(12) United States Patent
Ohkawa et al.

(10) Patent No.: US 7,208,495 B2
(45) Date of Patent: Apr. 24, 2007

(54) BENZO-FUSED 5-MEMBERED HETROCYCLE COMPOUNDS, PROCESS FOR PREPARATION OF THE SAME, AND USE THEREOF

(75) Inventors: Shigenori Ohkawa, Takatsuki (JP); Masaomi Miyamoto, Takarazuka (JP); Masahiro Okura, Mino (JP); Tetsuya Tsukamoto, Akashi (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 323 days.

(21) Appl. No.: 10/481,367

(22) PCT Filed: Jul. 4, 2002

(86) PCT No.: PCT/JP02/06776

§ 371 (c)(1),
(2), (4) Date: Dec. 18, 2003

(87) PCT Pub. No.: WO03/004485

PCT Pub. Date: Jan. 16, 2003

(65) Prior Publication Data

US 2004/0167171 A1    Aug. 26, 2004

(30) Foreign Application Priority Data

Jul. 5, 2001    (JP) ............... 2001-204586

(51) Int. Cl.
    A61K 31/497    (2006.01)
    A61K 31/445    (2006.01)
    C07D 405/00    (2006.01)
    C07D 401/00    (2006.01)

(52) U.S. Cl. .................. 514/252.2; 514/320; 544/376; 546/196

(58) Field of Classification Search ............... 544/376; 546/196; 514/252.2, 320
    See application file for complete search history.

(56) References Cited

U.S. PATENT DOCUMENTS

| 4,558,043 | A | 12/1985 | Wenk et al. |
| 5,681,954 | A | 10/1997 | Yamamoto et al. |
| 6,479,536 | B1 | 11/2002 | Ohkawa et al. |
| 6,867,226 | B2 * | 3/2005 | Kobayashi et al. ......... 514/375 |
| 6,900,222 | B1 * | 5/2005 | De Bruyn et al. .......... 514/274 |
| 6,967,201 | B1 * | 11/2005 | Briner et al. ......... 514/254.11 |
| 7,008,950 | B1 * | 3/2006 | Ohkawa et al. ............. 514/278 |

FOREIGN PATENT DOCUMENTS

| EP | 0 471 609 B1 | 6/1991 |
| JP | 04-149546 | 5/1992 |
| WO | WO 97/29105 | 8/1997 |
| WO | WO 98/55454 | 12/1998 |
| WO | WO 99/05140 | 2/1999 |
| WO | WO 00/34262 | 6/2000 |
| WO | WO 01/09111 A1 | 2/2001 |
| WO | WO 01/87878 A1 | 11/2001 |
| WO | WO 02/074768 | 9/2002 |

OTHER PUBLICATIONS

Debets, A.J.J., "Zone Electrophoretic Sample Treatment Coupled On-Line with Column Liquid Chromatography for the Determination of Basic and Acidic Compounds in Biological Samples", *Chromatographia* (1992), vol. 34, No. 11-12, pp. 581-588.

Jurd, L., "Quinones and Quinone Methides. III. A Novel Side-Chain Amination Reaction of 2-(1-Phenylethyl)-1,4-benzoquinones", *Aust. J. Chem.* (1978) 31(2), pp. 347-352.

* cited by examiner

Primary Examiner—Deborah C. Lambkin
(74) Attorney, Agent, or Firm—Elaine M. Ramesh; Mark Chao

(57) ABSTRACT

A compound represented by the formula:

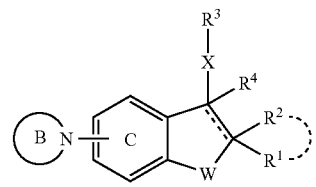

(wherein, $R^1$ and $R^2$ are the same or different and each represents a hydrogen atom, hydrocarbon group or heterocyclic group, or $R^1$ and $R^2$ may form, together with the adjacent carbon atom, a 3–8 membered iso- or heterocyclic group, $R^3$ represents a cyclic group, a hydroxy group, a mercapto group that may have oxo, or an amino group, $R^4$ represents a hydrogen atom, a hydrocarbon group, a hydroxy group, a mercapto group which may have oxo, or an amino group, or $R^2$ and $R^4$ may link together to form a double bond, X represents a bond or a linear hydrocarbon group, W represents an oxygen atom or a sulfur atom, ring B represents a 5–8 membered nitrogen-containing heterocyclic group, ring C represents a benzene ring, and— represents a single bond or a double bond), or a salt or a prodrug thereof that has excellent neurodegenerative inhibitory activity and brain penetrability, and is useful as an agent for preventing/treating neurodegenerative diseases.

46 Claims, No Drawings

BENZO-FUSED 5-MEMBERED HETROCYCLE COMPOUNDS, PROCESS FOR PREPARATION OF THE SAME, AND USE THEREOF

This application is the National Phase filing of International Patent Application No. PCT /JP02/06776, filed Jul. 4, 2002.

TECHNICAL FIELD

The present invention relates to novel benzo-fused 5-membered heterocyclic compounds, and particularly to benzofuran or benzothiophene derivatives, methods for producing them, and pharmaceutical compositions containing the same. More particularly, the present invention relates to compounds exhibiting excellent pharmacological activities such as neurotrophic factor-like activity, neurotrophic factor activity-enhancing activity, neurodegeneration inhibitory activity, neurogenesis enhancing activity, neuroregeneration enhancing activity, inhibiting activity of β-amyloid cytotoxicity, and the like, and are effective as a medicine for preventing/treating neurodegenerative diseases and the like.

BACKGROUND ART

Neurodegenerative diseases are progressive diseases that cause destructive damage known as nerve cell death. The major neurodegenerative diseases are exemplified by central nerve diseases such as Alzheimer's disease, Parkinson's disease, amyotrophic lateral sclerosis (ALS), Huntington's disease and the like, and peripheral nerve disorders such as diabetic neuropathy and the like. Most of these diseases are related to aging, and the onset thereof increases with age. However, these diseases also occasionally appear in middle age or even younger ages.

As a result of research related to the structure and function of the brain, the roles of neurotransmitters, neurotrophic factors, and the like are gradually being elucidated, but there is still much that is unknown about the causes of neurodegenerative diseases. Only with Parkinson's disease has the connection between it and a specific neurotransmitter, i.e., dopamine, been clearly shown, and thus a precursor of dopamine, L-Dopa, is used as a drug to relieve the neurological symptoms thereof and recover function. However, L-Dopa does not inhibit the progress of neurodegeneration, and as the condition progresses, i.e., the degeneration/loss of dopamine neurons, the effect of the L-Dopa will be gradually lost. In addition, Alzheimer's disease is a disease in which a large variety of neurons such as acetylcholine neurons, monoamine system neurons, and the like degenerate and/or are lost, and cholinesterase inhibitors are either now on the market or being developed as drugs to treat this disease. However here, like with L-Dopa in Parkinson's disease, these are still in the area of palliative treatment that temporarily improves the neurological symptoms thereof.

Thus, there are no current reports of drugs that protect neurons from the toxicity of factors causing cell death and inhibit the progress of neurodegenerative diseases including Alzheimer's disease and Parkinson's disease.

In addition, it is said that cell death in neurodegenerative diseases is caused by the toxicity of the factors specific to each respective disease. For example, in Alzheimer's disease, endogenous β-amyloid is considered to be a factor that causes cell death. β-amyloid is a protein composed of between 40 to 43 amino acids, and forms the senile plaque that is a neuropathological hallmark seen in the brains of Alzheimer's disease patients. It has been clearly shown that neuronal cell death is caused when this β-amyloid is added to a primary culture of hippocampus neurons [Science, Vol. 245, pp 417–420 (1989)], and it has been demonstrated that the aggregation of β-amyloid is essential for the manifestation of this toxicity and the like [Neurobiology of Aging, Vol. 13, pp 587–590 (1992) and Journal of Molecular Biology, Vol. 218, pp 149–163 (1991)]. With regard to the mechanism by which the toxicity of β-amyloid is manifested, it is thought that 1) β-amyloid forms ion channels and occurs calcium ions influx, 2) β-amyloid enhances free radicals generation, 3) β-amyloid activates tau-protein kinase I (TPK-I) to promote the phosphorylation of tau, 4) β-amyloid activates microglia, and neurotoxin is secreted from the microglia, and the like.

Recently, it has been clearly shown that neurotrophic factors such as IGF-1 (insulin-like growth factor), NGF (nerve growth factor) and the like inhibit neuronal apoptosis caused by β-amyloid and the like, and that the inhibition of TPK-I/GSK-3β (glycogen synthase kinase-3) caused by the activation of PI-3 kinase played a role in this mechanism [J. Neurosci, Vol. 11, pp 2552–2563 (1991), Science, Vol. 267, pp 2003–2006 (1995), and J. Biol. Chem. Vol. 272, pp 154–161 (1997)]. When TPK-I/GSK-3 β is activated through PI-3 kinase inhibition by β-amyloid and the acetylcholine synthesis reaction system is influenced by the inhibition of pyruvate dehydrogenase (PDH), and thus the content of acetylcholine is also reduced. This concurs with the reduction of the quantity of acetylcholine in brains of Alzheimer's disease patients, and conversely, by activating PI-3 kinase, it is anticipated that nerve cell death will not only be prevented, but that this will cause the quantity of intracerebral acetylcholine to increase, and the neurological symptoms to improve. Furthermore, by inhibiting TPK-I/GSK-3β, an increase in intracerebral glucose utilization that is reduced in Alzheimer's disease can also be expected [J. Biol. Chem Vol. 269, pp 3568–3573 (1994), and Endocrinology, Vol. 125, pp 314–320 (1989)].

In addition, the following compounds have been reported as compounds having a condensed nitrogen-containing heterocyclic group on a benzene ring condensed with a 5-membered heterocyclic, e.g., a furan ring or dihydrofuran ring, or a benzothiophene ring or dihydrobenzothiophene ring.

1) Compounds represented by the following formula and which have bone resorption and bone metabolism inhibitory activity:

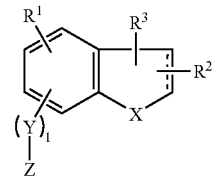

(wherein, $R^1$ is hydrogen, lower alkyl, an acyl group, amino, acylamino, nitro, halogen or hydroxy-lower alkyl which may have one or more suitable substituents, $R^2$ is hydrogen, lower alkyl, an acyl group, lower alkoxy, acyl-lower alkyl, aryl, cyano, mono-(or di- or tri-)-halo-lower alkyl. lower alkylthio or hydroxy-lower alkyl which may have one or more suitable substituents, $R^3$ is hydrogen, lower alkyl, lower alkenyl, cyclo-lower alkyl-lower alkyl, halogen, an acyl group, acyl-lower alkyl, acylamino, acylamino-lower alkyl, acyl(lower)alkenyl, acyloxy-lower alkyl, acyl-lower alkylthio-lower alkyl, amino-lower alkyl, mono-(or di-) lower alkylamino, lower alkylthio-lower alkyl, hydroxy-imino-lower alkyl which may have one or more suitable substituents, hydroxy-lower alkyl which may have one or more suitable substituents, hydroxy-lower alkylthio-lower alkyl, cyano-lower alkyl, mono-(or di-)lower alkoxy-lower alkyl which may have one or more suitable substituents, lower alkyl substituted with aryl which may have one or more suitable substituents, mono-(or di-)lower alkylamino-lower alkyl, lower alkyl substituted with heterocyclic group which may have one or more suitable substituents, the heterocyclic group which may have one or more suitable substituents, heterocyclicthio, heterocyclicthio-lower alkyl, heterocyclicoxy, heterocyclicoxy-lower alkyl, heterocycli-caminoimino-lower alkyl, aryl, amino or nitro, $R^2$ and $R^3$ may be linked together to form (1) lower alkylene which may have one or more suitable substituents, (2) lower alkenylene which may have one or more suitable substituents, or (3) a group of the formula $—(A^1)_m—W—(A^2)_n—$ (wherein $A^1$ and $A^2$ are each lower alkylene which may have one or more suitable substituents or lower alkenylene which may have one or more suitable substituents, W is S—, —S(O)— or $N(R^5)$—(wherein $R^5$ is hydrogen, lower alkyl or an acyl group) and m and n are each integer 0 or 1, X is O or S, Y is vinylene or a group of the formula —NHCO—, —NHSO$_2$—, —OCO—, —OCH$_2$—, —NHCOCO—, —NHCOCH=CH—, —NHCOCH$_2$—, —NHCONH— or $N(R^6)$CO—(wherein $R^6$ is lower alkyl), Z is heterocyclic group which may have one, or more suitable substituents, or aryl which may have one or more suitable substituents, 1 is an integer 0 or 1, and— represents a single bond or a double bond), and pharmaceutically acceptable salts thereof, and more specifically

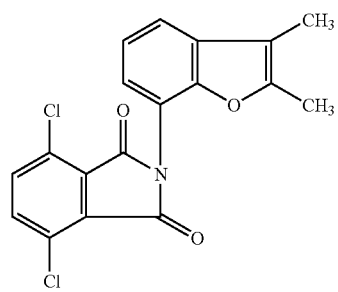

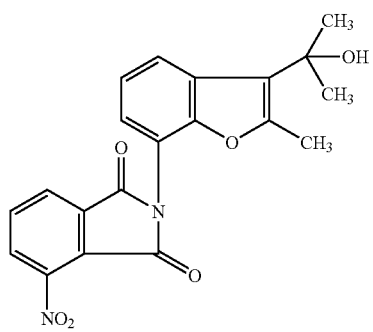

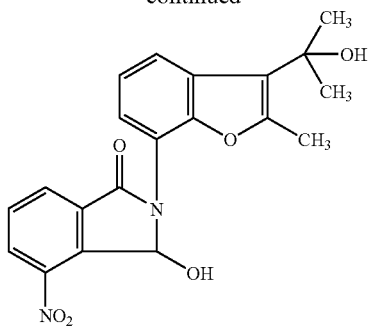

(WO 95/29907 and JP 9-512795 A).

2) 3,5-dihydroxy heptanoic acids having lipid peroxide formation inhibition activity, represented by the formula:

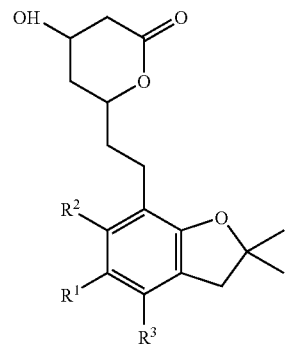

(wherein $R^1$ is a hydrogen atom, a nitro group, a group represented by —N($R^4$) $R^5$, wherein $R^4$ and $R^5$ are each an hydrogen atom, lower alkyl group, lower alkenyl group, aryl group, aralkyl group, acyl group, aroyl group, substituted or unsubstituted carbamoyl group, or substituted or unsubstituted thiocarbamoyl group, and $R^4$ and $R^5$ may be combined to form a cyclic amino group. $R^2$ and $R^3$ are each an hydrogen atom or lower alkyl), and 3,5-dihydroxy heptanoic acids represented by the formula:

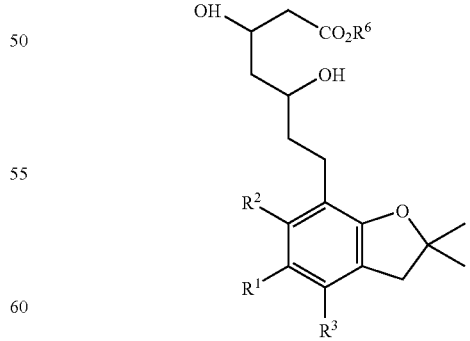

(wherein, $R^1$ is a hydrogen atom, nitro group, a group represented by —N($R^4$)$R^5$, and wherein $R^4$ and $R^5$ are each a hydrogen atom, lower alkyl group, lower alkenyl group, aryl group, aralkyl group, acyl group, aroyl group, substituted or unsubstituted carbamoyl group, or substituted or unsubstituted thiocarbamoyl group, and $R^4$ and $R^5$ may be combined together to form a amino group, $R^2$ and $R^3$ are each an hydrogen atom or lower alkyl, $R^6$ is an hydrogen atom, lower alkyl group, alkali metal or alkaline earth metal) (JP 5-194466 A).

3) Compounds used as a herbicide and represented by the formula:

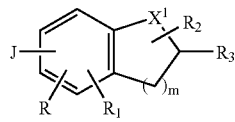

(wherein, R is H, Cl, F, $C^1$–$C^2$ alkyl or $C_1$–$C_2$ alkoxy, $R^1$ is H, F, Cl, Br, $CH_3$, $OCH_3$, CN, $CF_3$, $OCF_3$ or $OCF_2H$,. $X^1$ is O; $R^2$ is H, $CH_3$ or $CH_2CH_3$, $R^3$ is H, $C_1$–$C_4$ haloalkyl, $CR_2R_7CN$, CN, $CR_2R_4R_7$, COCl, $COR_4$, $C(NOR_6)$ $R_2$, $CO_2R_4$, $CONR_4R_2$, $CHR_2OH$, $CO_2$ $(CH_2)_2Si$ $(CH_3)_3$, $CONR_2SO_2CH_3$, $CHR_2CO_2R_4$, $CONHCH(CH_3)$ CONHCH $(CH_3)$ $CO_2CH_3$, $CHR_2COR_4$, $CHR_2OSO_2(C_1$–$C_4$ alkyl), $CHR_2OC(O)R_4$, $CHR_2OC(O)N(R_2)_2$, $CHR_2OC(O)N(R_2)$ $OCH_3$, $CHR_2OC(O)N(R_2)Ph$, $HC=CH_2$ or $C\equiv CH$; $R^4$ is H, $C_1$–$C_4$ alkyl, $C_1$–$C_4$ haloalkyl, $C_2$–$C_6$ alkenyl, $C_3$–$C_6$ alkynyl, $C_2$–$C_4$ halo alkenyl, phenyl, $C_1$–$C_4$ alkylphenyl, $C_3$–$C_6$ alkoxycarbonyl alkyl or $(CH_2CH_2O)_bR_2$; b is 1–6; m is 1; n is 1 or 2; J is

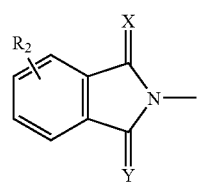

J-1

(wherein, X and Y respectively represent O or S). (U.S. Pat. No. 4,881,967).

4) Compounds having antibacterial activity and represented by the formula:

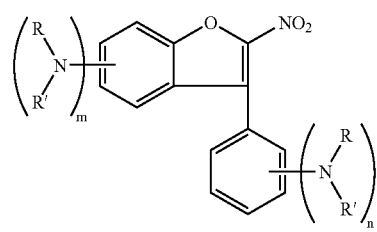

(wherein, m and n are 0 or 1, and the sum of m and n is 1, R is hydrogen or lower alkyl, R' is R,

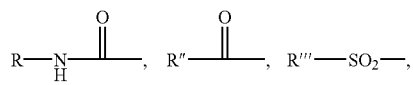

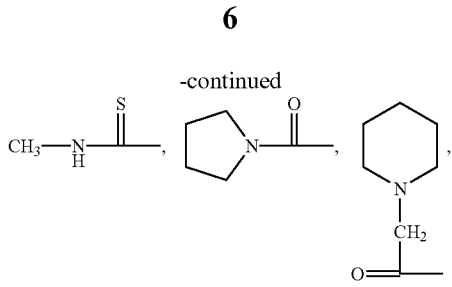

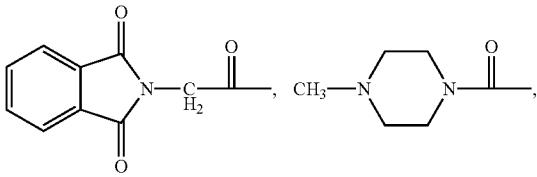

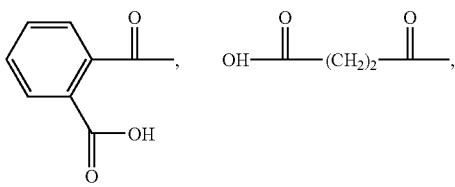

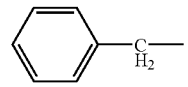

or R and R' together form $(CH_3)_2N-N=$,

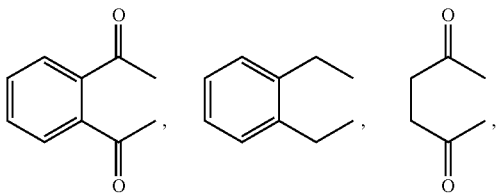

or form a pyrrole or pyrrolidine, R″ is R, lower alkyl $CF_3—$ or $ClCH_2—$, R‴ is a lower alkyl or $CF_3—$), or pharmacologically acceptable salts thereof (U.S. Pat. No. 4,212,865).

5) The compound which is a synthetic intermediate and represented by the formula:

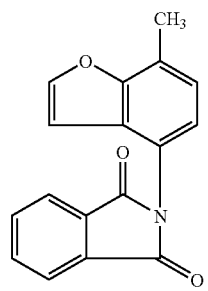

[Tetrahedron Letters, Vol. 37, No. 51, pp 9183–9186, (1996)].

6) The compounds or salts thereof having lipid peroxide formation inhibition activity and represented by the formula:

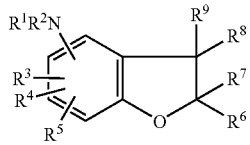

(wherein, $R^1$ and $R^2$ are the same or different and each is a hydrogen atom, acyl group, alkoxycarbonyl group, aliphatic group, optionally substituted aliphatic group, or an optionally substituted aromatic group, $R^3$, $R^4$ and $R^5$ are the same or different and each is an optionally acylated hydroxy group, an optionally substituted amino group, an optionally substituted alkoxy group, or an optionally substituted aliphatic group, or two of $R^3$, $R^4$ and $R^5$ may form an optionally substituted carbon homocyclic group, $R^6$ and $R^7$ are the same or different and each is an optionally substituted aliphatic group, and moreover at least one of $R^6$ and $R^7$ has methylene at the α-position, $R^8$ and $R^9$ are the same or different and each is a hydrogen atom or an optionally substituted aliphatic group or an optionally substituted aromatic group), or a salt thereof (EP-A-483772 and JP 5-140142 A).

7) The compounds having bone resorption inhibitory activity and represented by the formula:

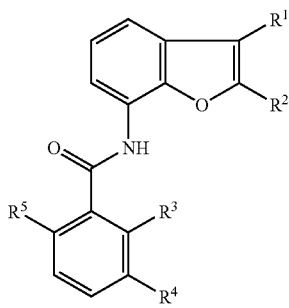

(wherein, $R^1$ is formyl, carbamoyl-lower alkyl, thiomorpholino carbonyl-lower alkyl, thiomorpholino carbonyl-lower alkyl S-oxide, pyridylamino carbonyl-lower alkyl, pyrazolylamino carbonyl-lower alkyl, triazolylamino carbonyl-lower alkyl, quinolylamino carbonyl-lower alkyl which may have one or more suitable substituents, 3-pyridyl-lower alkyl aminocarbonyl-lower alkyl, 4-pyridyl-lower alkyl aminocarbonyl-lower alkyl, pyridyl ethylamino carbonyl-lower alkyl, pyridyl-lower alkylaminocarbonyl-lower alkyl N-oxide, benzimidazolyl-lower alkylaminocarbonyl-lower alkyl, N-pyridyl-lower alkyl-N-acyl-lower alkylaminocarbonyl-lower alkyl, N-pyridyl-lower alkyl-N-lower alkylaminocarbonyl-lower alkyl, -lower alkylaminocarbonyl-lower alkyl, di-lower alkylaminocarbonyl methyl, quinolyl, 2-hydroxyethyl-2-hydroxy-2-methylpropyl, cyano-lower alkyl, di-lower alkylamino-lower alkyl, pyridyl-lower alkyl, triazolyl-lower alkyl, pyrazolyl-lower alkyl which may have one or more suitable substituents, pyrimidinyl-lower alkyl which may have one or more suitable substituents, dihydrophthalidinyl-lower alkyl which may have one or more suitable substituents, oxadiazolyl-lower alkyl which may have one or more suitable substituents, heterocyclic lower alkenyl which may have one or more suitable substituents, (lower alkoxy)-lower alkylamino-lower alkyl which may have one or more suitable substituents, aryl-lower alkylaminocarbonyl-lower alkyl which may have one or more suitable substituents, arylamino carbonyl-lower alkyl which may have one or more suitable substituents, arylthio-lower alkyl which may have one or more suitable substituents, lower alkyl, or imidazolyl-lower alkyl, $R^2$ is lower alkyl, protected carboxy or cyano, $R^3$ is halogen or lower alkyl, $R^4$ is hydrogen, nitro or amino, and $R^5$ is halogen, lower alkyl or nitro. However, when 1) $R^1$ is methyl, $R^2$ is protected carboxy or cyano, and 2) when $R^1$ is imidazolylmethyl, $R^2$ is protected carboxy or cyano), or salts thereof (JP 9-124633 A).

8) Compounds having sodium channel modulation activity and which are represented by following formula:

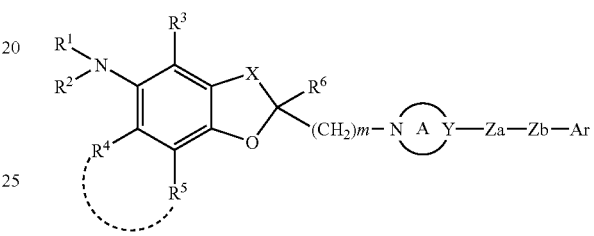

(wherein, $R^1$ and $R^2$ are each a hydrogen atom, a lower alkyl which may be substituted, or acyl, $R^3$, $R^4$ and $R^5$ are each a lower alkyl which may be substituted or a lower alkoxy with may be substituted, or $R^4$ and $R^5$ may link together to form a 5- or 6-membered carbon homocyclic group, $R^6$ is lower alkyl, Ar is an aromatic group which may be substituted, ring A is a 5- to 8-membered nitrogen-containing heterocyclic ring C which may be substituted, X is a lower alkylene which may be substituted, Y is a carbon atom or a nitrogen atom, Za is group represented by the formula $CH_2$, $COCH(R^7)$, $OCH(R^7)$, $SCH(R^7)$ or $N(R^{10})CH(R^7)$ (wherein, $R^7$ is a hydrogen atom or aromatic group which may be substituted, and $R^{10}$ is a hydrogen atom, hydrocarbon group which may be substituted, or acyl), Zb is a divalent aliphatic hydrocarbon group which may have a binding bond or a substitutent and may be bonded via an oxygen atom, nitrogen atom or sulfur atom, and m is an integer of 1–3), or salts thereof (WO98/08842).

It is thought that compounds which exhibit excellent brain permeability and which have neurotrophic factor-like activity, neurotrophic factor reactivity-enhancing activity, and activity that promotes neuropoiesis and neuroregeneration enhancing after neurodegeneration, will inhibit nerve cell death in neurodegenerative diseases such as Alzheimer's disease and the like, and can improve the symptoms of the same. Accordingly, it is desirable to develop compounds having neurotrophic factor-like activity and neurotrophic factor reactivity-enhancing activity, and further have excellent pharmacological activities such as activity which inhibits the cytotoxicity of β-amyloid and the like in order to protect neurons, or activity which protects neurons from toxicity factors which cause cell death, and thus are useful as a pharmaceutical for preventing/treating neurodegenerative diseases and the like.

The present applicant took this situation into consideration, and first, successfully synthesized compounds or the salts thereof represented by the formula:

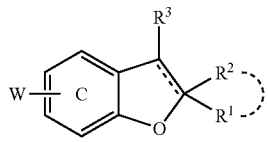

wherein (i) a group is represented by the formula:

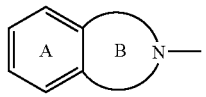

(Wa)

(in the formula, ring A represents a benzene ring which may be substituted, and ring B represents a 5- to 7-membered nitrogen-containing heterocyclic group which may be substituted with a halogen or an optionally substituted hydrocarbon group) or
(ii) a group is represented by the formula:

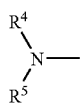

(Wb)

(in the formula, $R^4$ represents (1) a aliphatic hydrocarbon group which may be substituted with an aromatic group that may be substituted, and wherein the aliphatic hydrocarbon group may have further substituents or (2) an acyl group that includes an aromatic group that may be substituted, $R^5$ represents hydrogen, $C_{1-6}$ alkyl or an acyl group),
when W is Wa, $R^3$ represents a hydrogen atom, a hydrocarbon group that may be substituted, or a heterocyclic group that may be substituted, ring C represents a benzene ring which, other than the group represented by Wa, may also have a substituent selected from a halogen, a lower alkyl that may be halogenated, lower alkoxy that may be halogenated, and a lower alkylthio which may be halogenated,
when W is Wb, $R^3$ represents a $C_{6-14}$ aryl group that may be substituted, and ring C represents a benzene ring which may also have further substituents in addition to the group represented by Wb. However, when— represents a double bond, the partial structure

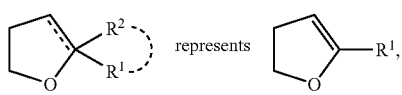 represents 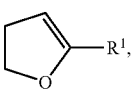, the applicant then discovered that the compounds have pharmaceutical activities such as neurotrophic factor-like activity, neurotrophic factor reactivity-enhancing activity, inhibiting activity of β-amyloid cytotoxicity, and the like, and moreover, discovered that these compounds had extremely low toxicity, excellent brain penetrability properties, and thus could be sufficiently satisfactory as a pharmaceutical having neurodegeneration inhibitory activity, and filed a patent application (WO00/34262).

OBJECT OF INVENTION

It is an object of the present invention to provide additional novel benzo-fused 5-membered heterocyclic compounds having pharmaceutical activity such as neurotrophic factor-like activity, neurotrophic factor reactivity-enhancing activity, neurogenesis enhancing activity, neuroregeneration enhancing activity, and inhibiting activity of β-amyloid cytotoxicity, and having excellent brain penetrability properties and neurodegeneration inhibition activity.

DISCLOSURE OF INVENTION

As a result of extensive studies, the present inventors discovered that the novel compounds represented by following formula (I) have surprisingly excellent pharmaceutical activity such as neurotrophic factor-like activity, neurotrophic factor reactivity-enhancing activity, neurogenesis enhancing activity, neuroregeneration enhancing activity, and inhibiting activity of β-amyloid cytotoxicity, and moreover discovered that the compounds had extremely low toxicity and excellent brain penetrability properties. The present invention was completed based on this discovery.

More specifically, the present invention invention provides,
(1) Compounds represented by formula:

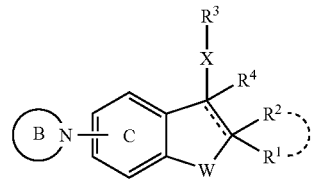

(I)

(wherein, $R^1$ and $R^2$ are the same or different and each represents a hydrogen atom, optionally substituted hydrocarbon group or optionally substituted heterocyclic group, or $R^1$ and $R^2$ may form, together with the adjacent carbon atom, a 3–8 membered iso- or heterocyclic group which may optionally substituted, $R^3$ represents an optionally substituted cyclic group, X represents a bond or a spacer of 1–3 atoms, and $R^4$ represents a hydrogen atom, an optionally substituted hydrocarbon group, optionally substituted hydroxy group, optionally substituted mercapto group which may have oxo, or an optionally substituted amino group, or $R^2$ and $R^4$ may link together to form a double bond, W represents an oxygen atom or a sulfur atom, ring B represents an optionally substituted 4–8 membered nitrogen-containing heterocyclic group, and ring C represents a benzene ring which may also be optionally substituted in addition to the group represented by ring B but not via a nitrogen atom, and— represents a single bond or a double bond), or a salt thereof.
(2) The compounds as defined in item (1), wherein $R^1$ and $R^2$ are the same or different and represent (i) a hydrogen atom, (ii) C1–6 alkyl group, C2–6 alkenyl group, C2–6 alkynyl group, C3–8 cycloalkyl group or C6–14 aryl group each of which may have 1–5 substituents selected from (1)

halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5-or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and a 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy, or (iii) 5–14 membered heterocyclic group including, other than carbon atoms, 1–4 heteroatoms selected from nitrogen atoms, sulfur atoms, and oxygen atoms, optionally containing 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally containing 1–3 substituents selected from C1–6 alkyl, C6–14 aryl and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo, and (24) C6–14 aryloxy, or (iv) $R^1$ and $R^2$, together with the adjacent carbon atom, may form C3–8 cycloalkane or 3–8 membered heterocyclic group including, other than carbon atoms, 1–4 heteroatoms selected from nitrogen atoms, sulfur atoms, and oxygen atoms, which may respectively include 1–5 substituents selected from the following, (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, thiocarbamoyl, C6–14 aryl-carbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino, and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally including 1–3 substituents which are selected from C1–6 alkyl, C6–14 aryl and a 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy;

$R^3$ represents (1) C6–14 aryl, (2) optionally-halogenated C3–8 cycloalkyl or (3) 5–10 membered heterocyclic group including, other than carbon atoms, 1–4 heteroatoms selected from nitrogen atoms, sulfur atoms, and oxygen atoms, which may respectively include 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino,

(16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5 or 6 membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy, X is the bond,

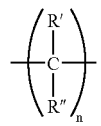

(wherein, R' and R" represent a hydrogen atom, C1–6 alkyl group, C3–8 cycloalkyl group or C6–14 aryl group, and n is an integer of 1–3, and when n is 2 or 3, R' and R" may be different in each repeating unit), —CO—, —O—, —S—, —SO—, —SO$_2$— or NR$^5$— (wherein, R$^5$ represents a hydrogen atom or C1–6 alkyl group, C2–6 alkenyl group, C2–6 alkynyl group, C3–8 cycloalkyl group, C6–14 aryl group, each of which may respectively contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally containing 1–3 substituents selected from C1–6 alkyl, C6–14 aryl and 5–10 membered aromatic heterocyclic group including, other than carbon atoms, 1–4 heteroatoms selected from nitrogen atoms, sulfur atoms, and oxygen atoms (22) 5–10 membered aromatic heterocyclic group including, other than carbon atoms, 1–4 heteroatoms selected from nitrogen atoms, sulfur atoms, and oxygen atoms (23) sulfo, and (24) C6–14 aryloxy), and a divalent group combining 1–3 of these may be formed;

R$^4$ represents a hydrogen atom or C1–6 alkyl group, C2–6 alkenyl group, C2–6 alkynyl group or C3–8 cycloalkyl group, C6–14 aryl group, hydroxy group, mercapto group which may have oxo, or amino group, which may respectively include 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) the acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5-or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino, and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy, or $R^2$ and $R^4$ may link together to form a double bond, and ring B via —Y— is (i) a hydrogen atom, (ii) halogen, (iii) oxo, (iv) [1] halogen or [2] C1–6 alkyl group, C2–6 alkenyl group, C2–6 alkynyl group, C3–8 cycloalkyl group, C6–14 aryl group or 4–8 membered nitrogen-containing ring which may contain 5–10 membered aromatic heterocyclic group including, other than carbon atoms, 1–4 heteroatoms selected from nitrogen atoms, sulfur atoms, and oxygen atoms, and which may respectively include 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5 or 6 membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy; wherein Y is a bond, —CO—, —O—, —S—, —SO—, —SO₂— or $NR^6$— ($R^6$ is a hydrogen atom or C1–6 alkyl group, C2–6 alkenyl group, C2–6 alkynyl group, C3–8 cycloalkyl group, C6–14 aryl group, which may respectively contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl which includes 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy), and;

ring C represents a benzene ring which may further include, in addition to ring B, 1–3 substituents selected from (1) halogen, (2) C1–3 alkylenedioxy, (3) nitro, (4) cyano, (5) optionally halogenated C1–8 alkyl, (6) optionally halogenated C2–8 alkenyl, (7) optionally halogenated C2–8 alkynyl, (8) optionally halogenated C3–8 cycloalkyl, (9) optionally halogenated C6–14 aryl, (10) optionally halogenated C1–6 alkoxy, (11) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino and C6–14 aryl sulfonyl amino, (19) 4–8 membered saturated cyclic amino optionally containing 1–3 substituents selected from C1–6 alkyl, C6–14 aryl, and 5–10 membered aromatic heterocyclic group including, other than carbon atoms, 1–4 heteroatoms selected from nitrogen atoms, sulfur atoms, and oxygen atoms, (20) 5–10 membered aromatic heterocyclic group including, other than carbon atoms, 1–4 heteroatoms selected from nitrogen atoms, sulfur atoms, and oxygen atoms, and (21) sulfo, (3) The compounds as defined in item (1), wherein W is an oxygen atom, (4) The compounds as defined in item (1), wherein X is a bond, (5) The compounds as defined in item (1), wherein X is

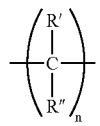

(wherein, R' and R" represent a hydrogen atom, C1–6 alkyl group, C3–8 cycloalkyl group or C6–14 aryl group, and n is an integer of 1–3, and when n is 2 or 3, R' and R" may be different in each repeating unit),
(6) The compounds as defined in item (1), wherein— is a single bond,
(7) The compounds as defined in item (1), wherein R3 is optionally substituted C6–14 aryl group,
(8) The compounds as defined in item (1), wherein R3 is an optionally substituted heterocyclic group,
(9) The compounds as defined in item (1), wherein X is a bond, and R3 is an optionally substituted phenyl group,
(10) The compounds as defined in item (1), wherein X is a bond, R3 is a phenyl group which may respectively contain 1–5 substituents selected from (1) halogen, (2) optionally halogenated C1–6 alkyl, (3) optionally halogenated C6–14 aryl, (4) optionally halogenated C1–6 alkoxy, and (5) di-C1–6 alkylamino,
(11) The compounds as defined in item (1), wherein X is a bond, R3 is a 5–8 membered heterocyclic group including 1–3 nitrogen atoms, as heteroatoms, on the ring structure, which may also contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl and 5–10 membered aromatic heterocyclic group including, other than carbon atoms, 1–4 heteroatoms selected from nitrogen atoms, sulfur atoms, and oxygen atoms, (22) 5–10 membered aromatic heterocyclic group including, other than carbon atoms, 1–4 heteroatoms selected from nitrogen atoms, sulfur atoms, and oxygen atoms, (23) sulfo and (24) C6–14 aryloxy,
(12) The compounds as defined in item (1), wherein X is a bond, and R3 is piperidino, morpholino, piperazinyl, pyridyl or pyrrolidinyl group which may respectively contain 1–3 substituents selected from (1) halogen, (2) optionally halogenated C1–6 alkyl, (3) optionally halogenated C6–14 aryl and (4) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl and C7–16 aralkyloxy-carbonyl,
(13) The compounds as defined in item (1), wherein ring B includes 1–4 groups (that may be respectively the same or different when a plurality is included) represented by the formula —Y—Ar [wherein, Y represents —(CH$_2$)$_m$13 (m represents an integer of 1 to 6), —CO—, —O—, —S—, —SO—, —SO$_2$— or —NR$^6$— (wherein R$^6$ represents a hydrogen atom or optionally substituted hydrocarbon group) or a bond, and Ar represents optionally substituted aromatic group],
(14) The compounds as defined in item (1), wherein ring B is a piperidine ring, piperazine ring or pyrrolidine ring,
(15) The compounds as defined in item (1), wherein ring B is substituted in the 5 position of a (dihydro) benzo thiophene ring or a (dihydro) benzofuran ring,
(16) The compound as defined in item (13), wherein the aromatic ring represented by Ar is a optionally substituted phenyl group,
(17) The compound as defined in item (13), wherein Y is a bond,
(18) The compounds as defined in item (1), wherein R1 and R2 are respectively C1–6 alkyl group,
(19) The compounds as defined in item (1), wherein R4 is a hydrogen atom,
(20) The compounds as defined in item (1), wherein ring C further includes, in addition to ring B, 1–3 substituents selected from (1) halogen, (2) C1–3 alkylenedioxy, (3) nitro, (4) cyano, (5) optionally halogenated C1–8 alkyl, (6) optionally halogenated C2–8 alkenyl, (7) optionally halogenated C2–8 alkynyl, (8) optionally halogenated C3–8 cycloalkyl, (9) optionally halogenated C6–14 aryl, (10) optionally halogenated C1–6 alkoxy, (II) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonylamino, and C6–14 arylsulfonylamino, (19) 4–8 membered saturated cyclic amino which may contain 1–3 substituents selected from C1–6 alkyl, C6–14 aryl, and 5–10 membered aromatic heterocyclic group including, other than carbon atoms, 1–4 heteroatoms selected from nitrogen atoms, sulfur atoms, and oxygen atoms, (20) 5–10 membered aromatic heterocyclic group including, other than carbon atoms, 1–4 heteroatoms selected from nitrogen atoms, sulfur atoms, and oxygen atoms, and (21) sulfo,

(21) The compounds as defined in item (1), wherein ring C further includes, in addition to ring B, 1–3 substituents selected from (1) halogen, (2) C1–3 alkylenedioxy, (3) nitro, (4) cyano, (5) C1–8 alkyl, (6) C2–8 alkenyl, (7) C2–8 alkynyl, (8) optionally halogenated C3–8 cycloalkyl, (9) optionally halogenated C6–14 aryl, (10) C1–6 alkoxy, (11) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, mono-C1–6 alkyl-carbamoyl, di-C1–6 alkyl-carbamoyl, C6–14 aryl-carbamoyl, thiocarbamoyl, C1–6 alkylsulfonyl; C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino, and C6–14 arylsulfonyl amino and (19) sulfo,

(22) The compounds as defined in item (1), wherein ring C further includes, in addition to ring B, 1 to 3 C1–6 alkyl groups,

(23) The compounds as defined in item (1), wherein ring C further includes, in addition to ring B, 3 C1–6 alkyl groups,

(24) The compounds as defined in item (1), wherein ring C includes, in addition to ring B, 3 methyl groups,

(25) 4-(3,4-dimethoxyphenyl)-1-(2,2,4,6,7-pentamethyl-3-(4-methylphenyl)-2,3-dihydro-1-benzofuran-5-yl) piperazine, (3R)-4-(4-methoxyphenyl)-1-(2,2,4,6,7-pentamethyl-3-(4-methylphenyl)-2,3-dihydro-1-benzofuran-5-yl) piperidine, 1-(2,2,4,6,7-pentamethyl-3-(4-methylphenyl)-2,3-dihydro-1-benzofuran-5-yl)-4-(4-methoxyphenyl) piperazine, N-phenyl-5-(4-(4-methoxyphenyl) piperazin-1-yl)-2,2,4,6,7-pentamethyl-2,3-dihydro-1-benzofuran-3-amine, 4-(4-methoxyphenyl)-1-(2,2,4,6,7-pentamethyl-3-piperidino-2,3-dihydro-1-benzofuran-5-yl) piperazine, 1-(3-(4-(trifluoromethyl)phenyl)-2,2,4,6,7-pentamethyl-2,3-dihydro-1-benzofuran-5-yl)-4-(4-methoxyphenyl) piperazine, 4-(3,4-dimethoxyphenyl)-1-(3-(4-methylphenyl)-2,2,4,6,7-pentamethyl-2,3-dihydro-1-benzofuran-5-yl) piperidine, 1-(3-(4-isopropylphenyl)-2,2,4,6,7-pentamethyl-2,3-dihydro-1-benzofuran-5-yl)-4-(3,4-dimethoxyphenyl) piperidine, 1-(4-methoxyphenyl)-4-(2,2,4,6,7-pentamethyl-3-[pyrrolidin-1-yl]-2,3-dihydro-1-benzofuran-5-yl) piperazine, 1-(5-(4-(4-methoxyphenyl) 1-piperazinyl)-(2,2,4,6,7-pentamethyl-2,3-dihydro-1-benzofuran-3-yl) indoline, 1-(4-methoxyphenyl)-4-(2,2,4,6,7-pentamethyl-3-pyridine-2-yl-2,3-dihydro-1-benzofuran-5-yl) piperazine, 1-(3-(6-fluoropyridin-3-yl)-2,2,4,6,7-pentamethyl-2,3-dihydro-1-benzofuran-5-yl)-4-(4-methoxyphenyl) piperazine, 1-(3,4-dimethoxyphenyl)-4-(2,2,4,6,7-pentamethyl-3-piperidino-2,3-dihydro-1-benzofuran-5-yl) piperazine, 1-(4-methoxyphenyl)-4-(2,2,4,6,7-pentamethyl-3-(6-methyl-3-pyridinyl)-2,3-dihydro-1-benzofuran-5-yl) piperazine, 4-(4-methoxyphenyl)-1-(2,2,4,5,7-pentamethyl-3-(4-methylphenyl)-2,3-dihydro-1-benzofuran-6-yl) piperazine, 1-(3-benzyl-2,2,4,6,7-pentamethyl-2,3-dihydro-1-benzofuran-5-yl)-4-(4-methoxyphenyl) piperazine, or 1-(4-methoxyphenyl)-4-(2,2,4,6,7-pentamethyl-3–4-phenoxy) methyl)-2,3-dihydro-1-benzofuran-5-yl) piperazine,

(26) A prodrug of the compounds as defined in item (1),

(27) A neurodegeneration inhibitor which includes a compound as defined in item (1), a salt thereof, or a prodrug thereof,

(28) The inhibitor as defined in item (27), which is a β-amyloid toxicity inhibitor,

(29) The inhibitor as defined in item (27), which is a neurotrophic factor like agent,

(30) The inhibitor as defined in item (27), which is an agent for preventing/treating neurodegenerative diseases,

(31) A inhibitor as defined in item (27), which is an agent for preventing/treating Alzheimer's disease or Parkinson's disease,

(32) A inhibitor as defined in item (27), which is therapeutic agent for mild cognitive impairment or mild memory loss,

(33) A neurogenesis promotion agent or a neuroregeneration promotion agent that includes a compound as defined in item (1), a salt thereof, or a prodrug thereof,

(34) The agent as defined in item (33), which is a proliferation/differentiation promotion agent for stem cells and/or neural precursor cells,

(35) The agent as defined in item (33), wherein the stem cells are embryonic stem cells or neural stem cells,

(36) The agent as defined in item (33), which is a survival/differentiation promotion agent for neural stem cells and/or nerve cell grafts,

(37) The agent as defined in item (33), which is a proliferation/differentiation promotion agent for neural stem cells and/or neural cells,

(38) The agent as defined in item (33), which is a proliferation/differentiation promotion agent for endogenus neural stem cells,

(39) The agent as defined in item (33), which is for preventing/treating central nervous system diseases,

(40) A proliferation/differentiation promotion agent for culturing neural stem cells and/or neural precursor cells for transplantation which includes a compound as defined in item (1) or a salt thereof,

(41) Use of compounds as defined in item (1) or salts thereof as a proliferation/differentiation promotion agent when culturing neural stem cells and/or neural precursor cells for transplantation,

(42) Protein kinase B (PKB) activator which includes a compound defined in item (1), a salt thereof, or a prodrug thereof,

(43) The PKB activator as defined in item (42), which is an agent for preventing/treating Parkinson's disease, Alzheimer's disease, amyotrophic lateral sclerosis (ALS) or Huntington's disease,

(44) The PKB activator as defined in item (42), which is an agent for preventing/treating depression, anxiety, manic depression or PTSD (post-traumatic stress disorder),

(45) Use of the PKB activator as defined in item (42) for the production of an agent for preventing/treating Parkinson's disease, Alzheimer's disease, ALS or Huntington's disease,

(46) A process for the therapy or prevention of Parkinson's disease, Alzheimer's disease, ALS or Huntington's disease in a mammal, comprising the adminstration of the PKB activator as defined in item (42) to a mammal requiring prevention/treatment of Parkinson's disease, Alzheimer's disease, ALS or Huntington's disease,

(47) Use of the PKB activator as defined in item (42) for the production of an agent for preventing/treating depression, anxiety, manic depression or PTSD,

(48) A process for the prevention/treatment of depression, anxiety, manic depression or PTSD in a mammal, comprising the adminstration of the PBK activator as defined in item

(42) to a mammal requiring prevention/treatment of depression, anxiety, manic depression or PTSD,

(49) A neurodegeneration inhibitor that includes a compound, a salt thereof, or a prodrug thereof, and is represented by the formula

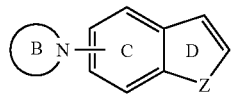

(wherein, ring B represents an optionally substituted 5–8 membered nitrogen-containing heterocyclic group, ring C represents a benzene ring which may further contain substituents in addition to the group represented by ring B, ring D represents an optionally substituted 5-membered ring, Z represents a carbon atom, nitrogen atom, oxygen atom or sulfur atom, and— represents a single bond or a double bond),

(50) The inhibitor as defined in item (49), wherein Z is an oxygen atom,

(51) The inhibitor as defined in item (49), which is a β-amyloid toxicity inhibitor,

(52) The inhibitor as defined in item (49), which is a neurotrophic factor like agent,

(53) The inhibitor as defined in item (49), which is an agent for preventing/treating neurodegenerative diseases,

(54) The inhibitor as defined in item (49), which is an agent for preventing/treating Alzheimer's disease, Parkinson's disease, ALS or Huntington's disease,

(55) The inhibitor as defined in item (49), which is a therapeutic agent for mild cognitive impairment or mild memory loss,

(56) A PKB activator which includes a compound as defined in item (49), a salt thereof, or prodrug thereof,

(57) A neurogenesis promotion agent or a neuroregeneration promotion agent which includes a compound as defined in item (49), a salt thereof, or prodrug thereof,

(58) The agent as defined in item (57), which is a proliferation/differentiation promotion agent for stem cells and/or neural precursor cells,

(59) The agent as defined in item (57), wherein Z is an oxygen atom,

(60) The agent as defined in item (57), wherein the stem cells are embryonic stem cells or neural stem cells,

(61) The agent as defined in item (57), which is a survive/differentiation promotion agent for neural stem cells and/or neural cell grafts,

(62) The agent as defined in item (57), which is a proliferation/differentiation promotion agent for neural stem cells and/or neural cells for transplantation,

(63) The agent as defined in item (57), which is a proliferation/differentiation promotion agent for endogenous neural stem cells,

(64) The agent as defined in item (57), which is for preventing/treating central nervous system diseases,

(65) A proliferation/differentiation promotion agent for stem cells and/or neural precursor cells for neural stem cell culture that include a compound as defined in item (49), or a salt thereof,

(66) The agent as defined in item (65), wherein Z is an oxygen atom,

(67) Use of compounds as defined in item (49) or salts thereof as a proliferation/differentiation promotion agent for stem cells and/or neural precursor cells for neural stem cell culture,

(68) Use as defined in item (67), wherein Z is an oxygen atom,

(69) A process for producing compounds as defined in item (1) or salts thereof, comprising the step of reacting compounds represented by the formula:

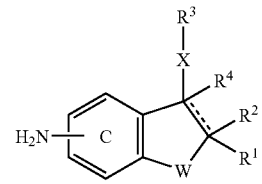

(wherein each symbol has the same meaning as in item (1)) or salts thereof with compounds represented by the formula:

$L^1$-E-$L^2$ (wherein, $L^1$ and $L^2$ represent leaving groups, and E represents a partial sequence of the ring structure of ring B other than the nitrogen atom) or salts thereof, and

(70) The production process as defined in item (69), in which the reaction occurs in the presence of base.

DETAILED DESCRIPTION OF INVENTION

In the aforementioned formula, W is an oxygen atom or sulfur atom. In other words, compounds or salts thereof represented by the aforementioned formula (I) of the invention (hereinafter simply referred to as compound (I)) are benzofuran or benzothiophene derivatives. Preferably, W is an oxygen atom.

In the aforementioned formula— represents a single bond or a double bond.

When— represents a double bond, R2 and R4 will not be present. In other words, in the aforementioned formula, (i) when— represents a single bond, the partial structure

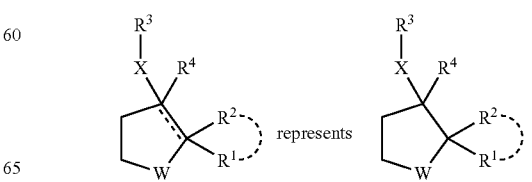

(ii) when ═ represents a double bond, the partial structure represents

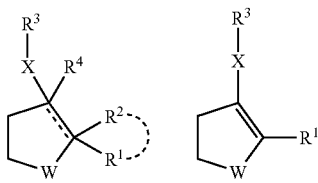

but, in the present specification, (i) and (ii) are together represented with the formula:

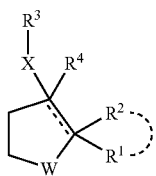

for the sake of convenience.

In the aforementioned formula, R1 and R2 are the same or different and represent a hydrogen atom, optionally substituted hydrocarbon group or optionally substituted heterocyclic group, or R1 and R2 together with the adjacent carbon atom may form a 3–8 membered homocyclic or heterocyclic group.

As the "hydrocarbon group" of the "optionally substituted hydrocarbon group" represented by R1 or R2, for example, a linear or cyclic hydrocarbon group (for example, alkyl, alkenyl, alkynyl, cycloalkyl, aryl and the like) and the like are exemplified. From amongst these, a 1–16 member carbon chain or a cyclic hydrocarbon group and the like are preferred.

As the "alkyl", for example C1–6 alkyl (for example, methyl, ethyl, propyl, isopropyl, butyl, isobutyl, sec-butyl, tert-butyl, pentyl, hexyl and the like) and the like are preferred.

As the "alkenyl", for example C2–6 alkenyl (for example, vinyl, allyl, isopropenyl, butenyl, isobutenyl, sec-butenyl and the like) and the like are preferred.

As the "alkynyl", for example C2–6 alkynyl (for example, ethynyl, propargyl, butenyl, 1-hexynyl and the like) and the like are preferred.

As the "cycloalkyl", for example C3–8 cycloalkyl (for example, cyclopropyl, cyclobutyl, cyclopentyl, cyclohexyl and the like) and the like are preferred.

As the "aryl", for example C6–14 aryl (for example, phenyl, 1-naphthyl, 2-naphthyl, biphenyl, 2-anthryl and the like) and the like are preferred.

As the "C6–14 aryl which may be substituted by halogen", C6–14 aryl such as is described above that is optionally substituted with fluorine, chlorine, bromine, iodine is preferred.

As the "substituent" of the "optionally substituted hydrocarbon group" represented by R1 or R2, for example (1) halogen atom (for example, fluorine, chlorine, bromine, iodine and the like), (2) C1–3 alkylenedioxy (for example, methylenedioxy, ethylenedioxy and the like), (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) C6–14 aryl which may be substituted by halogen (for example, phenyl, fluorine substituted phenyl, 1-naphthyl, 2-naphthyl, biphenyl, 2-anthryl and the like),

(10) optionally halogenated C1–6 alkoxy, (11) optionally halogenated C1–6 alkylthio or mercapto, (12) hydroxy, (13) amino, (14) mono-C1–6 alkylamino (for example, methylamino, ethylamino and the like), (15) mono-C6–14 arylamino (for example, phenylamino, 1-naphthyl amino, 2-naphthyl amino and the like), (16) di-C1–6 alkylamino (for example, dimethylamino, diethylamino and the like), (17) di-C6–14 arylamino (for example, diphenylamino and the like), (18) acyl, (19) acylamino, (20) acyloxy, (21) optionally substituted 4–8 membered saturated cyclic amino, (22) 5–10 membered aromatic heterocyclic group (for example, 2- or 3-thienyl, 2-, 3- or 4-pyridyl, 2-,3-,4-,5- or 8-quinolyl, 1-,3-,4- or 5-isoquinolyl, 1-, 2- or 3-indolyl, 2-benzothiazolyl, 2-benzo[b]thienyl, benzo[b]furanyl and the like), (23) sulfo, (24) C6–14 aryloxy (for example, phenyloxy, naphthyloxy and the like) and the like are exemplified.

The "hydrocarbon group" may have 1–5, preferably 1–3, of the above-mentioned substituents in the positions which can be substituted, and each substituent may be the same or different when there are two or more substituents.

As the aforementioned "optionally halogenated C1–6 alkyl", C1–6 alkyl and the like (for example, methyl, ethyl, propyl, isopropyl, butyl, isobutyl, sec-butyl, tert-butyl, pentyl, hexyl and the like) which may include for example 1–5, preferably 1–3, halogen atoms, (for example, fluorine, chlorine, bromine, iodine and the like) are exemplified. As specific examples, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like are exemplified.

As the aforementioned "optionally halogenated C2–6 alkenyl", C2–6 alkenyl and the like (for example, vinyl, allyl, isopropenyl, butenyl, isobutenyl, sec-butenyl and the like) which may contain for example 1–5, and preferably 1–3, halogen atoms, (for example, fluorine, chlorine, bromine, iodine and the like) are exemplified. As specific examples, vinyl, allyl, isopropenyl, butenyl, isobutenyl, sec-butenyl, 3,3,3-trifluoro-1-propenyl, 4,4,4-trifluoro-1-butenyl and the like are exemplified.

As the aforementioned "optionally halogenated C2–6 alkynyl", C2–6 alkynyl (for example, ethynyl, propargyl, butenyl, 1-hexynyl and the like) and the like which may contain for example 1–5, and preferably 1–3, halogen atoms, (for example, fluorine, chlorine, bromine, iodine and the like) of are exemplified. As specific examples, ethynyl, propargyl, butenyl, 1-hexynyl, 3,3,3-trifluoro-1-propynyl, 4,4,4-trifluoro-1-butenyl and the like are exemplified.

As the aforementioned "optionally halogenated C3–8 cycloalkyl", C3–8 cycloalkyl and the like (for example, cyclopropyl, cyclobutyl, cyclopentyl, cyclohexyl and the like) which may contain for example 1–5, preferably 1–3 halogen atom (for example, fluorine, chlorine, bromine, iodine and the like) are exemplified. As specific examples, cyclopropyl, cyclobutyl, cyclopentyl, cyclohexyl, 4,4-dichlorocyclohexyl, 2,2,3,3-tetrafluorocyclopentyl, 4-chlorocyclohexyl and the like are exemplified.

As the aforementioned "optionally halogenated C1–6 alkoxy", C1–6 alkoxy (for example, methoxy, ethoxy, propoxy, isopropoxy, butoxy, iso butoxy, sec-butoxy, pentyloxy, hexyloxy and the like) and the like which may contain for example 1–5, preferably 1–3 halogen atom (for example, fluorine, chlorine, bromine, iodine and the like) are exemplified. As specific examples, for example methoxy, difluoromethoxy, trifluoromethoxy, ethoxy, 2,2,2-trifluoroethoxy, propoxy, isopropoxy, butoxy, 4,4,4-trifluorobutoxy, iso butoxy, sec-butoxy, pentyloxy, hexyloxy and the like are exemplified.

As the aforementioned "optionally halogenated C1–6 alkylthio", C1–6 alkylthio and the like (for example, methylthio, ethylthio, propylthio, isopropylthio, butylthio, sec-butylthio, tert-butylthio and the like) which may contain for example 1–5, and preferably 1–3, halogen atom (for example, fluorine, chlorine, bromine, iodine and the like) are exemplified. As specific examples, methylthio, difluoromethylthio, trifluoromethylthio, ethylthio, propylthio, isopropylthio, butylthio, 4,4,4-trifluorobutylthio, pentylthio, hexylthio and the like are exemplified.

As the aforementioned "acyl", for example formyl, carboxy, carbamoyl, C1–6 alkyl-carbonyl (for example, acetyl, propionyl and the like), C3–8 cycloalkyl-carbonyl (for example, cyclopropylcarbonyl, cyclopentylcarbonyl, cyclohexylcarbonyl and the like), C1–6 alkoxy-carbonyl (for example, methoxycarbonyl, ethoxycarbonyl, propoxycarbonyl, tert butoxycarbonyl and the like), C6–14 aryl-carbonyl (for example, benzoyl, 1-naphthoyl, 2-naphthoyl and the like), C7–16 aralkyl-carbonyl (for example, phenylacetyl, phenylpropionyl and the like), C6–14 aryloxy-carbonyl (for example, phenoxycarbonyl and the like), C7–16 aralkyloxy-carbonyl (for example, benzyloxycarbonyl, phenethyl oxycarbonyl and the like), 5- or 6-membered heterocyclic carbonyl (for example, nicotinoyl, isonicotinoyl, 2-thenoyl, 3-thenoyl, 2-furoyl, 3-furoyl, morpholino carbonyl, thio morpholino carbonyl, piperidino carbonyl, 1-pyrrolidinyl-carbonyl and the like), mono-C1–6 alkyl-carbamoyl (for example, methylcarbamoyl, ethyl carbamoyl and the like), di-C1–6 alkyl-carbamoyl (for example, dimethylcarbamoyl, diethylcarbamoyl, ethylmethyl carbamoyl and the like), C6–14 aryl-carbamoyl (for example, phenylcarbamoyl, 1-naphthylcarbamoyl, 2-naphthylcarbamoyl and the like), thiocarbamoyl, 5 or 6 membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), C1–6 alkylsulfonyl (for example, methylsulfonyl, ethylsulfonyl and the like), C6–14 arylsulfonyl (for example, phenylsulfonyl, 1-naphthyl sulfonyl, 2-naphthyl sulfonyl and the like), C1–6 alkylsulfinyl (for example, methylsulfinyl, ethyl sulfinyl and the like), C6–14 arylsulfinyl (for example, phenylsulfinyl, 1-naphthyl sulfinyl, 2-naphthyl sulfinyl and the like) and the like are exemplified.

As the aforementioned "acylamino", for example formyl amino, C1–6 alkyl-carbonylamino (for example, acetylamino and the like), C6–14 aryl-carbonylamino (for example, phenyl carbonylamino, naphthylcarbonylamino and the like), C1–6 alkoxy-carboxynylamino(example, methoxycarbonylamino, ethoxycarbonylamino, propoxycarbonylamino, butoxycarbonyl amino and the like), C1–6 alkylsulfonyl amino (for example, methylsulfonylamino, ethylsulfonyl amino and the like), C6–14 arylsulfonylamino (for example, phenylsulfonyl amino, 2-naphthyl sulfonyl amino, 1-naphthyl sulfonyl amino and the like) and the like are exemplified.

As the aforementioned "acyloxy", for example C1–6 alkyl-carbonyl oxy (for example, acetoxy, propionyloxy and the like), C6–14 aryl-carbonyl oxy (for example, benzoyloxy, naphthylcarbonyl oxy and the like), C1–6 alkoxy-carbonyl oxy (for example, methoxycarbonyloxy, ethoxycarbonyloxy, propoxycarbonyloxy, butoxycarbonyl oxy and the like), mono-C1–6 alkyl-carbamoyloxy (for example, methylcarbamoyloxy, ethyl carbamoyloxy and the like), di-C1–6 alkyl-carbamoyloxy (for example, dimethylcarbamoyloxy, diethylcarbamoyloxy and the like), C6–14 arylcarbamoyloxy (for example, phenylcarbamoyloxy, naphthyl carbamoyloxy and the like), nicotinoyloxy and the like are exemplified.

As the "4–8 membered saturated cyclic amino" of the aforementioned "optionally substituted 4–8 membered saturated cyclic amino", for example morpholino, thiomorpholino, piperazine-1-yl, piperidino, pyrrolidin-1-yl and the like are exemplified. As "substituents" of the "optionally substituted 4–8 membered saturated cyclic amino", for example, 1 to 3 substituents of C1–6 alkyl (for example, methyl, ethyl, propyl, isopropyl, butyl, isobutyl, sec-butyl, tert-butyl, pentyl, hexyl and the like), C6–14 aryl (for example, phenyl, 1-naphthyl, 2-naphthyl, biphenyl, 2-anthryl and the like), 5–10 membered aromatic heterocyclic group (for example, 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl and the like) and the like are exemplified.

As the "heterocyclic group" of the "optionally substituted heterocyclic group" represented by R1 or R2, 5–14 membered heterocyclic group (aromatic heterocyclic group, saturated or unsaturated non-aromatic aliphatic heterocyclic group) and the like that includes, other than carbon atoms, 1–4 heteroatoms selected from nitrogen atoms, sulfur atoms, and oxygen atoms, are exemplified.

As the "aromatic heterocyclic group", for example 5–14 membered, preferably 5–10 membered aromatic heterocyclic group and the like that includes one or more (for example 1–4) heteroatoms, other than carbon atoms, selected from oxygen atoms, sulfur atoms, and nitrogen atoms, are exemplified. More specifically, an aromatic heterocyclic group such as for example, thiophene, benzothiophene, benzofuran, benzimidazole, benzoxazole, benzothiazole, benzisothiazole, naphth[2,3-b]thiophene, furan, isoindolizine, xanthene, phenoxathium, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazan, phenoxazine, and the like, and a monovalent group that can remove an arbitrary hydrogen atom from a ring formed by the condensation of these rings (preferably monocyclic) with 1 or a plurality of (preferably 1 or 2) aromatic rings (for example, a benzene ring and the like) are exemplified.

As preferred examples of the "aromatic heterocyclic group", a 5- or 6-membered aromatic heterocyclic group which may be condensed with 1 benzene ring and the like are exemplified. As specific examples, 2. 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl and the like are exemplified. More preferably, 2- or 3-thienyl, 2-, 3- or 4-pyridyl, 2- or 3-quinolyl, 1-isoquinolyl, 1- or 2-indolyl, 2-benzothiazolyl and the like.

As the "non-aromatic heterocyclic group", for example a 3–8 membered (preferably 5 or 6 membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl and the like are exemplified.

As the "substituents" of the "optionally substituted heterocyclic group" represented by R1 or R2, the same number of substituents are used as that in the "optionally substituted hydrocarbon group" represented by the aforementioned R1 or R2.

As the "3–8 membered homocyclic ring" of the "optionally substituted 3–8 membered homocyclic ring" formed by R1 and R2, for example cyclopropane, cyclobutane, cyclopentane, cyclohexane, C3–8 cycloalkane and the like are exemplified.

As the "3–8 membered heterocyclic group" of the "optionally substituted 3–8 membered heterocyclic group" formed by R1 and R2, a 3–8 membered heterocyclic group that includes, other than the carbon atoms, 1–4 heteroatoms selected from oxygen atoms, sulfur atoms, and nitrogen atoms, are exemplified, such as for example aziridine, azetidine, morpholine, thiomorpholine, piperazine, piperidine, pyrrolidine, hexamethyleneimine, heptamethyleneimine, hexahydropyrimidine and the like.

As the "substituents" of the "optionally substituted 3–8 membered homocyclic or heterocyclic group" formed by R1 and R2, the same number of substituents are used as that in the "substituents" of the "optionally substituted hydrocarbon group" represented by the aforementioned R1 or R2.

R3 represents a cyclic group which may have substituents.

As the "cyclic group" in the "optionally substituted cyclic group" represented by R3, for example (1) C6–14 aryl (2) optionally halogenated C3–8 cycloalkyl, (3) cyclic group selected from 5–14 membered aromatic heterocyclic group including at least 1 (for example, 1–4) heteroatoms, other than carbon atoms, selected from oxygen atoms, sulfur atoms and nitrogen atoms, are exemplified. Specific examples of (1), are for example a C6–14 aryl such as phenyl, 1-naphthyl, 2-naphthyl, biphenyl, anthryl and the like, and preferably for example a C6–10 aryl such as phenyl, 1-naphthyl, 2-naphthyl and the like are exemplified. Phenyl is particularly preferred. As (2) and (3), the same groups as exemplified in the aforementioned R1 and R2 are exemplified.

When X is a bond, it is particularly preferred that R3 is a phenyl group optionally substituted by 1–5 substituents selected from (1) halogen, (2) optionally halogenated C1–6 alkyl, (3) C6–14 aryl that may be substituted by halogen, (4) optionally halogenated C1–6 alkoxy and (5) di-C1–6 alkylamino. In addition, when X is a bond, R3 is preferably a 5–8 membered heterocyclic group that includes 1–3 nitrogen atom as the ring structure heteroatoms, and which may respectively contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl (9) C6–14 aryl which may be substituted by halogen (10) optionally halogenated C1–6 alkoxy (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than the carbon atoms, 1–4 heteroatoms selected from oxygen atoms, sulfur atoms, and nitrogen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than the carbon atoms, 1–4 heteroatoms selected from oxygen atoms, sulfur atoms, and nitrogen atoms, C1–6 alkylsulfonyl, C6–14 arylsulfonyl, C1–6 alkylsulfinyl and C6–14 arylsulfinyl (19) acylamino selected from formyl amino, C1–6 alkyl-carbonylamino, C6–14 aryl-carbonylamino, C1–6 alkoxy-carbonylamino, C1–6 alkylsulfonyl amino and C6–14 arylsulfonylamino (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy (21) 4–8 membered saturated cyclic amino, which may contain 1–3 substituents selected from C1–6 alkyl, C6–14 aryl, and a 5–10 membered aromatic heterocyclic group including, other than the carbon atoms, 1–4 heteroatoms selected from oxygen atoms, sulfur atoms, and nitrogen atoms, (22) 5–10 membered aromatic heterocyclic group including, other than the carbon atoms, 1–4 heteroatoms selected from oxygen atoms, sulfur atoms, and nitrogen atoms, (23) sulfo and (24) C6–14 aryloxy; and even more preferably compounds that are piperidino, morpholino, piperazinyl, pyridyl or pyrrolidinyl groups which optionally have 1–3 substituents selected from (1) halogen, (2) optionally halogenated C1–6 alkyl (3) C6–14 aryl which may be substituted by halogen, and (4) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl and C7–16 aralkyloxy-carbonyl.

Specific examples of the spacer with 1–3 atoms, represented by X include

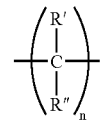

(wherein, R' and R" represent a hydrogen atom, C1–6 alkyl group, C3–8 cycloalkyl group or C6–14 aryl group, and n is an integer of 1–3, and when n is 2 or 3, R' and R" may be different in each repeating unit), —CO—, —O—, —S—, —SO—, —SO$_2$— or NR$^5$—, and even a divalent group in which 1–3 of these are combined may also be used. As the C1–6 alkyl group, C3–8 cycloalkyl group and C6–14 aryl group represented by R' and R", the same groups cited as examples in R1 and R2 are exemplified, but C1–6 alkyl is particularly preferred.

As the "substituents" of the "optionally substituted cyclic group", the same "substituents" of the "optionally substituted hydrocarbon group" represented by the aforementioned R1 or R2 are used in the same number.

The C1–6 alkyl group, C3–8 cycloalkyl group, and C6–14 aryl group represented by R' and R" may each have 1–3 substituents in a substitutable position, and when there are two or more substituents, these may be the same or different. As such "substituents", the same "substituents" of the "optionally substituted hydrocarbon group" represented by the aforementioned R1 or R2 are used in the same number.

As the R$^5$ of the group NR$^5$ represented by X, a hydrogen atom, and a C1–6 alkyl group, C2–6 alkenyl group, C2–6 alkynyl group, C3–8 cycloalkyl group, or a C6–14 aryl group which may have 1–5 substituents selected from the same examples cited with respect to the "substituents" of the "optionally substituted hydrocarbon group" of aforementioned $R^1$ and $R^2$, for example (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl (9) C6–14 aryl which may be substituted by halogen, (10) optionally halogenated C1–6 alkoxy (II) optionally halogenated C1–6 alkylthio or mercapto, (12) hydroxy, (13) amino, (14) mono-C1–6 alkylamino, (15) mono-C6–14-arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 arylcarbonyl, C7–16 aralkyl-carbonyl, C6–14 aryloxy-carbonyl, C7–16 aralkyloxy-carbonyl, 5- or 6-membered heterocyclic carbonyl including, other than the carbon atoms, 1–4 heteroatoms selected from oxygen atoms, sulfur atoms, and nitrogen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than the carbon atoms, 1–4 heteroatoms selected from oxygen atoms, sulfur atoms, and nitrogen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonylamino, (20) acyloxy selected from C1–6 alkylcarbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may have 1–3 substituents selected from C1–6 alkyl, C6–14 aryl, and 5–10 membered aromatic heterocyclic group including, other than the carbon atoms, 1–4 heteroatoms selected from oxygen atoms, sulfur atoms, and nitrogen atoms, (22) 5–10 membered aromatic heterocyclic group including, other than the carbon atoms, 1–4 heteroatoms selected from oxygen atoms, sulfur atoms, and nitrogen atoms, (23) sulfo, and (24) C6–14 aryloxy are exemplified.

Ring B represents an optionally substituted 4–8 membered nitrogen-containing heterocyclic group, for example, a 4–8 membered nitrogen-containing heterocyclic group which may be substituted by halogen or by a optionally substituted hydrocarbon group, and a 4–8 membered nitrogen-containing heterocyclic group that may be substituted by a heterocyclic group, wherein said heterocyclic group may be substituted through Y.

As the "4–8 membered nitrogen-containing heterocyclic group" represented by ring B, a 4–8 membered nitrogen-containing heterocyclic group and the like such as for example pyrrole (for example, 1H-pyrrole and the like), dihydropyrrole (for example, 2,5-dihydro-1H-pyrrole and the like), dihydropyridine (for example, 1,2-dihydropyridine and the like), tetrahydropyridine (for example, 1,2,3,4-tetrahydropyridine and the like), piperidine, piperazine, azepin (for example, 1H-azepin and the like), dihydroazepin (for example, 2,3-dihydro-1H-azepin, 2,5-dihydro-1H-azepin, 2,7-dihydro-1H-azepin and the like), tetrahydroazepin (for example, 2,3,6,7-tetrahydro-1H-azepin, 2,3,4,7-tetrahydro-1H-azepin and the like), penta hydroazepin, and 1,4-diazepane and the like are exemplified.

As the "halogen" which may be included as the "substituent" on ring B, for example fluorine, chlorine, bromine, iodine and the like are exemplified.

As the "optionally substituted hydrocarbon group" which may be included as a "substituent" on ring B, the same "optionally substituted hydrocarbon group" represented by the aforementioned R1 or R2 is used.

As the "heterocyclic group which may be substituted" that may be included on ring B, the same group as the "heterocyclic group which may be substituted" in the aforementioned R1 and R2 is exemplified.

Y represents a bond, —CO—, —O—, —S—, —SO—, —SO$_2$— or NR$^6$—. When Y is a bond, the heterocyclic group is directly bonded to ring B.

Examples of R6 include a hydrogen atom, and a C1–6 alkyl group, C2–6 alkenyl group, C2–6 alkynyl group, C3–8 cycloalkyl group, or a C6–14 aryl group which may have 1–5 substituents selected from the same examples cited with respect to the "substituent" of the "optionally substituted hydrocarbon group" of the aforementioned R1 and R2, such as for example (1) halogen, (2) C1–3 alkylenedioxy, (3) nitro, (4) cyano, (5) optionally halogenated C1–6 alkyl, (6) optionally halogenated C2–6 alkenyl (7) optionally halogenated C2–6 alkynyl, (8) optionally halogenated C3–8 cycloalkyl, C6–14 aryl which may be substituted by (9) halogen, (10) optionally halogenated C1–6 alkoxy, (II) optionally halogenated C1–6 alkylthio or mercapto, (12) hydroxy, (13) amino, (14) mono-C1–6 alkylamino, (15) mono-C$_{6-14}$ arylamino, (16) di-C1–6 alkylamino (17) di-C6–14 arylamino (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than the carbon atoms, 1–4 heteroatoms selected from oxygen atoms, sulfur atoms, and nitrogen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than the carbon atoms, 1–4 heteroatoms selected from oxygen atoms, sulfur atoms, and nitrogen atoms, C1–6 alkylsulfonyl, C6–14 arylsulfonyl, C1–6 alkylsulfinyl and C6–14 arylsulfinyl (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonylamino (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy (21) 4–8 membered saturated cyclic amino optionally having 1–3 substituents selected from C1–6 alkyl, C6–14 aryl and, 5–10 membered aromatic heterocyclic group including, other than the carbon atoms, 1–4 heteroatoms selected from oxygen atoms, sulfur atoms, and nitrogen atoms, (22) 5–10 membered aromatic heterocyclic group including, other than the carbon atoms, 1–4 heteroatoms selected from oxygen atoms, sulfur atoms, and nitrogen atoms, (23) sulfo and (24) C6–14 aryloxy.

Ring B may have 1–5 of these substituents at the positions which can be substituted, and when the number of subsituents is two or more, each substituent may be the same or different.

Ring C represents a benzene ring which may have additional substituents in addition to ring B.

Examples of these substituents include the same substituents as those cited as examples of the "substituents" of the "optionally substituted hydrocarbon group" of the aforementioned $R^1$ and $R^2$, namely (1) halogen, (2) C1–3 alkylenedioxy, (3) nitro, (4) cyano, (5) optionally halogenated C1–8 alkyl, (6) optionally halogenated C2–8 alkenyl, (7) optionally halogenated C2–8 alkynyl, (8) optionally halogenated C3–8 cycloalkyl, (9) optionally halogenated C6–14 aryl, (10) optionally halogenated C1–6 alkoxy, (11) hydroxy, (12) amino, (13) mono-C1–6 alkylamino, (14) mono-C6–14 arylamino, (15) di-C$_{1-6}$ alkylamino, (16) di-C6–14 arylamino (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl including, other than the carbon atoms, 1–4 heteroatoms selected from oxygen atoms, sulfur atoms, and nitrogen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than the carbon atoms, 1–4 heteroatoms selected from oxygen atoms, sulfur atoms, and nitrogen atoms, C1–6 alkylsulfonyl, C6–14 arylsulfonyl, C1–6 alkylsulfinyl, and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonylamino, (19) 4–8 membered saturated cyclic amino which may contain 1–3 substituents selected from C1–6 alkyl, C6–14 aryl, and 5–10 membered aromatic heterocyclic group including, other than the carbon atoms, 1–4 heteroatoms selected from oxygen atoms, sulfur atoms, and nitrogen atoms, (20) 5–10 membered aromatic heterocyclic group including, other than the carbon atoms, 1–4 heteroatoms selected from oxygen atoms, sulfur atoms, and nitrogen atoms, and (21) sulfo; more preferable examples of these substituents include (1) halogen (2) C1–3 alkylenedioxy, (3) nitro, (4) cyano, (5) C1–8 alkyl, (6) C2–8 alkenyl, (7) C2–8 alkynyl, (8) optionally halogenated C3–8 cycloalkyl, (9) optionally halogenated C6–14 aryl, (10) C1–6 alkoxy, (11) hydroxy, (12) amino, (13) mono-C1–6 alkylamino, (14) mono-C6–14 arylamino, (15) di-C1–6 alkylamino, (16) di-C6–14 arylamino (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, mono-C1–6 alkyl-carbamoyl, di-C1–6 alkyl-carbamoyl, C6–14 aryl-carbamoyl, thiocarbamoyl, C1–6 alkylsulfonyl, C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonylamino, and (19) sulfo.

Or, the substituents which ring C may have in addition to the aforementioned ring B may be selected from halogen, optionally halogenated lower alkyl, optionally halogenated lower alkoxy, and optionally halogenated lower alkyl thio. Examples of the "halogen" of this "substituent" include, for example, fluorine, chlorine, bromine, iodine and the like. Examples of the "lower alkyl which may be halogenated" include, for example, C1–6 alkyl (for example, methyl, ethyl, propyl, isopropyl, butyl, isobutyl, sec-butyl, tert-butyl, pentyl, hexyl and the like) and the like which may contain 1–5, preferably 1–3, halogen atoms, (for example, fluorine, chlorine, bromine, iodine and the like), and more specifically, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl. Examples of the "lower alkoxy which may be halogenated" include, for example, C1–6 alkoxy (for example, methoxy, ethoxy, propoxy, isopropoxy, butoxy, iso butoxy, sec-butoxy, pentyloxy, hexyloxy and the like) and the like which may contain 1–5, preferably 1–3, halogen atoms, (for example, fluorine, chlorine, bromine, iodine and the like). More specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like. Examples of the "lower alkyl thio which may be halogenated" include, for example, C1–6 alkylthio (for example, methylthio, ethylthio, propylthio, isopropylthio, butylthio, sec-butylthio, tert-butylthio and the like) and the like which may contain 1–5, preferably 1–3, halogen atoms, (for example, fluorine, chlorine, bromine, iodine and the like). More specific examples include methylthio, difluoromethylthio, trifluoromethylthio, ethylthio, propylthio, isopropylthio, butylthio, 4,4,4-trifluorobutylthio, pentyl thio, hexylthio, and the like.

In the aforementioned formula, the number of substituents on ring C in addition to ring B is 1–3, and when there are two or more thereof each substituent may be the same or different.

In the aforementioned formula, $R^4$ may be hydrogen or, like with the aforementioned $R^3$, may be a optionally substituted hydrocarbon group, optionally substituted hydroxy group, oxolated mercapto group which may be substituted, or an optionally substituted amino group. Examples of the "substituent" of the "optionally substituted hydroxy group" are the same as the examples of the "substituent" in the "optionally substituted hydrocarbon group" of the aforementioned R1 and R2, namely C1–6 alkyl, C2–6 alkenyl, C2–6 alkynyl, C3–8 cycloalkyl, C6–14 aryl (for example, phenyl, 1-naphthyl, 2-naphthyl, biphenyl, 2-anthryl and the like), optionally substituted acyl, optionally substituted 4–8 membered saturated cyclic amino, 5–10 membered aromatic heterocyclic group (for example, 2- or 3-thienyl, 2-, 3- or 4-pyridyl, 2-,3-,4-,5- or 8-quinolyl, 1-,3-,4- or 5-isoquinolyl, 1-, 2- or 3-indolyl, 2-benzothiazolyl, 2-benzo[b] thienyl, benzo[b]furanyl and the like) and the like.

Examples of "the optionally oxolated mercapto group" of "the optionally oxolated mercapto group which may be substituted" include a mercapto group, sulfanyl group, sulfinyl group and sulfonyl group. Examples of the substituents thereof are the same as the examples of the "substituent" in the "optionally substituted hydrocarbon group" of the aforementioned R1 and R2, namely C1–6 alkyl, C2–6 alkenyl, C2–6 alkynyl, C3–8 cycloalkyl, C6–14 aryl (for example, phenyl, 1-naphthyl, 2-naphthyl, biphenyl, 2-anthryl and the like), C1–6 alkoxy, optionally substituted amino, acyl, optionally substituted 4–8 membered saturated cyclic amino, 5–10 membered aromatic heterocyclic group (for example, 2- or 3-thienyl, 2-, 3- or 4-pyridyl, 2-,3-,4-,5- or 8-quinolyl, 1-,3-,4- or 5-isoquinolyl, 1-, 2- or 3-indolyl, 2-benzothiazolyl, 2-benzo[b] thienyl, benzo[b]furanyl and the like) and the like.

Examples of the "optionally substituted amino group" include amino, mono-C1–6 alkylamino (for example, methylamino, ethylamino and the like), mono-C6–14 arylamino (for example, phenylamino, 1-naphthyl amino, 2-naphthyl amino and the like), di-C1–6 alkylamino (for example, dimethylamino, diethylamino and the like), di-C6–14 arylamino (for example, diphenylamino and the like), acylamino and the like.

Examples of the acylamino include, like with the aforementioned R1 and R2, formyl amino, C1–6 alkyl-carbonylamino (for example, acetylamino and the like), C6–14 aryl-carbonylamino (for example, phenylcarbonylamino, naphthylcarbonylamino and the like), C1–6 alkoxy-carbonylamino (for example, methoxycarbonylamino, ethoxycarbonylamino, propoxycarbonylamino, butoxycarbonyl amino and the like), C1–6 alkylsulfonyl amino (for example, methylsulfonylamino, ethylsulfonyl amino and the like), C6–14 arylsulfonylamino (for example, phenylsulfonyl amino, 2-naphthyl sulfonyl amino, 1-naphthyl sulfonyl amino and the like) and the like.

When R4 forms a double bond together with R2, R4 is not present.

Specific examples of compounds represented by formula (I) of the present invention include, for example, 4-(3,4-dimethoxyphenyl)-1-(2,2,4,6,7-pentamethyl-3-(4-methylphenyl)-2,3-dihydro-1-benzofuran-5-yl) piperazine, (3R)-4-(4-methoxyphenyl)-1-(2,2,4,6,7-pentamethyl-3-(4-methylphenyl)-2,3-dihydro-1-benzofuran-5-yl) piperidine, 1-(2,2,4,6,7-pentamethyl-3-(4-methylphenyl)-2,3-dihydro-1-benzofuran-5-yl)-4-(4-methoxyphenyl) piperazine, N-phenyl-5-(4-(4-methoxyphenyl) piperazin-1-yl)-2,2,4,6,7-pentamethyl-2,3-dihydro-1-benzofuran-3-amine, 4-(4-methoxyphenyl)-1-(2,2,4,6,7-pentamethyl-3-piperidino-2,3-dihydro-1-benzofuran-5-yl) piperazine, 1-(3-(4-(trifluoromethyl) phenyl)-2,2,4,6,7-pentamethyl-2,3-dihydro-1-benzofuran-5-yl)-4-(4-methoxyphenyl) piperazine, 4-(3,4-dimethoxyphenyl)-1-(3-(4-methylphenyl)-2,2,4,6,7-pentamethyl-2,3-dihydro-1-benzofuran-5-yl) piperidine, 1-(3-(4-isopropylphenyl)-2,2,4,6,7-pentamethyl-2,3-dihydro-1-benzofuran-5-yl)-4-(3,4-dimethoxyphenyl) piperidine, 1-(4-methoxyphenyl)-4-(2,2,4,6,7-pentamethyl-3-(pyrrolidine-1-yl)-2,3-dihydro-1-benzofuran-5-yl) piperazine, 1-(5-(4-(4-methoxyphenyl)-1-piperazinyl)-(2,2,4,6,7-pentamethyl-2,3-dihydro-1-benzofuran-3-yl) indoline, 1-(4-methoxyphenyl)-4-(2,2,4,6,7-pentamethyl-3-pyridin-2-yl-2,3-dihydro-1-benzofuran-5-yl) piperazine, 1-(3-(6-fluoropyridin-3-yl)-2,2,4,6,7-pentamethyl-2,3-dihydro-1-benzofuran-5-yl)-4-(4-methoxyphenyl) piperazine, 1-(3,4-dimethoxyphenyl)-4-(2,2,4,6,7-pentamethyl-3-piperidino-2,3-dihydro-1-benzofuran-5-yl) piperazine, 1-(4-methoxyphenyl)-4-(2,2,4,6,7-pentamethyl-3-(6-methyl-3-pyridinyl)-2,3-dihydro-1-benzofuran-5-yl) piperazine, 4-(4-methoxyphenyl)-1-(2,2,4,5,7-pentamethyl-3-(4-methylphenyl)-2,3-dihydro-1-benzofuran-6-yl) piperazine, 1-(3-benzyl-2,2,4,6,7-pentamethyl-2,3-dihydro-1-benzofuran-5-yl)-4-(4-methoxyphenyl) piperazine, 1-(4-methoxyphenyl)-4-(2,2,4,6,7-pentamethyl-3-((4-methylphenoxy) methyl)-2,3-dihydro-1-benzofuran-5-yl) piperazine, and the like.

In addition to the aformentioned compound (I), the present inventors also discovered that compounds and the salts thereof represented by the formula (I') (hereinafter simply referred to as compound (I')):

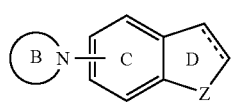 (I')

(each symbol has the same meaning as above) have the same activity/effect as compound (I). In other words, the present inventors discovered that the compound (I'), characterized by a structure in which a nitrogen-containing heterocyclic group such as ring B is substituted at the N position on a condensed ring made up of ring C and a ring D is useful as a neurodegeneration inhibitor in the same way as compound (I). Here, examples of substituents of ring D include hydrogen atoms, optionally substituted hydrocarbon groups, or optionally substituted heterocyclic groups like those represented by R1 and R2, and those previously listed as these substitutents, namely (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino (18) acyl selected from formy, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl, mono-C1–6 alkyl-carbamoyl, di-C1–6 alkyl-carbamoyl, C6–14 aryl-carbamoyl, thiocarbamoyl, 5- or 6-membered heterocyclic carbamoyl including, other than the carbon atoms, 1–4 heteroatoms selected from oxygen atoms, sulfur atoms, and nitrogen atoms, C1–6 alkylsulfonyl, C6–14 arylsulfonyl, C1–6 alkylsulfinyl and C6–14 arylsulfinyl (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonylamino (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy (21) 4–8 membered saturated cyclic amino which may contain 1–3 substituents selected from C1–6 alkyl, C6–14 aryl, and 5–10 membered aromatic heterocyclic group including, other than the carbon atoms, 1–4 heteroatoms selected from oxygen atoms, sulfur atoms, and nitrogen atoms, (22) 5–10 membered aromatic heterocyclic group including, other than carbon atoms, 1–4 heteroatoms selected from nitrogen atoms, sulfur atoms, and oxygen atoms, (23) sulfo, and (24) C6–14 aryloxy, with 1–3 of these substituted in positions that can be substituted.

As the salts of the aforementioned compound (I) and compound (I'), when a compound has an acidic group such as —COOH and the like, the salt may be for example a metal salt, an ammonium salt, a salt with an organic base and the like, and when a compound has a basic group such as NH₂ and the like, the salt may be for example an inorganic acid, or an organic salt other than a salt with a basic or acidic amino acid and the like. Examples of suitable metal salts include alkali metal salt such as for example sodium salt, potassium salt and the like, alkaline earth metal salt such as for example calcium salt, magnesium salt, barium salt and the like, and aluminium salt and the like. Examples of suitable salts with organic bases include, for example, trimethylamine, triethylamine, pyridine, picoline, ethanolamine, diethanolamine, triethanolamine, dicyclohexylamine, N,N-dibenzylethylenediamine and the like. Examples of suitable salts with inorganic acids include, for example, hydrochloric acid, hydrobromic acid, nitric acid, sulfuric acid, phosphoric acid and the like. Examples of suitable salts with organic acids include, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Examples of suitable salts with basic amino acids include, for example, arginine, lysine, ornithine and the like, and examples of suitable salts with acidic amino acids include, for example, aspartic acid, glutamic acid and the like.

From amongst these, pharmacologically acceptable salts are preferred. For example, when there is an acidic functional group in the compound, preferred examples include inorganic salts such as alkali metal salts (for example, sodium salt, potassium salt and the like), alkaline earth metal salts (for example, calcium salt, magnesium salt, barium salt and the like), and ammonium salts, and when there is a basic functional group in the compound, inorganic salts such as hydrochloride, sulfate, phosphate, and hydrobromide and the like, or organic salts such as acetate, maleate, fumarate, succinate, methanesulfonate, p-toluenesulfonate, citrate, and tartrate and the like.

Next, processes for producing compound (I) and compound (I') of the present invention, as well as later-described compounds (Ia), (Ib), (Ic), (Id), (Ie) and (If), will be described.

Compound (I) and compound (I') of the present invention can be produced by the processes shown below or by processes corresponding to these.

Each symbol of the compounds in the following reaction equation diagrams has the same meaning as above. The compounds in the reaction equations also include the salts formed therefrom, and examples of the salts are those that are the same as the salts of compound (I) and compound (I') and the like.

Reaction equation 1

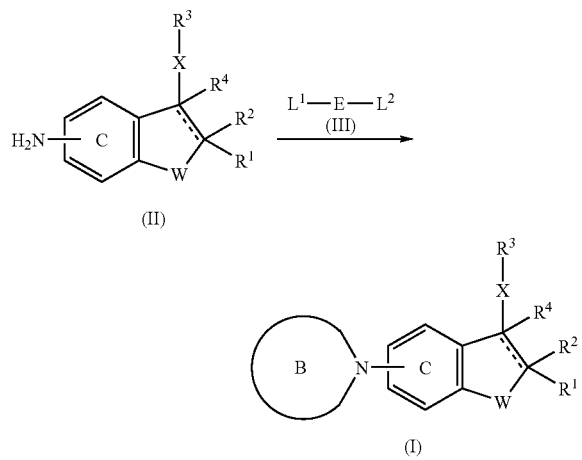

In the reaction equation 1, L1 and L2 are leaving groups, and E represents a ring component other than the nitrogen atom of ring B. The other symbols have the same meaning as above.

The compound (I) is produced according to reaction equation 1 by reacting compound (II) and a compound (III) represented by the formula:

as required in the presence of base.

The "substituents which may be further included in addition to —$NH_2$" on ring C of compound (II) are the same as "the substituents which may be further included" on ring C of compound (I), and the same number thereof are used.

The compound (III) is readily available as a commercial product, and moreover is produced by per se well-known processes.

Examples of the "leaving group" represented by $L^1$ and $L^2$ include hydroxy, halogen atom (for example, fluorine, chlorine, bromine, iodine and the like), optionally halogenated $C_{1-5}$ alkylsulfonyloxy (for example, methanesulfonyloxy, ethane sulfonyloxy, trichloromethane sulfonyloxy and the like), optionally substituted $C_{6-10}$ arylsulfonyloxy and the like. Examples of the "optionally substituted $C_{6-10}$ arylsulfonyloxy" include $C_{6-10}$ arylsulfonyloxy (for example, phenylsulfonyloxy, naphthyl sulfonyloxy and the like) and the like which may contain 1–3 substituents selected from, for example, $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro, and specific examples include benzensulfonyloxy, m-nitrobenzene sulfonyloxy, p-toluenesulfonyloxy and the like.

Compound (III) is a compound which can form a optionally substituted 4–8 membered nitrogen containing heterocyclic group represented by the formula:

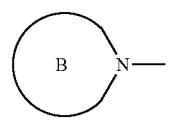

(In the formula, each symbol has same meaning as above) together with the nitrogen atom of the amino group substituted to ring C of compound (II).

The amount of compound (III) is about 0.8–about 5.0 moles and preferably about 1.0–about 2.0 moles with respect to 1 mole of compound (II).

Examples of the "base" include basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as sodium methoxide, sodium ethoxide, potassium tert-butoxide and the like.

The amount of base used is about 0.5–about 10.0 moles and preferably about 1.0–about 3.0 moles with respect to 1 mole of compound (II). In addition, in accordance with requirements, it is produced by reacting in the presence of quaternary ammonium salt and base.

Examples of the "quaternary ammonium salt" include tetrabutyl ammonium iodide and the like.

The amount of quaternary ammonium salt used is about 0.1–about 3.0 moles and preferably about 0.5–about 1.0 mole with respect to 1 mole of compound (II).

This reaction is advantageously conducted using a solvent inert in the reaction. This type of solvent is not particularly limited so long as the reaction proceeds. However, for example, solvents such as for example alcohols such as for example methanol, ethanol, propanol, butanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitriles such as for example acetonitrile, propionitrile and the like, sulfoxides such as for example dimethylsulfoxide and the like or mixed solvent thereof and the like are preferred.

The reaction time is usually for about 30 minutes to about 72 hours, and preferably about three hours to about 24 hours. The reaction temperature is usually about −20–about 200° C. and preferably about 20–about 150° C.

The compound (I) and compound (Ia) which is included in compound (I) are produced by the process as defined in the following reaction equation 2.

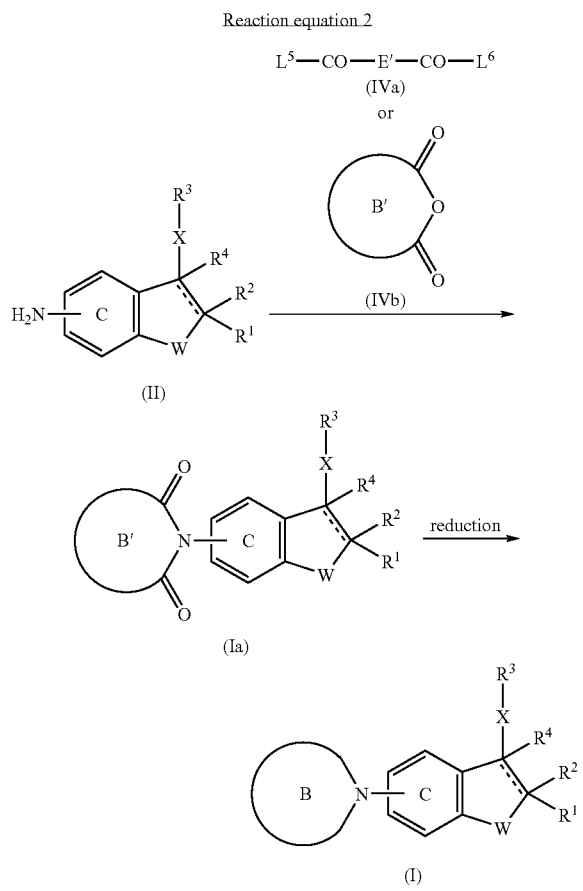

$L^5$ and $L^6$ in reaction equation 2 represent leaving groups, and ring B' represents a 4–8 membered heterocyclic group that may contain substituents in addition to the oxo group, and —CO—E'—CO— represents a partial sequence of the ring structure other than nitrogen atom of the B' ring in compound (Ia). The other symbols have the same meaning as above.

Examples of the "leaving group" represented by $L^5$ and $L^6$ include, for example, hydroxy, halogen atom (for example, fluorine, chlorine, bromine, iodine and the like), $C_{1-6}$ alkylsulfonyloxy (for example, methanesulfonyloxy, ethane sulfonyloxy and the like), optionally substituted $C_{6-10}$ arylsulfonyloxy, and the like.

Examples of "optionally substituted $C_{1-6}$ arylsulfonyloxy" include, for example, $C_{6-10}$ arylsulfonyloxy (for example, benzensulfonyloxy, naphthylsulfonyloxy and the like) and the like which may contain 1–3 substituents selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), halogen (for example, chloro, bromo, iodo and the like) and nitro, and specific examples include benzensulfonyloxy, p-toluenesulfonyloxy, p-bromobenzenesulfonyloxy, m-nitrobenzenesulfonyloxy and the like.

Compounds (IVa) and (IVb) are compounds which can form the group represented by the formula:

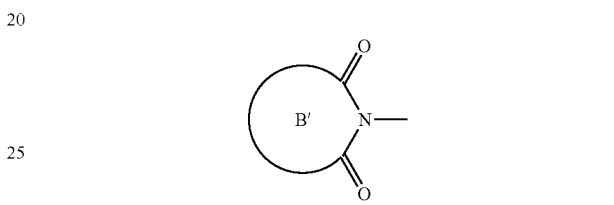

(each symbol has the same definition as above) together with the nitrogen atom of the amino group that is a substituent of ring C of compound (II).

The compounds (IVa) and (IVb) are readily available as commercial products, and moreover are produced by per se well-known processes.

Compound (Ia) is obtained by reacting compound (IVa) and compound (II) according to reaction equation 2 in the presence of base as required.

The amount of compound (IVa) used is about 0.8–about 5.0 moles and preferably about 1.0–about 2.0 moles with respect to 1 mole of compound (II).

Examples of the "base" include, for example, basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxide such as for example sodium methoxide, sodium ethoxide, potassium t-butoxide and the like. The amount of base used is about 0.5–about 10.0 moles and preferably about 2.0–about 3.0 moles with respect to 1 mole of compound (II).

This reaction is advantageously conducted using a solvent inert in the reaction. Preferrable solvents include, for example, alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide hexamethyl phosphoric triamide and the like, sulfoxides such as for example dimethylsulfoxide and the like, dichloromethane, chloroform, carbon tetrachloride, halocarbons such as for example 1,2-dichloroethane and the like, nitrites such as acetonitrile, propionitrile and the like, or mixed solvents thereof.

The reaction time is usually about 10 minutes to about 8 hours, preferably about 30 minutes to about 3 hours. The reaction temperature is usually about 0–about 120° C. and preferably about 25–about 100° C.

The product can be used in the next reaction as the reaction mixture or as crude product, but it can be isolated from the reaction mixture in accordance with normal methods, and can be readily purified using ordinary separation means (for example, recrystallization, distillation, chromatography and the like).

The compound (Ia) is synthesised by a process in which compound (II) and compound (IVa) are reacted together in the presence of a suitable condensing agent.

The amount of compound (IVa) used is about 1.0–about 5.0 moles and preferably about 0.8–about 2.0 moles with respect to 1 mole of compound (II).

Examples of the "condensing agent" that can be used include, for example N,N'-dicarboximides such as for example N,N-dicyclohexylcarbodiimide, 1-ethyl-3-(3-dimethylaminopropyl) carbodiimide (WSC) hydrochloride and the like, azolides such as for example N,N-carbonyl imidazole and the like, dehydrating agents such as for example N-ethoxycarbonyl-2-ethoxy-1,2-dihydroquinoline, phosphorus oxychloride, acetic anhydride and the like, and 2-halogeno pyridinium salts such as for example 2-chloromethylpyridinium iodide and 2-fluoro-1-chloromethylpyridinium iodide.

The amount of condensing agent used is about 1.0–about 5.0 moles and preferably about 2.0–about 3.0 moles with respect to 1 mole of compound (II).

In addition, a base may be copresent with the condensing agent as required, and it may be reacted. Examples of the "base" include, for example basic salts such as for example potassium acetate, sodium acetate and the like, and 1-hydroxy-1H-benzotriazole (HOBt)-hydrate and the like. The amount of base used is about 0.5–about 5.0 moles and preferably about 2.0–about 3.0 moles with respect to 1 mole of compound (II).

This reaction is advantageously conducted using a solvent inert in the reaction. Preferrable solvents include, for example, alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide, hexamethyl phosphoric triamide and the like, sulfoxides such as for example dimethylsulfoxide and the like, halocarbons such as for example dichloromethane, chloroform, carbon tetrachloride, 1,2-dichloroethane and the like, nitriles such as acetonitrile, propionitrile and the like, acid anhydrides and the like such as for example acetic anhydride and the like, or mixed solvents thereof.

The reaction time is usually about 10 minutes to about 48 hours, preferably about 30 minutes to about 24 hours. The reaction temperature is usually about 0–about 120° C. and preferably about 25–about 100° C.

The product can be used in the next reaction as the reaction mixture or as crude product, but it can be isolated from the reaction mixture in accordance with normal methods, and can be readily purified using ordinary separation means (for example, recrystallization, distillation, chromatography and the like).

Instead of the aforementioned reaction, the compound (II) and compound (IVb) may be reacted in the presence of a suitable condensing agent.

The amount of compound (IVb) used is about 0.8–about 5.0 moles and preferably about 0.8–about 2.0 moles with respect to 1 mole of compound (II).

Examples of the "condensing agent" that can be used include N,N'-dicarboximides such as for example N,N-dicyclohexylcarbodiimide, 1-ethyl-3-(3-dimethylaminopropyl) carbodiimide (WSC) hydrochloride and the like, azolides such as for example N,N-carbonyl imidazole and the like, dehydrating agents such as for example N-ethoxycarbonyl-2-ethoxy-1,2-dihydroquinoline, phosphorus oxychloride, acetic anhydride and the like, 2-halogeno pyridinium salts such as for example 2-chloromethylpyridinium iodide, 2-fluoro-1-chloromethylpyridinium iodide and the like.

The amount of condensing agent used is about 0.8–about 5.0 moles and preferably about 2.0–about 3.0 moles with respect to 1 mole of compound (II).

In addition, the reaction may take place in the presence of a base and the condensing agent as required. Examples of the "base" include, for example basic salts such as for example potassium acetate, sodium acetate and the like, and 1-hydroxy-1H-benzotriazole (HOBt)-hydrate and the like. The amount of base used is about 0.5–about 5.0 moles and preferably about 2.0–about 3.0 moles with respect to 1 mole of compound (II).

This reaction is advantageously conducted using a solvent inert in the reaction. Preferrable solvents include, for example, alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide hexamethyl phosphoric triamide and the like, sulfoxides such as for example dimethylsulfoxide and the like, halocarbons such as for example dichloromethane, chloroform, carbon tetrachloride, 1,2-dichloroethane and the like, nitriles such as acetonitrile, propionitrile and the like, acid anhydrides such as for example acetic anhydride and the like, or mixed solvents thereof.

The reaction time is usually about 10 minutes to about 48 hours, preferably about 30 minutes to about 24 hours. The reaction temperature is usually about 0–about 120° C. and preferably about 25–about 100° C.

The product can be used in the next reaction as the reaction mixture or as crude product, but it can be isolated from the reaction mixture in accordance with normal methods, and can be readily purified using ordinary separation means (for example, recrystallization, distillation, chromatography and the like).

Instead of the aforementioned reaction, the compound (Ia) is synthesised by reaction of the compound (II) and compound (IVb) following the cyclization in the presence of suitable condensing agent.

The amount of compound (IVb) used is about 0.8–about 5.0 moles and preferably about 1.0–about 2.0 moles with respect to 1 mole of compound (II).

Examples of the "condensing agent" that can be used include N,N'-dicarboximides such as for example N,N-dicyclohexylcarbodiimide, 1-ethyl-3-(3-dimethylaminopropyl) carbodiimide (WSC) hydrochloride and the like, azolides such as for example N,N-carbonyl imidazole and the like, dehydrating agents such as for example N-ethoxy-carbonyl-2-ethoxy-1,2-dihydroquinoline, phosphorus oxychloride, acetic anhydride and the like, and 2-halogeno pyridinium salts such as for example 2-chloromethylpyridinium iodide, 2-fluoro-1-chloromethylpyridinium iodide and the like.

The amount of condensing agent used is about 0.8–about 5.0 moles and preferably about 1.0–about 3.0 moles with respect to 1 mole of compound (II).

In addition, the reaction may take place in the presence of a base and the condensing agent as required. Examples of the "base" include, for example, basic salts such as for example potassium acetate, sodium acetate and the like, and 1-hydroxy-1H-benzotriazole (HOBt)-hydrate and the like. The amount of base used is about 0.8–about 5.0 moles and preferably about 1.0–about 3.0 moles with respect to 1 mole of compound (II).

This reaction is advantageously conducted using a solvent inert in the reaction. Preferrable solvents include, for example, alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide hexamethyl phosphoric triamide and the like, sulfoxides such as for example dimethylsulfoxide and the like, halocarbons such as for example dichloromethane, chloroform, carbon tetrachloride, 1,2-dichloroethane and the like, nitrites such as acetonitrile, propionitrile and the like, acid anhydrides such as acetic anhydride and the like or mixed solvents thereof and the like.

The reaction time is usually about 10 minutes to about 48 hours, preferably about 30 minutes to about 24 hours. The reaction temperature is usually about 0–about 120° C. and preferably about 25–about 100° C.

The product can be used in the next reaction as the reaction mixture or as crude product, but it can be isolated from the reaction mixture in accordance with normal methods, and can be readily purified using ordinary separation means (for example, recrystallization, distillation, chromatography and the like).

Compound (I) is produced by reducing compound (Ia) with a reducing agent. Examples of the "reducing agent" that can be used include metal hydrides such as for example sodium borohydride, lithium aluminium hydride and the like, and boranes such as for example borane tetrahydrofuran complex and the like.

The amount of reducing agent used is about 0.5–about 10 moles and preferably about 1.0–about 6.0 moles with respect to 1 mole of compound (Ia).

In addition, an acid catalyst may be added to the reducing agent as required. Examples of the "acid catalyst" that can be used includes Lewis acids such as boron trifluoride, and aluminum chloride and the like. The amount of the "acid catalyst" used is about 0.5–about 10 moles and preferably about 1.0–about 6.0 moles with respect to 1 mole of compound (Ia).

This reaction is advantageously conducted using a solvent inert in the reaction or in the absence of solvent. These types of solvents are not particularly limited so long as the reaction progresses. However, for example, alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxy-ethane and the like, amides such as for example N,N-dimethylformamide, N,N-dimethylacetamide hexamethyl phosphoric triamide and the like, sulfoxides such as for example dimethylsulfoxide and the like, halocarbons such as for example dichloromethane, chloroform, carbon tetrachloride, 1,2-dichloroethane and the like, N,N-dimethylaniline, anilines such as for example N,N-diethylaniline and the like, organic acids such as for example formic acid, acetic acid and the like, or mixed solvent thereof and the like may be used.

The reaction time is usually about 10 minutes to about 24 hours, preferably about 30 minutes to about 12 hours. The reaction temperature is usually about −40–about 120° C. and preferably about −10–about 100° C.

In accordance with normal methods, the product can be isolated from the reaction mixture, and can be readily purified using ordinary separation means (for example, recrystallization, distillation, chromatography and the like).

Compound (I) is produced by the process as defined in the following reaction equation 3 using compound (V) instead of compound (II).

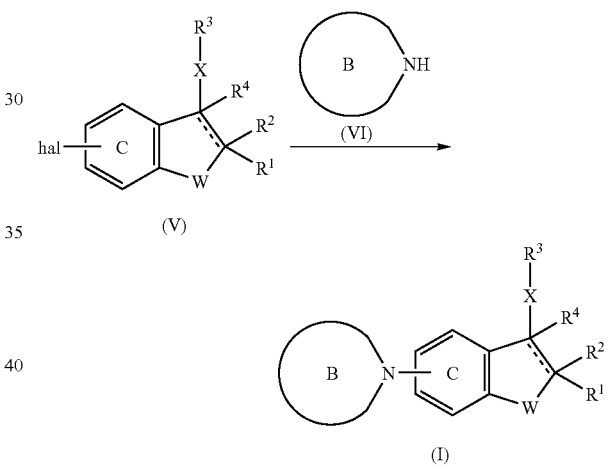

In reaction equation 3, hal represents halogen. The other symbols have the same meaning as above.

According to reaction equation 3, compound (I) is produced by reacting compound (V) and a 4–8 membered cycloamino compound (VI) which is represented by the formula:

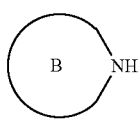

(in the formula, ring B has the same meaning as above) in the presence of base as required. In accordance with need, catalysts such as for example copper, copper salt and the like may be used, and catalysts such as palladium, nickel and the like may be used with a ligand (for example phosphine and pyridines and the like) in accordance with Chemistry Letters, 1983, pp 927–928.

The amount of compound (VI) used is about 0.8–about 10.0 moles and preferably about 1.0–about 5.0 moles with respect to 1 mole of compound (V).

Examples of the "base" include basic salts such as for example sodium carbonate, potassium carbonate, cesium carbonate, sodium bicarbonate and the like, aromatic amine species such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydride species such as for example sodium hydride, potassium hydride and the like, metallic amide species such as for example sodium amide, lithium diisopropylamide, lithium hexamethyl disilazide and the like, and metalalkoxide species such as for example sodium methoxide, sodium ethoxide, sodium tert butoxide, potassium t-butoxide and the like.

The amount of base used is about 0.8–about 10.0 moles and preferably about 1.0–about 5.0 moles with respect to 1 mole of compound (V).

This reaction is advantageously conducted using a solvent inert in the reaction. This type of solvent is not particularly limited so long as the reaction proceeds. However, for example, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, or mixed solvent thereof are preferred.

Examples of the copper catalyst used include copper, copper halide (CuI, CuBr, CuCl and the like), copper oxide (CuO) and the like.

The amount of copper catalyst used is about 0.1–about 10.0 moles and preferably about 0.5–about 2.0 moles with respect to 1 mole of compound (V).

It is preferable that phosphine is used as the ligand, but trialkylphosphine, triarylphosphine, trialkoxy phosphine and the like may also be used, and, as the palladium catalyst, palladium acetate, palladium chloride, tetrakis (triphenylphosphine) palladium, bis (dibenzylideneacetone) palladium and the like may be used.

The amount of phosphine is about 0.001–about 10.0 moles and preferably about 0.01–about 1.0 mole with respect to 1 mole of compound (V). The amount of palladium catalyst is about 0.0001–about 5.0 moles and preferably about 0.01–about 0.5 mole with respect to 1 mole of compound (V).

The reaction time is usually about 30 minutes to about 72 hours, preferably about one hour to about 48 hours. The reaction temperature is usually about –20–about 200° C. and preferably about 0–about 150° C.

Reaction equation 4

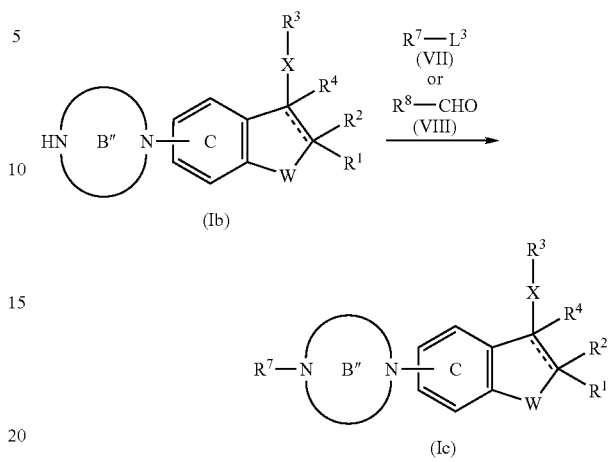

The B" ring in reaction equation 4 represents an optionally substituted 5–8 membered nitrogen containing heterocyclic group, a portion of the ring included in the aforementioned ring B is represented, $L^3$ represents a leaving group, and $R^8$ represents a group in which one methylene was removed from $R^7$. The other symbols have the same meaning as above.

Examples of $R^7$ include, for example, optionally substituted acyl group, optionally substituted aliphatic hydrocarbon group, optionally substituted aromatic hydrocarbon group, or heterocyclic group.

According to reaction equation 4, compound (Ic) is produced by reacting compound (Ib) and compound (VII) represented by the formula $R^7$—$L^3$, or condensing compound (Ib) and compound (VIII) represented by the formula $R^8$—CHO and reducing with a reducing agent.

Examples of the "leaving group" represented by $L^3$ include hydroxy, halogen atom (for example, fluorine, chlorine, bromine, iodine and the like), optionally halogenated $C_{1-5}$ alkylsulfonyloxy (for example, methanesulfonyloxy, ethane sulfonyloxy, trichloromethane sulfonyloxy and the like), optionally substituted $C_{6-10}$ arylsulfonyloxy, and the like.

Examples of "optionally substituted $C_{6-10}$ arylsulfonyloxy" include $C_{6-10}$ arylsulfonyloxy (for example, phenylsulfonyloxy, naphthyl sulfonyloxy and the like) and the like which may contain 1–3 substituents selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro, and more specifically benzensulfonyloxy, m-nitrobenzene sulfonyloxy, p-toluenesulfonyloxy and the like.

(1) The reaction conditions when $R^7$ is a "optionally substituted acyl group" is described below.

The reaction of compound (Ib) and compound (VII) is performed in the presence of base or acid as required.

The amount of compound (VII) used is about 0.8–about 5.0 moles and preferably about 1.0–about 2.0 moles with respect to 1 mole of compound (Ib).

Examples of the "base" include basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as for example sodium methoxide, sodium ethoxide, potassium t-butoxide and the like.

Examples of the "acid" include methanesulfonic acid, p-toluenesulfonic acid, camphor sulfonic acids, and Lewis acids and the like such as for example aluminum chloride, zinc chloride and the like.

The amount of the "base" used is about 0.1–about 10 moles and preferably about 0.8–about 2 moles with respect to 1 mole of compound (Ib).

The amount of the "acid" used is about 0.1–about 10 moles and preferably about 0.8–about 3 moles with respect to 1 mole of compound (Ib).

This reaction is advantageously conducted using a solvent inert in the reaction or absence of solvent. This type of solvent is not particularly limited so long as the reaction progresses. However, for example, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, nitrogen containing aromatic hydrocarbons and the like such as for example pyridine, lutidine, quinoline and the like, or mixed solvents thereof are preferred. The reaction temperature is about −20–about 150° C. and preferably about 0–about 100° C. The reaction time is usually about 5 minutes to about 24 hours, preferably about 10 minutes to about 5 hours.

Instead of the aforementioned reaction, the compound (Ib) and compound (VII) may be reacted in the presence of a suitable condensing agent.

The amount of compound (VII) used is about 0.8–about 5.0 moles and preferably about 1.0–about 2.0 moles with respect to 1 mole of compound (Ib).

Examples of the condensing agent that can be used include N, N'-dicarbodiimides such as for example N,N'-dicyclohexylcarbodiimide, 1-ethyl-3-(3-dimethylaminopropyl) carbodiimide (WSC) hydrochloride and the like, azorides such as for example N,N'-carbonyldiimidazole and the like, dehydrating agents such as for example N-ethoxycarbonyl-2-ethoxy-1,2-dihydroquinoline, phosphorus oxychloride and the like, and 2-halogeno pyridinium salts such as for example 2-chloromethylpyridinium iodide, 2-fluoro-1-chloromethyl-pyridinium iodide and the like.

The amount of condensing agent used is about 0.8–about 5.0 moles and preferably about 1.0–about 2.0 moles with respect to 1 mole of compound (Ib).

This reaction is advantageously conducted using a solvent inert in the reaction, but this type of solvent is not particularly limited so long as the reaction proceeds. However, for example, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, or mixed solvent thereof are preferred.

The reaction time is usually about 5 minutes to about 48 hours, preferably about 30 minutes to about 24 hours. The reaction temperature is usually about −20–about 200° C. and preferably about 0–about 100° C.

(2) The reaction conditions when $R^7$ is an "optionally substituted aliphatic hydrocarbon group" are described below.

Compound (Ib) and compound (VII) represented by the formula $R^7$—$L^3$ are reacted in the presence of base as required.

The amount of compound (VII) used is about 0.8–about 5.0 moles and preferably about 1.0–about 2.0 moles with respect to 1 mole of compound (Ib).

Examples of the "base" include basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as for example sodium methoxide, sodium ethoxide, potassium t-butoxide and the like.

The amount of base used is about 0.8–about 5.0 moles and preferably about 1.0–about 2.0 moles with respect to 1 mole of compound (Ib).

This reaction is advantageously conducted using a solvent inert in the reaction, but this type of solvent is not particularly limited so long as the reaction proceeds. However, for example, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, or mixed solvents thereof are preferred.

The reaction time is usually about 30 minutes to about 48 hours, preferably about one hour about 24 hours. The reaction temperature is usually about −20–about 200° C. and preferably about 0–about 150° C.

(3) The reaction conditions when $R^7$ is an "optionally substituted aromatic hydrocarbon group or heterocyclic group" are described below.

Compound (Ib) and compound (VII) represented by the formula $R^7$—$L^3$ are reacted in the presence of base as required. A catalyst such as for example copper, cuprate and the like may be used as needed, and acatalyst such as nickel, palladium, and the like may be used with a ligand (phosphine and pyridine and the like) in accordance with the process disclosed in Chemistry Letters 1983, pp 927–928.

The amount of compound (VII) used is about 0.8–about 5.0 moles and preferably about 1.0–about 2.0 moles with respect to 1 mole of compound (Ib).

Examples of the "base" include, for example, basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine., 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as for example sodium methoxide, sodium ethoxide, sodium tert butoxide, potassium t-butoxide and the like.

The amount of base used is about 0.8–about 5.0 moles and preferably about 1.0–about 2.0 moles with respect to 1 mole of compound (Ib).

This reaction is advantageously conducted using a solvent inert in the reaction, but this type of solvent is not particularly limited so long as the reaction proceeds. However, for example, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, or mixed solvents thereof are preferred.

Examples of the copper catalyst that can be used include, for example, copper, copper halide (CuI, CuBr, CuCl and the like), copper oxide (CuO) and the like.

The amount of copper catalyst is about 0.1–about 10.0 moles and preferably about 0.5–about 2.0 moles with respect to 1 mole of compound (Ib).

It is preferable that phosphine is used as the ligand, but trialkylphosphine, triarylphosphine, trialkoxy phosphine and the like may also be used, and, as the palladium catalyst, palladium acetate, palladium chloride, tetrakis (triphenylphosphine) palladium, bis (dibenzylideneacetone) palladium and the like may be used.

The amount of phosphine used is about 0.01–about 10.0 moles and preferably about 0.1–about 1.0 moles with respect to 1 mole of compound (Ib). The amount of palladium catalyst used is about 0.01–about 5.0 moles and preferably about 0.1–about 0.5 mole with respect to 1 mole of compound (Ib).

The reaction time is usually about 30 minutes to about 48 hours, preferably about one hour to about 24 hours. The reaction temperature is usually about −20–about 200° C. and preferably about 0–about 150° C.

In addition, instead of the aforementioned reation, compound (Ic) can be synthesized by reductive amination reaction.

The amount of compound (VIII) used is about 0.8–about 5.0 moles and preferably about 1.0–about 2.0 moles with respect to 1 mole of compound (Ib).

Examples of the "reducing agent" that can be used include metal hydrides such as for example sodium borohydride, sodium cyanoborohydride, lithium aluminium hydride and the like, boranes such as for example borane tetrahydrofuran complex and the like, hydrosilanes such as for example triethylsilane and the like, or formic acid and the like. In addition, an acid catalyst may be added to the reducing agent as required. Examples of the acid catalyst that can be used include, for example, mineral acids such as for example hydrochloric acid, hydrobromic acid, sulfuric acid and the like, sulfonic acids such as for example methanesulfonic acid, p-toluenesulfonic acid and the like, organic acids such as for example acetic acid, propionic acid, trifluoro acetic acid and the like, Lewis acids such as for example zinc chloride, aluminum chloride and the like.

The amount of "reducing agent" used is about 0.25–about 5.0 moles and preferably about 0.5–about 2.0 moles with respect to 1 mole of compound (Ib).

The amount of acid catalyst with, for example, mineral acids is about 1–about 100 moles and preferably about 1–about 20 moles with respect to 1 mole of compound (Ib).

This reaction is advantageously conducted using a solvent inert in the reaction, but this type of solvent is not particularly limited so long as the reaction proceeds. However, for example, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides and the like such as for example N,N-dimethylformamide, N,N-dimethylacetamide and the like, or mixed solvents thereof are preferred.

The reaction time is usually about 5 minutes to about 48 hours, preferably about 30 minutes to about 24 hours. The reaction temperature is usually about −20–about 200° C. and preferably about 0–about 100° C.

After the condensation of compound (Ib) and compound (VIII), instead of reduction with a reducing agent, the reaction can be carried out by a catalytic hydrogenation reaction in which various kinds of catalysts are copresent in a hydrogen atmosphere. Examples of the catalyst which can be used include, platinum oxide, platinised activated carbon, palladium activated carbon, nickel, copper-chromium oxide, rhodium, cobalt, ruthenium and the like. The amount of catalyst used is about 1–about 1000 wt. %, and is preferably about 5–about 50 wt. % with respect to compound (Ib).

This reaction is advantageously conducted using a solvent inert in the reaction but this type of solvent is not particularly limited so long as the reaction proceeds. However, alcohols such as for example methanol, ethanol, propanol and the like, ethers such as for example diethyl ether, tetrahydrdfuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, water, or mixed solvents thereof are preferred.

The reaction time is usually about 30 minutes to about 48 hours, preferably about 30 minutes to about 24 hours. The reaction temperature is usually about 0–about 120° C. and preferably about 20–about 80° C.

Instead of the aforementioned reaction, a process can be used that reduces the acylamido synthesized in the aforementioned (1) with a reducing agent.

Examples of the reducing agent include metal hydrides such as for example sodium borohydride, lithium aluminium hydride and the like, and boranes and the like such as for example borane tetrahydrofuran complex and the like.

In addition, an acid catalyst may be added to the reducing agent as required. Examples of the acid catalyst that can be used include Lewis acids such as for example boron trifluoride diethylether complex, aluminum chloride and the like.

The amount of said reducing agent is respectively about 0.25–about 10 moles and preferably about 0.5–about 5 moles with respect to acylamido body 1 mole.

The amount of the Lewis acids is respectively about 0.1–about 10 moles and preferably about 0.5–about 5 moles with respect to 1 mole of the acylamido.

This reaction is advantageously conducted using a solvent inert in the reaction, but this type of solvent is not particularly limited so long as the reaction proceeds. However, for example, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, water and the like, or mixed solvents thereof are preferred.

The reaction time is usually about 30 minutes to about 24 hours, preferably about one hour to about 16 hours. The reaction temperature is usually about 0–about 150° C. and preferably about 20–about 100° C.

Product (Ic) obtained as above can be isolated from the reaction mixture using well known isolation means, and it is readily purified by separation means such as for example recrystallization, distillation, chromatography and the like.

In addition, compound (Id) that is included in compound (I) is produced by the process as defined in the following reaction equation 5.

Reaction equation 5

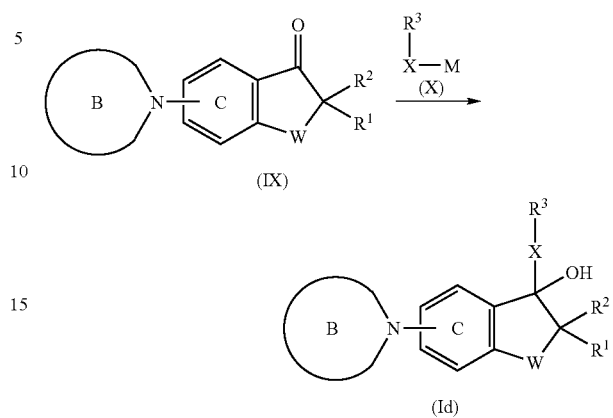

In reaction equation 5, M represents a metal, and the other symbols have the same meaning as above.

In the formula, an organometallic compound (X) represented by $R^3$—X—M is readily available as a commercial product, and it is produced by per se well known processes, for example the process described in the 4th Edition of Jikken Kagaku Kouza, 25 (edited by The Chemical Society of Japan) and published by Maruzen KK.

According to reaction equation 5, compound (Id) is obtained by reacting compound (IX) and organometallic compound (X).

As the organometallic compound (X), a Grignard reagent and a organolithium agent are preferred.

The amount of compound (X) used is about 0.8–about 30 moles and preferably about 1.0–about 20 moles with respect to 1 mole of compound (IX).

This reaction is advantageously conducted using a solvent inert in the reaction or in the absence of a solvent. These types of solvents are not particularly limited so long as the reaction progresses. However, for example alcohols such as for example methanol, ethanol, propanol and the like, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide hexamethyl phosphoric triamide and the like, sulfoxides such as for example dimethylsulfoxide and the like, halocarbons such as for example dichloromethane, chloroform, carbon tetrachloride, 1,2-dichloroethane and the like, or mixed solvents thereof and the like may be used.

The reaction time is usually about 10 minute to about 24 hours, preferably about 30 minutes to about 12 hours. The reaction temperature is usually about −100–about 120° C. and preferably about −80–about 60° C.

The product can be used for the next reaction as the reaction mixture itself or as crude product, but it can be isolated from the reaction mixture in accordance with normal methods, and it is readily purified using ordinary separation means (for example, recrystallization, distillation, chromatography and the like).

Compound (I) and the following compound (Ie) that includes the compound (I) are produced by the process as defined in the following reaction equation 6.

Reaction equation 6

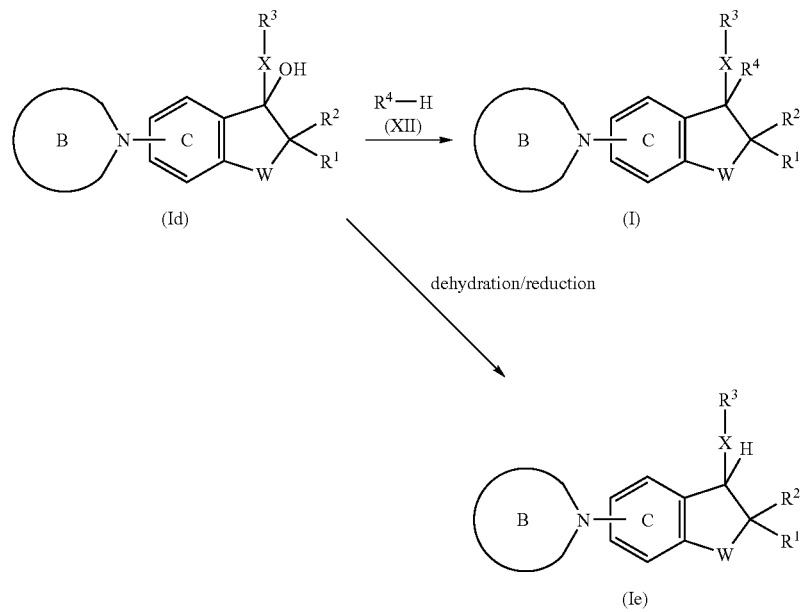

Each symbol in reaction equation 6 has the same meaning as above.

Compound (Id) is separately subjected to the well known acylation reaction, etherification reaction, amination reaction, halogenation reaction, or alkylation reaction, or a reaction in which two or more of these reactions are combined thereof to thereby produce compound (I).

For example, when $R^4$ is alkoxy (for example, methoxy, ethoxy, phenoxy and the like), compound (I) is obtained by reacting compound (Id) with an alcohol (for example, methanol, ethanol, phenol and the like) in the presence of an acid catalyst.

Examples of the "acid catalyst" that can be used include an organic acid such as for example formic acid, acetic acid, trifluoroacetic acid, p-toluenesulfonic acid and the like, a mineral acid such as for example sulfuric acid, hydrochloric acid, hydrobromic acid and the like, and a Lewis acid such as for example zinc chloride and the like.

The amount of alcohol used is about 0.8 mole to an excess amount with respect to 1 mole of compound (Id). The amount of acid catalyst is respectively about 0.1–about 100 moles and preferably about 0.1–about 50 moles with respect to 1 mole of compound (Id).

This reaction is advantageously conducted using a solvent inert in the reaction or in the absence of solvent. These types of solvents are not particularly limited so long as the reaction progresses. However, hydrocarbons such as for example hexane, cyclohexane, benzene, toluene, xylene and the like, ethers such as diethyl ether, diisopropyl ether, tetrahydrofuran, dioxane, 1,2-dimethoxyethane and the like, amides such as for example N,N-dimethylformamide, N,N-dimethylacetamide hexamethyl phosphoric triamide and the like, sulfoxides such as for example dimethylsulfoxide and the like, halocarbons such as for example dichloromethane, chloroform, carbon tetrachloride, 1,2-dichloroethane and the like, nitrites such as acetonitrile, propionitrile and the like, or mixed solvents thereof are preferred.

The reaction time is usually about 10 minutes to about 48 hours, preferably about 30 minutes to about 12 hours. The reaction temperature is usually about 0–about 200° C. and preferably about 25–about 100° C.

The product can be used in the next reaction as the reaction mixture itself or as crude product, but it can be isolated from the reaction mixture in accordance with normal methods, and it is readily purified using ordinary separation means (for example, recrystallization, distillation, chromatography and the like).

In addition, compound (Ie) can be produced by subjecting compound (Id) to a reductive dehydration reaction.

Examples of the reductive dehydration reaction include the well-known catalytic reduction method, and the method using an organic silyl reagent (alkylsilane reagent and the like).

In the catalytic reduction method, compound (Ie) can be produced by reacting compound (Id) with a metal catalyst in a hydrogen atmosphere. A suitable acid catalyst may be added as required.

Examples of the "metal catalyst" that can be used include Raney nickel, platinum oxide, metal palladium, palladium activated carbon and the like. The amount of the "metal catalyst" used is usually about 1–about 1000 wt. % and preferably about 5–about 20 wt. % with respect to compound (Id).

Examples of the "acid catalyst" that can be used include an organic acid such as for example formic acid, acetic acid, trifluoroacetic acid, p-toluenesulfonic acid and the like, a mineral acid such as for example sulfuric acid, hydrochloric acid, hydrobromic acid and the like. The amount of the "acid catalyst" used is respectively about 0.1 to an excess amount with respect to 1 mole of compound (Id).

This reaction is advantageously conducted using a solvent inert in the reaction. This type of solvent is not particularly limited so long as the reaction progresses. However, alcohols such as for example methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such a N,N-dimethylformamide, N,N-dimethylacetamide and the like, organic acids such as for example acetic acid and the like, water, or mixed solvents thereof are preferred. Hydrogen pressure is usually about 1–about 100 atmospheres, preferably about 1–about 5 atmosphere. The reaction time is usually about 30 minutes to about 48 hours, preferably about 1 hour to 24 hours. The reaction temperature is usually about 0–about 120° C. and preferably about 20–about 80° C.

The product can be isolated from the reaction mixture according to normal methods after eliminating the catalyst, and it is readily purified using ordinary separation means (for example, recrystallization, distillation, chromatography and the like).

With a process that uses an organic silyl reagent (alkylsilane reagent), compound (Ie) can be produced by reacting compound (Id) with alkylsilane reagent and an acid.

Examples of the alkylsilane reagent include triethylsilane, phenyl dimethylsilane and the like. The amount of the "alkylsilane reagent" used is about 0.8–about 20 moles and preferably about 1–about 10 moles with respect to 1 mole of compound (Id).

Examples of the acid that can be used includes an organic acid such as trifluoroacetic acid and the like. The amount of acid used is about 0.1 to an excess amount with respect to 1 mole of compound (Id).

This reaction is advantageously conducted using a solvent inert in the reaction. This type of solvent is not particularly limited so long as the reaction progresses. However, ethers such as diethyl ether, tetrahydrofuran, dioxane, 1,2-dimethoxyethane and the like, hydrocarbons such as for example benzene, toluene, cyclohexane, hexane and the like, organic acids such as for example acetic acid, trifluoroacetic acid and the like, or mixed solvents thereof are preferred.

In accordance with normal methods, product can be isolated from the reaction mixture, and it is readily purified using ordinary separation means (for example, recrystallization, distillation, chromatography and the like).

The following compound (Ie) that includes compound (I) is produced by the process described in the following reaction equation 7.

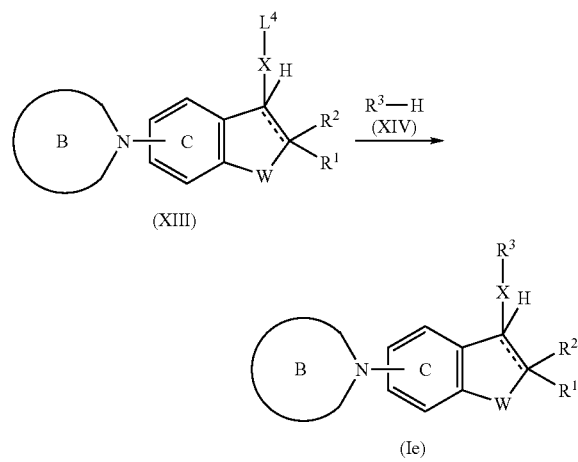

In reaction equation 7, $L^4$ is a leaving group, and each symbol has the same meaning as above.

The compound (XIV) represented by $R^3$—H is readily available as a commercial product, and moreover it is produced by per se well known processes.

Examples of the "leaving group" represented by $L^4$ include hydroxy, halogen atom (for example, fluorine, chlorine, bromine, iodine and the like), optionally halogenated $C_{1-5}$ alkylsulfonyloxy (for example, methanesulfonyloxy, ethane sulfonyloxy, trichloromethane sulfonyloxy and the like), and optionally substituted $C_{6-10}$ arylsulfonyloxy. Examples of "optionally substituted $C_{6-10}$ arylsulfonyloxy" include $C_{6-10}$ arylsulfonyloxy (for example, phenylsulfonyloxy, naphthylsulfonyloxy and the like) which may contain 1–3 substituents selected from for example $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro, and specific examples include benzensulfonyloxy, m-nitrobenzenesulfonyloxy, p-toluenesulfonyloxy and the like.

According to reaction equation 7, compound (Ie) can be obtained by reacting compound (XIII) and compound (XIV) in the presence of acid catalyst or base.

Examples of the "acid catalyst" that can be used include an organic acid such as for example formic acid, acetic acid, trifluoroacetic acid, p-toluenesulfonic acid and the like, a mineral acid such as for example sulfuric acid, hydrochloric acid, hydrobromic acid and the like, and a Lewis acid such as for example zinc chloride and the like.

Examples of the "base" include basic salts such as sodium carbonate, potassium carbonate, cesium carbonate, sodium bicarbonate and the like, aromatic amines such as pyridine, lutidine and the like, tertiary amines such as triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metallic amides such as sodium amide, lithium diisopropylamide, lithium hexamethyl disilazide and the like, and metalalkoxides such as sodium methoxide, sodium ethoxide, potassium t-butoxide and the like.

The amount of acid catalyst used is about 0.1 mole to an excess amount with respect to 1 mole of compound (XIII), and preferably about 0.1–about 50 moles.

The amount of base used is about 1.0–5.0 moles and preferably about 1.0–2.0 moles with respect to 1 mole of compound (XIII).

This reaction is advantageously conducted using a solvent inert in the reaction or in the absence of solvent. It is not restricted in particular so long as reaction progresses. However, alcohols such as for example methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N dimethylformamide, N,N dimethylacetamide and the like, halogenated hydrocarbons such as dichloromethane, chloroform, carbon tetrachloride, 1,2-dichloroethane and the like, nitrites such as acetonitrile, propionitrile and the like, sulfoxides such as dimethylsulfoxide and the like, or mixed solvents thereof are preferred.

The reaction time is usually about 10 minutes to about 48 hours, preferably about 30 minutes to about 24 hours. The reaction temperature is usually −20–200° C., and preferably 0–150° C.

Instead of the aforementioned reaction, the Mitsunobu reaction (Synthesis, 1981, pp. 1–27) can be used.

This reaction is carried out by reacting compound (XIV) and compound (XIII) in which L is OH in the presence of a azo dicarboxylates (for example, diethylazo dicarboxylate and the like) and a phosphines (for example, triphenylphosphine, tributylphosphine and the like).

The amount of compound (XIV) used is about 1.0–5.0 moles and preferably about 1.0–2.0 moles with respect to 1 mole of compound (XIII).

The amount of the "azo dicarboxylates" and "phosphines" is respectively about 1.0–5.0 moles and preferably about 1.0–2.0 moles with respect to 1 mole of compound (XIII).

This reaction is advantageously conducted using a solvent inert in the reaction, but this type of solvent is not particularly limited so long as the reaction proceeds. However, ethers such as diethyl ether, tetrahydrofuran, dioxane, 1,2-dimethoxyethane and the like, hydrocarbons such as benzene, toluene, cyclohexane, hexane and the like, amides such as N,N dimethylformamide, N,N dimethylacetamide and the like, halogenated hydrocarbons such as dichloromethane, chloroform, carbon tetrachloride, 1,2-dichloroethane and the like, nitrites such as acetonitrile, propionitrile and the like, sulfoxides such as dimethylsulfoxide and the like, or mixed solvents thereof are preferred.

The reaction time is usually about five minutes to 48 hours, preferably 30 minutes to 24 hours. The reaction temperature is usually 20–200° C., and preferably 0–100° C.

The product can be used for the next reaction as the reaction mixture itself or crude product, but it can be isolated from the reaction mixture in accordance with normal methods, and it is readily purified using ordinary separation means (for example, recrystallization, distillation, chromatography and the like).

The following compound (Ie) that includes compound (I) is produced by the process described in the following reaction equation 8.

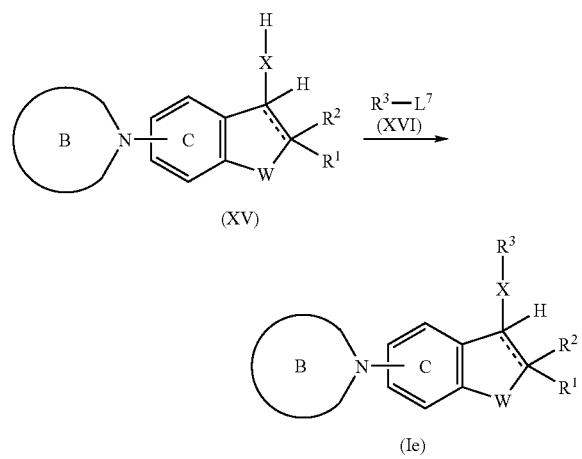

In reaction equation 8, $L^7$ is a leaving group, and each symbol has the same meaning as above.

Compound (XVI) represented by $R^3$—$L^7$ is readily available as a commercial product and moreover it is produced by per se well known processes.

Examples of the "leaving group" represented by $L^7$ include a halogen atom (for example, fluorine, chlorine, bromine, iodine and the like), optionally halogenated $C_{1-5}$ alkylsulfonyloxy (for example, methanesulfonyloxy, ethanesulfonyloxy, trichloromethanesulfonyloxy and the like), optionally substituted $C_{6-10}$ arylsulfonyloxy and the like. Examples of "optionally substituted $C_{6-10}$ arylsulfonyloxy" include $C_{6-10}$ arylsulfonyloxy (for example, phenylsulfonyloxy, naphthylsulfonyloxy and the like) which may contain 1–3 substituents selected from for example $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like) and nitro, and the like, and specific examples include benzensulfonyloxy, m-nitrobenzene sulfonyloxy, p-toluenesulfonyloxy and the like.

According to reaction equation 8, compound (Ie) is obtained by reacting compound (XV) and compound (XVI) in the presence of base.

The amount of compound (XVI) used is about 0.8–5.0 moles and preferably about 1.0–2.0 moles with respect to 1 mole of compound (XV).

Examples of the "base" include basic salts such as sodium carbonate, potassium carbonate, cesium carbonate, sodium bicarbonate and the like, aromatic amines such as pyridine, lutidine and the like, tertiary amines such as triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metallic amides such as sodium amide, lithium diisopropylamide, lithium hexamethyl disilazide and the like, and metalalkoxides such as sodium methoxide, sodium ethoxide, potassium t-butoxide and the like.

The amount of base used is about 1.0–5.0 moles and preferably about 1.0–2.0 moles with respect to 1 mole of compound (XV).

This reaction is advantageously conducted using a solvent inert in the reaction or in the absence of solvent. It is not restricted in particular so long as reaction progresses. However, alcohols such as for example methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N dimethylformamide, N,N dimethylacetamide and the like, halogenated hydrocarbons such as dichloromethane, chloroform, carbon tetrachloride, 1,2-dichloroethane and the like, nitriles such as acetonitrile, propionitrile and the like, sulfoxides such as dimethylsulfoxide and the like, or mixed solvents thereof are preferred.

The reaction time is usually about 10 minutes to about 48 hours, preferably about 30 minutes to about 24 hours. The reaction temperature is usually −20–200° C., and preferably 0–150° C.

The following compound (If) that includes compound (I) is produced by a reductive amination reaction in accordance with following reaction equation 9.

Reaction equation 9

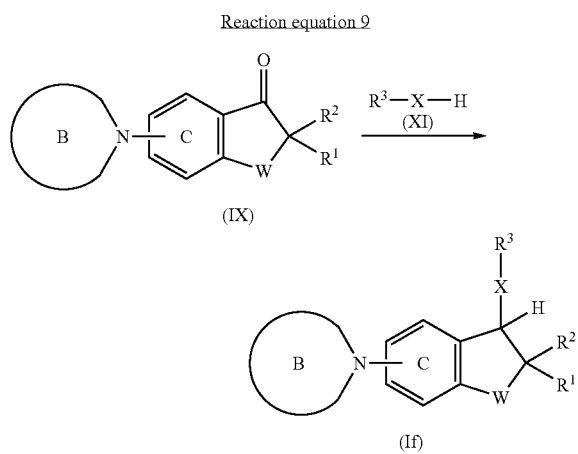

In reaction equation 9, $R^3$—H (XI) is amine, and the other symbols have the same meaning as above.

Compound (If) is produced by condensing compound (IX) and (XI) and reducing with a reducing agent.

The amount of compound (XI) used is about 1.0–about 5.0 moles and preferably about 1.0–about 2.0 moles with respect to 1 mole of compound (IX).

Examples of the "reducing agent" include metal hydrides such as for example sodium borohydride, sodium cyanoborohydride, lithium aluminium hydride and the like, boranes such as for example borane tetrahydrofuran complex and the like, and hydrosilanes such as for example triethylsilane or formic acid and the like. In addition, an acid catalyst may be added to the reducing agent as required. Examples of the acid catalyst include mineral acids such as for example hydrochloric acid, hydrobromic acid, sulfuric acid and the like, sulfonic acids such as for example methanesulfonic acid, p-toluenesulfonic acid and the like, organic acids such as for example acetic acid, propionic acid, trifluoro acetic acid and the like, and Lewis acids such as for example zinc chloride, aluminum chloride and the like.

The amount of the "reducing agent" used is respectively about 0.25–about 5.0 moles and preferably about 0.5–about 2.0 moles with respect to 1 mole of compound (IX).

The amount of the acid catalyst used is usually about 1–about 100 moles and preferably about 1–about 20 moles with respect to 1 mole of compound (IX) when for example a mineral acids is used.

This reaction is advantageously conducted using a solvent inert in the reaction, but this type of solvent is not particularly limited so long as the reaction proceeds. However, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N dimethylacetamide and the like, or mixed solvents thereof are preferred.

The reaction time is usually about 5 minutes to about 48 hours, preferably about 30 minutes to about 24 hours. The reaction temperature is usually about −20–about 200° C. and preferably about 0–about 100° C.

After the condensation of compound (IX) and compound (XI), instead of reduction with the reducing agent, the reaction is carried out by a catalytic hydrogenation reaction in which various kinds of catalysts are copresent under a hydrogen atmosphere. Examples of the catalyst which are used include platinum oxide, platinised activated carbon, palladium activated carbon, nickel, copper-chromium oxide, rhodium, cobalt, ruthenium and the like. The amount of the catalyst used is about 5–about 1000 wt. %, and preferably about 5–about 1000 wt. % with respect to compound (IX).

This reaction is advantageously conducted using a solvent inert in the reaction, but this type of solvent is not particularly limited so long as the reaction proceeds. However, alcohols such as for example methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N dimethylformamide, N,N dimethylacetamide and the like, water and the like, or mixed solvents thereof are preferred.

The reaction time is usually about 30 minutes to about 48 hours, preferably about 30 minutes to about 24 hours. The reaction temperature is usually about 0–about 120° C. and preferably about 20–about 80° C.

In accordance with normal methods, the product can be isolated from the reaction mixture, and it is readily purified using ordinary separation means (for example, recrystallization, distillation, chromatography and the like).

Compound (II) is produced by using per se well-known processes, for example the processes disclosed in JP05-140142A or processes based on these.

In addition, when compound (II) is dihydro-benzofuran, it is produced by the process as defined in the following reaction equation.

Reaction equation 10

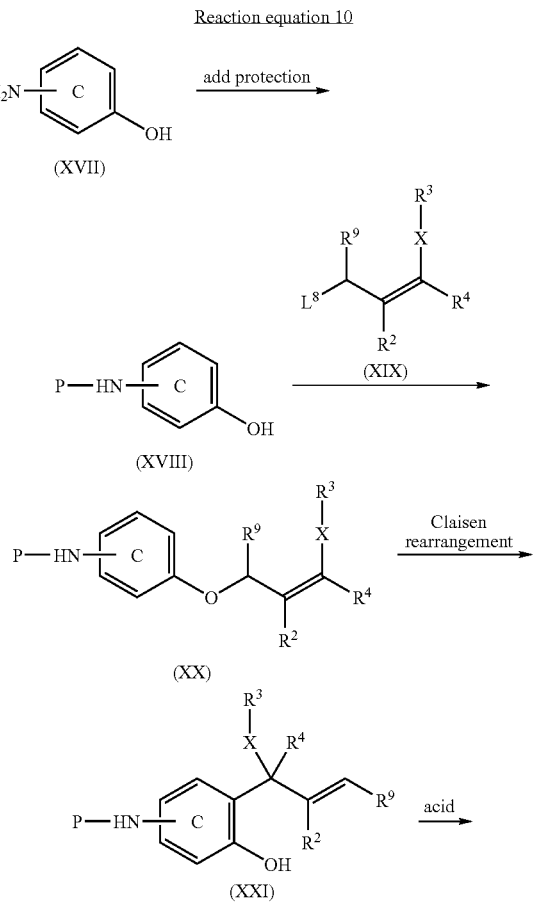

-continued

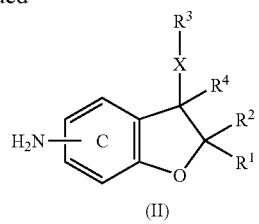

(II)

In reaction equation 10, $L^8$ represents a leaving group, $R^9$ represents a hydrogen atom or a group in which one methylene was removed from $R^1$. The other symbols have the same meaning as above.

Examples of the "leaving group" represented by $L^8$ include hydroxy, halogen atom (for example, fluorine, chlorine, bromine, iodine and the like), $C_{1-6}$ alkylsulfonyloxy (for example, methylsulfonyloxy, ethylsulfomyl oxy and the like), and optionally substituted $C_{6-10}$ arylsulfonyloxy and the like.

Examples of "optionally substituted $C_{6-10}$ arylsulfonyloxy" include for example $C_{6-10}$ arylsulfonyloxy (for example, phenylsulfonyloxy, naphthyl sulfonyloxy and the like) which may contain 1–3 substituents selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), nitro and the like, and specific examples include benzensulfonyloxy, m-nitrobenzene sulfonyloxy, p-toluenesulfonyloxy and the like.

Compound (XVII) and compound (XIX) are readily available as commercial products and are produced by per se well-known processes.

Compound (XVIII) is produced by carrying out a protecting group addition reaction generally used in peptide chemistry and the like on compound (XVII).

Examples of the protecting groups (P) that can be used include formyl or respectively optionally substituted $C_{1-6}$ alkyl-carbonyl (for example acetyl, propionyl and the like), phenylcarbonyl, $C_{1-6}$ alkoxy-carbonyl (for example methoxycarbonyl, ethoxycarbonyl, tert butoxycarbonyl and the like), phenyloxycarbonyl, $C_{7-10}$ aralkyl-oxycarbonyl (for example benzyloxycarbonyl and the like), trityl, phthaloyl and the like. Examples of the substituents of these that can be used include halogen atom (for example fluorine, chlorine, bromine, iodine and the like), $C_{1-6}$ alkyl-carbonyl (for example acetyl, propionyl, valeryl and the like), nitro and the like, and number of substituents is 1–3.

Compound (XX) is produced by reacting a phenolate anion created by processing compound (XVIII) into a base with the compound (XIX) represented by the formula $R^9$—$CHL^5$—$CR^2$=$CR^3R^4$.

The amount of compound (XIX) used is about 0.8–about 5.0 moles and preferably about 1.0–about 2.0 moles with respect to 1 mole of compound (XVIII).

Examples of the "base" include inorganic bases such as alkali metal hydroxides like sodium hydroxide, potassium hydroxide and the like, alkali metal alcoholates such as for example sodium methoxide, sodium ethoxide, potassium t-butoxide and the like, alkali metal hydrides such as for example sodium hydride, potassium hydride and the like, metallic amides such as for example sodium amide, lithium diisopropylamide, lithium hexamethyl disilazide and the like, and basic salts such as for example potassium hydrogencarbonate, sodium carbonate, potassium carbonate, sodium acetate and the like.

The amount of base used is about 0.5–about 5.0 moles and preferably about 1.0–about 3.0 moles with respect to 1 mole of compound (XVIII).

This reaction is advantageously conducted using a solvent inert in the reaction. Preferrable solvents include, for example, alcohols such as for example methanol, ethanol, propanol and the like, hydrocarbons such as for example cyclohexane, hexane, benzene, toluene, xylene and the like, ethers such as for example tetrahydrofuran, dioxane, 1,2-dimethoxyethane, diethyl ether, diisopropyl ether and the like, amides such as for example N,N-dimethylformamide, N,N-dimethylacetamide, hexamethyl phosphoric triamide and the like, sulfoxides such as for example dimethylsulfoxide and the like, halogenated hydrocarbons such as for example dichloromethane, chloroform, carbon tetrachloride, 1,2-dichloroethane and the like, water, or mixed solvents thereof.

The reaction time is usually about 10 minutes to about 8 hours, preferably about 30 minutes to about 3 hours. The reaction temperature is usually about 0–about 120° C. and preferably about 25–about 100° C.

The product can be used in the next reaction as the reaction mixture itself or as crude product, but it can be isolated from the reaction mixture in accordance with normal methods, and it can be readily purified using ordinary separation means (for example, recrystallization, distillation, chromatography and the like).

Compound (XXI) is produced by performing a Claisen rearrangement of compound (XX).

This reaction is advantageously conducted using a solvent inert in the reaction or in the absence of solvent. These types of solvents are not particularly limited so long as the reaction progresses. However, alcohols such as for example methanol, ethanol, propanol and the like, hydrocarbons such as for example cyclohexane, hexane, benzene, toluene, xylene, mesitylene and the like, organic acids such as for example formic acid, acetic acid and the like, ethers such as for example tetrahydrofuran, dioxane, 1,2-dimethoxyethane, diethyl ether, diisopropyl ether and the like, anilines such as for example N,N-dimethylaniline, N,N-diethylaniline and the like, halogenated hydrocarbons such as for example dichloromethane, chloroform, carbon tetrachloride, 1,2-dichloroethane and the like, or mixed solvents thereof can be used.

In addition, this reaction may be carried out using an acid catalyst as required.

Examples of the acid catalyst that can be used include Lewis acids such as for example aluminum chloride, boron trifluoride and the like.

When a Lewis acid is used, the amount of acid catalyst used will usually be about 0.1–about 20 moles and preferably about 0.1–about 5.0 moles with respect to 1 mole of compound (XX).

The reaction time is usually about 30 minutes to about 24 hours, and preferably about 1–about 6 hours. The reaction temperature is usually about −70–about 300° C. and preferably about 150–about 250° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (II) is produced by cyclization of compound (XXI) with acid catalyst. Examples of acid catalyst that can be used include mineral acids such as for example hydrochloric acid, hydrobromic acid, sulfuric acid and the like, sulfonic acids such as for example p-toluenesulfonic acid, camphor sulfonic acid and the like, and Lewis acids such as for example aluminum chloride, boron trifluoride and the like.

The amount of acid catalyst used when the acid catalyst is for example a mineral acids is normally about 0.8–about 100 moles and preferably about 10–about 50 moles with respect to 1 mole of compound (XXI), and the amount of acid catalyst used when the acid catalyst is for example a sulfonic acid is about 0.1–about 20 moles and preferably about 0.1–about 5 mole with respect to 1 mole of compound (XXI).

This reaction is advantageously conducted using a solvent inert in the reaction or in the absence of solvent. These types of solvents are not particularly limited so long as the reaction progresses. For example when mineral acids are being used as a solvent, a mixed solvent of water and an organic solvent such as alcohols such as for example methanol, ethanol, propanol and the like, saturated hydrocarbons such as for example cyclohexane, hexane and the like, aromatic hydrocarbons such as for example benzene, toluene, xylene and the like, ethers such as for example tetrahydrofuran, dioxane, 1,2-dimethoxyethane, diethyl ether, diisopropyl ether and the like, amides such as for example N,N-dimethylformamide, N,N-dimethylacetamide, hexamethyl phosphoric triamide and the like, sulfoxides such as for example dimethylsulfoxide and the like, halogenated hydrocarbons such as for example dichloromethane, chloroform, carbon tetrachloride, 1,2-dichloroethane and the like, or water is preferred.

The reaction time is usually about 30 minutes to about 24 hours, preferably about 30 minutes to about 6 hours. The reaction temperature is usually about –78–about 200° C. and preferably about –20–about 150° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

In addition, it is produced by the process as defined in the following reaction equation.

Reaction equation 11

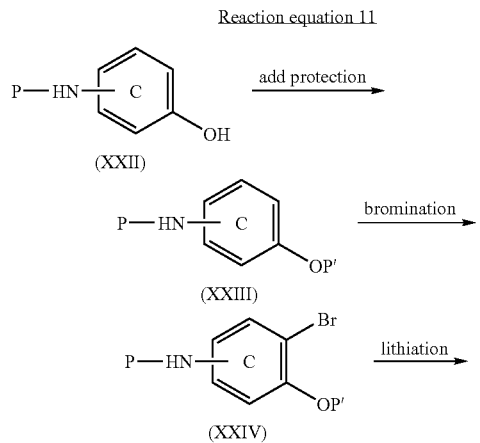

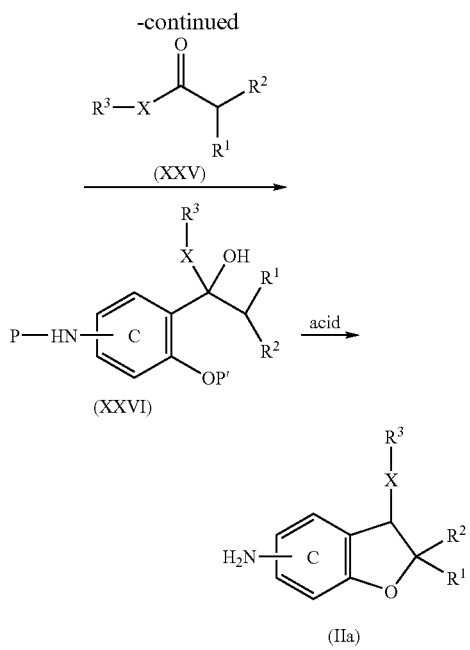

In reaction equation 11, P' represents a hydroxy protecting group, and the other symbols have the same meaning as above.

Compound (XXIII) is produced by performing a protecting group addition reaction generally used in peptide chemistry and the like on compound (XXII).

Examples of the hydroxy protecting group (P'–j that can be used include respectively, optionally substituted $C_{1-6}$ alkyl (for example methyl, ethyl, propyl, isopropyl, butyl, tert-butyl and the like), phenyl, $C_{7-11}$ aralkyl (for example benzyl and the like), formyl, $C_{1-6}$ alkyl-carbonyl (for example acetyl, propionyl and the like) phenyloxycarbonyl, $C_{7-11}$ aralkyl-oxycarbonyl (for example benzyloxycarbonyl and the like), tetrahydropyranyl, tetrahydrofuranyl, silyl and the like. Examples of substituents of these groups include halogen atom (for example fluorine, chlorine, bromine, iodine and the like), $C_{1-6}$ alkyl (for example methyl, ethyl, tert-butyl and the like), $C_{7-11}$ aralkyl (for example benzyl and the like), $C_{6-10}$ aryl (for example phenyl, naphthyl and the like), and nitro and the like, and the number of these substituents is 1–4.

Compound (XXIV) is produced by reacting compound (XXIII) and a bromination reagent.

Examples of the "bromination reagent" that may be used include bromine, imides such as for example N-bromosuccinimide and the like, halogen adducts and the like such as for example benzyl trimethyl ammonium tribromide and the like. The amount of the halogenation reagent is about 1.0–about 5.0 moles and preferably about 1.0–about 2.0 moles with respect to 0.8 mole of compound (XXIII).

This reaction is advantageously conducted using a solvent inert in the reaction. These types of solvents are not particularly limited so long as the reaction progresses. However, ethers such as for example diethyl ether, tetrahydrofuran, dioxane, 1,2-dimethoxyethane and the like, alcohols such as for example methanol, ethanol, propanol and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, organic acids such as for example acetic acid, propionic acid and the like, nitroalkanes such as for example nitromethane and the like, aromatic amines such as for example pyridine, lutidine, quinoline and the like, or mixed solvents thereof may be used.

This reaction is performed in the presence of base, a Lewis acid or iron as required.

Examples of the "base" include basic salts such as for example sodium carbonate, calcium carbonate, cesium carbonate, sodium bicarbonate, sodium acetate, potassium acetate and the like, aromatic amines such as for example pyridine, lutidine and the like, tertiary amines and the like such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like.

The amount of base used is about 0.8–about 10 moles with respect to 1 mole of compound (XXIII).

Examples of the "Lewis acid" include ferric chloride, aluminum chloride, boron trifluoride and the like. The amount of Lewis acid used is about 0.01–about 1 mole with respect to 1 mole of compound (XXIII).

As for "iron", the amount thereof used is about 0.01–about 1 mole with respect to 1 mole of compound (XXIII).

The reaction temperature is usually about −50–about 150° C. and preferably about 0–about 100° C. The reaction time is usually about 5 minutes to about 24 hours, preferably about 10 minutes to about 12 hours.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (XXVI) is produced by reacting ketone (XXV) after lithiating compound (XXIV).

Examples of the "lithiation reagent" that can be used include alkyllithiums and the like such as for example n-butyllithium and the like. The amount of lithiation reagent used is about 0.8–about 5.0 moles and preferably about 1.0–about 3.0 moles with respect to 1 mole of compound (XXIV).

This reaction is advantageously conducted using a solvent inert in the reaction. These types of solvents are not particularly limited so long as the reaction progresses. However, for example ethers such as for example diethyl ether, tetrahydrofuran, dioxane, 1,2-dimethoxyethane and the like, hydrocarbons such as for example benzene, toluene, cyclohexane, hexane and the like, halogenated hydrocarbons such as for example dichloromethane, chloroform, carbon tetrachloride, 1,2-dichloroethane and the like or mixed solvents thereof and the like may be used.

The reaction temperature is usually about −78–about 100° C. and preferably about −78–about 50° C. The reaction time is usually about 5 minutes to about 24 hours, preferably about 10 minutes to about 3 hours.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (IIa) is produced by a deprotection and cyclization of compound (XXVI) with an acid catalyst.

Examples of the acid catalyst that can be used include mineral acids such as for example hydrochloric acid, hydrobromic acid, sulfuric acid and the like, sulfonic acids such as for example p-toluenesulfonic acid, camphor sulfonic acid and the like, and Lewis acids such as for example aluminum chloride, boron trifluoride and the like.

The amount of acid catalyst used when the acid catalyst is for example a mineral acids is normally about 0.5–about 100 moles and preferably about-10–about 50 moles with respect to 1 mole of compound (XXVI), and the amount of acid catalyst used when the acid catalyst is for example a sulfonic acids is normally about 0.1–about 20 moles and preferably about 0.1–about 5 moles with respect to 1 mole of compound (XXVI).

This reaction is advantageously conducted using a solvent inert in the reaction or in the absence of solvent. These types of solvents are not particularly limited so long as the reaction progresses. For example when mineral acids are being used as the solvent, a mixed solvent of water and an a organic solvent such as alcohols such as for example methanol, ethanol, propanol and the like, saturated hydrocarbons such as for example cyclohexane, hexane and the like, aromatic hydrocarbons such as for example benzene, toluene, xylene and the like, ethers such as for example tetrahydrofuran, dioxane, 1,2-dimethoxyethane, diethyl ether, diisopropyl ether and the like, amides such as for example N,N-dimethylformamide, N,N-dimethylacetamide, hexamethyl phosphoric triamide and the like, sulfoxides such as for example dimethylsulfoxide and the like, halogenated hydrocarbons and the like such as for example dichloromethane, chloroform, carbon tetrachloride, 1,2-dichloroethane and the like, or water are preferred.

The reaction time is usually about 30 minutes to about 24 hours, preferably about 30 minutes to about 6 hours. The reaction temperature is usually about −78–about 200° C. and preferably about −20–about 150° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

In addition, in each of the aforementioned reactions, when a functional group such as for example an amino group, hydroxy group, carboxy group and the like are present, a protecting group generally used in peptide chemistry may be introduced and thereafter be subjected to reaction, and the target compound can be obtained by removing the protecting group after the reaction according to need.

Examples of the protecting groups that can be used include formyl or respectively optionally substituted $C_{1-6}$ alkyl-carbonyl (for example, acetyl, propionyl and the like), phenylcarbonyl, $C_{1-6}$ alkoxy-carbonyl (for example, methoxycarbonyl, ethoxycarbonyl and the like), phenyloxycarbonyl, $C_{7-10}$ aralkyloxy-carbonyl (for example, benzyloxycarbonyl and the like), trityl, phthaloyl and the like. Examples of substituents of these groups that may be used include halogen atoms, (for example, fluorine, chlorine, bromine, iodine and the like), $C_{1-6}$ alkyl-carbonyl (for example, acetyl, propionyl, valeryl and the like), nitro and the like, and the number of substituents is 1–3.

In addition, the protecting groups may be removed according to per known methods such as treatment with for example acid, base, UV light, hydrazine, phenylhydrazine, N-methyl dithiocarbamate sodium, tetrabutyl ammonium fluoride, palladium acetate or the like, and a reduction reaction.

In addition, when compound (II) is benzofuran, it is produced by the process described in the following reaction equation.

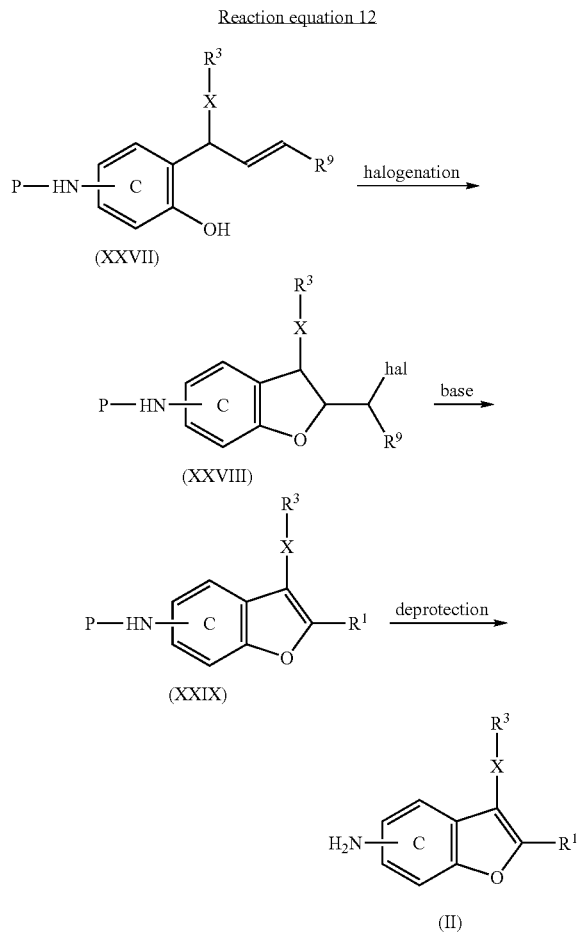

In reaction equation 12, hal represents halogen atom (for example, fluorine, chlorine, bromine, iodine and the like), and the other symbols have the same meaning as above.

Compound (XXVIII) is produced by reacting a compound (XXVII) synthesised in the same way as compound (XXI) with a halogenation reagent.

Examples of the "halogenation reagent" that can be used include halogens such as for example bromine, chlorine, iodine and the like, imides such as for example N-bromosuccinimide and the like, halogen adducts and the like such as for example benzyl trimethyl ammonium iodo dichloride, benzyl trimethyl ammonium tribromide and the like. The amount of halogenation reagent is about 0.8–about 5.0 moles and preferably about 1.0–about 2.0 moles with respect to 1 mole of compound (XXVII).

This reaction is advantageously conducted using a solvent inert in the reaction. These types of solvents are not particularly limited so long as the reaction progresses. However, alcohols such as for example methanol, ethanol, propanol and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitriles such as for example acetonitrile, propionitrile and the like, sulfoxides such as for example dimethylsulfoxide and the like, organic acids such as for example acetic acid, propionic acid and the like, nitroalkanes such as for example nitromethane and the like, aromatic amines such as for example pyridine, lutidine, quinoline and the like, or mixed solvents thereof may be used.

This reaction is carried out in the presence of a base or a radical initiator, or under photoirradiation, as required.

Examples of the "base" include basic salts such as for example sodium carbonate, calcium carbonate, cesium carbonate, sodium bicarbonate, sodium acetate, potassium acetate and the like, aromatic amines such as for example pyridine, lutidine and the like, tertiary amines and the like such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like. The amount of base used is about 0.8–about 10 moles with respect to 1 mole of compound (XXVII).

Examples of the "radical initiator" include benzoyl peroxide, azobisisobutyronitrile and the like. The amount of the radical initiator used is about 0.01–about 1 mole with respect to 1 mole of compound (XXVII).

When photoirradiation is performed, it is possible to use a halogen lamp and the like.

The reaction temperature is usually about −50–about 150° C. and preferably about 0–about 100° C. The reaction time is usually about 5 minutes to about 24 hours, preferably about 10 minutes to about 12 hours.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (XXIX) is produced by treating compound (XXVIII) with a base.

Examples of the "base" include inorganic bases such as for example alkali metal hydroxide and the like such as for example sodium hydroxide, potassium hydroxide and the like, organic base such as for example triethylamine, 1,8-diazabicyclo[5,4,0]-7-undecene, pyridine and the like, alkali metal alcoholates such as for example sodium methoxide, sodium ethoxide, potassium t-butoxide and the like, hydrides of alkali metal such as for example sodium hydride, potassium hydride and the like, metallic amides such as for example sodium amide, lithium diisopropylamide, lithium hexamethyl disilazide and the like, basic salts and the like such as for example potassium hydrogen carbonate, sodium carbonate, potassium carbonate, sodium acetate and the like.

The amount of base used is about 0.5–about 10 moles and preferably about 1.0–about 5.0 moles with respect to 1 mole of compound (XXVIII).

This reaction is advantageously conducted using a solvent inert in the reaction. Preferable solvents include alcohols such as for example methanol, ethanol, propanol and the like, hydrocarbons such as for example cyclohexane, hexane, benzene, toluene, xylene and the like, ethers such as for example tetrahydrofuran, dioxane, 1,2-dimethoxyethane, diethyl ether, diisopropyl ether and the like, amides such as for example N,N-dimethylformamide, N,N-dimethylacetamide, hexamethyl phosphoric triamide and the like, sulfoxides such as for example dimethylsulfoxide and the like, halogenated hydrocarbons such as for example dichloromethane, chloroform, carbon tetrachloride, 1,2-dichloroethane and the like, water, or mixed solvents thereof.

The reaction time is usually about 10 minutes to about 24 hours, preferably about 30 minutes to about 12 hours. The reaction temperature is usually about 0–about 120° C. and preferably about 25–about 100° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (II) is produced by carrying out a deprotecting reaction on compound (XXIX).

The protecting groups may be removed according to per known methods such as treatment with acid, base, UV light, hydrazine, phenylhydrazine, N-methyl dithiocarbamate sodium, tetrabutyl ammonium fluoride, palladium acetate and the like, or a reduction reaction.

Compound (XXXIV) can be produced by per se well-known processes, for example the process disclosed in the Journal of American Chemical Society, Vol. 104, pp. 2659–2661, (1982), Tetrahedron Asymmetry, Vol. 8–1, pp. 45–55, (1997), and the like, or processes that correspond to these.

In addition, when compound (XXXIV) is dihydrobenzofuran, it is produced by the process described in the following reaction equation.

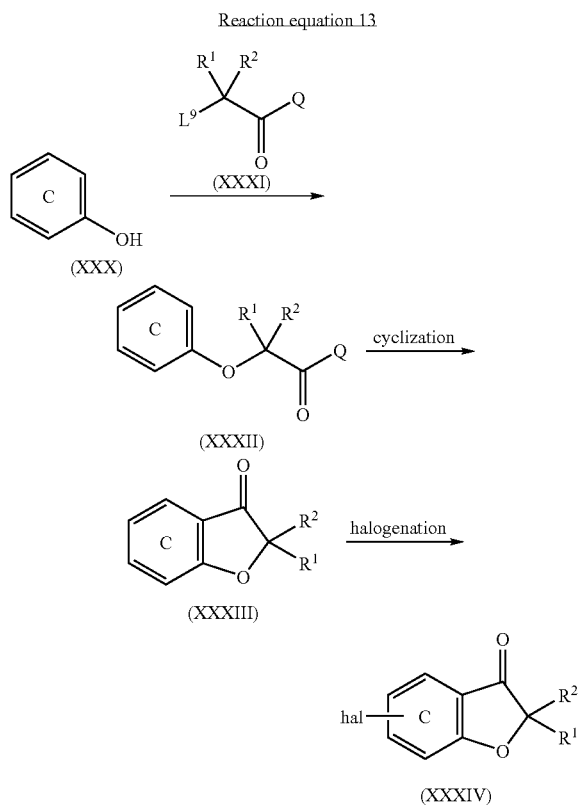

In reaction equation 13, the group represented by —CO—Q represents carboxylic acid or reactive derivative thereof, L$^9$ represents a leaving group, and the other symbols have the same meaning as above.

Compound (XXX) is readily available as a commercial product, and moreover it is produced by per se well-known processes, for example the process disclosed in the 4th Edition of Jikken Kagaku Kouza 20 (edited by The Chemical Society of Japan), pp 111–185, published by Matuzen KK and processes corresponding to this.

Compound (XXXII) is produced by reacting compound (XXX) and compound (XXXI) in the presence of base as required.

Examples of the "leaving group" represented by L$^9$ include hydroxy, halogen atom (for example, fluorine, chlorine, bromine, iodine and the like), $C_{1-6}$ alkylsulfonyloxy (for example, methanesulfonyloxy, ethane sulfonyloxy and the like), optionally substituted $C_{6-10}$ arylsufonyloxy and the like.

Examples of "optionally substituted $C_{6-10}$ arylsulfonyloxy" include $C_{6-10}$ arylsulfonyloxy (for example, benzensulfonyloxy, naphthyl sulfonyloxy and the like) which may contain 1–3 substituents selected from $C_{1-6}$ alkyl (for example, methyl, ethyl, propyl, isopropyl, butyl, isobutyl, sec-butyl, tert-butyl, pentyl, hexyl and the like), $C_{1-6}$ alkoxy (for example, methoxy, ethoxy, propoxy, isopropoxy, butoxy, isobutoxy, sec-butoxy, pentyloxy, hexyloxy and the like), halogen (for example, chloro, bromo, iodo and the like) and nitro, and the like, and specific examples include benzensulfonyloxy, p-toluenesulfonyloxy, p-bromobenzene sulfonyloxy, m-nitrobenzene sulfonyloxy and the like.

Examples of the "base" include basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as for example sodium methoxide, sodium ethoxide, potassium t-butoxide and the like.

The amount of compound (XXXI) is about 0.8–about 5.0 moles and preferably about 1.0–about 3.0 moles with respect to 1 mole of compound (XXX).

The amount of base used is about 0.8–about 5.0 moles and preferably about 1.0–about 3.0 moles with respect to 1 mole of compound (XXX). In addition, compound (XXXI) can be produced by reacting it in the presence of quaternary ammonium salt and base as required.

Examples of the "quaternary ammonium salt" include tetrabutyl ammonium iodide and the like.

The amount of quaternary ammonium salt used is about 0.1–about 2.0 moles and preferably about 0.5–about 1.0 moles with respect to 1 mole of compound (XXX).

This reaction is advantageously conducted using a solvent inert in the reaction, but this type of solvent is not particularly limited so long as the reaction proceeds. However, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitriles such as for example acetonitrile, propionitrile and the like, sulfoxides such as for example dimethylsulfoxide and the like, or mixed solvents thereof are preferred.

The reaction time is usually about 30 minutes to about 96 hours, preferably about one hour to about 72 hours. The reaction temperature is usually about 0–about 120° C. and preferably about 0–about 60° C.

Instead of the aforementioned reaction, the Mitsunobu reaction (Synthesis, 1981, pp. 1–27) can be used.

This reaction reacts compound (XXX) and compound (XXXI) in which $L^9$ is OH in the presence of azodicarboxylates (for example, diethylazodicarboxylate and the like) and phosphines (for example, triphenylphosphine, tributylphosphine and the like).

The amount of compound (XXXI) used is about 0.8–about 5.0 moles and preferably about 1.0–about 3.0 moles with respect to 1 mole of compound (XXX).

The amount of the "azodicarboxylates" and "phosphines" used is respectively about 0.8–about 5.0 moles and preferably about 1.0–about 3.0 moles with respect to 1 mole of compound (XXX).

This reaction is advantageously conducted using a solvent inert in the reaction, but this type of solvent is not particularly limited so long as the reaction proceeds. However, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitriles such as for example acetonitrile, propionitrile and the like, sulfoxides such as for example dimethylsulfoxide and the like, or mixed solvents thereof and the like are preferred.

The reaction time is usually about 5 minutes to about 48 hours, preferably about 30 minutes to about 24 hours. The reaction temperature is usually about –20–about 200° C. and preferably about 0–about 100° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

Compound (XXXIII) is prepared from compound (XXXII) by well-known cyclization reaction.

The cyclization reaction is carried out using an acid.

In this reaction, Q is preferably hydroxy, halogen and the like. In this reaction, compound (XXXII) is reacted with an acid as required to obtain compound (XXXIII).

Examples of the "acid" that can be used include a Lewis acid such as for example aluminum chloride, ferric chloride, stannic chloride, titanium tetrachloride, boron trifluoride diethyl ether and the like, a mineral acid such as for example polyphosphoric acid, sulfuric acid and the like, an organic acid and the like such as for example trifluoroacetic acid, methanesulfonic acid, p-toluenesulfonic acid, trifluoromethanesulfonic acid and the like.

The amount of the "acid" used is a catalytic amount to an excess amount, and is preferably about 0.8–about 5 mole with respect to 1 mole of compound (XXXII).

This reaction is advantageously conducted using a solvent inert in the reaction or in the absence of solvent. These types of solvents are not particularly limited so long as the reaction progresses. However, nitroalkanes such as for example carbon disulfide, nitromethane and the like, nitro aryls such as for example nitrobenzene and the like, halocarbons such as for example dichloromethane, 1,2-dichloroethane, 1,2-dichlorobenzene and the like, organic acids such as for example acetic acid, trifluoroacetic acid and the like, acid anhydride and the like such as for example acetic anhydride, anhydrous trifluoroacetic acid and the like, or mixed solvents thereof are preferred.

The reaction time is usually about 10 minutes to about 96 hours, preferably about 10 minutes to about 12 hours. The reaction temperature is usually about –70–about 200° C. and preferably about –40–about 150° C.

The product can be used in the next reaction as the reaction mixture itself or crude product, but it can be isolated from the reaction mixture in accordance with normal methods, and it is readily purified using ordinary separation means (for example, recrystallization, distillation, chromatography and the like).

Compound (XXXIV) is produced by reacting compound (XXXIII) and a halogenation reagent.

Examples of the "halogenation reagent" that can be used include imides such as for example chlorine, bromine, iodine, N-chloro succinimide and N-bromosuccinimide and the like, and halogen adducts such as for example benzyl trimethyl ammonium tri bromide and the like. The amount of halogenation reagent used is about 0.8–about 5.0 moles and preferably about 1.0–about 2.0 moles with respect to 1 mole of compound (XXXIII).

This reaction is advantageously conducted using a solvent inert in the reaction. These types of solvents are not particularly limited so long as the reaction progresses. However, for example ethers such as for example diethyl ether, diisopropyl ether, tetrahydrofuran, dioxane, 1,2-dimethoxyethane and the like, alcohols such as for example methanol, ethanol, propanol and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, organic acids such as for example acetic acid, propionic acid and the like, nitroalkanes such as for example nitromethane and the like, aromatic amines such as for example pyridine, lutidine, quinoline and the like, or mixed solvents thereof and the like may be used.

This reaction is performed in the presence of a base, a Lewis acid, or iron as required.

Examples of the "base" include basic salts such as for example sodium carbonate, calcium carbonate, cesium carbonate, sodium bicarbonate, sodium acetate, potassiumacetate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like. The amount of base used is about 0.8–about 10 moles with respect to 1 mole of compound (XXXIII).

Examples of the "Lewis acid" include ferric chloride, aluminum chloride, boron trifluoride and the like. The amount of Lewis acid used is about 0.01–about 5 mole with respect to 1 mole of compound (XXXIII).

The amount of "iron" used is about 0.01–about 5 mole with respect to 1 mole of compound (XXXIII).

The reaction temperature is usually about –50–about 150° C. and preferably about –20–about 100° C. The reaction time is usually about 5 minutes to about 24 hours, preferably about 10 minutes to about 12 hours.

In addition, when a halogen atom is substituted on ring C of compound (XXX), compound (XXXIV) can be produced without carrying out halogenation.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

In addition, compound (IX) is produced by the process described in the following reaction equation.

Reaction equation 14

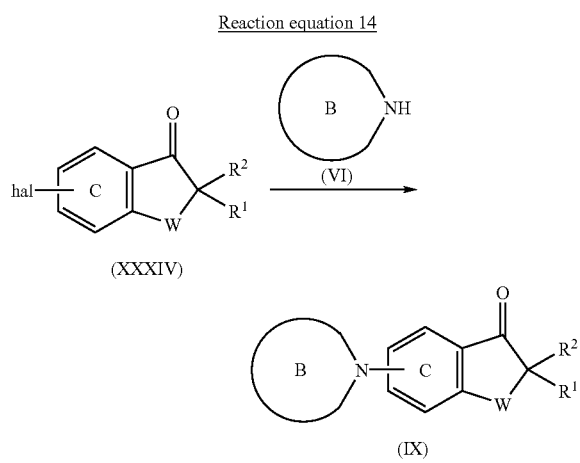

Each symbol in reaction equation 14 has the same meaning as above.

According to reaction equation 14, compound (IX) is produced by reacting compound (XXXIV) and a 4–8 membered cycloamino compound (VI) (in the formula, ring B has the same meaning as above) in the presence of base as required. In accordance with need, catalysts such as for example copper, cuprate and the like may be used, and a catalyst such as palladium, nickel and the like with a ligand (for example phosphine and pyridines and the like) in accordance with the process disclosed in Chemistry Letters 1983, pp 927–928.

The amount of compound (VI) used is about 0.8–about 10.0 moles and preferably about 1.0–about 5.0 moles with respect to 1 mole of compound (XXXIV).

Examples of the "base" include basic salts such as for example sodium carbonate, potassium carbonate, cesium carbonate, sodium bicarbonate and the like, aromatic amines such as for example pyridine, lutidine and the like, tertiary amines such as for example triethylamine, tripropylamine, tributyl amine, cyclohexyl dimethylamine, 4-dimethylaminopyridine, N,N-dimethylaniline, N-methylpiperidine, N-methylpyrrolidine, N-methylmorpholine and the like, alkali metal hydrides such as for example sodium hydride, potassium hydride and the like, metallic amides such as for example sodium amide, lithium diisopropylamide, lithium hexamethyl disilazide and the like, and metalalkoxides such as for example sodium methoxide, sodium ethoxide, sodium tert butoxide, potassium t-butoxide and the like.

The amount of base used is about 0.8–about 10.0 moles and preferably about 1.0–about 5.0 moles with respect to 1 mole of compound (XXXIV).

This reaction is advantageously conducted using a solvent inert in the reaction, but this type of solvent is not particularly limited so long as the reaction proceeds. However, alcohols such as for example methanol, ethanol, propanol and the like, ethers such as for example diethyl ether, tetrahydrofuran, dioxane, 1,2-dimethoxyethane and the like, hydrocarbons such as for example benzene, toluene, cyclohexane, hexane and the like, amides such as for example N,N-dimethylformamide, N,N-dimethylacetamide and the like, halogenated hydrocarbons such as for example dichloromethane, chloroform, carbon tetrachloride, 1,2-dichloroethane and the like, nitrites such as for example acetonitrile, propionitrile and the like, sulfoxides such as for example dimethylsulfoxide and the like, or mixed solvents thereof are preferred.

Examples of the copper catalyst that can be used include copper, copper halide (CuI, CuBr, CuCl and the like), copper oxide (CuO) and the like.

The amount of copper catalyst used is about 0.1–about 10.0 moles and preferably about 0.5–about 2.0 moles with respect to 1 mole of compound (XXXIV).

Phosphine is preferred as the ligand, and examples thereof include trialkylphosphine, triarylphosphine, trialkoxy phosphine and the like. Examples of the palladium catalyst that can be used include palladium acetate, palladium chloride, tetrakis (triphenylphosphine) palladium, bis (dibenzylideneacetone) palladium and the like.

The amount of phosphine used is about 0.001–about 10.0 moles and preferably about 0.01–about 1.0 mole with respect to 1 mole of compound (XXXIV). The amount of palladium catalyst used is about 0.0001–about 5.0 moles and preferably about 0.01–about 0.5 mole with respect to 1 mole of compound (XXXIV).

The reaction time is usually about 30 minutes to about 72 hours, preferably about one hour to about 48 hours. The reaction temperature is usually about −20–about 200° C. and preferably about 0–about 150° C.

The product can be used in the next reaction as the reaction mixture itself or a crude product, but it can be isolated from the reaction mixture in accordance with normal methods, and it can be readily purified using ordinary separation means (for example, recrystallization, distillation, chromatography and the like).

The starting materials of aforementioned compound (I) and compound (I') may be in salt form and are not particularly limited so long as the reaction is achieved. However, for example, the same salt as the salt which the aforementioned compound (I) may form and the like is used.

With respect to the configurational isomers (E, Z isomers) of compound (I) and the compounds (Ia), (Ib), (Ic), (Id), (Ie), and (If) which are included in compound (I) (hereinafter described as compound (I)) and compound (I'), the isolation and purification thereof can be carried out by standard separation means such as for example extraction, recrystallization, distillation, chromatography and the like at a point in time isomerization occured, and pure compound can be produced thereby. In addition, according to the processes disclosed in Shin Jikken Kagaku Kouza 14 (edited by The Chemical Society of Japan), pp. 251–253, the 4th Edition of Jikken Kagaku Kouza 19 (edited by The Chemical Society of Japan), pp. 273–274, and processes corresponding to these, isomerization of double bonds proceeds by heating, an acid catalyst, a transition metal complex, a metal catalyst, a radical species catalyst, photoirradiation or a strong base catalyst and the like, and a corresponding pure isomer can be obtained thereby.

Note that compound (I) and (I') produce stereoisomers depending on the species of the substituents, but are included in the present invention regardless of whether the isomers are isolated or in mixture.

Compound (I) and (I') may be hydrate or non-hydrate.

In either case, it is possible to synthesize compound (I) and (I') by carrying out a deprotecting reaction, an acylation reaction, an alkylation reaction, a hydrogenation reaction, an oxidation reaction, a reductive reaction, a carbon chain extension reaction, or a substituent exchange reaction either alone or in a combination of two or more thereof as required.

In the aforementioned reaction, when a target substance is obtained in the free state, it may be converted into a salt in accordance with standard methods, and when it is obtained as a salt, it can be converted into a free form or another salt in accordance with standard methods. Compound (I) and (I') obtained in this way can be isolated and purified from a reaction solution by using well known means, for example solvent transfer, concentration, solvent extraction, fractionation, crystallization, recrystallization, chromatography and the like.

Note that when compound (I) and (I') are present as configuration isomers, diastereomers, conformers and the like, it is possible to respectively isolate these using the aforementioned separation and purification means as required. In addition, when compound (I) and (I') are a racemic mixture, it is possible to separated into d- and l-isomers by standard optical resolution means.

In addition, in each of the aforementioned reactions, when a functional group such as for example amino group, hydroxy group, carboxy group and the like is present, the reaction may be carried out after a protecting group which is generally used in peptide chemistry is introduced, and the target compound may be obtained by removing the protecting group after the reaction in accordance with needed.

Examples of the protecting groups that can be used include formyl or respectively optionally substituted $C_{1-6}$ alkyl-carbonyl (for example, acetyl, propionyl and the like), phenylcarbonyl, $C_{1-6}$ alkoxy-carbonyl (for example, methoxycarbonyl, ethoxycarbonyl and the like), phenyloxycarbonyl, $C_{7-10}$ aralkyloxy-carbonyl (for example, benzyloxycarbonyl and the like), trityl, phthaloyl and the like. Substituents of these groups that may be used include halogen atom (for example, fluorine, chlorine, bromine, iodine and the like), $C_{1-6}$ alkyl-carbonyl (for example, acetyl, propionyl, valeryl and the like), nitro and the like, and the number of substituents is 1–3.

In addition, per se well-known processes by which the protecting groups are removed or processes corresponding thereto can be used, and include treatment with for example acid, base, UV light, hydrazine, phenylhydrazine, N-methyldithiocarbamate sodium, tetrabutyl ammonium fluoride, palladium acetate and the like, and a reduction reaction.

A prodrug of compound (I) and (I') of the present invention may be a compound which is converted into compound (I) or (I') by a reaction with an enzyme, gastric acid, and the like under physiological conditions in vivo, in other words, it may be a compound which is changed into compound (I) or (I') by enzymatic oxidation, reduction, hydrolysis and the like, or a compound which is changed into compound (I) or (I') by hydrolysis and the like with gastric acid and the like.

Examples of a prodrug of compound (I) and (I') include a compound in which an amino group of compound (I) and (I') is acylated, alkylated, phosphorylated (for example a compound in which an amino group of compound (I) and (I') is converted into eicosanoylamino, alanylamino, pentylaminocarbonylamino, (5-methyl-2-oxo-1,3-dioxolene-4-yl)methoxycarbonylamino, tetrahydrofuranylamino, pyrrolidylmethylamino, pivaloyloxymethylamino, tert-butylamino and the like); a compound in which a hydroxy group of compound (I) and (I') is acylated, alkylated, phosphorylated, or borylated (for example a compound in which a hydroxy group of compound (I) and (I') is converted into acetylatoxy, palmitoyloxy, propanoyloxy, pivaloyloxy, succinyloxy, fumaryloxy, alanyloxy, dimethylaminomethylcarbonyloxy, and the like); a compound in which a carboxyl group of compound (I) and (I') is converted into an ester or an amide, for example an ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolene-4-yl)methyl ester, cyclohexyloxycarbonylethyl ester, or a methyl amide), and the like. These compounds can be produced from compound (I) or (I') by per se well known processes.

In addition, the prodrug of the compounds (I) and (I') of the present invention may be converted into compound (I) or (I') under physiological conditions as described in the publication "Pharmaceutical Research and Development" Vol. 7, Molecular Design, pp. 163–198, published in 1990 by Hirokawa Shoten.

Compound (I) and (I'), salts thereof, or prodrugs thereof (hereinafter abbreviated to the compound of the present invention) on mammals (for example, mouse, rat, hamster, rabbit, cat, dog, cattle, sheep, monkey, human and the like) as a neurotrophic factor like agent, a neurotrophic factor activity-enhancing agent, neurodegeneration inhibition agent, neurogenesis promotion agent, or as a β-amyloid toxicity inhibition agent, and it inhibits neuronal cell death, promotes neuroregeneration and improves mild cognitive impairment or mild memory loss. In addition, the compound of the present invention acts to activate the choline system (for example, activation of choline acetyltransferase), increases the contents of acetylcholine, and activates neural function. Furthermore, as a stem cell (for example, embryonic stem cell, neural stem cell and the like) proliferation promoting agent, and neural precursor cell differentiation promoting agent, or as a neurotrophic factor like agent, neurotrophic factor activity-enhancing agent, and a neurodegeneration inhibition agent, the compound of the present invention inhibits neuronal cell death and promotes the regeneration of neural system/function by neurogenesis and axonal extension. Furthermore, it is used in transplantation, and is useful for the preparation of neural stem cells/neurons (including neural precursor cells) from fetus brain/patient brain tissue and embryonic stem cells, and at the same time promotes survival/differentiation and functional differentiation of neural stem cells/neurons after transplantation.

In addition, the compound of the present invention, and more particularly compound (I), the salts thereof or prodrugs thereof (hereinafter abbreviated to compound (I)), is useful as a PKB activator, and it displays neurodegeneration inhibitory activity, neuroregeneration enhancing activity, neural stem cell self-renewal promotion activity, stem cell (for example, embryonic stem cell, neural stem cell and the like) proliferating activity, neural precursor cell differentiation promotion activity by activating PKB or inhibition of the signal transduction of GSK as a substrate of PKB, demonstrates pharmaceutical activity such as neural stem cell self-renewal promotion activity, stem cell (for example, embryonic stem cell, neural stem cell and the like) proliferating promotion activity, neural stem cell differentiating activity, neurotrophic factor like activity, neurotrophic factor activity-enhancing activity, neurodegeneration inhibition activity, neurogenesis acceleration activity, antioxidant activity, or β-amyloid induced neuronal cell death inhibition activity, and it is believed to prevent and/or treat diseases such as Parkinson's disease, Alzheimer's disease and the like. More particularly, because compound (I) of the present invention has excellent properties as a pharmaceutical such as for example low toxicity, few side effects, and the like, it is useful to prevent/treat diseases such as for example Parkinson's disease, Alzheimer's disease, ALS, Huntington's disease and the like.

In addition, the compound of the present invention is useful as an agent for preventing/treating Post-traumatic Stress Disorder (PTSD), anxiety, manic depression or trauma.

In addition, as a proliferation and/or differentiation promotion agent for stem cells and/or neural precursor cells by activating PKB, or as neurotrophic factor like agent, neurotrophic factor activity-enhancing agent, and a neurodegeneration inhibition agent, the compound of the present invention inhibits neuronal cell death and promotes regeneration of neural system/function by enhancing neurogenesis and nerve axonal elongation, and thus it is used as an agent for preventing/treating diseases such as for example neurodegenerative disease (for example, Parkinson's disease, Alzheimer's disease, mild cognitive impairment (MCI), amyotrophic lateral sclerosis (ALS), Huntington's disease, spinocerebellar degeneration, multiple sclerosis (MS), Pick disease and the like), other psychiatric diseases (for example, depression, anxiety, manic depression or PTSD, schizophrenia, anxiety neurosis, compulsive neurosis and the like), head trauma, spinal cord injuries, cerebral blood vessel disorders, multiinfarct dementia, asymptomatic cerebral infarction, polyglutamine disease (dentatorubral/pallidoluysian atrophy, Kennedy-Alter-Sung disease, Machado-Jacob disease, spinocerebellar ataxia 6 type), prion disease (Creutzfeldt-Jacob disease, Gerstmann-Straussler-Scheinker disease), cerebral cortex basal ganglion degeneration, progressive supranuclear paralysis, AIDS encephalopathy, myodystrophy, diabetic neuropathy and the like. And as a nutrional factor like agent and nutritional factor activity-enhancing agent, it inhibits cell death and promotes regeneration of tissue/function by the generation and regeneration of cells, and thus it is used as an agent for preventing/treating diseases such as for example diabetic retinopathy, diabetic nephropathy, cirrhosis, alcoholic hepatitis and the like, as well as being useful in treatments such as the regeneration of pancreas β-cells and the like, the treatment of osteoporosis by the regeneration of osteoblasts, and the like.

The compound of the present invention has low toxicity and can be produced into pharmaceutical compositions according to per se well known means as is or in a mixture of pharmacologically acceptable carriers, for example tablets (including sugar coated tablets, film coated tablets, tablets that dissolve in the oral cavity, and the like), powders, granules, encapsulated formulations (including soft capsules), liquids, injections, suppositories, controlled release agents, patchs and the like, and may be safely administered orally or non-orally (for example, topically, rectally, intravenously, and the like).

The amount of the compound of the present invention in the pharmaceutical composition of the present invention is about 0.01 wt %–about 100 wt %.

The dose varies depending upon the subject to which it is administered, the administration route, the disease, and the like, for example when it is administered orally to an adult as a treatment for Alzheimer's disease, the dose may be about 0.1–about 20 mg/kg body weight, preferably about 0.2–about 10 mg/kg body weight and more preferably about 0.5–about 10 mg/kg body weight, in terms of the compound of the present invention as the active ingredient, and it may be administered once a day or divided over several times a day.

In addition to the compound of the present invention, other active ingredients may be used together therewith that are suitable for treating diseases such as neurodegeneration disease (for example, Alzheimer's disease, Parkinson's disease, amyotrophic lateral sclerosis (ALS), Huntingdon's disease, spinocerebellar degeneration, multiple sclerosis (MS) and the like), psychiatric diseases (for example, depression, anxiety, manic depression or PTSD, schizophrenia and the like), head trauma, spinal cord injuries, cerebral blood vessel disorders, multiinfarct dementia, asymptomatic cerebral infarction, polyglutamine disease (tastigiobulbar fibers-pallidoluysian atrophy, Kennedy-Alter-Sung disease, Machado-Jacob disease, spinocerebellar ataxia 6 type), prion disease (Creutzfeldt-Jacob disease, Gerstmann-Straussler-Scheinker disease), cerebral cortex basal ganglion degeneration, progressive supranuclear palsy, AIDS encephalopathy, muscular dystrophy, diabetic neuropathy, diabetic retinopathy, diabetic nephropathy, cirrhosis, alcoholic hepatitis, osteoporosis, and the like, and for regeneration therapy such as pancreatic β-cells. Preferred examples of other active ingredients that can be used with the compound of the present invention include acetylcholinesterase inhibitor (for example, donepezil, rivastigmine, galanthamine, zanapezil [TAK-147] and the like), β-amyloid protein production, secretion, accumulation, agglutination and/or deposition inhibitor [β-secretase inhibitor (for example 6-(4-biphenylyl) methoxy-2-[2-(N,N-dimethylamino) ethyl] tetralin, 6-(4-biphenylyl) methoxy-2-(N,N-dimethylamino) methyl tetralin, 6-(4-biphenylyl) methoxy-2-(N,N-dipropylamino) methyl tetralin, 2-(N,N-dimethylamino) methyl-6-(4'-methoxybiphenyl-4-yl) methoxy tetralin, 6-(4-biphenylyl) methoxy-2-[2-(N,N-diethylamino) ethyl]tetralin, 2-[2-(N,N-dimethylamino) ethyl]-6-(4'-methylbiphenyl-4-yl) methoxy tetralin, 2-[2-(N, N-dimethylamino) ethyl]-6-(4'-methoxybiphenyl-4-yl) methoxy tetralin, 6-(2',4'-dimethoxy biphenyl-4-yl) methoxy-2-[2-(N,N-dimethylamino) ethyl]tetralin, 6-[4-(1,3-benzodioxole-5-yl) phenyl]methoxy-2-(2-(N,N-dimethylamino) ethyl]tetralin, 6-(3',4'-dimethoxybiphenyl-4-yl) methoxy-2-[2-(N,N-dimethylamino) ethyl]tetralin, optically active agents thereof, salts thereof, and hydrates thereof, OM99–2 (WO01/00663)), γ-secretase inhibitor, β-amyloid protein agglutination inhibitor (for example, PTI-00703, ALZHEMED (NC-531), PPI-368 (JP 11-514333 A), PPI-558 (JP 2001-500852 A), SKF-74652 [Biochem. J. (1999), 340 (1), 283–289)), β-amyloid vaccine, β-amyloid catabolic enzyme, cerebral function activator (for example, aniracetam, nicergoline and the like), other Parkinson's disease therapeutic agents [(for example, dopamine receptor agonist (L-Dopa, bromocriptine, pergolide, talipexole, pramipexole, cabergoline, amantadine, and the like), monoamine oxidase (MAO) inhibitor (deprenyl, selugiline (selegiline), remacemide, riluzole, and the like), anticholinergic agents (for example, trihexyphenidyl, biperiden, and the like), COMT inhibitor (for example, entacapone and the like)], amyotrophic lateral sclerosis therapeutic agent (for example, riluzole and the like, neurotrophic factor and the like), hyperlipidemia therapeutic agents such as cholesterol lowering agents [statins (for example, pravastatin sodium, atolovastatin, simvastatin, rosuvastatin and the like), fibrate (for example, clofibrate and the like), squalene synthase inhibitor], therapeutic agent for abnormal behavior accompanied by progressive dementia (for example, sedatives, anxiolytic agents and the like) apoptosis inhibitor (for example, CPI-1189, IDN-6556, CEP-1347, and the like), neurodifferentiation/regeneration promotor (for example, leteprinim, xaliproden (SR-57746-A), SB-216763, and the like), antihypertensive agents, diabetes mellitus therapeutic agents, antidepressants, anxiolytic agents, nonsteroidal anti-inflammatory agents (for example, meloxicam, tenoxicam, indomethacin, ibuprofen, celecoxib, rofecoxib, aspirin, indomethacin and the like), disease-modifying anti-rheumatic drugs (DMARDs), anticytokine agent (TNF inhibitor, MAP kinase inhibitor, and the like), steroids (for example, dexamethasone, hexestrol, cortisone acetate and the like), sex hormones or derivatives thereof (for example, progesterone, estradiol, estradiol benzoate and the like), parathyroid hormone (PTH), calcium receptor antagonist and the like. More particularly, the use of a β-secretase inhibitor such as for 6-(4-biphenylyl)methoxy-2-[2-(N,N-dimethylamino) ethyl]tetralin hydrochloride monohydrate and the like with the compound of the present invention is preferred.

The other active ingredient and the compound of the present invention are mixed together and formulated into one pharmaceutical composition (for example, a tablet, a powder, granules, a capsule (including soft capsules), a liquid, an injection, suppository, a sustained release preparation, and the like) according to per se well-known processes, and may be formulated separately and administered to the same subject simultaneously or over a period of time.

Examples of pharmacologically acceptable carriers which may be used in the production of the formulation of the present invention include various types of conventionally used organic or inorganic carrier substances, for example excipients, lubricants, binders, disintegrators, and the like for solid preparations, and solvents, solubilizers, suspending agents, isotonizing agents, buffers, soothing agents and the like for liquid preparations. In addition, additives such as standard preservatives, anti-oxidants, colorants, sweeteners, adsorbents, wetting agent and the like can be used in accordance with need.

Examples of excipients include lactose, refined sugar, D-mannitol, starch, corn starch, crystalline cellulose, light anhydrous silicic acid and the like.

Examples of lubricants include magnesium stearate, calcium stearate, talc, colloidal silica and the like.

Examples of binders include crystalline cellulose, refined sugar, D-mannitol, dextrin, hydroxypropylcellulose, hydroxypropyl methyl cellulose, polyvinylpyrrolidone, starch, sucrose, gelatin, methyl cellulose, carboxymethylcellulose sodium and the like.

Examples of disintegrators include starch, carboxymethylcellulose, carboxymethylcellulose calcium, crosscarmellose sodium, carboxymethyl starch sodium, L-hydroxypropylcellulose and the like.

Examples of solvents include water for injections, alcohol, propylene glycol, macrogol, sesame oil, corn oil, olive oil and the like.

Examples of solubilizers include polyethyleneglycol, propylene glycol, D-mannitol, benzyl benzoate, ethanol, trisaminomethane, cholesterol, triethanolamine, sodium carbonate, sodium citrate and the like.

Examples of suspending agents include surfactants such as stearyl triethanolamine, sodium lauryl sulfate, lauryl amino propionic acid, lecithin, benzalkonium chloride, benzethonium chloride, glyceryl monostearate and the like; and hydrophilic polymers such as polyvinyl alcohol, polyvinyl pyrrolidone, carboxymethylcellulose sodium, methyl cellulose, hydroxymethyl cellulose, hydroxyethyl cellulose, hydroxypropylcellulose and the like.

Examples of the isotonizing agents include dextrose, D-sorbitol, sodium chloride, glycerol, D-mannitol and the like.

Examples of the buffers include liquid buffers of phosphates, acetates, carbonates, citrates and the like.

Examples of the soothing agents include benzyl alcohol.

Examples of the preservatives include parahydroxybenzoic acid esters, chlorobutanol, benzyl alcohol, phenethyl alcohol, dehydroacetic acid, sorbic acid and the like.

Examples of the anti-oxidants include sulfite, ascorbic acid, α-tocopherol and the like.

This invention is described in detail by means of the following Reference Examples, Examples, Preparation Examples and Experimental Examples, but they are merely examples, and the present invention is not limited to these examples and may vary in a range which does not depart from the scope of the present invention.

In the following Examples and Reference Examples, "room temperature" usually indicates about 10–about 35° C. % indicates percentage by weight unless specifically stated otherwise.

Other abreviations used in the text indicate the following meanings.
s: singlet
d: doublet
dd: doublet of doublets
dt: doublet of triplets
t: triplet
q: quartet
septet: septet
m: multiplet
br: broad
J: coupling constant
Hz: Hertz
THF: tetrahydrofuran
DMF: N,N-dimethylformamide
BINAP: 2,2'-bis (diphenylphosphino)-1,1'-binaphthyl
CDCl3: deuterated chloroform
DMSO-$d_6$: deuterated dimethyl sulfoxide
$^1$H-NMR: proton nuclear magnetic resonance In addition, with regard to $^1$H-NMR of the compounds that are formed into salts, data for the free form of the compounds has been disclosed. In addition, abnormally broad peak of the proton on the hydroxy group and the amino group are not disclosed herein.

In the silica gel chromatography, Kieselgel 60 made by Merck Corp. was used and, in the basic silica gel chromatography, Chromatorex NH made by Fuji Sylysia Chemical was used.

In addition, activated alumina (basic) made by ICN Pharmaceuticals was used for the basic alumina chromatography.

REFERENCE EXAMPLE 1 methyl 3-(4-fluorophenyl)-2-propenoate

To a solution of 3-(4-fluorophenyl)-2-propenoic acid (24.2 g, 146 mmol) in DMF (120 ml) were added methyl iodide (31.1 g, 219 mmol) and potassium carbonate (40.4 g, 292 mmol) at room temperature and the mixture was stirred for 72 hours. The resulting mixture was poured into water and extracted with ethyl acetate. The organic layer was washed with water and saturated aqueous sodium chloride, dried over anhydrous sodium sulfate, and concentrated under reduced pressure. The residue was crystallized from hexane to obtain 24.5 g (yield 93%) of the title compound. mp. 43–46° C.

$^1$H-NMR (CDCl3) δ: 3.81 (3H, s), 6.37 (1H, d, J=16.2 Hz), 7.00–7.16 (2H, m), 7.46–7.58 (2H, m), 7.66 (1H, d, J=16.2 Hz).

REFERENCE EXAMPLE 2 methyl 3-(4-methylphenyl)-2-propenoate

To a solution of 3-(4-methylphenyl)-2-propenoic acid (10.0 g, 61.7 mmol) in THF (100 ml) were added 1,4-diazabicyclo[5.4.0]-7-undecene (11.0 mL, 73.6 mmol) and methyl iodide (4.3 mL, 69.1 mmol) under ice cooling and the mixture was stirred at room temperature for 24 hours. The resulting mixture was poured into water and extracted with ethyl acetate. The organic layer was washed with aqueous sodium sulfite, saturated aqueous sodium bicarbonate, water and saturated aqueous sodium chloride, and dried over anhydrous sodium sulfate, and concentrated under reduced pressure. The residue was crystallized from hexane to obtain 9.10 g (yield 84%) of the title compound. mp. 56–58° C.

$^1$H-NMR (CDCl3) δ: 2.37 (3H, s), 3.80 (3H, s), 6.39 (1H, d, J=16.1 Hz), 7.19 (2H, d, J=8.1 Hz), 7.42 (2H, d, J=8.1 Hz), 7.67 (1H, d, J=16.1 Hz).

REFERENCE EXAMPLE 3 methyl 3-(3,4-dimethoxyphenyl)-2-propenoate

To a suspension of 3-(3,4-dimethoxyphenyl)-2-propenoic acid (21.8 g, 105 mmol) in methanol (220 ml) was added thionyl chloride (23.0 mL, 315 mmol) under ice cooling and the mixture was stirred at 60° C. for 12 hours. The resulting mixture was concentrated under reduced pressure, and the residue was added to water and extracted with ethyl acetate. The organic layer was washed with saturated aqueous sodium bicarbonate, water and saturated aqueous sodium chloride, and dried over anhydrous sodium sulfate, and concentrated under reduced pressure. The residue was crystallized from ethyl acetate-hexane to obtain 18.7 g (yield 80%) of the title compound. mp. 72–74° C.

$^1$H-NMR (CDCl3) δ: 3.80 (3H, s), 3.91 (6H, s), 6.31 (1H, d, J=15.8 Hz), 6.86 (1H, d, J=8.2 Hz), 7.05 (1H, d, J=1.8 Hz), 7.11 (1H, dd, J=8.2, 1.8 Hz), 7.64 (1H, d, J=15.8 Hz).

REFERENCE EXAMPLE 4

3-phenylglutaric anhydride

To acetic anhydride (5 ml) was added 3-phenylglutaric acid (2.20 g, 10.6 mmol). The mixture was refluxed for 3 hours. The resulting mixture was concentrated under reduced pressure. The residue was crystallized from diisopropyl ether to obtain 1.8 g (yield 90%) of the title compound.

$^1$H-NMR (CDCl3) δ: 2.87 (2H, dd, J=17.2, 11.4 Hz), 3.13 (2H, dd, J=17.2, 4.5 Hz), 3.32–3.56 (1H, m), 7.10–7.50 (5H, m).

REFERENCE EXAMPLE 5

3-(4-fluorophenyl)glutaric anhydride

Dimethyl malonate (14.7 g, 111 mmol) was added dropwise to the mixture of sodium methoxide in methanol (methanol solution 28%, 19.3 g, 100 mmol) and methanol (30 ml) under ice cooling and stirred for 15 minutes. To the mixture was added a solution of methyl (2E)-3-(4-fluorophenyl)-2-propenoate (10.0 g, 55.5 mmol) obtained in Reference Example 1 in THF (50 ml) under ice cooling and the mixture was refluxed for 12 hours. The resulting mixture was concentrated under reduced pressure, and the residue was diluted with water. The aqueous layer was acidified with dilute hydrochloric acid, extracted with ethyl acetate. The organic layer was washed with water and saturated aqueous sodium chloride, and dried over anhydrous sodium sulfate, and concentrated under reduced pressure. The residue was purified using silica gel column chromatography (hexane/ethyl-acetate=8/1) to obtain 12.7 g (yield 73%) of 2-(4-fluorophenyl)-1,1,3-trimethoxy carbonyl propane via recrystallization (ethyl acetate-hexane). mp. 75–76° C.

$^1$H-NMR (CDCl3) δ: 2.72 (1H, dd, J=15.8, 9.3 Hz), 2.86 (1H, dd, J=15.8, 5.1 Hz), 3.50 (3H, s), 3.54 (3H, s), 3.74 (1H, d, J=9.8 Hz), 3.75 (3H, s), 3.82–4.04 (1H, m), 6.90–7.08 (2H, m), 7.14–7.32 (2H, m).

An aqueous solution of sodium hydroxide (3N, 23 mL, 69 mmol) was added to a solution of 2-(4-fluorophenyl)-1,1,3-trimethoxy carbonyl propane (6.7 g, 21.5 mmol) in methanol (100 ml) at room temperature and the mixture was stirred for 12 hours. The resulting mixture was concentrated under reduced pressure, and then water (20 ml) and concentrated hydrochloric acid (10 ml) were added under ice cooling. The aqueous mixture was refluxed for 12 hours. The reaction mixture was extracted with ethyl acetate. The organic extract was washed with water and saturated sodium chloride, and dried over anhydrous sodium sulfate. The solvent was removed under reduced pressure, and the residue was crystallized from ethyl acetate-hexane to obtain 4.5 g of 3-(4-fluorophenyl) glutaric acid (yield 93%). mp. 145–147° C.

$^1$H-NMR (DMSO-d$_6$) δ: 2.48 (2H, dd, J=15.8, 8.8 Hz), 2.64 (2H, dd, J=15.8, 6.2 Hz), 3.20–3.56 (1H, m), 7.00–7.20 (2H, m), 7.22–7.40 (2H, m), 12.1(2H, br s).

To acetic anhydride (5 ml) was added 3-(4-fluorophenyl) glutaric acid (2.00 g, 8.84 mmol) and the mixture was refluxed for 3 hours. The resulting mixture was concentrated under reduced pressure, and the residue was crystallized from ethyl acetate-hexane to obtain 1.4 g (yield 76%) of the title compound. mp. 99–104° C.

$^1$H-NMR (CDCl3) δ: 2.84 (2H, dd, J=17.2, 11.2 Hz), 3.11 (2H, dd, J=17.2, 4.4 Hz), 3.32–3.56 (1H, m), 7.02–7.34 (4H, m).

REFERENCE EXAMPLE 6

3-(4-methylphenyl)glutaric anhydride

Using methyl 3-(4-methylphenyl)-2-propenoate obtained in Reference Example 2, the title compound was synthesized.

Yield 41%. mp. 160–162° C. (ethyl acetate-hexane).

$^1$H-NMR (CDCl3) δ: 2.35 (3H, s), 2.84 (2H, dd, J=17.2, 11.2 Hz), 3.09 (2H, dd, J=17.2, 4.5 Hz), 3.28–3.50 (1H, m), 7.08 (2H, d, J=8.5 Hz), 7.20 (2H, d, J=8.5 Hz).

REFERENCE EXAMPLE 7

3-(4-methoxyphenyl) glutaric anhydride

Using ethyl 3-(4-methoxyphenyl)-2-propenoate, the title compound was synthesized in the same manner as in Reference Example 5. Yield 38%. mp. 144–149° C. (ethyl acetate-hexane).

$^1$H-NMR (CDCl3) δ: 2.82 (2H, dd, J=17.0, 11.4 Hz), 3.09 (2H, dd, J=17.0, 4.4 Hz), 3.26–3.50 (1H, m), 3.81 (3H, s), 6.86–6.98 (2H, m), 7.06–7.18 (2H, m).

REFERENCE EXAMPLE 8

3-(3,4-dimethoxyphenyl)glutaric anhydride

Using methyl 3-(3,4-dimethoxyphenyl)-2-propenoate obtained in Reference Example 3, the title compound was synthesized in the same manner as in Reference Example 5. Yield 54%. mp. 118–120° C. (diisopropyl ether).

$^1$H-NMR (CDCl3) δ: 2.85 (2H, dd, J=16.9, 11.2 Hz), 3.16 (2H, dd, J=16.9, 4.4 Hz), 3.28–3.50 (1H, m), 3.88 (3H, s), 3.89 (3H, s), 6.66–6.80 (2H, m), 6.87 (1H, d, J=8.0 Hz).

REFERENCE EXAMPLE 9 methyl 2-(2,3,5-trimethyl phenoxy)isobutyrate

To a solution of 2,3,5-trimethylphenol (20.0 g, 147 mmol) in dimethylsulfoxide (100 ml) was added methyl 2-bromoisobutyrate (52.2 g, 288 mmol) and potassium carbonate (40.0 g, 289 mmol) at room temperature. The mixture was stirred for 36 hours. The resulting mixture was poured into water and extracted with ethyl acetate. The organic extract was washed with water and saturated aqueous sodium chloride, dried over anhydrous sodium sulfate, and concentrated under reduced pressure. The residue was purified using basic silica gel column chromatography (hexane/ethyl acetate=50/1) to obtain 30.3 g (yield 87%) of oily title compound.

$^1$H-NMR (CDCl3) δ: 1.57 (6H, s), 2.11 (3H, s), 2.21 (6H, s), 3.79 (3H, s), 6.33 (1H, s), 6.46 (1H, s).

REFERENCE EXAMPLE 10

2-(2,3,5-trimethyl phenoxy)isobutyric acid

An aqueous solution of 8N sodium hydroxide (30 mL, 240 mmol) was added to a solution of methyl 2-(2,3,5-trimethylphenoxy)isobutyrate (29.0 g, 123 mmol) obtained in Reference Example 9 in methanol (290 ml) at room temperature and the mixture was stirred for 12 hours. The resulting mixture was concentrated under reduced pressure, and the residue was diluted with water. The aqueous layer was acidified by hydrochloric acid and extracted with ethyl acetate. The organic extract was washed with water and saturated aqueous sodium chloride, and dried over anhydrous sodium sulfate. The solvent was removed under reduced pressure, and the residue was crystallized from hexane to obtain 20.5 g (yield 75%) of the title compound. mp. 91–94° C.

$^1$H-NMR (CDCl3) δ: 1.59 (6H, s), 212 (3H, s), 2.22 (3H, s), 2.23 (3H, s), 6.53 (1H, s), 6.71 (1H, s).

REFERENCE EXAMPLE 11

2,2,4,6,7-pentamethyl-2,3-dihydro-1-benzofuran-3-one

To 2-(2,3,5-trimethyl phenoxy) isobutyric acid (1.00 g, 4.5 mmol) obtained in Reference Example 10 was added polyphosphoric acid (8 g) and the mixture was stirred at 100° C. for 30 minutes. The reaction mixture was diluted with water and extracted with diisopropyl ether. The organic extract was washed with water, saturated aqueous sodium bicarbonate, water and saturated aqueous sodium chloride, and dried over anhydrous sodium sulfate. The solvent was removed under reduced pressure, and the residue was crystallized from hexane to obtain 300 mg (yield 33%) of the title compound. mp. 99–101° C.

$^1$H-NMR (CDCl3) δ: 1.44 (6H, s), 2.16 (3H, s), 2.30 (3H, s), 2.52 (3H, s), 6.63 (1H, s).

REFERENCE EXAMPLE 12

5-bromo-2,2,4,6,7-pentamethyl-2,3-dihydro-1-benzofuran-3-one

To a solution of 2,2,4,6,7-pentamethyl-2,3-dihydro-1-benzofuran-3-one (12.8 g, 63 mmol) obtained in Reference Example 11 in acetic acid (130 ml) was added dropwise bromine (3.9 mL, 76 mmol) at room temperature. The mixture was stirred for 1 hour and concentrated under reduced pressure. The residue was diluted with 5% sodium sulfite aqueous and extracted with ethyl acetate. The organic extract was washed with water, saturated aqueous sodium bicarbonate, water and saturated aqueous sodium chloride, and dried over anhydrous sodium sulfate. The solvent was removed under reduced pressure, and the residue was crystallized from methanol to obtain 12.9 g (yield 73%) of the title compound. mp. 92–93° C.

$^1$H-NMR (CDCl3) δ: 1.44 (6H, s), 2.26 (3H, s), 2.47 (3H, s), 2.66 (3H, s).

REFERENCE EXAMPLE 13

4-(4-methoxyphenyl)-1-(2,2,4,6,7-pentamethyl-2,3-dihydro-1-benzofuran-3-on-5-yl)piperazine Palladium acetate (150 mg, 0.67 mmol) and BINAP (1.30 g, 2.1 mmol) were added to toluene (80 ml) at room temperature and the mixture was stirred for 5 minutes under argon atmosphere. To the reaction mixture was added 5-bromo-2,2,4,6,7-pentamethyl-2,3-dihydro-1-benzofuran-3-on (4.0 g, 14 mmol) obtained in Reference Example 12 and 1-(4-methoxyphenyl)piperazine (8.1 g, 42 mmol) at room temperature. The mixture was stirred for 10 minutes under argon atmosphere, and then sodium tert butoxide (3.8 g, 40 mmol) was added at room temperature. The mixture was refluxed for 18 hours under argon atmosphere. The reaction mixture was diluted with water and extracted with ethyl acetate. The organic extract was washed with water and saturated aqueous sodium chloride, and dried over anhydrous sodium sulfate. The solvent was removed under reduced pressure and the residue was purified using basic alumina column chromatography (ethyl acetate) and silica gel column chromatography (hexane/ethyl acetate=8/1) to obtain 1.66 g (yield 30%) of the title compound via recrystallization (ethyl acetate-hexane). mp. 144–146° C.

$^1$H-NMR (CDCl3) δ: 1.43 (6H, s), 2.18 (3H, s), 2.35 (3H, s), 2.61 (3H, s), 3.02–3.46 (8H, m), 3.79 (3H, s), 6.86 (2H, d, J=9.3 Hz), 6.97 (2H, d, J=9.3 Hz).

REFERENCE EXAMPLE 14

1-benzyl-4-(3,4-dimethoxyphenyl)piperidine-4-ol

A solution of n-butyllithium in hexane (1.56 M, 93.0 mL, 145 mmol) was added dropwise a solution of 4-bromo-1,2-dimethoxybenzene (34.4 g, 158 mmol) in THF (350 ml) under −70° C. and stirred for 30 minutes under argon atmosphere. A solution of 1-benzyl piperidin-4-one (25.0 g, 132 mmol) in THF (50 ml) was added dropwise to the reaction mixture under −60° C., and the mixture was allowed to warm to 0° C. and stirred under ice cooling for 30 minutes. The reaction mixture was diluted with water, concentrated under reduced pressure, and extracted with ethyl acetate. The organic extract was washed with water and saturated aqueous sodium chloride, dried over anhydrous sodium sulfate, and concentrated under reduced pressure. The residue was purified using silica gel column chromatography and the obtained crystals were washed with hexane to obtain 26.6 g (yield 71%) of the title compound. mp. 112–114° C.

$^1$H-NMR (CDCl3) δ: 1.50–1.84 (2H, m), 2.02–2.28 (2H, m), 2.36–2.58 (2H, m), 2.70–2.90 (2H, m), 3.58 (2H, s), 3.87 (3H, s), 3.89 (3H, s), 6.83 (1H, d, J=8.4 Hz), 6.94–7.14 (2H, m), 7.18–7.44 (5H, m).

REFERENCE EXAMPLE 15

1-benzyl-4-(3,4-dimethoxyphenyl)-1,2,3,6-tetrahydropyridine

To acetic acid (130 ml) was added 1-benzyl-4-(3,4-dimethoxyphenyl)piperidine-4-ol (26.0 g, 79.4 mmol) obtained in Reference Example 14. The mixture was refluxed for 3 hours. The reaction mixture was concentrated, and the residue was made to basic with a solution of potassium carbonate and extracted with ethyl acetate. The organic extract was washed with water and saturated aqueous sodium chloride, dried over anhydrous sodium sulfate, and concentrated under reduced pressure. The residual crystals were washed with hexane to obtain 22.0 g (yield 90%) of the title compound. mp. 94–96° C.

$^1$H-NMR (CDCl3) δ: 2.46–2.64(2H, m), 2.71 (2H, d, J=5.5 Hz), 3.10–3.24 (2H, m), 3.64 (2H, s), 3.87 (3H, s), 3.88 (3H, s), 5.92–6.04 (1H, m), 6.81 (1H, d, J=8.8 Hz), 7.86–7.98 (2H, m), 7.20–7.46 (5H, m).

REFERENCE EXAMPLE 16

4-(3,4-dimethoxyphenyl)piperidine

A mixture of 1-benzyl-4-(3,4-dimethoxyphenyl)-1,-2,3,6-tetrahydropyridine (10.0 g, 32.3 mmol) obtained in Reference Example 15 and 10% palladium-carbon (2.0 g) in methanol (200 ml) was stirred at room temperature under hydrogen pressure of 4 to 5 atmospheres for 10 hours. The catalyst was removed by filtration and the filtrate was concentrated under reduced pressure. The residual crystals were washed with hexane to obtain 6.58 g (yield 92%) of the title compound. mp. 98–100° C.

$^1$H-NMR (CDCl3) δ: 1.48–1.94 (4H, m), 2.46–2.88 (3H, m), 3.08–3.28 (2H, m), 3.86 (3H, s), 3.88 (3H, s), 6.70–6.90 (3H, m). 1H is unconfirmed.

REFERENCE EXAMPLE 17

5-(4-(3,4-dimethoxyphenyl)piperidino)-2,2,4,6,7-pentamethyl-2,3-dihydro-1-benzofuran-3(2H)-one Using 4-(3,4-dimethoxyphenyl)piperidine obtained in Reference Example 16, the title compound was synthesized in the same manner as in Reference Example 13. Yield 34%. mp. 175–177° C. (ethyl acetate). $^1$H-NMR (CDCl3) δ: 1.43 (6H, s), 1.70–1.98 (4H, m), 2.17 (3H×0.39, s), 2.20 (3H×0.61, s), 2.30 (3H×0.39, s), 2.39 (3H×0.61, s), 2.44–2.74 (1H, m), 2.60 (3H×0.61, s), 2.61 (3H×0.39, s), 2.86–3.08 (2H, m), 3.22–3.52 (2H, m), 3.88 (3H, s), 3.92 (3H, s), 6.74–6.94 (3H, m).

REFERENCE EXAMPLE 18

5-(4-(4-methoxyphenyl)piperazin-1-yl)-2,2,4,6,7-pentamethyl-2,3-dihydro-1-benzofuran-3-ol Sodium borohydride (300 mg, 7.93 mmol) was added to a solution of 4-(4-methoxyphenyl)-1-(2,2,4,6,7-pentamethyl-2,3-dihydro-1-benzofuran-3-on-5-yl)piperazine (740 mg, 1.88 mmol) obtained in Reference Example 13 in THF (7 ml) and methanol (7 ml) at room temperature and stirred for 2 hours. The resulting mixture was concentrated under reduced pressure, and the residue was diluted 1 N potassium carbonate and extracted with ethyl acetate. The organic extract was washed with water and saturated aqueous sodium chloride, dried over anhydrous sodium sulfate, and concentrated under reduced pressure. The residual crystals were washed with hexane to obtain 670 mg (yield 90%) of the title compound. mp. 159–161° C.

$^1$H-NMR (CDCl3) δ: 1.30 (3H, s), 1.51 (3H, s), 2.09 (3H, s), 2.26 (3H, s), 2.39 (3H, s), 3.00–3.42 (8H, m), 3.78 (3H, s), 4.72 (1H, d, J=8.8 Hz), 6.86 (2H, d, J=9.2 Hz), 6.97 (2H, d, J=9.2 Hz).

REFERENCE EXAMPLE 19

5-(4-(3,4-dimethoxyphenyl)piperidino)-2,2,4,6,7-pentamethyl-2,3-dihydro-1-benzofuran-3-ol Using 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Reference Example 18. Yield 96%. mp. 140–142° C. (hexane). $^1$H-NMR (CDCl3) δ: 1.31 (3H, s), 1.43 (1H, d, J=9.0 Hz), 1.51 (3H, s), 1.66–1.98 (4H, m), 2.08 (3H×0.5, s), 2.11 (3H×0.5, s), 2.20 (3H×0.5, s), 2.30 (3H×0.5, s), 2.38 (3H, s), 2.44–2.70 (1H, m), 2.86–3.12 (2H, m), 3.16–3.52 (2H, m), 3.88 (3H, s), 3.92 (3H, s), 4.72 (1H, d, J=9.0 Hz), 6.74–6.94 (3H, m).

REFERENCE EXAMPLE 20

3-bromo-2, 4, 5-trimethylbenzaldehyde

Aluminum chloride (48.0 g, 360 mmol) was added to a solution of 2,4,5-trimethylbenzaldehyde (21.3 g, 144 mmol) in methylene chloride (200 ml) under ice cooling and the mixture was allowed to warm to room temperature. To the mixture was added dropwise bromine (7.80 ml, 151 mmol) at room temperature. The mixture was stirred for 4 hours, poured into water. Methylene chloride was removed under reduced pressure. The residue was extracted with ethyl acetate, and the organic extract was washed with water, saturated aqueous sodium bicarbonate, 5% aqueous sodium sulfite, water and saturated sodium chloride, and dried over anhydrous sodium sulfate. The solvent was removed under reduced pressure to obtain 32.5 g (yield 100%) of the title compound. mp. 108–110° C.

$^1$H-NMR (CDCl3) δ: 2.38 (3H, s), 2.46 (3H, s), 2.73 (3H, s), 7.54 (1H, s), 10.21 (1H, s).

REFERENCE EXAMPLE 21

3-bromo-2, 4, 5-trimethylphenol

To a solution of 3-bromo-2, 4, 5-trimethylbenzaldehyde (32.0 g, 141 mmol) obtained in Reference Example 21 in THF (100 ml) and methanol (200 ml) was added p-toluenesulfonic acid monohydrate (5.40 g, 28.4 mmol) under ice cooling. To the reaction mixture was added dropwise hydrogen peroxide water (30%, 24.0 g, 212 mmol) at 10° C. or less. The mixture was allowed to warm to room temperature and stirred for 12 hours. The reaction mixture was heated at 50° C. for 36 hours and the resulting mixture was diluted with aqueous sodium sulfite. Methanol and THF were removed under reduced pressure. The residue was extracted with ethyl acetate, and the organic extract was washed with water and saturated aqueous sodium chloride, dried over anhydrous sodium sulfate. The solvent was removed under reduced pressure, and the residue was purified using silica gel column chromatography (hexane then hexane/ethyl acetate=10/1) and thereafter the obtained crystals were washed with hexane to obtain 9.1 g (yield 30%) of the title compound. mp. 86–88° C.

$^1$H-NMR (CDCl3) δ: 2.25 (3H, s), 2.30 (3H, s), 2.32 (3H, s), 4.63 (1H, s), 6.56 (1H, s).

REFERENCE EXAMPLE 22 methyl 2-(3-bromo-2,4,5-trimethyl phenoxy) isobutyrate

Using 3-bromo-2,4,5-trimethylphenol obtained in Reference Example 21, the title compound was synthesized in the same manner as in Reference Example 9. Yield 41%. mp. 66–68° C. (hexane). $^1$H-NMR (CDCl3) δ: 1.56 (6H, s), 2.24 (3H, s), 2.31 (3H, s), 2.32 (3H, s), 3.80 (3H, s), 6.48 (1H, s).

REFERENCE EXAMPLE 23

2-(3-bromo-2,4,5-trimethyl phenoxy)isobutyric acid

Using methyl 2-(3-bromo-2,4,5-trimethylphenoxy)isobutyrate obtained in Reference Example 22, the title compound was synthesized in the same manner as in Reference Example 15. Yield 97%. mp. 151–153° C. (hexane). $^1$H-NMR (CDCl3) δ: 1.59 (6H, s), 2.26 (3H, s), 2.33 (6H, s), 6.67 (1H, s), 9.60 (1H, br s).

REFERENCE EXAMPLE 24

6-bromo-2,2,4,5,7-pentamethyl-2,3-dihydro-1-benzofuran-3(2H)-one

Oxalyl chloride (9.00 mL, 101 mmol) was added dropwise to a solution of 2-(3-bromo-2, 4, 5-trimethyl phenoxy) isobutyric acid (20.2 g, 67.1 mmol) obtained in Reference Example 23 in THF (200 ml) and DMF (0.1 mL) under ice cooling. The mixture was allowed to warm to room temperature and stirred for one hour. The resulting mixture was concentrated under reduced pressure. The residue was dissolved in methylene chloride (200 ml) and then aluminum chloride (22.4 g, 168 mmol) was added at −70° C. or less. The mixture was allowed to warm to room temperature over a period of 30 minutes, poured into water under ice cooling. Methylene chloride was removed under reduced pressure and the aqueous residue was extracted with ethyl acetate. The organic extract was washed with water, saturated aqueous sodium bicarbonate, water and saturated aqueous sodium chloride, and dried over anhydrous sodium sulfate. The solvent was removed under reduced pressure, and the residue was crystallized from methanol to obtain 18.5 g (yield 97%) of the title compound. mp. 125–127° C.

$^1$H-NMR (CDCl3) δ: 1.44 (6H, s), 2.34 (3H, s), 2.37 (3H, s), 2.60 (3H, s).

REFERENCE EXAMPLE 25

6-(4-(4-methoxyphenyl)piperazin-1-yl-2,2,4,5,7-pentamethyl-2,3-dihydro-1-benzofuran-3(2H)-one Using 6-bromo-2,2,4,5,7-pentamethyl-2,3-dihydro-1-benzofuran-3(2H)-one obtained in Reference Example 24 and 1-(4-methoxyphenyl)piperazine, the title compound was synthesized in the same manner as in Reference Example 13. Yield 74%. mp. 162–164° C. (ethyl acetate). $^1$H-NMR (CDCl3) δ: 1.43 (6H, s), 2.22 (3H, s), 2.26 (3H, s), 2.53 (3H, s), 2.94–3.56 (8H, m), 3.79 (3H, s), 6.87 (2H, d, J=9.2 Hz), 6.98 (2H, d, J=9.2 Hz).

REFERENCE EXAMPLE 26

1-(2,2,3,4,6,7-hexamethyl-3-hydroxy-2,3-dihydro-1-benzofuran-5-yl)-4-(4-methoxyphenyl)piperazine A solution of methyllithium in diethyl ether (1.14 M, 5.60 mL, 6.38 mmol) was added dropwise to a solution of 4-(4-methoxyphenyl)-1-(2,2,4,6,7-pentamethyl-2,3-dihydro-1-benzofuran-3-on-5-yl)piperazine (2.00 g, 5.06 mmol) obtained in Reference Example 13 in THF (20 ml) under ice cooling and the mixture was stirred for 10 minutes. The reaction mixture was diluted with water and extracted with ethyl acetate. The organic extract was washed with water and saturated aqueous sodium chloride, and dried over anhydrous sodium sulfate. The solvent was removed under reduced pressure, and the residue was crystallized from hexane to obtain 2.00 g (yield 96%) of the title compound. mp. 139–141° C.

$^1$H-NMR (CDCl3) δ: 1.31 (3H, s), 1.41 (3H, s), 1.56 (3H, s), 1.70 (1H, s), 2.08 (3H, s), 2.24 (3H, s), 2.43 (3H, s), 3.00–3.40 (8H, m), 3.78 (3H, s), 6.86 (2H, d, J=9.2 Hz), 6.97 (2H, d, J=9.2 Hz).

REFERENCE EXAMPLE 27

4-(4-methoxyphenyl)-1-(3-methylene-2,2,4,6,7-pentamethyl-2,3-dihydro-1-benzofuran-5-yl)piperazine A solution of 10% hydrochloric acid (5 ml) was added to a solution of 1-(2,2,3,4,6,7-hexamethyl-3-hydroxy-2,3-dihydro-1-benzofuran-5-yl)-4-(4-methoxyphenyl)piperazine (1.70 g, 4.14 mmol) obtained in Reference Example 26 in acetonitrile (15 ml) at room temperature and the mixture was stirred for 6 hours. The resulting mixture was concentrated under reduced pressure, and the residue was made to basic with 10% aqueous potassium carbonate. The aqueous layer was extracted with ethyl acetate. The organic extract was washed with water and saturated aqueous sodium chloride, and dried over anhydrous sodium sulfate. The solvent was removed under reduced pressure and the residue was crystallized from ethanol to obtain 1.50 g (yield 92%) of the title compound. mp. 134–136° C.

$^1$H-NMR (CDCl3) δ: 1.46 (6H, s), 2.12 (3H, s), 2.29 (3H, s), 2.45 (3H, s), 3.04–3.42 (8H, m), 3.79 (3H, s), 4.82 (1H, s), 5.32 (1H, s), 6.86 (2H, d, J=9.5 Hz), 6.98 (2H, d, J=9.5 Hz).

REFERENCE EXAMPLE 28

2,2,4,6,7-pentamethyl-5-(4-phenylpiperazin-1-yl)-1-benzofuran-3(2H)-one

Using 1-phenylpiperazine, the title compound was obtained in the same manner as in Reference Example 13. Yield 22%.

$^1$H-NMR (CDCl3) δ: 1.43 (6H, s), 2.18 (3H, s), 2.35 (3H, s), 2.60 (3H, s), 3.10–3.26 (4H, m), 3.32–3.43 (4H, m), 6.88 (1H, t, J=7.2 Hz), 6.99 (2H, dd, J=1.0, 8.8 Hz), 7.25–7.33 (2H, m).

REFERENCE EXAMPLE 29

5-(4-(2-methoxyphenyl)piperazin-1-yl)-2,2,4,6,7-pentamethyl-1-benzofuran-3(2H)-one Using 1-(2-methoxyphenyl)piperazine, the title compound was obtained as amorphous state powder in the same manner as in Reference Example 13. Yield 38%.

$^1$H-NMR (CDCl3) δ: 1.43 (6H, s), 2.18 (3H, s), 2.37 (3H, s), 2.63 (3H, s), 3.04–3.28 (6H, m), 3.34–3.42 (2H, m), 3.89 (3H, s), 6.86–7.05 (4H, m).

REFERENCE EXAMPLE 30

2,2,4,6,7-pentamethyl-5-(4-phenylpiperazin-1-yl)-2,3-dihydro-benzofuran-3-ol

Using 2,2,4,6,7-pentamethyl-5-(4-phenylpiperazin-1-yl)-1-benzofuran-3(2H)-one obtained in Reference Example 28, the title compound was obtained in the same manner as in Reference Example 18. Yield 22% mp. 142–144° C.

$^1$H-NMR (CDCl3) δ: 1.30 (3H, s), 1.40 (1H, d, J=9.0 Hz), 1.51 (3H, s),2.09 (3H, s), 2.26 (3H, s), 2.38 (3H, s), 3.17–3.38 (8H, m), 4.71 (1H, d, J=9.0 Hz), 6.81–6.89 (1H, m), 6.99 (2H, brd, J=8.0 Hz), 7.24–7.34 (2H, m).

REFERENCE EXAMPLE 31

5-(4-(2-methoxyphenyl)piperazin-1-yl)-2,2,4,6,7-pentamethyl-2,3-dihydro-benzofuran-3-ol Using 5-(4-(2-methoxyphenyl)piperazin-1-yl)-2,2,4,6,7-pentamethyl-1-benzofuran-3(2H)-one obtained in Reference Example 29, the title compound was obtained as an amorphous powder in the same manner as in Reference Example 18. Yield 58%. $^1$H-NMR (CDCl3) δ: 1.30 (3H, s), 1.41 (1H, d, J=9.0 Hz), 1.51 (3H, s), 2.09 (3H, s), 2.28 (3H, s), 2.41 (3H, s), 3.05–3.38 (8H, m), 3.89 (3H, s), 4.71 (1H, d, J=9.0 Hz), 6.83–7.03 (4H, m).

REFERENCE EXAMPLE 32

5-bromo-2, 2, 4, 6-tetramethyl-3-(4-methylphenyl)-2,3-dihydro-1-benzofuran

N-bromosuccinimide (2.1 g, 11.6 mmol) was added to a solution of 2,2,4,6-tetramethyl-3-(4-methylphenyl)-2,3-dihydro-1-benzofuran (3.1 g, 11.6 mmol) in acetonitrile (30 ml) with ice cooling and the mixture was stirred at room temperature for 1.5 hours. The resulting mixture was concentrated under reduced pressure. After the remaining solids were removed with filtration, the filtrate was concentrated under reduced pressure. The residue was purified using silica gel column chromatography (hexane) to obtain 2.67 g (yield 67%) of the title compound via recrystallization (methanol). mp. 116–118° C.

$^1$H-NMR (CDCl3) δ: 1.01 (3H, s), 1.49 (3H, s), 1.99 (3H, s), 2.31 (3H, s), 2.40 (3H, s), 4.10 (1H, s), 6.63 (1H, s), 6.80–7.20 (4H, m).

REFERENCE EXAMPLE 33

5-bromo-2,2,4,6-tetramethyl-3-(4-methylphenyl)-2,3-dihydro-1-benzofuran-7-carbaldehyde Titanium tetrachloride (1.5 mL, 13.6 mmol) was added to a solution of 5-bromo-2,2,4,6-tetramethyl-3-(4-methylphenyl)-2,3-dihydro-1-benzofuran (2.60 g, 7.53 mmol) obtained in Reference Example 32 and 1,1-dichloromethyl methyl ether (0.95 g, 8.28 mmol) in methylene chloride (10 ml) with ice cooling under an argon atmosphere and the mixture was stirred for 20 minutes at the same temperature. The resulting mixture was poured into water and extracted with methylene chloride. The organic extract was washed with saturated aqueous sodium bicarbonate, and dried over anhydrous sodium sulfate, and concentrated under reduced pressure. The residue was crystallized (ethyl acetate-hexane) to obtain 2.54 g (yield 90%) of the title compound. mp. 128–130° C.

$^1$H-NMR (CDCl3) δ: 1.07 (3H, s), 1.54 (3H, s), 2.06 (3H, s), 2.32 (3H, s), 2.76 (3H, s), 4.13 (1H, s), 6.40–7.20 (4H, m), 10.4(1H, s).

REFERENCE EXAMPLE 34

5-bromo-7-(1,3-dioxolan-2-yl)-2,2,4,6-tetramethyl-3-(4-methylphenyl)-2,3-dihydro-1-benzofuran A mixture of 5-bromo-2,2,4,6-tetramethyl-3-(4-methylphenyl)-2,3-dihydro-1-benzofuran-7-carbaldehyde obtained (2.42 g, 6.48 mmol) in Reference Example 33, ethylene glycol (2.0 mL, 35.8 mmol) and p-toluenesulfonic acid monohydrate (50 mg, 0.263 mmol) in toluene (30 ml) was refluxed for 3 hours, and the water formed was removed using a Dean-Stark trap. The solvent was concentrated under reduced pressure. The residue was diluted with water and extracted with ethyl acetate. The organic extract was washed with saturated aqueous sodium bicarbonate and water, and dried over anhydrous sodium sulfate, and concentrated under reduced pressure. The residue was crystallized (ethyl acetate-hexane) to obtain 1.89 g (yield 70%) of the title compound. mp. 169–172° C.

$^1$H-NMR (CDCl3) δ: 1.00 (3H, s), 1.48 (3H, s), 2.00 (3H, s), 2.30 (3H, s), 2.52 (3H, s), 4.00–4.27 (5H, m), 6.17 (1H, s), 6.50–7.10 (4H, m).

REFERENCE EXAMPLE 35

5-(4-(3,4-dimethoxyphenyl)-1-piperazinyl)-2,2,4,6,7-pentamethyl-1-benzofuran-3(2H)-one Using 5-bromo-2,2,4,6,7-pentamethyl-2,3-dihydro-1-benzofuran-3-one obtained in Reference Example 12 and 1-(3,4-dimethoxyphenyl)piperazine, the title compound was obtained in the same manner as in Reference Example 13. Yield 63% mp. 153–154° C. (ethyl acetate-hexane).

$^1$H-NMR (CDCl3) δ: 1.43 (6H, s), 2.18 (3H, s), 2.36 (3H, s), 2.61 (3H, s), 3.03–3.42 (8H, m), 3.85 (3H, s), 3.89 (3H, s), 6.52 (1H, dd, J=8.8, 2.6 Hz), 6.65 (1H, d, J=2.6 Hz), 6.82 (1H, d, J=8.8 Hz).

REFERENCE EXAMPLE 36

2,2,4,6,7-pentamethyl-5-(4-(4-(trifluoromethyl)phenyl)-1-piperazinyl)-1-benzofuran-3(2H)-one Using 5-bromo-2,2,4,6,7-pentamethyl-2,3-dihydro-1-benzofuran-3(2H)-one obtained in Reference Example 12 and 1-(4-(trifluoromethyl)phenyl)piperazine, the title compound was obtained in the same manner as in Reference Example 13.
Yield 33% mp. 188–190° C. (ethyl acetate-hexane).
$^1$H-NMR (CDCl3) δ: 1.43 (6H, s), 2.18 (3H, s), 2.35 (3H, s), 2.59 (3H, s), 3.10–3.52 (8H, m), 6.98 (2H, d, J=8.6 Hz), 7.50 (2H, d, J=8.6 Hz).

REFERENCE EXAMPLE 37

5-(4-(3,4-dimethoxyphenyl)-1-piperazinyl)-2,2,4,6,7-pentamethyl-1-benzofuran-3-ol Using 5-(4-(3,4-dimethoxyphenyl)-1-piperazinyl)-2,2,4,6,7-pentamethyl-1-benzofuran-3(2H)-one obtained in Reference Example 35, the title compound was obtained in the same manner as in Reference Example 18. Yield 88% mp. 150–151° C. (ethyl acetate-hexane).
$^1$H-NMR (CDCl3) δ: 1.30 (3H, s), 1.45 (1H, d, J=8.8 Hz), 1.51 (3H, s), 2.09 (3H, s), 2.26 (3H, s), 2.39 (3H, s), 3.09–3.40 (8H, m), 3.85 (3H, s), 3.89 (3H, s), 4.72 (1H, d, J=8.8 Hz), 6.52 (1H, dd, J=8.6, 2.8 Hz)-, 6.65 (1H, d, J=2.8 Hz), 6.81 (1H, d, J=8.6 Hz).

REFERENCE EXAMPLE 38

2,2,4,6,7-pentamethyl-5-(4-(4-(trifluoromethyl)phenyl)-1-piperazinyl)-1-benzofuran-3-ol Using 2,2,4,6,7-pentamethyl-5-(4-(4-(trifluoromethyl)phenyl)-1-piperazinyl)-1-benzofuran-3(2H)-one obtained in Reference Example 36, the title compound was obtained in the same manner as in Reference Example 18.
Yield 77% mp. 212–214° C. (ethyl acetate-hexane).
$^1$H-NMR (CDCl3) δ: 1.30 (3H, s), 1.42 (1H, d, J=8.7 Hz), 1.51 (3H, s), 2.08 (3H, s), 2.25 (3H, s), 2.37 (3H, s), 3.18–3.45 (8H, m), 4.71 (1H, d, J=8.7 Hz), 6.97 (2H, d, J=8.7 Hz), 7.49 (2H, d, J=8.7 Hz).

REFERENCE EXAMPLE 39

(5-(4-(4-methoxyphenyl)piperazin-1-yl)-2,2,4,6,7-pentamethyl-2,3-dihydro-1-benzofuran-3-yl) methanol Borane THF complex (THF solution 1.0M, 20.0 mL, 20.0 mmol) was added to a solution of 4-(4-methoxyphenyl)-1-(3-methylene-2,2,4,6,7-pentamethyl-2,3-dihydro-1-benzofuran-5-yl)piperazine (2.0 g, 5.10 mmol) obtained in Reference Example 27 in THF (20 ml) with ice cooling under argon atmosphere and the mixture was stirred for 1 hour at room temperature. The mixture was diluted with water (2.0 mL) and stirred until hydrogen was not generated. To the resulting mixture was added 1N sodium hydroxide (5.0 mL) and 30% hydrogen peroxide water (2.0 mL), and the mixture was stirred for 1 hour at 50° C. The resulting mixture was diluted with water and extracted with ethyl acetate. The organic extract was washed with water and saturated aqueous sodium chloride solution, dried over anhydrous sodium sulfate, and concentrated under reduced pressure. The residue was purified using silica gel column chromatography (hexane/ethyl acetate=4/1) to obtain 1.87 g (yield 89%) of the title compound via recrystallization (ethyl acetate-hexane). mp. 140–141° C.
$^1$H-NMR (CDCl3) δ: 1.22–1.30 (1H, m), 1.33 (3H, s), 1.63 (3H, s), 2.07 (3H, s), 2.23 (3H, s), 2.28 (3H, s), 3.04 (1H, t, J=3.6 Hz), 3.08–3.32 (8H, m), 3.71–3.85 (5H, m), 6.85 (2H, d, J=9.0 Hz), 6.96 (2H, d, J=9.0 Hz).

REFERENCE EXAMPLE 40

(5-(4-(4-methoxyphenyl)piperazin-1-yl)-2,2,4,6,7-pentamethyl-2,3-dihydro-1-benzofuran-3-yl)methyl methanesulfononate Methanesulfonyl chloride (0.38 mL, 4.97 mmol) was added to a solution of (5–4-(4-methoxyphenyl)piperazin-1-yl)-2,2,4,6,7-pentamethyl-2,3-dihydro-1-benzofuran-3-yl) methanol (1.7 g, 4.14 mmol) and triethylamine (0.69 mL, 4.97 mmol) obtained in Reference Example 39 in methylene chloride (30 ml) under ice cooling and the mixture was stirred for 1 hour at room temperature. The resulting mixture was poured into water and extracted with methylene chloride. The organic extract was washed with 1N hydrochloric acid and water, dried over anhydrous sodium sulfate, and concentrated under reduced pressure. The residue was crystallized (ethyl acetate-hexane) to obtain 1.50 g (yield 74%) of the title compound. mp. 150–151° C.
$^1$H-NMR (CDCl3) δ: 1.36 (3H, s), 1.61 (3H, s), 2.07 (3H, s), 2.24 (3H, s), 2.31 (3H, s), 2.89 (3H, s), 3.10–3.38 (9H, m), 3.79 (3H, s), 4.21–4.30 (2H, m), 6.87 (2H, d, J=9.0 Hz), 6.98 (2H, d, J=9.0 Hz).

REFERENCE EXAMPLE 41

5-(4-benzyl piperazin-1-yl)-2,2,4,6,7-pentamethyl-2,3-dihydro-1-benzofuran-3 (2H)-one Using 5-bromo-2,2,4,6,7-pentamethyl-2,3-dihydro-1-benzofuran-3 (2H)-one obtained in Reference Example 12 and 1-benzyl piperazine, the title compound was obtained in the same manner as in Reference Example 13. Yield 75%.
$^1$H-NMR (CDCl3) δ: 1.41 (6H, s), 2.16 (3H, s), 2.32 (3H, s), 2.40–2.64 (7H, m), 2.92–3.06 (2H, m), 3.13–3.30 (2H, m), 7.24–7.38 (5H, m).

REFERENCE EXAMPLE 42

5-(4-benzylpiperazin-1-yl)-2,2,4,6,7-pentamethyl-2,3-dihydro-1-benzofuran-3-ol

Using 5-(4-benzylpiperazin-1-yl)-2,2,4,6,7-pentamethyl-2,3-dihydro-1-benzofuran-3 (2H)-one obtained in Reference Example 41, the title compound was obtained as an morphous powder in the same manner as in Reference Example 18. Yield 93%. $^1$H-NMR (CDCl3) δ: 1.29 (3H, s), 1.42–1.55 (4H, m), 2.07 (3H, s), 2.23 (3H, s), 2.35 (3H, s), 2.42–2.63 (4H, m), 2.98–3.20 (4H, m), 3.57 (2H, s), 4.69 (1H, br), 7.20–7.42 (5H, m).

REFERENCE EXAMPLE 43 tert-butyl 4-(2,2,4,6,7-pentamethyl-2,3-dihydro-1-benzofuran-3 (2H)-one-5-yl)piperazine carboxylate Using tert-butyl piperazine carboxylate, the title compound was obtained in the same manner as in Reference Example 13. Yield 75% mp. 123–125° C. (hexane-ethyl acetate).

¹H-NMR (CDCl3) δ: 1.42 (6H, s), 1.49 (9H, s), 2.17 (3H, s), 2.31 (3H, s), 2.55 (3H, s), 2.90–2.98 (2H, m), 3.07–3.17 (2H, m), 3.33–3.43 (2H, m), 3.3.6–3.71 (2H, m).

REFERENCE EXAMPLE 44 tert-butyl 4-(3-hydroxy-2,2,4,6,7-pentamethyl-2,3-dihydro-1-benzofuran-5-yl)piperazine carboxylate Using tert butyl 4-(2,2,4,6,7-pentamethyl-2,3-dihydro-1-benzofuran-3-one-5-yl)piperazine carboxylate obtained in Reference Example 43, the title compound was obtained as an amorphous powder in the same manner as in Reference Example 18. Yield 98%.

¹H-NMR (CDCl3) δ: 1.23–1.32 (4H, m), 1.47–1.54 (12H, m), 2.07 (3H, s), 2.21 (3H, s), 2.33 (3H, s), 2.94–3.08 (4H, m), 3.40–3.49 (2H, m), 3.52–3.60 (2H, m), 4.69 (1H, d, J=9.0 Hz).

REFERENCE EXAMPLE 45

5-(4-(4-fluorophenyl)piperazin-1-yl)-2,2,4,6,7-pentamethyl-1-benzofuran-3 (2H)-one Using 1-(4-fluorophenyl)piperazine, the title compound was obtained in the same manner as in Reference Example 13.

Yield 22% mp. 176–179° C. (hexane-ethyl acetate).

¹H-NMR (CDCl3) δ: 1.44 (6H, s), 2.18 (3H, s), 2.35 (3H, s), 2.60 (3H, s), 3.07–3.41 (8H, m), 6.94–6.99 (4H, m).

EXAMPLE 1

1-(2,2,4,6,7-pentamethyl-3-(4-methylphenyl)-2,3-dihydro-1-benzofuran-5-yl)piperazine hydrochloride Bis(2-chloroethyl)amine hydrochloride (18.7 g, 105 mmol) was added to a suspension of 2,2,4,6,7-pentamethyl-3-(4-methylphenyl)-2,3-dihydro-1-benzofuran-5-amine (29.5 g, 100 mmol) in 1-butanol (300 mL) and the mixture was refluxed for 24 hours under argon atmosphere. The reaction mixture was cooled to room temperature and then sodium carbonate (12.7 g, 120 mmol) was added. The resulting mixture was refluxed for 24 hours and concentrated under reduced pressure. The residue was diluted with water (500 ml) and extracted with ethyl acetate. The extract was washed with saturated aqueous sodium chloride, dried over anhydrous sodium sulfate, and the solvent was removed under reduced pressure. The residue was purified on basic silica gel column chromatography (hexane/ethyl acetate=10/1) to obtain a free base of the title compound as an oil residue.

The residue was dissolved in ethyl acetate and treated with 4N-hydrogenchloride in ethyl acetate to obtain 10.3 g (yield 26%) of the title compound. mp. 224–225° C. (hexane-ethanol).

¹H-NMR (CDCl3) δ: 0.99 (3H, s), 1.48 (3H, s), 1.87 (3H, s), 2.14 (3H, s), 2.26 (3H, s), 2.31 (3H, s), 2.85–3.05 (8H, m), 4.07 (1H, s), 6.65 (2H, br), 7.03 (2H, br).

EXAMPLE 2

(1-(2,2,4,6,7-pentamethyl-3-(4-methylphenyl),-2,3-dihydro-1-benzofuran-5-yl)-4-(phenylmethyl))piperazine hydrochloride Benzyl bromide (119 mL, 1 mmol) was added to a suspension of 1-(2,2,4,6,7-pentamethyl-3-(4-methylphenyl)-2,3-dihydro-1-benzofuran-5-yl)piperazine hydrochloride obtained (364 mg, 1.0 mmol) in Example 1 and potassium carbonate (138 mg, 1 mmol) in DMF (5 ml) and the mixture was stirred at room temperature for 5 hours. The resulting mixture was poured into water and extracted with ethyl acetate. The extract was washed with saturated aqueous sodium chloride, dried over anhydrous sodium sulfate, and the solvent was removed under reduced pressure. The residue was purified on silica gel column chromatography (hexane/ethyl acetate=10/1) to obtain a free base of the title compound as an oil residue. The residue was dissolved in ethyl acetate and treated with 4N-hydrogenchloride in ethyl acetate to obtain 218 mg (yield 44%) of the title compound. mp. 278–280° C. (hexane-ethanol).

¹H-NMR (CDCl3) δ: 0.98 (3H, s), 1.47 (3H, s), 1.87 (3H, s), 2.13 (3H, s), 2.25 (3H, s), 2.30 (3H, s), 2.45–2.56 (4H, m), 3.00–3.16 (4H, m), 3.56 (2H, s), 4.06 (1H, s), 6.78 (2H, br), 7.04 (2H, d, J=7.0 Hz), 7.23–7.40 (5H, m).

EXAMPLE 3

4-(4-methoxyphenylmethyl)-1-(2,2,4,6,7-pentamethyl-3-(4-methylphenyl)-2,3-dihydro-1-benzofuran-5-yl)piperazine hydrochloride Using 4-methoxybenzyl bromide, the title compound was obtained in the same manner as in Example 2. Yield 70% mp. 229–230° C. (hexane-ethanol).

¹H-NMR (CDCl3) δ: 0.98 (3H, s), 1.47 (3H, s), 1.86 (3H, s), 2.13 (3H, s), 2.24 (3H, s), 2.30 (3H, s), 2.42–2.52 (4H, m), 2.98–3.07 (4H, m), 3.48 (2H, s), 3.80 (3H, s), 4.06 (1H, s), 6.70 (2H, br), 6.86 (2H, d, J=8.7 Hz), 7.03 (2H, br), 7.25 (2H, d, J=7.7 Hz).

EXAMPLE 4

4-(4-fluorophenylmethyl)-1-(2,2,4,6,7-pentamethyl-3-(4-methylphenyl)-2,3-dihydro-1-benzofuran-5-yl)piperazine hydrochloride Using 4-fluorobenzyl bromide, the title compound was obtained in the same manner as in Example 2. Yield 44% mp. 272–274° C. (hexane-ethanol).

¹H-NMR (CDCl3) δ: 0.98 (3H, s), 1.47 (3H, s), 1.86 (3H, s), 2.13 (3H, s), 2.25 (3H, s), 2.30 (3H, s), 2.43–2.51 (4H, m), 2.98–3.07 (4H, m), 3.50 (2H, s), 4.06 (1H, s), 6.70 (2H, br), 6.95–7.08 (4H, m), 7.25–7.35 (4H, m).

EXAMPLE 5

4-(2-methoxyphenylmethyl)-1-(2,2,4,6,7-pentamethyl-3-(4-methylphenyl)-2,3-dihydro-1-benzofuran-5-yl)piperazine hydrochloride Using 2-methoxybenzyl bromide, the title compound was obtained in the same manner as in Example 2. Yield 64% mp. 122–123° C. (hexane-ethanol).

¹H-NMR (CDCl3) δ: 0.98 (3H, s), 1.47 (3H, s), 1.87 (3H, s), 2.13 (3H, s), 2.25 (3H, s), 2.30 (3H, s), 2.52–2.59 (4H, m), 3.01–3.12 (4H, m), 3.61 (2H, s), 3.82 (3H, s), 4.06 (1H, s), 6.70 (2H, br), 6.87 (1H, d, J=8.1 Hz), 6.93 (1H, dt, J=0.9 Hz, 7.6 Hz), 7.03 (2H, br), 7.18–7.24 (1H, m), 7.41 (1H, dd, J=1.7 Hz, 7.6 Hz)

EXAMPLE 6

4-(3-methoxyphenylmethyl)-1-(2,2,4,6,7-pentamethyl-3-(4-methylphenyl)-2,3-dihydro-1-benzofuran-5-yl)piperazine hydrochloride Using 3-methoxybenzyl bromide, the title compound was obtained in the same manner as in Example 2. Yield 64% mp. 234–236° C. (hexane-ethanol).

$^1$H-NMR (CDCl3) δ: 0.98 (3H, s), 1.47 (3H, s), 1.87 (3H, s), 2.13 (3H, s), 2.25 (3H, s), 2.30 (3H, s), 2.46–2.53 (4H, m), 3.00–3.07 (4H, m), 3.52 (2H, s), 3.81 (3H, s), 4.06 (1H, s), 6.75 (2H, br), 6.79 (1H, dd, J=2.5 Hz, 8.0 Hz), 6.92–6.95 (2H, m), 7.03 (2H, br), 7.22 (1H, t, J=8.0 Hz)

EXAMPLE 7

1-(2,2,4,6,7-pentamethyl-3-(4-methylphenyl)-2,3-dihydro-1-benzofuran-5-yl)-4-(3-pyridylmethyl)piperazine dihydrochloride Using 3-(chloromethyl)pyridine hydrochloride, the title compound was obtained in the same manner as in Example 2. Yield 62% mp. 226–229° C. (ethyl acetate-ethanol)

$^1$H-NMR (CDCl3) δ: 0.99 (3H, s), 1.47 (3H, s), 1.86 (3H, s), 2.13 (3H, s), 2.25 (3H, s), 2.30 (3H, s), 2.43–2.55 (4H, m), 2.98–3.10 (4H, m), 3.55 (2H, s), 4.06 (1H, s), 6.85 (2H, br), 7.00–7.09 (2H, m), 7.235–7.30 (1H, m) 7.66–7.75 (1H, m), 8.50 (1H, dd, J=1.8 Hz, 4.8 Hz), 8.56 (d, J=1.8 Hz).

EXAMPLE 8

4-methyl-1-(2,2,4,6,7-pentamethyl-3-(4-methylphenyl)-2,3-dihydro-1-benzofuran-5-yl)piperazine Using methyl iodide, the title compound was obtained in the same manner as in Example 2. Yield 51% mp. 188–190° C. (hexane-ethanol).

$^1$H-NMR (CDCl3) δ: 0.99 (3H, s), 1.48 (3H, s), 1.87 (3H, s), 2.14 (3H, s), 2.25 (3H, s), 2.31 (3H, s), 2.35 (3H, s), 2.45–2.57 (4H, m), 3.00–3.15 (4H, m), 4.06 (1H, s), 6.85 (2H, br), 7.04 (2H, d, J=6.8 Hz).

EXAMPLE 9

(4-benzoyl-1-(2,2,4,6,7-pentamethyl-3-(4-methylphenyl),-2,3-dihydro-1-benzofuran-5-yl))piperazine Triethylamine (–0.31 mL, 2.25 mmol) and benzoyl chloride (96 mL) were added to a suspension of 1-(2,2,4,6,7-pentamethyl-3-(4-methylphenyl)-2,3-dihydro-1-benzofuran-5-yl)piperazine hydrochloride obtained in Example 1 (301 mg, 0.75 mmol) in THF (5 ml) at room temperature and the mixture was stirred at the same temperature for 5 hours. The resulting mixture was poured into saturated aqueous sodium bicarbonate and extracted with ethyl acetate. The extract was washed with saturated aqueous sodium chloride, dried over anhydrous sodium sulfate, and the solvent was removed under reduced pressure. The residue was purified on silica gel column chromatography (hexane/ethyl acetate=10/1) and crystallized from hexane to obtain 350 mg (yield 100%) of the title compound. mp. 137–138° C. (hexane-ethyl acetate).

$^1$H-NMR (CDCl3) δ: 0.99 (3H, s), 1.48 (3H, s), 1.87 (3H, s), 2.14 (3H, s), 2.25 (3H, s), 2.31 (3H, s), 2.92–3.20 (4H, m), 3.38–3.55 (2H, m), 3.70–4.02 (2H, m), 4.07 (1H, s), 6.70 (2H, br), 7.05 (2H, br), 7.41 (5H, s).

EXAMPLE 10

4-(4-fluorobenzoyl)-1-(2,2,4,6,7-pentamethyl-3-(4-methylphenyl)-2,3-dihydro-1-benzofuran-5-yl)piperazine Using 4-fluorobenzoyl chloride, the title compound was obtained in the same manner as in Example 9. Yield 52% mp. 241–142° C. (hexane-ethyl acetate).

$^1$H-NMR (CDCl3) δ: 1.00 (3H, s), 1.47 (3H, s), 1.86 (3H, s), 2.14 (3H, s), 2.24 (3H, s), 2.31 (3H, s), 3.06 (4H, br), 3.60 (4H, br), 4.06 (1H, s), 6.80 (2H, br), 7.00–7.14 (4H, m), 7.43 (2H, dd, J=5.4 Hz, 8.6 Hz).

EXAMPLE 11

4-acetyl-1-(2,2,4,6,7-pentamethyl-3-(4-methylphenyl)-2,3-dihydro-1-benzofuran-5-yl)piperazine Using Acetic anhydride, the title compound was obtained in the same manner as in Example 9. Yield 83% mp. 272–274° C. (hexane-ethyl acetate).

$^1$H-NMR (CDCl3) δ: 1.00 (3H, s), 1.48 (3H, s), 1.84 (3H, s), 2.11 (3H, d, J=2.6 Hz), 2.14 (3H, s), 2.23 (3H, s), 2.31 (3H, s), 2.95–3.08 (4H, m), 3.43–3.57 (2H, m), 3.62–3.73 (2H, m), 4.06 (1H, s), 6.80 (2H, br), 7.05 (2H, d, J=7.2 Hz).

EXAMPLE 12

4-(4-methoxybenzoyl)-1-(2,2,4,6,7-pentamethyl-3-(4-methylphenyl)-2,3-dihydro-1-benzofuran-5-yl)piperazine Using 4-methoxybenzoyl chloride, the title compound was obtained in the same manner as in Example 9. Yield 58% mp. 163–165° C. (hexane-ethyl acetate).

$^1$NMR (CDCl3) δ: 0.99 (3H, s), 1.48 (3H, s), 1.86 (3H, s), 2.14 (3H, s), 2.24 (3H, s), 2.31 (3H, s), 3.05 (4H, br), 3.65 (4H, br), 3.83 (3H, s), 4.06 (1H, s), 6.80 (2H, br), 6.90 (2H, d, J=8.8 Hz), 7.04 (2H, d, J=7.2 Hz), 7.40 (2H, d, J=8.8 Hz).

EXAMPLE 13

4-(4-cyanobenzoyl)-1-(2,2,4,6,7-pentamethyl-3-(4-methylphenyl)-2,3-dihydro-1-benzofuran-5-yl)piperazine Using 4-cyanobenzoyl chloride, the title compound was obtained in the same manner as in Example 9. Yield 49% mp. 159–161° C. (hexane-ethyl acetate).

$^1$H-NMR (CDCl3) δ: 1.00 (3H, s), 1.48 (3H, s), 1.86 (3H, s), 2.14 (3H, s), 2.24 (3H, s), 2.31 (3H, s), 3.05 (4H, br), 3.38 (2H, br), 3.80 (2H, br), 4.06 (1H, s), 6.80 (2H, br), 7.04 (2H, d, J=7.2 Hz), 7.52 (2H, d, J=7.9 Hz), 7.71 (2H, d, J=7.9 Hz).

EXAMPLE 14

1-(2,2,4,6,7-pentamethyl-3-(4-methylphenyl)-2,3-dihydro-1-benzofuran-5-yl)-4-(4-nitrophenyl)piperazine Triethylamine (0.31 mL, 2.25 mmol) and 4-fluoronitrobenzene (159 μL, 1.5 mmol) were added to a suspension of 1-(2,2,4,6,7-pentamethyl-3-(4-methylphenyl)-2,3-dihydro-1-benzofuran-5-yl)piperazine hydrochloride obtained in Example 1 (301 mg, 0.75 mmol) in acetonitrile (6 ml) at room temperature and the mixture was refluxed for 10 hours. The resulting mixture was cooled, diluted with saturated aqueous sodium bicarbonate, and extracted with ethyl acetate. The organic extract was washed with saturated aqueous sodium chloride, dried over anhydrous sodium sulfate, and the solvent was removed under reduced pressure. The residue was purified on silica gel column chromatography (hexane/ethyl acetate=4/1) and crystallized from hexane to obtain 312 mg (yield 86%) of the title compound. mp. 203–205° C. (hexane-ethyl acetate).

$^1$H-NMR (CDCl3) δ: 1.00 (3H, s), 1.49 (3H, s), 1.88 (3H, s), 2.15 (3H, s), 2.26 (3H, s), 2.31 (3H, s), 3.16–3.25 (4H, m), 3.42–3.53 (4H, m), 4.07 (1H, s), 6.75 (2H, br), 6.84 (2H, d, J=9.6 Hz), 7.05 (2H, brd, J=6.6 Hz), 8.12 (2H, d, J=9.6 Hz).

EXAMPLE 15

1-(2,2,4,6,7-pentamethyl-3-(4-methylphenyl)-2,3-dihydro-1-benzofuran-5-yl)-4-(2-nitrophenyl)piperazine Using 2-fluoro nitrobenzene, the title compound was obtained in the same manner as in Example 14. Yield 91% mp. 178–180° C. (hexane-ethyl acetate).

$^1$H-NMR (CDCl3) δ: 1.00 (3H, s), 1.49 (3H, s), 1.90 (3H, s), 2.15 (3H, s), 2.28 (3H, s), 2.31 (3H, s), 3.05–3.22 (8H, m), 4.08 (1H, s), 6.75 (2H, br), 7.01–7.09 (3H, m), 7.17 (1H, d, J=8.24 Hz), 7.47 (1H, t, J=8.8 Hz), 7.77 (1H, d, J=8.8 Hz).

EXAMPLE 16

1-(2,2,4,6,7-pentamethyl-3-(4-methylphenyl)-2,3-dihydro-1-benzofuran-5-yl)-4-(4-methylphenyl)piperazine BINAP(140 mg, 0.225 mmol) was added to a mixture of 1-(2,2,4,6,7-pentamethyl-3-(4-methylphenyl)-2,3-dihydro-1-benzofuran-5-yl)piperazine hydrochloride (301 mg, 0.75 mmol) obtained in Example 1, sodium tert butoxide (360 mg, 3.75 mmol), 4-bromotoluene (185 μL, 1.5 mmol), and palladium acetate (17 mg, 0.075 mmol) in toluene (6 ml) at room temperature and the mixture was refluxed for 24 hours under argon atmosphere. The resulting mixture was cooled, diluted with saturated aqueous sodium bicarbonate and extracted with ethyl acetate. The organic extract was washed with saturated aqueous sodium chloride, dried over anhydrous sodium sulfate, and the solvent was removed under reduced pressure. The residue was purified on silica gel column chromatography (hexane/ethyl acetate=4/1) and crystallized from hexane to obtain 281 mg (yield 82%) of the title compound. mp. 157–158° C. (hexane-ethyl acetate).

$^1$H-NMR (CDCl3) δ: 1.00 (3H, s), 1.49 (3H, s), 1.89 (3H, s), 2.15 (3H, s), 2.27 (6H, s), 2.31 (3H, s), 3.10–3.28 (8H, m), 4.08 (1H, s), 6.88 (2H, d, J=8.7 Hz), 7.00 (2H, br), 7.05 (2H, br), 7.08 (2H, d, J=8.7 Hz).

EXAMPLE 17

4-(acetamidophenyl)-1-(2,2,4,6,7-pentamethyl-3-(4-methylphenyl)-2,3-dihydro-1-benzofuran-5-yl)piperazine Using 4-bromoacetanilide, the title compound was obtained in the same manner as in Example 16. Yield 17%.

$^1$H-NMR (CDCl3) δ: 1.00 (3H, s), 1.49 (3H, s), 1.89 (3H, s), 2.15 (3H, s), 2.27 (3H, s), 2.31 (3H, s), 3.13–3.25 (8H, m), 4.07 (1H, s), 6.80 (2H, br), 6.85–7.08 (5H, m), 7.36 (2H, d, J=8.4 Hz).

EXAMPLE 18

4-(4-(trifluoromethyl)phenyl)-1-(2,2,4,6,7-pentamethyl-3-(4-methylphenyl)-2,3-dihydro-1-benzofuran-5-yl)piperazine Using 4-trifluoromethyl-1-bromobenzene, the title compound was obtained in the same manner as in Example 16. Yield 67% mp. 180–181° C. (hexane-ethyl acetate).

$^1$H-NMR (CDCl3) δ: 1.00 (3H, s), 1.49 (3H, s), 1.89 (3H, s), 2.15 (3H, s), 2.27 (3H, s), 2.31 (3H, s), 3.15–3.25 (4H, m), 3.28–3.38 (4H, m), 4.08 (1H, s), 6.80 (2H, br), 6.95 (2H, d, J=8.6 Hz), 7.05 (2H, brd, J=6.9 Hz), 7.48 (2H, d, J=8.6 Hz).

EXAMPLE 19

4-(3,4-dimethoxyphenyl)-1-(2,2,4,6,7-pentamethyl-3-(4-methylphenyl)-2,3-dihydro-1-benzofuran-5-yl)piperazine Using 4-bromoveratrol, the title compound was obtained in the same manner as in Example 16. Yield 35% mp. 136–139° C. (hexane-ethyl acetate).

$^1$H-NMR (CDCl3) δ: 1.00 (3H, s), 1.49 (3H, s), 1.91 (3H, s), 2.15 (3H, s), 2.29 (3H, s), 2.31 (3H, s), 3.07–3.30 (8H, m), 3.84 (3H, s), 3.87 (1H, s), 6.49 (1H, dd, J=2.6 Hz, 8.8 Hz), 6.62 (1H, d, J=2.6 Hz), 6.79 (1H, d, J=8.8 Hz), 6.85 (2H, br), 7.06 (2H, brd, J=7.7 Hz), 8.12 (2H, d, J=9.6 Hz).

EXAMPLE 20

4-(4-cyanophenyl)-1-(2,2,4,6,7-pentamethyl-3-(4-methylphenyl)-2,3-dihydro-1-benzofuran-5-yl)piperazine Using 4-bromobenzonitrile, the title compound was obtained in the same manner as in Example 16. Yield 45% mp. 216–217° C. (hexane-ethyl acetate).

$^1$H-NMR (CDCl3) δ: 1.00 (3H, s), 1.48 (3H, s), 1.87 (3H, s), 2.15 (3H, s), 2.26 (3H, s), 2.31 (3H, s), 3.13–3.25 (4H, m), 3.30–3.43 (4H, m), 4.07 (1H, s), 6.80 (2H, br), 6.87 (2H, d, J=9.2 Hz), 7.05 (2H, brd, J=7.0 Hz), 7.49 (2H, d, J=9.2 Hz).

EXAMPLE 21

1-(2,2,4,6,7-pentamethyl-3-(4-methylphenyl)-2,3-dihydro-1-benzofuran-5-yl)-4-(3-pyridyl)piperazine Using 3-bromopyridine, the title compound was obtained in the same manner as in Example 16. Yield 40% mp. 136–137° C. (hexane-ethyl acetate).

¹H-NMR (CDCl3) δ: 1.00 (3H, s), 1.49 (3H, s), 1.89 (3H, s), 2.15 (3H, s), 2.28 (3H, s), 2.31 (3H, s), 3.18–3.34 (8H, m), 4.08 (1H, s), 6.80 (2H, br), 7.05 (2H, brd, J=7.6 Hz), 7.10–7.21 (2H, m), 8.10 (1H, dd, J=1.8 Hz, 4.6 Hz), 8.35 (1H, d, J=1.8 Hz).

EXAMPLE 22

1-(2,2,4,6,7-pentamethyl-3-(4-methylphenyl)-2,3-dihydro-1-benzofuran-5-yl)-4-(2-pyridyl)piperazine Using 2-bromopyridine, the title compound was obtained in the same manner as in Example 16. Yield 63% mp. 190–191° C. (hexane-ethyl acetate).
¹H-NMR (CDCl3) δ: 1.00 (3H, s), 1.48 (3H, s), 1.88 (3H, s), 2.15 (3H, s), 2.27 (3H, s), 2.31 (3H, s), 3.10–3.21 (8H, m), 3.45–3.70 (4H, m), 4.08 (1H, s), 6.80 (2H, br), 7.05 (2H, brd, J=7.6 Hz), 7.10–7.21 (2H, m), 8.10 (1H, dd, J=1.8 Hz, 4.6 Hz), 8.35 (1H, d, J=1.8 Hz).

EXAMPLE 23

(3R)-1-(2,2,4,6,7-pentamethyl-3-(4-methylphenyl)-2,3-dihydro-1-benzofuran-5-yl)-4-phenylpipetidine-2,6-dione A mixture of (3R)-2,2,4,6,7-pentamethyl-3-(4-methylphenyl)-2,3-dihydro-1-benzofuran-5-amine (700 mg, 2.4 mmol) and 3-phenylglutaric anhydride (500 mg, 2.6 mmol) in THF (7 ml) was refluxed for 2 hours under an argon atmosphere. The resulting mixture was cooled to room temperature and then 1-ethyl-3-(3-dimethylaminopropyl)carbodiimide (WSC) hydrochloride (550 mg, 2.9 mmol) and 1-hydroxy-1H-benzotriazole (HOBt)-hydrate (450 mg, 2.9 mmol) were added. After the mixture was refluxed for 12 hours, the resulting mixture was cooled to room temperature, poured into water. The mixture was extracted with ethyl acetate. The organic extract was washed with 1N hydrochloric acid, water, saturated aqueous sodium bicarbonate and water, and dried over anhydrous sodium sulfate. The solvent was removed under reduced pressure and the residue was purified with silica gel column chromatography (hexane/ethyl acetate=5/1) to obtain 780 mg (yield 70%) of the title compound via recrystallization (ethyl acetate-hexane). mp. 118–122° C.
¹H-NMR (CDCl3) δ: 0.99 (3H, s), 1.49 (1.5H, s), 1.53 (3H, s), 1.61 (1.5H, s), 1.83 (1.5H, s), 2.02 (1.5H, s), 2.16 (1.5H, s), 2.18 (1.5H, s), 2.30 (3H, s), 2.84–3.28 (4H, m), 3.32–3.68 (1H, m), 4.19 (0.5H, s), 4.20 (0.5H, s), 6.50–7.50 (9H, m).

EXAMPLE 24

(3R)-4-(4-fluorophenyl)-1-(2,2,4,6,7-pentamethyl-3-(4-methylphenyl)-2,3-dihydro-1-benzofuran-5-yl)piperidine-2,6-dione Using 3-(4-fluorophenyl)glutaric anhydride obtained in Reference Example 5, the title compound was synthesized in the same manner as in Example 23. Yield 82%. mp. 151–154° C. (ethyl acetate-hexane).
[α]$_D$=+65.1° (c=0.491, chloroform).
¹H-NMR (CDCl3) δ: 0.99 (3H, s), 1.47 (1.5H, s), 1.53 (3H, s), 1.60 (1.5H, s), 1.88 (1.5H, s), 2.01 (1.5H, s), 2.16 (1.5H, s), 2.18 (1.5H, s), 2.30 (3H, s), 2.80–3.26 (4H, m), 3.34–3.68 (1H, m), 4.18 (0.5H, s), 4.20 (0.5H, s), 6.50–7.50 (8H, m).

EXAMPLE 25

(3R)-1-(2,2,4,6,7-pentamethyl-3-(4-methylphenyl)-2,3-dihydro-1-benzofuran-5-yl)-4-(4-methylphenyl)piperidine-2,6-dione Using 3-(4-methylphenyl)glutaric anhydride obtained in Reference Example 6, the title compound was synthesized in the same manner as in Example 23. Yield 97%. An amorphous powder.
[α]$_D$=+68.2° (c=0.4925, chloroform).
¹H-NMR (CDCl3) δ: 0.99 (3H, s), 1.50 (1.5H, s), 1.53 (3H, s), 1.60 (1.5H, s), 1.89 (1.5H, s), 2.01 (1.5H, s), 2.16 (1.5H, s), 2.18 (1.5H, s), 2.29 (3H, s), 2.34 (1.5H, s), 2.35 (1.5H, s), 2.80–3.26 (4H, m), 3.30–3.64 (1H, m), 4.18 (0.5H, s), 4.20 (0.5H, s), 6.50–7.40 (8H, m).

EXAMPLE 26

(3R)-4-(4-methoxyphenyl)-1-(2,2,4,6,7-pentamethyl-3-(4-methylphenyl)-2,3-dihydro-1-benzofuran-5-yl)piperidine-2,6-dione Using 3-(4-methoxyphenyl)glutaric anhydride obtained in Reference Example 7, the title compound was synthesized in the same manner as in Example 23. Yield 87%. mp. 207–209° C. (ethyl acetate-hexane).
[α]$_D$=+66.6 ° (c=0.496, chloroform).
¹H-NMR (CDCl3) δ: 0.99 (3H, s), 1.48 (1.5H, s), 1.53 (3H, s), 1.60 (1.5H, s), 1.88 (1.5H, s), 2.01 (1.5H, s), 2.16 (1.5H, s), 2.18 (1.5H, s), 2.30 (3H, s), 2.80–3.24 (4H, m), 3.28–3.64 (1H, m), 3.80 (1.5H, s), 3.82 (1.5H, s), 4.18 (0.5H, s), 4.20 (0.5H, s), 6.50–7.40 (8H, m).

EXAMPLE 27

(3R)-4-(3,4-dimethoxyphenyl)-1-(2,2,4,6,7-pentamethyl-3-(4-methylphenyl)-2,3-dihydro-1-benzofuran-5-yl)piperidine-2,6-dione Using 3-(3,4-dimethoxyphenyl)glutaric anhydride obtained in Reference Example 8, the title compound was synthesized in the same manner as in Example 23. Yield 100%. Amorphous powder.
[α]$_D$=+63.30 (c=0.499, chloroform).
¹H-NMR (CDCl3) δ: 0.99 (3H, s), 1.49 (1.5H, s), 1.54 (3H, s), 1.61 (1.5H, s), 1.89 (1.5H, s), 2.01 (1.5H, s), 2.16 (1.5H, s), 2.18 (1.5H, s), 2.29 (3H, s), 2.80–3.26 (4H, m), 3.30–3.64 (1H, m), 3.87 (1.5H, s), 3.89 (4.5H, s), 4.19 (0.5H, s), 4.20 (0.5H, s), 6.50–7.30 (7H, m).

EXAMPLE 28

(3R)-1-(2,2,4,6,7-pentamethyl-3-(4-methylphenyl)-2,3-dihydro-1-benzofuran-5-yl)-4-phenylpiperidine Aluminum chloride (913 mg, 6.9 mmol) was added to THF (10 mL) under ice cooling, and allowed to warm to room temperature so as to dissolve the aluminum chloride. The mixture was cooled with ice cooling and then lithium aluminium hydride (260 mg, 6.9 mmol) was added. After stirring for 15 minutes, A solution of (3R)-1-(2,2,4,6,7-pentamethyl-3-(4-methylphenyl)-2,3-dihydro-1-benzofuran-5-yl)-4-phenylpiperidine-2,6-dione obtained in Example 23 (640 mg, 1.4 mmol) in THF (5 ml) was added to the mixture under ice cooling. After the mixture was refluxed for 2 hours, the resulting mixture was cooled to room temperature, poured into water, and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=25/1) to obtain 350 mg (yield 58%) of the title compound via recrystallization (hexane). mp. 137–140° C.

$^1$H-NMR (CDCl3) δ: 0.99 (1.5H, s), 1.00 (1.5H, s), 1.49 (3H, s), 1.64–2.06 (4H, m), 1.88 (1.5H, s), 1.91 (1.5H, s), 2.14 (1.5H, s), 2.17 (1.5H, s), 2.22 (1.5H, s), 2.31 (3H, s), 2.32 (1.5H, s), 2.44–2.70 (1H, m), 2.84–3.08 (2H, m), 3.12–3.46 (2H, m), 4.08 (1H, s), 6.40–7.40 (9H, m).

EXAMPLE 29

(3R)-4-(4-fluorophenyl)-1-(2,2,4,6-pentamethyl-3-(4-methylphenyl)-2,3-dihydro-1-benzofuran-5-yl)piperidine Using (3R)-4-(4-fluorophenyl)-1-(2,2,4,6-pentamethyl-3-(4-methylphenyl)-2,3-dihydro-1-benzofuran-5-yl)piperidine-2,6-dione obtained in Example 24, the title compound was synthesized in the same manner as in Example 28. Yield 76%. mp. 141–144° C. (hexane).

$[α]_D$=+59.7° (c=0.495, chloroform).

$^1$H-NMR (CDCl3) δ: 0.99 (1.5H, s), 1.00 (1.5H, s), 1.49 (3H, s), 1.64–1.96 (4H, m), 1.88 (1.5H, s), 1.90 (1.5H, s), 2.13 (1.5H, s), 2.17 (1.5H, s), 2.22 (−1.5H, s), 2.31 (4.5H, s), 2.40–2.68 (1H, m), 2.84–3.08 (2H, m), 3.12–3.44 (2H, m), 4.08 (1H, s), 6.50–7.40 (8H, m).

EXAMPLE 30

(3R)-1-(2,2,4,6-pentamethyl-3-(4-methylphenyl)-2,3-dihydro-1-benzofuran-5-yl)-4-(4-methylphenyl)piperidine Using (3R)-1-(2,2,4,6-pentamethyl-3-(4-methylphenyl)-2,3-dihydro-1-benzofuran-5-yl)-4-(4-methylphenyl)piperidine-2,6-dione obtained in Example 25 the title compound was synthesized in the same manner as in Example 28, Yield 65%. mp. 165–167° C. (hexane). [α]D=+62.9° (c=0.4965, chloroform).

$^1$H-NMR (CDCl3) δ: 0.99 (1.5H, s), 1.00 (1.5H, s), 1.49 (3H, s), 1.64–1.96 (4H, m), 1.88 (1.5H, s), 1.90 (1.5H, s), 2.13 (1.5H, s), 2.17 (1.5H, s), 2.22 (1.5H, s), 2.31 (3H, s), 2.32 (4.5H, s), 2.40–2.66 (1H, m), 2.84–3.06 (2H, m), 3.12–3.46 (2H, m), 4.08 (1H, s), 6.40–7.40 (8H, m).

EXAMPLE 31

(3R)-4-(4-methoxyphenyl)-1-(2,2,4,6-pentamethyl-3-(4-methylphenyl)-2,3-dihydro-1-benzofuran-5-yl)piperidine Using (3R)-4-(4-methoxyphenyl)-1-(2,2,4,6-pentamethyl-3-(4-methylphenyl)-2,3-dihydro-1-benzofuran-5-yl)piperidine-2,6-dione obtained in Example 26, the title compound was synthesized in the same manner as in Example 28. Yield 59%. mp. 183–185° C. (ethyl acetate-hexane).

$[α]_D$=+60.6° (c=0.505, chloroform).

$^1$H-NMR (CDCl3) δ: 0.99 (1.5H, s), 1.00 (1.5H, s), 1.49 (3H, s), 1.62–1.96 (4H, m), 1.88 (1.5H, s), 1.90 (1.5H, s), 2.14 (1.5H, s), 2.17 (1.5H, s), 2.22 (1.5H, s), 2.31 (3H, s), 2.32 (1.5H, s), 2.40–2.66 (1H, m), 2.82–3.06 (2H, m), 3.12–3.46 (2H, m), 3.79 (1.5H, s), 3.80 (1.5H, s), 4.08 (1H, s), 6.40–7.40 (8H, m).

EXAMPLE 32

(3R)-4-(3,4-dimethoxyphenyl)-1-(2,2,4,6-pentamethyl-3-(4-methylphenyl)-2,3-dihydro-1-benzofuran-5-yl)piperidine Using (3R)-4-(3,4-dimethoxyphenyl)-1-(2,2,4,6-pentamethyl-3-(4-methylphenyl)-2,3-dihydro-1-benzofuran-5-yl)piperidine-2,6-dione obtained in Example 27, the title compound was synthesized in the same manner as in Example 28. Yield 54%. mp. 102–106° C. (hexane).

$[α]_D$=+60.50 ° (c=0.4915, chloroform).

$^1$H-NMR (CDCl3) δ: 0.99 (1.5H, s), 1.00 (1.5H, s), 1.49 (3H, s), 1.62–1.96 (4H, m), 1.89 (1.5H, s), 1.91 (1.5H, s), 2.14 (1.5H, s), 2.17 (1.5H, s), 2.22 (1.5H, s), 2.31 (3H, s), 2.33 (1.5H, s), 2.36–2.68 (1H, m), 2.82–3.08 (2H, m), 3.12–3.46 (2H, m), 3.86 (1.5H, s), 3.87 (1.5H, s), 3.88 (1.5H, s), 3.91 (1.5H, s), 4.08 (1H, s), 6.40–7.40 (7H, m).

EXAMPLE 33

1-(3-hydroxy-2,2,4,6-pentamethyl-3-(4-methylphenyl)-2,3-dihydro-1-benzofuran-5-yl)-4-(4-methoxyphenyl)piperazine n-Butyllithium (hexane solution 1.50 M, 3.40 mL, 5.10 mmol) was added dropwise to solution of 4-bromotoluene (1.10 g, 6.43 mmol) in THF (10 ml) under a stream of argon at −70° C. or less and the mixture was stirred for 30 minutes. To the mixture was added dropwise a solution of 4-(4-methoxyphenyl)-1-(2,2,4,6-pentamethyl-2,3-dihydro-1-benzofuran-3-on-5-yl)piperazine (1.00 g, 2.5 mmol) obtained in Reference Example 13 in THF (3 ml) at −70° C. or less and the mixture was allowed to warm to 0° C. After stirring under ice cooling for 30 minutes, the resulting mixture was poured into water and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=5/1) to obtain 1.11 g (yield 90%) of the title compound via recrystallization (ethyl acetate-hexane). mp. 145–147° C.

$^1$H-NMR (CDCl3) δ: 0.86 (3H, s), 1.51 (3H, s), 1.97 (3H, s), 2.08 (1H, s), 2.15 (3H, s), 2.30 (3H, s), 2.35 (3H, s), 3.02–3.36 (8H, m), 3.77 (3H, s), 6.60–7.90 (4H, m), 6.84 (2H, d, J=9.1 Hz), 6.95 (2H, d, J=9.1 Hz).

EXAMPLE 34

1-(3-hydroxy-2,2,4,6-pentamethyl-3-(2-naphthyl)-2,3-dihydro-1-benzofuran-5-yl)-4-(4-methoxyphenyl)piperazine Using 2-bromonaphthalene, the title compound was synthesized in the same manner as in Example 33. Yield 89%. mp. 189–190° C. (ethyl acetate-hexane).

$^1$H-NMR (CDCl3) δ: 0.90 (3H, br s), 1.58 (3H, s), 1.96 (3H, br s), 2.19 (3H, s), 2.21 (1H, s), 2.33 (3H, s), 3.02–3.36 (8H, m), 3.77 (3H, s), 6.84 (2H, d, J=9.4 Hz), 6.95 (2H, d, J=9.4 Hz), 7.00–8.40 (7H, m).

EXAMPLE 35

1-(3-hydroxy-2,2,4,6,7-pentamethyl-3-(1,1'-biphenyl-4-yl)-2,3-dihydro-1-benzofuran-5-yl)-4-(4-methoxyphenyl)piperazine Using 4-bromobipheny, the title compound was synthesized in the same manner as in Example 33. Yield 89%. mp. 182–184° C. (ethyl acetate-hexane).

$^1$H-NMR (CDCl3) δ: 0.92 (3H, s), 1.56 (3H, s), 2.02 (3H, s), 2.12 (1H, s), 2.17 (3H, s), 2.31 (3H, s), 3.02–3.40 (8H, m), 3.77 (3H, s), 6.85 (2H, d, J=9.2 Hz), 6.95 (2H, d, J=9.2 Hz), 6.80–8.00 (9H, m).

EXAMPLE 36

1-(3-hydroxy-2,2,4,6,7-pentamethyl-3-(3-thienyl)-2,3-dihydro-1-benzofuran-5-yl)-4-(4-methoxyphenyl)piperazine Using 3-bromothiophene, the title compound was synthesized in the same manner as in Example 33. Yield 76%. mp. 131–133° C. (diisopropyl ether-hexane).

$^1$H-NMR (CDCl3) δ: 0.97 (3H, s), 1.52 (3H, s), 2.02 (3H, s), 2.10 (1H, s), 2.14 (3H, s), 2.29 (3H, s), 3.00–3.38 (8H, m), 3.78 (3H, s), 6.80–7.04 (1H, m), 6.85 (2H, d, J=9.2 Hz), 6.96 (2H, d, J=9.2 Hz), 7.12–7.34 (2H, m).

EXAMPLE 37

1-(3-(3-furyl)-3-hydroxy-2,2,4,6,7-pentamethyl-2,3-dihydro-1-benzofuran-5-yl)-4-(4-methoxyphenyl)piperazine Using 3-bromofuran, the title compound was synthesized in the same manner as in Example 33. Yield 90%. mp. 148–149° C. (hexane).

$^1$H-NMR (CDCl3) δ: 1.09 (3H, s), 1.50 (3H, s), 2.00 (1H, s), 2.10 (3H, s), 2.13 (3H, s), 2.28 (3H, s), 3.02–3.36 (8H, m), 3.78 (3H, s), 6.23 (1H, dd, J=1.6, 1.0 Hz), 6.85 (2H, d, J=9.3 Hz), 6.96 (2H, d, J=9.3 Hz), 7.30–7.44 (2H, m).

EXAMPLE 38

1-(3-hydroxy-2,2,4,6,7-pentamethyl-3-(1-naphthyl)2,3-dihydro-1-benzofuran-5-yl)-4-(4-methoxyphenyl)piperazine Using 1-bromonaphthalene, the title compound was synthesized in the same manner as in Example 33. Yield 60%. Amorphous powder.

$^1$H-NMR (CDCl3) δ: 0.88 (1.5H, s), 0.95(1.5H, s), 1.59 (1.5H, s), 1.73(1.5H, s), 1.79(1.5H, s), 2.06(1.5H, s), 2.16 (1.5H, s), 2.23(1.5H, s), 2.34(1.5H, s), 2.35(1.5H, s), 2.48 (1H $ 2/3, s), 2.96–3.44 (8H, m), 3.76(1.5H, s), 3.77(1.5H, s), 6.7–8.0(10H, m), 8.10–8.22(0.5H, m), 8.88–9.04(0.5H, m).

EXAMPLE 39

1-(3-hydroxy-2,2,4,6,7-pentamethyl-3-phenyl-2,3-dihydro-1-benzofuran-5-yl)-4-(4-methoxyphenyl)piperazine Using 3-bromobenzene, the title compound was synthesized in the same manner as in Example 33. Yield 86%. mp. 123–125° C. (hexane).

$^1$H-NMR (CDCl3) δ: 0.86 (3H, s), 1.53 (3H, s), 1.97 (3H, s), 2.09 (1H, s), 2.15 (3H, s), 2.30 (3H, s), 3.04–3.36 (8H, m), 3.77 (3H, s), 6.4–8.2(5H, m), 6.85 (2H, d, J=9.2 Hz), 6.95 (2H, d, J=9.2 Hz).

EXAMPLE 40

1-(3-hydroxy-2,2,4,6,7-pentamethyl-3-(3-methylphenyl)-2,3-dihydro-1-benzofuran-5-yl)-4-(4-methoxyphenyl)piperazine Using 3-bromotoluene, the title compound was synthesized in the same manner as in Example 33. Yield 92%. mp. 122–125° C. (hexane).

$^1$H-NMR (CDCl3) δ: 0.86 (3H, s), 1.53 (3H, s), 1.97 (3H, s), 2.07 (1H, s), 2.15 (3H, s), 2.30 (3H, s), 2.35 (3H, br s), 3.02–3.38 (8H, m), 3.78 (3H, s), 6.40–8.00 (4H, m), 6.85 (2H, d, J=9.4 Hz), 6.96 (2H, d, J=9.4 Hz).

EXAMPLE 41

1-(3-hydroxy-2,2,4,6,7-pentamethyl-3-(2-thienyl)-2,3-dihydro-1-benzofuran-5-yl)-4-(4-methoxyphenyl)piperazine Using thiophene, the title compound was synthesized in the same manner as in Example 33. Yield 87%. mp. 154–155° C. (ethyl acetate-hexane).

$^1$H-NMR (CDCl3) δ: 1.02 (3H, s), 1.54 (3H, s), 2.09 (3H, s), 2.14 (3H, s), 2.29 (3H, s), 2.33 (1H, s), 3.00–3.38 (8H, m), 3.78 (3H, s), 6.64–6.78 (1H, m), 6.85 (2H, d, J=9.2 Hz), 6.88–7.02 (1H, m), 6.96 (2H, d, J=9.2 Hz), 7.20–7.36 (1H, m).

EXAMPLE 42

1-(3-(2-furyl)-3-hydroxy-2,2,4,6,7-pentamethyl-2,3-dihydro-1-benzofuran-5-yl)-4-(4-methoxyphenyl)piperazine Using furan, the title compound was synthesized in the same manner as in Example 33. Yield 91%. mp. 111–112° C. (hexane).

$^1$H-NMR (CDCl3) δ: 1.04 (3H, s), 1.53 (3H, s), 2.06 (3H, s), 2.12 (3H, s), 2.27 (1H, s), 2.28 (3H, s), 3.04–3.36 (8H, m), 3.78 (3H, s), 6.27 (1H, dd, J=2.2, 0.4 Hz), 6.39 (1H, dd, J=2.2, 1.4 Hz), 6.85 (2H, d, J=9.2 Hz), 6.96 (2H, d, J=9.2 Hz), 7.36–7.44 (1H, m).

EXAMPLE 43

1-(3-cyclohexyl-3-hydroxy-2,2,4,6,7-pentamethyl-2,3-dihydro-1-benzofuran-5-yl)-4-(4-methoxyphenyl)piperazine Cyclohexyl magnesium bromide (THF solution 1.0 M, 35 mL, 35 mmol) was added to a solution of 4-(4-methoxyphenyl)-1-(2,2,4,6,7-pentamethyl-2,3-dihydro-1-benzofuran-3-on-5-yl)piperazine (1.00 g, 2.53 mmol) obtained in Reference Example 13 in THF (10 ml) under ice cooling and the reaction mixture was allowed to warm to room temperature. After stirring for one hour, the resulting mixture was poured into water and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=8/1) to obtain 970 mg (yield 80%) of the title compound via recrystallization (hexane). mp. 166–167° C.

$^1$H-NMR (CDCl3) δ: 0.40–2.50 (11H, m), 1.30 (3H, s), 1.50 (3H, s), 1.75 (1H, s), 2.04 (3H, s), 2.24 (3H, s), 2.38 (3H, s), 3.02–3.42 (8H, m), 3.79 (3H, s), 6.86 (2H, d, J=9.1 Hz), 6.98 (2H, d, J=9.1 Hz).

EXAMPLE 44

1-(3-hydroxy-2,2,4,6,7-pentamethyl-3-(4-methylphenyl)-2,3-dihydro-1-benzofuran-5-yl)-4-(4-methoxyphenyl)piperazine To a methanol solution of hydrochloric acid (10%, 7 ml) was added 1-(3-methoxy-2,2,4,6,7-pentamethyl-3-(4-methylphenyl)-2,3-dihydro-1-benzofuran-5-yl)-4-(4-methoxyphenyl)piperazine (350 mg, 0.72 mmol) obtained in Example 33. After the mixture was refluxed for 30 minutes, the resulting mixture was concentrated under reduced pressure. The residue was made to basic with aqueous potassium carbonate and extracted with ethyl acetate. The organic extract was washed with water and saturated aqueous sodium chloride, dried over anhydrous sodium sulfate, and concentrated under reduced pressure. The residue was, crystallized from hexane to obtain 320 mg (yield 89%) of the title compound. mp. 180–182° C.

$^1$H-NMR (CDCl3) δ: 0.75 (3H, s), 1.50 (3H, s), 1.96 (3H, s), 2.15 (3H, s), 2.31 (3H, s), 2.35 (3H, s), 3.01 (3H, s), 3.00–3.40 (8H, m), 3.78 (3H, s), 6.5–7.8(4H, m), 6.85 (2H, d, J=9.3 Hz), 6.96. (2H, d, J=9.3 Hz).

EXAMPLE 45

1-(3-cyclohexylidene-2,2,4,6,7-pentamethyl-2,3-dihydro-1-benzofuran-5-yl)-4-(4-methoxyphenyl)piperazine hydrochloride Concentrated hydrochloric acid (0.5 mL) was added to a solution of 1-(3-cyclohexyl-3-hydroxy-2,2,4,6,7-pentamethyl-2,3-dihydro-1-benzofuran-5-yl)-4-(4-methoxyphenyl)piperazine (670 mg, 1.4 mmol) obtained in Example 43 in THF (5 ml) and methanol (5 ml) and the mixture was stirred at room temperature for 12 hours. The reaction mixture was concentrated under reduced pressure and the residue was made to basic with 10% aqueous potassium carbonate. The mixture was extracted with ethyl acetate. The organic extract was washed with water and saturated aqueous sodium chloride, dried over anhydrous sodium sulfate, and concentrated under reduced pressure. The crude product was treated with 4N hydrochloric acid in ethyl acetate solution and the title compound was crystallized from ethanol-diisopropyl ether to obtain 520 mg (yield 75%). mp. 220–222° C.

$^1$H-NMR (CDCl3) δ: 1.30–2.50 (10H, m), 1.58 (6H, s), 2.09 (3H, s), 2.17 (3H, s), 2.25 (3H, s), 3.02–3.46 (8H, m), 3.78 (3H, s), 6.86 (2H, d, J=9.4 Hz), 6.98 (2H, d, J=9.4 Hz).

EXAMPLE 46

1-(2,2,4,6,7-pentamethyl-3-(4-methylphenyl)-2,3-dihydro-1-benzofuran-5-yl)-4-(4-methoxyphenyl)piperazine To trifluoroacetic acid was added 1-(3-hydroxy-2,2,4,6,7-pentamethyl-3-(4-methylphenyl)-2,3-dihydro-1-benzofuran-5-yl)-4-(4-methoxyphenyl)piperazine (350 mg, 0.72 mmol) obtained in Example 33 (3.5 mL) under ice cooling. The mixture was warmed to room temperature, and then triethylsilane (0.3 mL, 1.9 mmol) was added at room temperature. The mixture was stirred for 15 minutes and concentrated under reduced pressure. The residue was made to basic with saturated aqueous sodium bicarbonate and extracted with ethyl acetate. The organic extract was washed with water and saturated aqueous sodium chloride, dried over anhydrous sodium sulfate, and concentrated under reduced pressure. The residue was crystallized from hexane to obtain 270 mg (yield 80%) of the title compound. mp. 189–191° C.

$^1$H-NMR (CDCl3) δ: 1.00 (3H, s), 1.49 (3H, s), 1.90 (3H, s), 2.15 (3H, s), 2.28 (3H, s), 2.31 (3H, s), 2.96–3.36 (8H, m), 3.77 (3H, s), 4.08 (1H, s), 6.40–7.40 (4H, m), 6.84 (2H, d, J=9.2 Hz), 6.95 (2H, d, J=9.2 Hz).

EXAMPLE 47

1-(2,2,4,6,7-pentamethyl-3-(2-naphthyl)-2,3-dihydro-1-benzofuran-5-yl)-4-(4-methoxyphenyl)piperazine Using 1-(3-hydroxy-2,2,4,6,7-pentamethyl-3-(2-naphthyl)-2,3-dihydro-1-benzofuran-5-yl)-4-(4-methoxyphenyl)piperazine obtained in Example 34, the title compound was synthesized in the same manner as in Example 46. Yield 88%. mp. 170–171° C. (ethanol).

$^1$H-NMR (CDCl3) δ: 1.03 (3H, s), 1.55 (3H, s), 1.89 (3H, s), 2.19 (3H, s), 2.31 (3H, s), 2.96–3.36 (8H, m), 3.76 (3H, s), 4.28 (1H, s), 6.60–8.20 (7H, m), 6.83 (2H, d, J=9.2 Hz), 6.93 (2H, d, J=9.2 Hz).

EXAMPLE 48

1-(2,2,4,6,7-pentamethyl-3-(1,1'-biphenyl-4-yl)-2,3-dihydro-1-benzofuran-5-yl)-4-(4-methoxyphenyl)piperazine Using 1-(3-hydroxy-2,2,4,6,7-pentamethyl-3-(1,1'-biphenyl-4-yl)-2,3-dihydro-1-benzofuran-5-yl)-4-(4-methoxyphenyl)piperazine obtained in Example 35, the title compound was synthesized in the same manner as in Example 46. Yield 82%. mp. 147–148° C. (ethanol).

$^1$H-NMR (CDCl3) δ: 1.06 (3H, s), 1.53 (3H, s), 1.94 (3H, s), 2.17 (3H, s), 2.30 (3H, s), 2.96–3.38 (8H, m), 3.77 (3H, s), 4.15 (1H, s), 6.5–7.8(9H, m), 6.84 (2H, d, J=9.0 Hz), 6.95 (2H, d, J=9.0 Hz).

EXAMPLE 49

1-(2,2,4,6,7-pentamethyl-3-(3-thienyl)-2,3-dihydro-1-benzofuran-5-yl)-4-(4-methoxyphenyl)piperazine Using 1-(3-hydroxy-2,2,4,6,7-pentamethyl-3-(3-thienyl)-2,3-dihydro-1-benzofuran-5-yl)-4-(4-methoxyphenyl)piperazine obtained in Example 36, the title compound was synthesized in the same manner as in Example 46. Yield 77%. mp. 128–131° C. (ethanol).

$^1$H-NMR (CDCl3) δ: 1.07 (3H, s), 1.47 (3H, s), 1.95 (3H, s), 2.13 (3H, s), 2.27 (3H, s), 2.96–3.38 (8H, m), 3.78 (3H, s), 4.22 (1H, s), 6.70 (1H, dd, J=4.8, 1.2 Hz), 6.76–6.90 (1H, m), 6.84 (2H, d, J=9.1 Hz), 6.95 (2H, d, J=9.1 Hz), 7.20 (1H, dd, J=4.8, 3.0 Hz).

EXAMPLE 50

1-(3-(3-furyl)-2,2,4,6,7-pentamethyl-2,3-dihydro-1-benzofuran-5-yl)-4-(4-methoxyphenyl)piperazine Using 1-(3-(3-furyl)-3-hydroxy-2,2,4,6,7-pentamethyl-2,3-dihydro-1-benzofuran-5-yl)-4-(4-methoxyphenyl)piperazine obtained in Example 37, the title compound was synthesized in the same manner as in Example 46. Yield 72%. mp. 110–113° C. (methanol).

$^1$H-NMR (CDCl3) δ: 1.18 (3H, s), 1.45 (3H, s), 2.02 (3H, s), 2.12 (3H, s), 2.26 (3H, s), 2.98–3.38 (8H, m), 3.78 (3H, s), 4.03 (1H, s), 6.03–6.12 (1H, m), 6.85 (2H, d, J=9.2 Hz), 6.96 (2H, d, J=9.2 Hz), 7.11 (1H, s), 7.30–7.35 (1H, m).

EXAMPLE 51

1-(2,2,4,6,7-pentamethyl-3-(1-naphthyl)-2,3-dihydro-1-benzofuran-5-yl)-4-(4-methoxyphenyl)piperazine Using 1-(3-hydroxy-2,2,4,6,7-pentamethyl-3-(1-naphthyl)-2,3-dihydro-1-benzofuran-5-yl)-4-(4-methoxyphenyl)piperazine obtained in Example 38, the title compound was synthesized in the same manner as in Example 46. Yield 63%. mp. 165–166° C. (ethanol).

$^1$H-NMR (CDCl3) δ: 0.92 (3H, s), 1.68 (3H, s), 1.81 (3H, s), 2.19 (3H, s), 2.32 (3H, s), 2.96–3.40 (8H, m), 3.76 (3H, s), 5.03 (1H, s), 6.64–6.82 (1H, m), 6.83 (2H, d, J=9.1 Hz), 6.94 (2H, d, J=9.1 Hz), 7.22–7.38 (1H, m), 7.42–7.68 (2H, m), 7.72 (1H, d, J=8.6 Hz), 7.84–7.96 (1H, m), 8.14 (1H, d, J=8.6 Hz).

EXAMPLE 52

1-(2,2,4,6,7-pentamethyl-3-phenyl-2,3-dihydro-1-benzofuran-5-yl)-4-(4-methoxyphenyl)piperazine Using 1-(3-hydroxy-2,2,4,6,7-pentamethyl-3-phenyl-2,3-dihydro-1-benzofuran-5-yl)-4-(4-methoxyphenyl)piperazine obtained in Example 39, the title compound was synthesized in the same manner as in Example 46. Yield 84%. mp. 126–128° C. (methanol).

$^1$H-NMR (CDCl3) δ: 1.00 (3H, s), 1.50 (3H, s), 1.90 (3H, s), 2.16 (3H, s), 2.28 (3H, s), 3.02–3.32 (8H, m), 3.77 (3H, s), 4.11 (1H, s), 6.40–7.60 (5H, m), 6.84 (2H, d, J=9.3 Hz), 6.94 (2H, d, J=9.3 Hz).

EXAMPLE 53

1-(2,2,4,6,7-pentamethyl-3-(3-methylphenyl)-2,3-dihydro-1-benzofuran-5-yl)-4-(4-methoxyphenyl)piperazine Using 1-(3-hydroxy-2,2,4,6,7-pentamethyl-3-(3-methylphenyl)-2,3-dihydro-1-benzofuran-5-yl)-4-(4-methoxyphenyl)piperazine obtained in Example 40, the title compound was synthesized in the same manner as in Example 46. Yield 86%. mp. 159–161° C. (ethanol).

$^1$H-NMR (CDCl3) δ: 1.01 (3H, s), 1.49 (3H, s), 1.90 (3H, s), 2.16 (3H, s), 2.29 (6H, br s), 3.00–3.34 (8H, m), 3.77 (3H, s), 4.07 (1H, s), 6.20–7.40 (4H, m), 6.84 (2H, d, J=9.1 Hz), 6.95 (2H, d, J=9.1 Hz).

EXAMPLE 54

1-(2,2,4,6,7-pentamethyl-3-(2-thienyl)-2,3-dihydro-1-benzofuran-5-yl)-4-(4-methoxyphenyl)piperazine Using 1-(3-hydroxy-2,2,4,6,7-pentamethyl-3-(2-thienyl)-2,3-dihydro-1-benzofuran-5-yl)-4-(4-methoxyphenyl)piperazine obtained in Example 41, the title compound was synthesized in the same manner as in Example 46. Yield 78%. mp. 139–141° C. (ethanol).

$^1$H-NMR (CDCl3) δ: 1.14 (3H, s), 1.48 (3H, s), 2.00 (3H, s), 2.14 (3H, s), 2.28 (3H, s), 3.04–3.34 (8H, m), 3.78 (3H, s), 4.37 (1H, s), 6.66 (1H, d, J=2.7 Hz), 6.85 (2H, d, J=9.0 Hz), 6.90–7.00 (1H, m), 6.95 (2H, d, J=9.0 Hz), 7.15 (1H, dd, J=5.0, 1.1 Hz).

EXAMPLE 55

1-(3-(2-furyl)-2,2,4,6,7-pentamethyl-2,3-dihydro-1-benzofuran-5-yl)-4-(4-methoxyphenyl)piperazine Using 1-(3-(2-furyl)-3-hydroxy-2,2,4,6,7-pentamethyl-2,3-dihydro-1-benzofuran-5-yl)-4-(4-methoxyphenyl)piperazine obtained in Example 42, the title compound was synthesized in the same manner as in Example 46. Yield 67%. mp. 110–111° C. (ethanol).

$^1$H-NMR (CDCl3) δ: 1.15 (3H, s), 1.48 (3H, s), 2.00 (3H, s), 2.12 (3H, s), 2.27 (3H, s), 3.04–3.36 (8H, m), 3.78 (3H, s), 4.24 (1H, s), 5.84–5.90 (1H, m), 6.28 (1H, dd, J=3.0, 1.8 Hz), 6.85 (2H, d, J=9.3 Hz), 6.96 (2H, d, J=9.3 Hz), 7.34 (1H, dd, J=1.8, 0.9 Hz).

EXAMPLE 56

1-(3-cyclohexyl-2,2,4,6,7-pentamethyl-2,3-dihydro-1-benzofuran-5-yl)-4-(4-methoxyphenyl)piperazine A mixture of 1-(3-cyclohexylidene-2,2,4,6,7-pentamethyl-2,3-dihydro-1-benzofuran-5-yl)-4-(4-methoxyphenyl)piperazine hydrochloride obtained in Example 45 (390 mg, 0.79 mmol), 10% palladium-carbon (300 mg) in ethanol (10 ml) and methanol (10 ml) was stirred at room temperature under hydrogen pressure of 4–5 atmospheres for 8 hours. The catalyst was removed by filtration and the filtrate was concentrated under reduced pressure. The residue was diluted with 10% aqueous potassium carbonate, and the aqueous layer was made alkaline and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=20/1) to obtain 95 mg (yield 26%) of the title compound via recrystallization (ethanol). mp. 119–121° C.

$^1$H-NMR (CDCl3) δ: 0.40–2.40 (11H, m), 1.21 (3H, s), 1.56 (3H, s), 2.06 (3H, s), 2.24 (6H, s), 2.64 (1H, d, J=2.6 Hz), 3.02–3.44 (8H, m), 3.79 (3H, s), 6.86 (2H, d, J=9.1 Hz), 6.98 (2H, d, J=9.1 Hz).

EXAMPLE 57

N-benzyl-5-(4-(4-methoxyphenyl)piperazin-1-yl)-2,2,4,6,7-pentamethyl-2,3-dihydro-1-benzofuran-3-amine Methane sulfonyl chloride (0.12 mL, 1.55 mmol) was added dropwise to a solution of 5-(4-(4-methoxyphenyl)

piperazin-1-yl)-2,2,4,6,7-pentamethyl-2,3-dihydro-1-benzofuran-3-ol (300 mg, 0.757 mmol) obtained in Reference Example 18 and triethylamine (0.4 mL, 2.87 mmol) in THF (3 ml) under ice cooling. The reaction mixture was stirred for 10 minutes and then benzylamine (0.4 mL, 3.66 mmol) was added. The resulting mixture was stirred under ice cooling for 1 hour. The reaction mixture was poured into 1N aqueous potassium carbonate and extracted with ethyl acetate. The organic extract was washed with water and saturated aqueous sodium chloride, dried over anhydrous sodium sulfate, and concentrated under reduced pressure. The residue was purified with silica gel column chromatography (hexane then hexane/ethyl acetate=5/1) to obtain 280 mg (yield 76%) of the title compound via recrystallization (ethanol). mp. 93–95° C.

$^1$H-NMR (CDCl3) δ: 1.32 (3H, s), 1.62 (3H, s), 2.08 (3H, s), 2.23 (3H, s), 2.27 (3H, s), 3.00–3.36 (8H, m), 3.78 (5H, s), 3.89 (1H, s), 6.86 (2H, d, J=9.2 Hz), 6.97 (2H, d, J=9.2 Hz), 7.14–7.42 (5H, m).

EXAMPLE 58

N-phenyl-5-(4-(4-methoxyphenyl)piperazin-1-yl)-2,2,4,6,7-pentamethyl-2,3-dihydro-1-benzofuran-3-amine Aniline (120 mg, 1.29 mmol) and p-toluenesulfonic acid monohydrate (25.0 mg, 0.131 mmol) were added to a solution of 5-(4-(4-methoxyphenyl)piperazin-1-yl)-2,2,4,6,7-pentamethyl-2,3-dihydro-1-benzofuran-3-ol (260 mg, 0.656 mmol) obtained in Reference Example 18 in methanol (3 ml) and the mixture was stirred at 60° C. for 120 hours. The resulting mixture was concentrated under reduced pressure. The residue was made to basic with 1N aqueous potassium carbonate and extracted with ethyl acetate. The organic extract was washed with water and saturated aqueous sodium chloride, dried over anhydrous sodium sulfate, and concentrated under reduced pressure. The residue was purified with basic column chromatography (hexane then hexane/ethyl acetate=25/1) to obtain 270 mg (yield 87%) of the title compound via recrystallization (methanol). mp. 90–94° C.

$^1$H-NMR (CDCl3) δ: 1.44 (3H, s), 1.47 (3H, s), 2.11 (3H, s), 2.21 (3H, s), 2.28 (3H, s), 3.00–3.40 (8H, m), 3.75 (1H, d, J=8.4 Hz), 3.78 (3H, s), 4.63 (1H, d, J=8.4 Hz), 6.58 (2H, d, J=7.6 Hz), 6.70 (1H, t, J=7.6 Hz), 6.85 (2H, d, J=9.1 Hz), 6.97 (2H, d, J=9.1 Hz), 7.19 (2H, t, J=7.6 Hz).

EXAMPLE 59

4-(4-methoxyphenyl)-1-(2,2,4,6,7-pentamethyl-3-piperidino-2,3-dihydro-1-benzofuran-5-yl)piperazine Using piperidine and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 57. Yield 80%.

mp. 146–148° C. (ethanol).

$^1$H-NMR (CDCl3) δ: 1.00–3.50 (18H, m), 1.21 (3H, s), 1.50 (3H, s), 2.07 (3H, s), 2.25 (3H, s), 2.30 (3H, s), 3.67 (1H, s), 3.79 (3H, s), 6.87 (2H, d, J=9.0 Hz), 6.98 (2H, d, J=9.0 Hz).

EXAMPLE 60

4-(4-methoxyphenyl)-1-(2,2,4,6,7-pentamethyl-3-(4-phenylpiperidino)-2,3-dihydro-1-benzofuran-5-yl)piperazine Using 4-phenylpiperidine and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 57. Yield 45%.

$^1$H-NMR (CDCl3) δ: 1.24 (3H, s), 1.40–3.50 (17H, m), 1.54 (3H, s), 2.08 (3H, s), 2.26 (3H, s), 2.34 (3H, S), 3.71 (1H, s), 3.79 (3H, s), 6.87 (2H, d, J=9.2 Hz), 6.99 (2H, d, J=9.2 Hz), 7.10–7.40 (5H, m).

EXAMPLE 61

4-(4-methoxyphenyl)-1-(2,2,4,6,7-pentamethyl-3-morpholino-2,3-dihydro-1-benzofuran-5-yl)piperazine Using morpholine and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 57. Yield 80%.

mp. 181–182° C. (ethanol).

$^1$H-NMR (CDCl3) δ: 1.23 (3H, s), 1.54 (3H, s), 1.60–4.00 (16H, m), 2.07 (3H, s), 2.25 (3H, s), 2.32 (3H, s), 3.65 (1H, s), 3.79 (3H, s), 6.87 (2H, d, J=9.2 Hz), 6.99 (2H, d, J=9.2 Hz).

EXAMPLE 62

3-(4-chlorophenyl)-5-(4-(4-methoxyphenyl)piperazin-1-yl)-2,2,4,6,7-pentamethyl-2,3-dihydro-1-benzofuran-3-ol Using 1-bromo-4-chlorobenzene and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 71%. mp. 153–155° C. (hexane).

$^1$H-NMR (CDCl3) δ: 0.87 (3H, s), 1.50 (3H, s), 1.96 (3H, s), 2.10 (1H, s), 2.14 (3H, s), 2.29 (3H, s), 2.98–3.38 (8H, m), 3.77 (3H, s), 6.60–8.20 (4H, m), 6.85 (2H, d, J=9.2 Hz), 6.95 (2H, d, J=9.2 Hz).

EXAMPLE 63

1-(3-(4-chlorophenyl)-2,2,4,6,7-pentamethyl-2,3-dihydro-1-benzofuran-5-yl)-4-(4-methoxyphenyl)piperazine Using 3-(4-chlorophenyl)-5-(4-(4-methoxyphenyl)piperazin-1-yl)-2,2,4,6,7-pentamethyl-2,3-dihydro-1-benzofuran-3-ol obtained in Example 62, the title compound was synthesized in the same manner as in Example 46. Yield 62%. mp. 181–183° C. (ethanol).

$^1$H-NMR (CDCl3) δ: 1.00 (3H, s), 1.49 (3H, s), 1.89 (3H, s), 2.15 (3H, s), 2.28 (3H, s), 3.02–3.32 (8H, m), 3.78 (3H, s), 4.07 (1H, s), 6.40–7.60 (4H, m), 6.85 (2H, d, J=9.3 Hz), 6.96 (2H, d, J=9.3 Hz).

EXAMPLE 64

3-(4-fluorophenyl)-5-(4-(4-methoxyphenyl)piperazin-1-yl)-2,2,4,6,7-pentamethyl-2,3-dihydro-1-benzofuran-3-ol Using 1-bromo-4-fluorobenzene and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 84%. mp. 142–144° C. (hexane).

$^1$H-NMR (CDCl3) δ: 0.86 (3H, s), 1.51 (3H, s), 1.96 (3H, s), 2.10 (1H, s), 2.14 (3H, s), 2.30 (3H, s), 2.98–3.38 (8H, m), 3.77 (3H, s), 6.60–8.20 (4H, m), 6.85 (2H, d, J=9.4 Hz), 6.95 (2H, d, J=9.4 Hz).

EXAMPLE 65

3-(4-(trifluoromethoxy)phenyl)-5-(4-(4-methoxyphenyl)piperazin-1-yl)-2,2,4,6,7-pentamethyl-2,3-dihydro-1-benzofuran-3-ol Using 1-bromo-4-(trifluoromethoxy)benzene and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 82%. mp. 175–176° C. (hexane).

$^1$H-NMR (CDCl3) δ: 0.86 (3H, s), 1.51 (3H, s), 1.96 (3H, s), 2.11 (1H, s), 2.15 (3H, s), 2.30 (3H, s), 3.00–3.38 (8H, m), 3.78 (3H, s), 6.60–8.20 (4H, m), 6.85 (2H, d, J=9.6 Hz), 6.95 (2H, d, J=9.6 Hz).

EXAMPLE 66

3-(4-methoxyphenyl)-5-(4-(4-methoxyphenyl)piperazin-1-yl)-2,2,4,6,7-pentamethyl-2,3-dihydro-1-benzofuran-3-ol Using 4-bromoanisole and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 95%. mp. 157–159° C. (hexane).

$^1$H-NMR (CDCl3) δ: 0.86 (3H, s), 1.51 (3H, s), 1.99 (3H, s), 2.05 (1H, s), 2.15 (3H, s), 2.30 (3H, s), 2.98–3.38 (8H, m), 3.78 (3H, s), 3.82 (3H, s), 6.60–8.20 (4H, m), 6.85 (2H, d, J=9.4 Hz), 6.96 (2H, d, J=9.4 Hz).

EXAMPLE 67

1-(3-(4-(trifluoromethoxy)phenyl)-2,2,4,6,7-pentamethyl-2,3-dihydro-1-benzofuran-5-yl)-4-(4-methoxyphenyl)piperazine Using 3-(4-(trifluoromethoxy)phenyl)-5-(4-(4-methoxyphenyl)piperazin-1-yl)-2,2,4,6,7-pentamethyl-2,3-dihydro-1-benzofuran-3-ol obtained in Example 65, the title compound was synthesized in the same manner as in Example 46. Yield 70%. mp. 147–148° C. (ethanol).

$^1$H-NMR (CDCl3) δ: 1.00 (3H, s), 1.49 (3H, s), 1.90 (3H, s), 2.15 (3H, s), 2.28 (3H, s), 2.98–3.36 (8H, m), 3.77 (3H, s), 4.10 (1H, s), 6.40–7.60 (4H, m), 6.84 (2H, d, J=9.1 Hz), 6.95 (2H, d, J=9.1 Hz).

EXAMPLE 68

4-(4-methoxyphenyl)-1-(3-(4-methoxyphenyl)-2,2,4,6,7-pentamethyl-2,3-dihydro-1-benzofuran-5-yl)piperazine Using 3-(4-methoxyphenyl)-5-(4-(4-methoxyphenyl)piperazin-1-yl)-2,2,4,6,7-pentamethyl-2,3-dihydro-1-benzofuran-3-ol obtained in Example 66, the title compound was synthesized in the same manner as in Example 46. Yield 88%. mp. 205–207° C. (ethanol).

$^1$H-NMR (CDCl3) δ: 1.00 (3H, s), 1.48 (3H, s), 1.91 (3H, s), 2.15 (3H, s), 2.28 (3H, s), 2.98–3.36 (8H, m), 3–0.77—(3H, s), 3.78 (3H, s), 4.06 (1H, s), 6.30–7.60 (4H, m), 6.84 (2H, d, J=9.1 Hz), 6.95 (2H, d, J=9.1 Hz).

EXAMPLE 69

3-(4-(trifluoromethyl)phenyl)-5-(4-(4-methoxyphenyl)piperazin-1-yl)-2,2,4,6,7-pentamethyl-2,3-dihydro-1-benzofuran-3-ol Using 1-bromo-4-(trifluoromethyl)benzene and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 91%. mp. 181–183° C. (hexane).

$^1$H-NMR (CDCl3) δ: 0.86 (3H, s), 1.52 (3H, s), 1.94 (3H, s), 2.15 (3H, s), 2.16 (1H, s), 2.30 (3H, s), 2.98–3.38 (8H, m), 3.77 (3H, s), 6.60–8.20 (4H, m), 6.84 (2H, d, J=9.0 Hz), 6.95 (2H, d, J=9.0 Hz).

EXAMPLE 70

1-(3-(4-(trifluoromethyl)phenyl)-2,2,4,6,7-pentamethyl-2,3-dihydro-1-benzofuran-5-yl)-4-(4-methoxyphenyl)piperazine Using 3-(4-(trifluoromethyl)phenyl)-5-(4-(4-methoxyphenyl)piperazin-1-yl)-2,2,4,6,7-pentamethyl-2,3-dihydro-1-benzofuran-3-ol obtained in Example 69, the title compound was synthesized in the same manner as in Example 46. Yield 93%. mp. 208–211° C. (ethanol).

$^1$H-NMR (CDCl3) δ: 1.00 (3H, s), 1.52 (3H, s), 1.88 (3H, s), 2.16 (3H, s), 2.29 (3H, s), 2.98–3.36 (8H, m), 3.77 (3H, s), 4.16 (1H, s), 6.40–7.80 (4H, m), 6.84 (2H, d, J=9.1 Hz), 6.95 (2H, d, J=9.1 Hz).

EXAMPLE 71

1-(3-(4-fluorophenyl)-2,2,4,6,7-pentamethyl-2,3-dihydro-1-benzofuran-5-yl)-4-(4-methoxyphenyl)piperazine Using 3-(4-fluorophenyl)-5-(4-(4-methoxyphenyl)piperazin-1-yl)-2,2,4,6,7-pentamethyl-2,3-dihydro-1-benzofuran-3-ol obtained in Example 64, the title compound was synthesized in the same manner as in Example 46. Yield 78%. mp. 139–141° C. (ethanol).

$^1$H-NMR (CDCl3) δ: 1.00 (3H, s), 1.49 (3H, s), 1.89 (3H, s), 2.15 (3H, s), 2.28 (3H, s), 2.98–3.36 (8H, m), 3.77 (3H, s), 4.08 (1H, s), 6.30–7.60 (4H, m), 6.84 (2H, d, J=9.3 Hz), 6.95 (2H, d, J=9.3 Hz).

EXAMPLE 72

3-(4-(2,2,4,6,7-pentamethyl-3-(4-methylphenyl)-2,3-dihydro-1-benzofuran-5-yl))piperazin-1-yl)benzoic acid Using ethyl 3-bromobenzoate, the title compound was obtained in the same manner as in Example 16. Yield 16% mp. 175–179° C. (decomposition) (hexane-ethyl acetate).
$^1$H-NMR (CDCl3) δ: 1.00 (3H, s), 1.49 (3H, s), 1.90 (3H, s) 2.15 (3H, s), 2.28 (3H, s), 2.31 (3H, s), 3.15–3.35 (8H, m), 4.08 (1H, s), 6.80 (2H, br), 7.05 (2H, brd, J=7.8 Hz), 7.20–7.38 (2H, m), 7.60 (2H, d, J=6.6 Hz), 7.70 (1H, s).

EXAMPLE 73

5-(4-(4-methoxyphenyl)piperazin-1-yl)-2,2,4,6,7-pentamethyl-3-(4-(dimethylamino)phenyl)-2,3-dihydro-1-benzofuran-3-ol Using 4-bromo-N,N-dimethylaniline and 4-(4-methoxyphenyl)-1-(2,2,4,6,7-pentamethyl-2,3-dihydro-1-benzofuran-3-on-5-yl)piperazine obtained in Reference Example 13, the title compound was synthesized in the same manner as in Example 33. Yield 73%. mp. 144–146° C. (ethyl acetate-hexane).
$^1$H-NMR (CDCl3) δ: 0.87 (3H, s), 1.52 (3H, s), 2.02 (4H, s), 2.15 (3H, s), 2.30 (3H, s), 2.96 (6H, s), 3.02–3.38 (8H, m), 3.78 (3H, s), 6.30–8.00 (4H, m), 6.85 (2H, d, J=9.2 Hz), 6.96 (2H, d, J=9.2 Hz).

EXAMPLE 74

1-(3-(benzyloxy)-2,2,4,6,7-pentamethyl-2,3-dihydro-1-benzofuran-5-yl)-4-(4-methoxyphenyl)piperazine Sodium hydride (60%, 0.06 g, 1.5 mmol) was added to a solution of 5-(4-(4-methoxyphenyl)piperazin-1-yl)-2,2,4,6,7-pentamethyl-2,3-dihydro-1-benzofuran-3-ol (0.30 g, 0.75 mmol) obtained in Reference Example 18 in DMF (5 ml) under ice cooling. The mixture was stirred for 30 minutes, and then benzyl bromide (0.14 g, 0.84 mmol) was added. After stirring for 30 minutes under ice cooling, the mixture was stirred for 30 minutes at room temperature. The resulting mixture was poured into water and extracted with ethyl acetate. The organic extract was washed with water and saturated aqueous sodium chloride, dried over anhydrous sodium sulfate, and concentrated. The residue was purified with silica gel column chromatography (hexane/ethyl acetate=9/1) to obtain 0.23 g (yield 62%) of the title compound via recrystallization (diisopropyl ether-methanol). mp. 98–99° C.
$^1$H-NMR (CDCl3) δ: 1.37 (3H, s), 1.60 (3H, s), 2.08 (3H, s), 2.24 (3H, s), 2.26 (3H, s), 3.09–3.30 (8H, m), 3.79 (3H, s), 4.53 (2H, s), 4.68 (1H, s), 6.86 (2H, d, J=9.0 Hz), 6.97 (2H, d, J=9.0 Hz), 7.26–7.34 (5H, m).

EXAMPLE 75

1-(4-methoxyphenyl)-4-(2,2,4,6,7-pentamethyl-3-(2-pyridylmethyl)oxy-2,3-dihydro-1-benzofuran-5-yl)piperazine Using 2-chloromethylpyridine hydrochloride and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 74. Yield 86%. mp. 120–121° C. (hexane-ethyl acetate). $^1$H-NMR (CDCl3) δ: 1.37 (3H, s), 1.59 (3H, s), 2.09 (3H, s), 2.25 (3H, s), 2.28 (3H, s), 3.05–3.28 (8H, m), 3.79 (3H, s), 4.67 (2H, s), 4.75 (1H, s), 6.86 (2H, d, J=9.2 Hz), 6.97 (2H, d, J=9.2 Hz), 7.15–7.21 (1H, m), 7.48 (1H, d, J=7.6 Hz), 7.68 (1H, t, J=7.6 Hz), 8.52 (1H, d, J=4.4 Hz).

EXAMPLE 76

1-(2,2,4,6,7-pentamethyl-3-(4-methylphenyl)-2,3-dihydro-1-benzofuran-5-yl)-4-(3,5-dimethylphenyl)piperazine Using 5-bromo-m-xylene, the title compound was obtained in the same manner as in Example 16. Yield 46% mp. 147–149° C. (hexane-ethyl acetate).
$^1$H-NMR (CDCl3) δ: 1.00 (3H, s), 1.49 (3H, s), 1.89 (3H, s), 2.15 (3H, s), 2.28 (9H, s), 2.31 (3H, s), 3.15–3.27 (8H, m), 4.08 (1H, s), 6.53 (1H, s), 6.60 (2H, s), 6.80 (2H, br), 7.05 (2H, brd, J=7.4 Hz).

EXAMPLE 77

4-(4-fluorophenyl)-1-(2,2,4,6,7-pentamethyl-3-(4-methylphenyl)-2,3-dihydro-1-benzofuran-5-yl)piperazine Using 4-bromofluorobenzene, the title compound was obtained in the same manner as in Example 17. Yield 38% mp. 159–162° C. (hexane-ethyl acetate).
$^1$H-NMR (CDCl3) δ: 1.00 (3H, s), 1.49 (3H, s), 1.90 (3H, s), 2.15 (3H, s), 2.28 (3H, s), 2.31 (3H, s), 3.07–3.25 (8H, m), 4.08 (1H, s), 6.80 (2H, br), 6.88–6.98 (4H, m), 7.05 (2H, brd, J=7.6 Hz).

EXAMPLE 78

5-(4-(3,4-dimethoxyphenyl)piperidino)-3-(4-methylphenyl)-2,2,4,6,7-pentamethyl-2,3-dihydro-1-benzofuran-3-ol Using 4-bromotoluene and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 89% mp. 133–135° C.
$^1$H-NMR (CDCl3) δ: 0.85 (3H×0.5, s), 0.86 (3H×0.5, s), 1.52 (3H, s), 1.64–2.00 (4H, m), 1.96 (3H×0.5, s), 1.99 (3H×0.5, s), 2.06 (1H×0.5, s), 2.07 (1H×0.5, s), 2.13 (3H×0.5, s), 2.17 (3H×0.5, s), 2.24 (3H×0.5, s), 2.346 (3H, s), 2.353 (3H×0.5, s), 2.40–2.68 (1H, m), 2.84–3.14 (2H, m), 3.16–3.48 (2H, m), 3.86 (3H×0.5, s), 3.87 (3H×0.5, s), 3.88 (3H×0.5, s), 3.91 (3H×0.5, s), 6.00–8.20 (7H, m).

EXAMPLE 79

4-(3,4-dimethoxyphenyl)-1-(3-(4-methylphenyl)-2,2,4,6,7-pentamethyl-2,3-dihydro-1-benzofuran-5-yl)piperidine Using 5-(4-(3,4-dimethoxyphenyl)piperidino)-3-(4-methylphenyl)-2,2,4,6,7-pentamethyl-2,3-dihydro-1-benzofuran-3-ol obtained in Example 78, the title compound was synthesized in the same manner as in Example 46. Yield 51%. mp. 103–105° C. (hexane-methanol).

¹H-NMR (CDCl3) δ: 0.99 (3H×0.5, s), 1.00 (3H×0.5, s), 1.49 (3H, s), 1.62–1.96 (4H, m), 1.89 (3H×0.5, s), 1.91 (3H×0.5, s), 2.14 (3H×0.5, s), 2.17 (3H×0.5, s), 2.22 (3H×0.5, s), 2.31 (3H, s), 2.33 (3H×0.5, s), 2.36–2.68 (1H, m), 2.82–3.08 (2H, m), 3.12–3.46 (2H, m), 3.86 (3H×0. 5, s), 3.87 (3H×0.5, s), 3.88 (3H×0.5, s), 3.91 (3H×0.5, s), 4.08 (1H, s), 6.40–7.40 (7H, m).

EXAMPLE 80

5-(4-(3,4-dimethoxyphenyl)piperidino)-2,2,4,6,7-pentamethyl-3-phenyl-2,3-dihydro-1-benzofuran-3-ol Using bromobenzene and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 96%. mp. 143–145° C. (hexane).

¹H-NMR (CDCl3) δ: 0.85 (3H×0.5, s), 0.86 (3H×0.5, s), 1.53 (3H, s), 1.64–2.00 (4H, m), 1.95 (3H×0.5, s), 1.99 (3H×0.5, s), 2.10 (1H×0.5, s), 2.11 (1H×0.5, s), 2.14 (3H×0.5, s), 2.17 (3H×0.5, s), 2.25 (3H×0.5, s), 2.35 (3H×0.5, s), 2.40–2.68 (1H, m), 2.84–3.14 (2H, m), 3.16–3.48 (–2H, m), 3.86 (3H×0.5, s), 3.87 (3H×0.5, s), 3.88 (3H×0.5, s), 3.91 (3H×0.5, s), 6.30–8.10 (8H, m).

EXAMPLE 81

4-(3,4-dimethoxyphenyl)-1-(2,2,4,6,7-pentamethyl-3-phenyl-2,3-dihydro-1-benzofuran-5-yl)piperidine Using 5-(4-(3,4-dimethoxyphenyl)piperidino)-2,2,4,6,7-pentamethyl-3-phenyl-2,3-dihydro-1-benzofuran-3-ol obtained in Example 80, the title compound was synthesized in the same manner as in Example 46. Yield 65%. mp. 118–120° C. (ethanol).

¹H-NMR (CDCl3) δ: 0.99 (3H×0.5, s), 1.00 (3H×0.5, s), 1.51 (3H, s), 1.62–2.00 (4H, m), 1.88 (3H×0.5, s), 1.90 (3H×0.5, s), 2.14 (3H×0.5, s), 2.17 (3H×0.5, s), 2.23 (3H×0.5, s), 2.33 (3H×0.5, s), 2.36–2.68 (1H, m), 2.82–3.08 (2H, m), 3.12–3.46 (2H, m), 3.86 (3H×0.5, s), 3.87 (3H×0.5, s), 3.88 (3H×0.5, s), 3.90 (3H×0.5, s), 4.11 (1H×0.5, s), 4.12 (1H×0.5, s), 6.00–8.00 (8H, m).

EXAMPLE 82

3-(4-fluorophenyl)-5-(4-(3,4-dimethoxyphenyl)piperidino)-2,2,4,6,7-pentamethyl-2,3-dihydro-1-benzofuran-3-ol Using 1-bromo-4-fluorobenzene and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 99%. mp. 150–152° C. (hexane)

¹H-NMR (CDCl3) δ: 0.85 (3H, s), 1.51 (3H, s), 1.64–2.00 (4H, m), 1.94 (3H×0.5, s), 1.98 (3H×0.5, s), 2.10 (1H×0.5, s), 2.11 (1H×0.5, s), 2.13 (3H×0.5, s), 2.16 (3H×0.5, s), 2.24 (3H×0.5, s), 2.34 (3H×0.5, s), 2.40–2.68 (1H, m), 2.84–3.14 (2H, m), 3.16–3.48 (2H, m), 3.86 (3H×0.5, s), 3.87 (3H×0.5, s), 3.88 (3H×0.5, s), 3.91 (3H×0.5, s), 6.20–8.20 (7H, m).

EXAMPLE 83

3-(4-isopropylphenyl)-5-(4-(3,4-dimethoxyphenyl)piperidino)-2,2,4,6,7-pentamethyl-2,3-dihydro-1-benzofuran-3-ol Using 1-bromo-4-isopropyl benzene and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 94%. Amorphous powder.

¹H-NMR (CDCl3) δ: 0.84 (3H×0.5, s), 0.85 (3H×0.5, s), 1.25 (6H, d, J=7.0 Hz), 1.52 (3H, s), 1.64–2.00 (4H, m), 1.96 (3H×0.5, s), 2.00 (3H×0.5, s), 2.08 (1H×0.5, s), 2.10 (1H×0.5, s), 2.13 (3H×0.5, s), 2.17 (3H×0.5, s), 2.24 (3H×0.5, s), 2.35 (3H×0.5, s), 2.40–2.68 (1H, m), 2.76–3.14 (3H, m), 3.16–3.48 (2H, m), 3.85 (3H×0.5, s), 3.87 (–3H×0.5, s), 3.88 (3H×0.5, s), 3.91 (3H×0.5, s), 6.20–8.00 (7H, m).

EXAMPLE 84

1-(3-(4-isopropylphenyl)-2,2,4,6,7-pentamethyl-2,3-dihydro-1-benzofuran-5-yl)-4-(3,4-dimethoxyphenyl)piperidine Using 3-(4-isopropylphenyl)-5-(4-(3,4-dimethoxyphenyl)piperidino)-2,2,4,6,7-pentamethyl-2,3-dihydro-1-benzofuran-3-ol obtained in Example 83, the title compound was synthesized in the same manner as in Example 46. Yield 90%. mp. 129–132° C. (hexane-methanol).

¹H-NMR (CDCl3) δ: 0.98 (3H, s), 1.22 (6H, d, J=7.0 Hz), 1.49 (3H, s), 1.62–2.00 (4H, m), 1.89 (3H×0.5, s), 1.91 (3H×0.5, s), 2.13 (3H×0.5, s), 2.17 (3H×0.5, s), 2.22 (3H×0.5, s), 2.33 (3H×0.5, s), 2.36–2.68 (1H, m), 2.70–3.08 (3H, m), 3.12–3.46 (2H, m), 3.86 (3H×0.5, s), 3.87 (3H×0.5, s), 3.88 (3H×0.5, s), 3.90 (3H×0.5, s), 4.09 (1H, s), 6.20–7.80 (7H, m).

EXAMPLE 85

3-(4-methoxyphenyl)-5-(4-(3,4-dimethoxyphenyl)piperidino)-2,2,4,6,7-pentamethyl-2,3-dihydro-1-benzofuran-3-ol Using 4-bromo anisole and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 98%. Amorphous powder.

¹H-NMR (CDCl3) δ: 0.85 (3H×0.5, s), 0.86 (3H×0.5, s), 1.51 (3H, s), 1.64–2.00 (4H, m), 1.97 (3H×0.5, s), 2.00 (3H×0.5, s), 2.08 (1H×0.5, s), 2.10 (1H×0.5, s), 2.13 (3H×0.5, s), 2.17 (3H×0.5, s), 2.24 (3H×0.5, s), 2.34 (3H×0.5, s), 2.40–2.68 (1H, m), 2.84–3.14 (2H, m), 3.16–3.48 (2H, m), 3.81 (3H×0.5, s), 3.82 (3H×0.5, s), 3.86 (3H×0.5, s), 3.87 (3H×0.5, s), 3.88 (3H×0.5, s), 3.91 (3H×0.5, s), 6.00–8.20 (7H, m).

EXAMPLE 86

1-(3-(4-methoxyphenyl)-2,2,4,6,7-pentamethyl-2,3-dihydro-1-benzofuran-5-yl)-4-(3,4-dimethoxyphenyl)piperidine Using 3-(4-methoxyphenyl)-5-(4-(3,4-dimethoxyphenyl)piperidino)-2,2,4,6,7-pentamethyl-2,3-dihydro-1-benzofuran-3-ol obtained in Example 85, the title compound was synthesized in the same manner as in Example 46. Yield 82%. mp. 154–156° C. (hexane-methanol).

$^1$H-NMR (CDCl3) δ: 1.00 (3H, s), 1.48 (3H, s), 1.62–2.00 (4H, m), 1.89 (3HX0.5, s), 1.91 (3HX0.5, s), 2.13 (3HX0.5, s), 2.17 (3HX0.5, s), 2.22 (3HX0.5, s), 2.33 (3HX0.5, s), 2.36–2.68 (1H, m), 2.82–3.08 (2H, m), 3.12–3.46 (2H, m), 3.778 (3HX0.5, s), 3.784 (3HX0.5, s), 3.86 (3HX0.5, s), 3.87 (3HX0.5, s), 3.88 (3HX0.5, s), 3.91 (3HX0.5, s), 4.07 (1HX0.5, s), 4.08 (1HX0.5, s), 6.20–7.80 (7H, m)

EXAMPLE 87

1-(3-(4-fluorophenyl)-2,2,4,6,7-pentamethyl-2,3-dihydro-1-benzofuran-5-yl)-4-(3,4-dimethoxyphenyl)piperidine Using 3-(4-fluorophenyl)-5-(4-(3,4-dimethoxyphenyl)piperidino)-2,2,4,6,7-pentamethyl-2,3-dihydro-1-benzofuran-3-ol obtained in Example 82, the title compound was synthesized in the same manner as in Example 46. Yield 72%. Amorphous powder.

$^1$H-NMR (CDCl3) δ: 0.99 (3H, s), 1.49 (3H, s), 1.62–2.00 (4H, m), 1.88 (3HX0.5, s), 1.90 (3HX0.5, s), 2.13 (3HX0.5, s), 2.16 (3HX0.5, s), 2.22 (3HX0.5, s), 2.32 (3HX0.5, s), 2.36–2.68 (1H, m), 2.82–3.08 (2H, m), 3.12–3.46 (2H, m), 3.86 (3HX0.5, s), 3.87 (3HX0.5, s), 3.88 (3HX0.5, s), 3.91 (3HX0.5, s), 4.09 (1HX0.5, s), 4.10 (1HX0.5, s), 6.20–7.80 (7H, m).

EXAMPLE 88

5-(4-(3,4-dimethoxyphenyl)piperidino)-2,2,4,6,7-pentamethyl-3-(3-thienyl)-2,3-dihydro-1-benzofuran-3-ol Using 3-bromothiophene and 5-(4-(3,4-dimethoxyphenyl)piperidino)-2,2,4,6,7-pentamethyl-2,3-dihydro-1-benzofuran-3(2H)-one obtained in Reference Example 17, the title compound was synthesized in the same manner as in Example 33. Yield 91%. mp. 125–128° C. (hexane).

$^1$H-NMR (CDCl3) δ: 0.96 (3HX0.5, s), 0.97 (3HX0.5, s), 1.52 (3H, s), 1.64–2.00 (4H, m), 2.00 (3HX0.5, s), 2.03 (3HX0.5, s), 2.11 (1H, s), 2.12 (3HX0.5, s), 2.16 (3HX0.5, s), 2.23 (3HX0.5, s), 2.33 (3HX0.5, s), 2.40–2.68 (1H, m), 2.84–3.14 (2H, m), 3.16–3.48 (2H, m), 3.86 (3HX0.5, s), 3.87 (3HX0.5, s), 3.89 (3HX0.5, s), 3.91 (3HX0.5, s), 6.70–7.36 (6H, m).

EXAMPLE 89

4-(3,4-dimethoxyphenyl)-1-(2,2,4,6,7-pentamethyl-3-(3-thienyl)-2,3-dihydro-1-benzofuran-5-yl)piperidine Using 5-(4-(3,4-dimethoxyphenyl)piperidino)-2,2,4,6,7-pentamethyl-3-(3-thienyl)-2,3-dihydro-1-benzofuran-3-ol obtained in Example 88 the title compound was synthesized in the same manner as in Example 46. Yield 82% mp. 111–113° C. (hexane-methanol).

$^1$H-NMR (CDCl3) δ: 1.10 (3H, s), 1.51 (3H, s), 1.62–2.00 (4H, m), 1.96 (3HX0.5, s), 1.98 (3HX0.5, s), 2.15 (3HX0.5, s), 2.18 (3HX0.5, s), 2.24 (3HX0.5, s), 2.34 (3HX0.5, s), 2.36–2.68 (1H, m), 2.82–3.12 (2H, m), 3.14–3.48 (2H, m), 3.89 (3HX0.5, s), 3.90 (3HX0.5, s), 3.91 (3HX0.5, s), 3.93 (3HX0.5, s), 4.25 (1HX0.5, s), 4.26 (1HX0.5, s), 6.66–6.96 (5H, m), 7.14–7.34 (1H, m).

EXAMPLE 90

N-phenyl-5-(4-(3,4-dimethoxyphenyl)piperidino)-2,2,4,6,7-pentamethyl-2,3-dihydro-1-benzofuran-3-amine Using aniline and 5-(4-(3,4-dimethoxyphenyl)piperidino)-2,2,4,6,7-pentamethyl-2,3-dihydro-1-benzofuran-3-ol obtained in Reference Example 19, the title compound was synthesized in the same manner as in Example 58. Yield 60%. mp. 138–140° C. (methanol).

$^1$H-NMR (CDCl3) δ: 1.44 (3H, s), 1.47 (3H, s), 1.70–1.96 (4H, m), 2.10 (3HX0.5, s), 2.13 (3HX0.5, s), 2.21 (3HX1.5, s), 2.32 (3HX0.5, s), 2.36–2.70 (1H, m), 2.86–3.08 (2H, m), 3.18–3.48 (2H, m), 3.68–3.84 (1H, m), 3.87 (3HX0.5, s), 3.88 (3HX0.5, s), 3.90 (3HX0.5, s), 3.91 (3HX0.5, s), 4.63 (1H, d, J=8.0 Hz), 6.59 (2H, d, J=7.7 Hz), 6.70 (1H, t, J=7.7 Hz), 6.74–6.90 (3H, m), 7.20 (2H, t, J=7.7 Hz).

EXAMPLE 91

N-benzyl-5-(4-(3,4-dimethoxyphenyl)piperidino)-2,2,4,6,7-pentamethyl-2,3-dihydro-1-benzofuran-3-amine Using benzylamine and 5-(4-(3,4-dimethoxyphenyl)piperidino)-2,2,4,6,7-pentamethyl-2,3-dihydro-1-benzofuran-3-ol obtained in Reference Example 19, the title compound was synthesized in the same manner as in Example 57. Yield 80%. Amorphous state powder.

$^1$H-NMR (CDCl3) δ: 1.32 (3H, s), 1.61 (3H, s), 1.62–2.00 (4H, m), 2.06 (3HX0.5, s), 2.10 (3HX0.5, s), 2.18 (3HX0.5, s), 2.26 (3HX0.5, s), 2.27 (3HX0.5, s), 2.28 (3HX0.5, s), 2.40–2.68 (1H, m), 2.84–3.08 (2H, m), 3.16–3.46 (2H, m), 3.79 (2H, d, J=1.8 Hz), 3.84–3.96 (1H, m), 3.87 (3H, s), 3.91 (3H, s), 6.76–6.92 (3H, m), 7.14–7.46 (5H, m).

EXAMPLE 92

3-(5-(4-[3,4-dimethoxyphenyl]piperidino)-2,2,4,6,7-pentamethyl-2,3-dihydro-1-benzofuran-3-yl)-2,3,4,5-tetrahydro-1H-3-benzoazepin Using 2,3,4,5-tetrahydro-1H-3-benzazepine and 5-(4-(3,4-dimethoxyphenyl)piperidino)-2,2,4,6,7-pentamethyl-2,3-dihydro-1-benzofuran-3-ol obtained in Reference Example 19, the title compound was synthesized in the same manner as in Example 57. Yield 54%. mp. 136–138° C. (hexane-methanol).

$^1$H-NMR (CDCl3) δ: 1.24 (3H, s), 1.53 (3HX0.5, s), 1.54 (3HX0.5, s), 1.62–2.00 (4H, m), 2.07 (3HX0.5, s), 2.11 (3HX0.5, s), 2.19 (3HX0.5, s), 2.25 (3H, s), 2.30 (3HX0.5, s), 2.34–3.50 (13H, m), 3.70–4.06 (1H, m), 3.87 (3H, s), 3.90 (3HX0.5, s), 3.91 (3HX0.5, s), 6.66–7.24 (7H, m).

EXAMPLE 93

1-(7-(1,3-dioxolan-2-yl)-2,2,4,6-tetramethyl-3-(4-methylphenyl)-2,3-dihydro-1-benzofuran-5-yl)-4-(4-methoxyphenyl)piperazine Using 5-bromo-7-(1,3-dioxolan-2-yl)-2,2,4,6-tetramethyl-3-(4-methylphenyl)-2,3-dihydro-1-benzofuran obtained in Reference Example 34 and 1-(4-methoxyphenyl)piperazine, the title compound was obtained in the same manner as in Reference Example 13. Yield 59%

Amorphous powder.

¹H-NMR (CDCl3) δ: 0.99 (3H, s), 1.47 (3H, s), 1.92 (3H, s), 2.31 (3H, s), 2.44 (3H, s), 3.03–3.30 (8H, m), 3.77 (3H, s), 3.99–4.32 (5H, m), 6.18 (1H, s), 6.40–7.20 (8H, m).

EXAMPLE 94

1-(2,2,4,6,7-pentamethyl-3-(4-methylphenyl)-2,3-dihydro-1-benzofuran-5-yl)-3-phenylpyrrolidine-2,5-dione A solution of 2,2,4,6,7-pentamethyl-3-(4-methylphenyl)-2,3-dihydro-1-benzofuran-5-amine (2.95 g, 10 mmol) and phenylsuccinic anhydride (1.94 g, 11 mmol) in toluene was refluxed for 6 hours. The reaction mixture was concentrated under reduced pressure. The residue was diluted with water and extracted with ethyl acetate. The extract was washed with saturated aqueous sodium chloride, dried over anhydrous sodium sulfate. The solvent was removed under reduced pressure. A mixture of the residue and sodium acetate (0.86 g, 10.5 mmol) in acetic anhydride (60 ml) was stirred at 90° C. for 1 hour. The reaction mixture was concentrated under reduced pressure. The residue was diluted with water and extracted with ethyl acetate. The extract was washed with saturated aqueous sodium chloride, dried over anhydrous sodium sulfate, and removed under reduced pressure. The residue was purified with silica gel column chromatography (hexane/ethyl acetate=4/1) to obtain 2.27 g (yield 50%) of the title compound. mp. 130–131° C. low polarity product, ¹H-NMR (CDCl3) δ: 1.00 (3H, s)=1.52 (3H, s), 1.64 (3H, s), 2.02 (3H, s), 2.16 (3H, s), 2.30 (3H, s), 3.00 (1H, dd, J=4.7, 18.5 Hz), 3.36 (1H, dd, J=9.5, 18.5 Hz), 4.15–4.25 (2H, m), 6.85 (2H, br), 7.06 (2H, brd, J=6.6 Hz), 7.30–7.47 (5H, m).

EXAMPLE 95

1-(2,2,4,6,7-tetramethyl-3-(4-methylphenyl)-2,3-dihydro-1-benzofuran-5-yl)-3-phenylpyrrolidine To a solution of aluminum chloride (3.33 g, 25 mmol) and lithium aluminium hydride (0.95 g, 25 mmol) in THF (30 ml) at 0° C. was added 1-(2,2,4,6,7-pentamethyl-3-(4-methylphenyl)-2,3-dihydro-1-benzofuran-5-yl)-3-phenylpyrrolidine-2,5-dione (2.27 g, 5 mmol) obtained in Example 94. The mixture was refluxed for 1 hour. The excess reducing agent was decomposed using saturated aqueous sodium chloride at 0° C. and the insoluble was removed by filtration. The filtrate was diluted with water and extracted with ethyl acetate. The extract was washed with saturated aqueous sodium chloride, dried over anhydrous sodium sulfate, and removed under reduced pressure. The residue was purified with silica gel column chromatography (hexane/ethyl acetate=8/1) to obtain 1.21 g (yield 57%) of the title compound. mp. 73–76° C.

¹H-NMR (CDCl3) δ: 1.05 (3H, s), 1.48 (3H, s), 1.91 (3H, s), 2.20 (3H, s), 2.31 (3H, s), 2.40–2.81 (4H, m), 3.31–3.85 (2H, m), 4.09 (1H, s), 4.25 (1H, br), 4.78 (1H, br), 4.97 (1H, br), 6.70 (2H, br), 7.06 (2H, br), 7.22–7.40 (3H, m), 7.76 (1H, br).

EXAMPLE 96

1-(4-methoxyphenyl)-4-(2,2,4,6,7-pentamethyl-3-(4-methylpiperazin-1-yl)-2,3-dihydro-1-benzofuran-5-yl)piperazine Using 5-(4-(4-methoxyphenyl)piperazin-1-yl)-2,2,4,6,7-pentamethyl-2,3-dihydro-1-benzofuran-3-ol obtained in Reference Example 18 and 1-methylpiperazine, the title compound was obtained in the same manner as in Example 57.

Yield 52% mp. 94–96° C. (methanol).

¹H-NMR (CDCl3) δ: 1.22 (3H, s), 1.50 (3H, s), 1.82–2.72 (18H, m), 2.82–3.35 (10H, m), 3.70 (1H, s), 3.79 (3H, s), 6.87 (2H, d, J=9.0 Hz), 6.98 (2H, d, J=9.0 Hz).

EXAMPLE 97

5-(4-(4-methoxyphenyl)piperazin-1-yl)-4-(2,2,4,6,7-pentamethyl-3-(3-pyridyl)-2,3-dihydro-1-benzofuran-3-ol Using 5-(4-(4-methoxyphenyl)-4-(4-methoxyphenyl)-1-(2,2,4,6,7-pentamethyl-2,3-dihydro-1-benzofuran-3-on-5-yl)piperazine obtained in Reference Example 13 and 3-bromopyridine, the title compound was obtained in the same manner as in Example 33. Yield 27% mp. 210–212° C. (hexane-ethyl acetate).

¹H-NMR (CDCl3) δ: 0.89 (3H, s), 1.53 (3H, s), 1.95 (3H, s), 2.15 (3H, s), 2.26 (1H, s), 2.30 (3H, s), 3.08–3.35 (8H, m), 3.77 (3H, s), 6.85 (2H, d, J=9.0 Hz), 6.95 (2H, d, J=9.0 Hz), 7.28 (1H, br s), 8.10 (2H, br s), 8.52 (1H, d, J=6.2 Hz).

EXAMPLE 98

1-(4-methoxyphenyl)-4-(2,2,4,6,7-pentamethyl-3-(3-pyridyl)-2,3-dihydro-1-benzofuran-5-yl)piperazine Using 5-(4-(4-methoxyphenyl)piperazin-1-yl)-4-(2,2,4,6,7-pentamethyl-3-(3-pyridyl)-2,3-dihydro-1-benzofuran-3-ol obtained in Example 97, the title compound was obtained in the same manner as in Example 46. Yield 79% mp. 159–161° C. (hexane-ethyl acetate).

¹H-NMR (CDCl3) δ: 1.03 (3H, s), 1.52 (3H, s), 1.90 (3H, s), 2.15 (3H, s), 2.28 (3H, s), 3.05–3.27 (8H, m), 3.77 (3H, s), 4.12 (1H, s), 6.84 (2H, d, J=9.0 Hz), 6.94 (2H, d, J=9.0 Hz), 7.14–7.22 (2H, m), 8.30 (1H, br s), 8.47 (1H, t, J=3.0 Hz).

EXAMPLE 99

1-(4-methoxyphenyl)-4-(2,2,4,6,7-pentamethyl-3-(pyrrolidinyl)-2,3-dihydro-1-benzofuran-5-yl)piperazine Using 5-(4-(4-methoxyphenyl)piperazin-1-yl)-2,2,4,6,7-pentamethyl-2,3-dihydro-1-benzofuran-3-ol and pyrrolidine obtained in Reference Example 18, the title compound was obtained in the same manner as in Example 57. Yield 48% mp. 124–126° C. (methanol).

¹H-NMR (CDCl3) δ: 1.24 (3H, s), 1.48 (3H, s), 1.62–1.78 (4H, m), 2.07 (3H, s), 2.20 (3H, s), 2.25 (3H, s), 2.48–2.75 (4H, m), 3.08–3.35 (8H, m), 3.78 (3H, s), 3.98 (1H, s), 6.85 (2H, d, J=9.0 Hz), 6.96 (2H, d, J=9.0 Hz).

EXAMPLE 100

1-(5-(4-(4-methoxyphenyl)piperazin-1-yl)-2,2,4,6,7-pentamethyl-2,3-dihydro-1-benzofuran-3-yl)indoline Using 5-(4-(4-methoxyphenyl)piperazin-1-yl)-2,2,4,6,7-pentamethyl-2,3-dihydro-1-benzofuran-3-ol obtained in Reference Example 18 and indoline, the title compound was obtained in the same manner as in Example 57. Yield 33% mp. 166–168° C. (methanol).

$^1$H-NMR (CDCl3) δ: 1.40 (6H, s), 2.08 (3H, s), 2.10 (3H, s), 2.27 (3H, s), 2.82–2.97 (3H, m), 3.05–3.30 (9H, m), 3.77 (3H, s), 4.69 (1H, s), 6.42 (1H, d, J=8.1 Hz), 6.55 (1H, d, J=7.2 Hz), 6.84 (2H, d, J=9.0 Hz), 6.91–7.09 (4H, m).

EXAMPLE 101

1-(5-(4-(4-methoxyphenyl)piperazin-1-yl)-2,2,4,6,7-pentamethyl-2,3-dihydro-1-benzofuran-3-yl)-1,2,3,4-tetrahydroquinoline Using 5-(4-(4-methoxyphenyl)piperazin-1-yl)-2,2,4,6,7-pentamethyl-2,3-dihydro-1-benzofuran-3-ol obtained in Reference Example 18 and 1,2,3,4-tetrahydroquinoline, the title compound was obtained in the same manner as in Example 57. Yield 52% mp. 188–190° C. (methanol).

$^1$H-NMR (CDCl3) δ: 1.39 (3H, s), 1.46 (3H, s), 1.68–1.82 (2H, m), 2.08 (3H, s), 2.11 (3H, s), 2.28 (3H, s), 2.60–2.90 (4H, m), 3.00–3.38 (8H, m), 3.78 (3H, s), 4.90 (1H, s), 6.56 (1H, d, J=7.0 Hz), 6.64 (1H, d, J=8.2 Hz), 6.85 (2H, d, J=9.2 Hz), 6.93–7.02 (3H, m), 7.08 (1H, t, J=8.2 Hz).

EXAMPLE 102

2-(5-(4-(4-methoxyphenyl)piperazin-1-yl)-2,2,4,6,7-pentamethyl-2,3-dihydro-1-benzofuran-3-yl)-1, 2, 3, 4-tetrahydroisoquinoline Using 5-(4-(4-methoxyphenyl)piperazin 1-yl)-2,2,4,6,7-pentamethyl-2,3-dihydro-1-benzofuran-3-ol obtained in Reference Example 18 and 1,2,3,4-tetrahydroisoquinoline, the title compound was obtained in the same manner as in Example 57. Yield 63% mp. 144–145° C. (methanol).

$^1$H-NMR (CDCl3) δ: 1.27 (3H, s), 1.52 (3H, s), 2.12 (3H, s), 2.27 (3H, s), 2.29 (3H, s), 1.68–1.82 (2H, m), 2.50–3.60 (13H, m), 3.78 (3H, s), 3.92 (1H, s), 4.18 (1H, br s), 6.85 (1H, d, J=9.0 Hz), 6.96 (1H, d, J=9.0 Hz), 7.07 (4H, s).

EXAMPLE 103

5-(4-(4-methoxyphenyl)piperazin-1-yl)-2,2,4,6,7-pentamethyl-3-(2-pyridyl)-2,3-dihydro-1-benzofuran-3-ol Using 4-(4-methoxyphenyl)-1-(2,2,4,6,7-pentamethyl-2, 3-dihydro-1-benzofuran-3-on-5-yl)piperazine obtained in Reference Example 13 and 2-bromopyridine, the title compound was obtained in the same manner as in Example 33.

Yield 34% mp. 113–115° C. (hexane-ethyl acetate).

$^1$H-NMR (CDCl3) δ: 0.90 (3H, s), 1.51 (3H, s), 1.91 (3H, s), 2.15 (3H, s), 2.28 (3H, s), 3.07–3.30 (8H, m), 3.76 (3H, s), 5.92 (1H, br s), 6.78–7.01 (5H, m), 7.16–7.01 (1H, m), 7.60 (1H, dt, J=7.8, 1.5 Hz), 8.56 (1H, dd, J=5.1, 1.5 Hz).

EXAMPLE 104

1-(4-methoxyphenyl)-4-(2,2,4,6,7-pentamethyl-3-(2-pyridyl)-2,3-dihydro-1-benzofuran-5-yl)piperazine Using 5-(4-(4-methoxyphenyl)piperazin-1-yl)-2,2,4,6,7-pentamethyl-3-(2-pyridyl)-2,3-dihydro-1-benzofuran-3-ol obtained in Example 103, the title compound was obtained in the same manner as in Example 46. Yield 37% mp. 123–125° C. (hexane-ethyl acetate).

$^1$H-NMR (CDCl3) δ: 1.04 (3H, s), 1.55 (3H, s), 1.91 (3H, s), 2.15 (3H, s), 2.28 (3H, s), 3.05–3.30 (8H, m), 3.77 (3H, s), 4.37 (1H, s), 6.75 (1H, d, J=7.8 Hz), 6.83 (2H, d, J=9.0 Hz), 6.94 (2H, d, J=9.0 Hz), 7.08–7.16 (1H, m), 7.53 (1H, dt, J=7.8, 1.8 Hz), 8.55 (1H, d, J=5.6 Hz).

EXAMPLE 105

5-(4-(4-methoxyphenyl)piperazin-1-yl)-2,2,4,6-tetramethyl-3-(4-methylphenyl)-2,3-dihydro-1-benzofuran-7-carbaldehyde Pyridinium p-toluenesulfonate (20 mg, 80 mmol) was added to a solution of 1-(7-(1,3-dioxolan-2-yl)-2,2,4,6-tetramethyl-3-(4-methylphenyl)-2,3-dihydro-1-benzofuran-5-yl)-4-(4-methoxyphenyl)piperazine (1.41 g, 2.67 mmol) obtained in Example 93 in acetone (15 ml) and water (1 ml) and the mixture was refluxed for 30 minutes. The reaction mixture was concentrated under reduced pressure. The residue was diluted with water and extracted with ethyl acetate. The organic extract was washed with water and saturated aqueous sodium chloride, dried over anhydrous sodium sulfate, and concentrated under reduced pressure. The residue was crystallized from hexane-ethyl acetate to obtain 1.04 g (yield 81%) of the title compound. mp. 175–177° C.

$^1$H-NMR (CDCl3) δ: 1.06 (3H, s), 1.54 (3H, s), 1.98 (3H, s), 2.32 (3H, s), 2.64 (3H, s), 3.00–3.30 (8H, m), 3.77 (3H, s), 4.07 (1H, s), 6.60–7.17 (8H, m), 10.4 (1H, s).

EXAMPLE 106

1-(5-(4-(4-methoxyphenyl)piperazin-1-yl)-2,2,4,6-tetramethyl-3-(4-methylphenyl)-2,3-dihydro-1-benzofuran-7-yl) ethanol To a solution of methyl magnesium bromide (THF solution 3.0 M, 1.0 mL, 3.0 mmol) in THF (5 ml) at −30° C. was added 5-(4-(4-methoxyphenyl)piperazin-1-yl)-2,2,4,6-tetramethyl-3-(4-methylphenyl)-2,3-dihydro-1-benzofuran-7-carbaldehyde (310 mg, 640 mmol) obtained in Example 105. The reaction mixture was stirred for 20 minutes under the same temperature. The resulting mixture was poured into water and extracted with ethyl acetate. The organic extract was washed with water and saturated aqueous sodium chloride, dried over anhydrous sodium sulfate, and concentrated under reduced pressure. The residue was crystallized from hexane-ethyl acetate to obtain 19.5 mg (yield 61%) of the title compound. mp. 149–151° C.

$^1$H-NMR (CDCl3) δ: 1.02 (3H, s), 1.50–1.60 (6H, m), 1.91 (3H, s), 2.31 (6H, s), 2.26 (1H, s), 3.00–3.30 (8H, m), 3.77 (3H, s), 3.92–4.04 (1H, m), 4.97–5.10 (1H, m), 6.50–7.17 (8H, m).

EXAMPLE 107

1-(5[4-(4-methoxyphenyl]piperazin-1-yl)-2,2,4,6,7-pentamethyl-2,3-dihydro-1-benzofuran-3-yl)-2,3,4,5,6,7-hexahydro-1H-azepin Using 5-(4-(4-methoxyphenyl)piperazin-1-yl)-2,2,4,6,7-pentamethyl-2,3-dihydro-1-benzofuran-3-ol obtained in Reference Example 18 and 2,3,4,5,6,7-hexahydro-1H-azepin, the title compound was obtained in the same manner as in Example 57. Yield 52% mp. 127–128° C. (methanol).

$^1$H-NMR (CDCl3) δ: 1.00–1.80 (14H, m), 2.08 (3H, s), 2.20–2.60 (8H, m), 2.83–3.37 (10H, m), 3.79 (3H, s), 3.86 (1H, s), 6.86 (2H, d, J=9.2 Hz), 6.98 (2H, d, J=9.2 Hz).

EXAMPLE 108

1-ethyl-4-(5-(4-(4-methoxyphenyl)piperazin-1-yl)-2,2,4,6,7-pentamethyl-2,3-dihydro-1-benzofuran-3-yl)piperazine Using 5-(4-(4-methoxyphenyl)piperazin-1-yl)-2,2,4,6,7-pentamethyl-2,3-dihydro-1-benzofuran-3-ol obtained in Reference Example 18 and 1-ethyl piperazine, the title compound was obtained in the same manner as in Example 57.

Yield 46-% mp. 98–100° C. (methanol).

$^1$H-NMR (CDCl3) δ: 1.04 (3H, t, J=7.2 Hz), 1.21 (3H, s), 1.51 (3H, s), 1.85–3.30 (27H, m), 3.69 (1H, s), 3.78 (3H, s), 6.85 (2H, d, J=9.0 Hz), 6.97 (2H, d, J=9.0 Hz).

EXAMPLE 109

1-acetyl-4-(5-(4-(4-methoxyphenyl)-1-piperazinyl)-(2,2,4,6,7-pentamethyl-2,3-dihydro-1-benzofuran-3-yl)piperazine Using 5-(4-(4-methoxyphenyl)piperazin-1-yl)-2,2,4,6,7-pentamethyl-2,3-dihydro-1-benzofuran-3-ol obtained in Reference Example 18 and 1-acetyl piperazine, the title compound was obtained in the same manner as in Example 57.

Yield 60% mp. 178–179° C. (methanol).

$^1$H-NMR (CDCl3) δ: 1.23 (3H, s), 1.52 (3H, s), 2.03 (3H, s), 2.07 (3H, s), 2.25 (3H, s), 2.27 (3H, s), 2.40–3.40 (16H, m), 3.71 (1H, s), 3.78 (3H, s), 6.86 (2H, d, J=9.2 Hz), 6.98 (2H, d, J=9.2 Hz).

EXAMPLE 110

1-(5-(4-(4-methoxyphenyl)piperazin-1-yl)-(2,2,4,6,7-pentamethyl-2,3-dihydro-1-benzofuran-3-yl)-4-phenylpiperazine Using 5-(4-(4-methoxyphenyl)piperazin-1-yl)-2,2,4,6,7-pentamethyl-2,3-dihydro-1-benzofuran-3-ol obtained in Reference Example 18 and 1-phenylpiperazine, the title compound was obtained in the same manner as in Example 57.

Yield 45% mp. 144–145° C. (hexane-ethyl acetate).

$^1$H-NMR (CDCl3) δ: 1.25 (3H, s), 1.54 (3H, s), 2.09 (3H, s), 2.26 (3H, s), 2.33 (3H, s), 2.40–3.37 (16H, m), 3.76 (1H, s), 3.78 (3H, s), 6.80–7.02 (7H, m), 7.21 (2H, d, J=8.6 Hz).

EXAMPLE 111

1-benzyl-4-(5-(4-(4-methoxyphenyl)piperazin-1-yl)-2,2,4,6,7-pentamethyl-2,3-dihydro-1-benzofuran-3-yl)piperazine Using 5-(4-(4-methoxyphenyl)piperazin-1-yl)-2,2,4,6,7-pentamethyl-2,3-dihydro-1-benzofuran-3-ol obtained in Reference Example 18 and 1-benzylpiperazine, the title compound was obtained in the same manner as in Example 57.

Yield 46% mp. 112–116° C. (methanol).

$^1$H-NMR (CDCl3) δ: 1.20 (3H, s), 1.50 (3H, s), 1.80–3.38 (25H, m), 3.46 (2H, s), 3.68 (1H, s), 3.78 (3H, s), 6.86 (1H, d, J=9.0 Hz), 6.97 (1H, d, J=9.0 Hz), 7.18–7.30 (5H, m).

EXAMPLE 112

3-(6-fluoropyridine-3-yl)-5-(4-(4-methoxyphenyl)piperazin-1-yl)-2,2,4,6,7-pentamethyl-2,3-dihydro-1-benzofuran-3-ol Using 4-(4-methoxyphenyl)-1-(2,2,4,6,7-pentamethyl-2,3-dihydro-1-benzofuran-on-5-yl)piperazine and 5-bromo-2-fluoropyridine obtained in Reference Example 13, the title compound was obtained in the same manner as in Example 33. Yield 67% mp. 129–131° C. (hexane-ethyl acetate).

$^1$H-NMR (CDCl3) δ: 0.90 (3H, s), 1.51 (3H, s), 1.96 (3H, s), 2.14 (3H, s), 2.19 (1H, s), 2.29 (3H, s), 3.08–3.28 (8H, m), 3.77 (3H, s), 6.84 (2H, d, J=9.0 Hz), 6.94 (2H, d, J=9.0 Hz), 7.60–8.70 (3H, m).

EXAMPLE 113

1-(3-(6-fluoropyridine-3-yl)-2,2,4,6,7-pentamethyl-2,3-dihydro-1-benzofuran-5-yl)-4-(4-methoxyphenyl)piperazine Using 3-(6-fluoropyridine-3-yl)-5-(4-(4-methoxyphenyl)piperazin-1-yl)-2,2,4,6,7-pentamethyl-2,3-dihydro-1-benzofuran-3-ol obtained in Example 112, the title compound was obtained in the same manner as in Example 46. Yield 72% mp. 87–88° C. (hexane-ethyl acetate).

$^1$H-NMR (CDCl3) δ: 1.04 (3H, s), 1.51 (3H, s), 1.91 (3H, s), 2.14 (3H, s), 2.28 (3H, s), 3.05–3.24 (8H, m), 3.77 (3H, s), 4.11 (1H, s), 6.76–6.86 (3H, m), 6.94 (2H, d, J=9.3 Hz), 7.25 (1H, br s), 7.95 (1H, br s).

EXAMPLE 114

1-(3-methoxyphenyl)-4-(2,2,4,6,7-pentamethyl-3-(pyrrolidinyl)-2,3-dihydro-1-benzofuran-5-yl)piperazine Using 5-(4-(3-methoxyphenyl)piperazin-1-yl)-2,2,4,6,7-pentamethyl-1-benzofuran-3-ol obtained in Reference Example 42 and pyrrolidine, the title compound was obtained in the same manner as in Example 57. Yield 39% mp. 106–107° C. (methanol).

$^1$H-NMR (CDCl3) δ: 1.23 (3H, s), 1.48 (3H, s), 1.60–1.78 (4H, m), 2.07 (3H, s), 2.21 (3H, s), 2.24 (3H, s), 2.47–2.77 (4H, m), 3.15–3.37 (8H, m), 3.80 (3H, s), 3.98 (1H, s), 6.43 (1H, dd, J=8.1, 2.1 Hz), 6.53 (1H, d, J=2.1 Hz), 6.60 (1H, dd, J=8.1, 2.1 Hz), 7.18 (1H, t, J=8.1 Hz).

EXAMPLE 115

4-(4-fluorophenyl)-1-(2,2,4,6,7-pentamethyl-3-(pyrrolidinyl)-2,3-dihydro-1-benzofuran-5-yl)piperazine hydrochloride Sodium borohydride (106 mg, 2.8 mmol) was added to a solution of 5-(4-(4-fluorophenyl)piperazin-1-yl)-2,2,4,6,7-pentamethyl-1-benzofuran-3(2H)-one (268 mg, 0.7 mmol) obtained in Reference Example 45 in THF (1.5 mL) and methanol (4.5 mL) at room temperature and stirred for 16 hours. The resulting mixture was cooled with ice, made to acidic by 1N hydrochloric acid, and extracted with ethyl acetate. The organic extract was washed with saturated aqueous sodium bicarbonate and saturated aqueous sodium chloride, dried over anhydrous sodium sulfate, and concentrated under reduced pressure. The residue was purified with silica gel column chromatography (hexane/ethyl acetate=4/1). The obtained crystals and triethylamine (0.084 mL, 0.6 mmol) were dissolved in dichloromethane (1 ml), and then methane sulfonyl chloride (0.023 mL, 0.3 mmol) was added under ice cooling. The reaction mixture was stirred for 30 minutes with ice cooling. To the mixture was added pyrrolidine (0.125 mL, 1.5 mmol). After stirring for 1 hour under ice cooling, the resulting mixture was diluted with saturated aqueous sodium bicarbonate and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=1/1) and it was treated with a solution of hydrogenchloride in ethyl acetate to obtain 27 mg (yield 8%) of the title compound.

$^1$H-NMR (CDCl3) δ: 1.24 (3H, s), 1.48 (3H, s), 1.64–1.75 (4H, m), 2.08 (3H, s), 2.22 (3H, s), 2.24 (3H, s), 2.45–2.62 (2H, m), 2.64–2.78 (2H, m), 3.12–3.35 (8H, m), 3.98 (1H, s), 6.92–7.02 (4H, m).

EXAMPLE 116

1-(2,2,4,6,7-pentamethyl-3-(pyrrolidinyl)-2,3-dihydro-1-benzofuran-5-yl)-4-phenylpiperazine hydrochloride Using pyrrolidine and 2,2,4,6,7-pentamethyl-5-(4-phenyl pyrazine-1-yl)-2,3-dihydro-benzofuran-3-ol obtained in Reference Example 30, the free base was obtained in the same manner as in Example 57. The free base was treated with a 4N hydrogenchloride in ethyl acetate (10 ml) to obtain the title compound. Yield 80%. Amorphous powder.

$^1$H-NMR (CDCl3) δ: 1.24 (3H, s), 1.48 (3H, s), 1.64–1.73 (4H, m), 2.04 (3H, s), 2.22 (3H, s), 2.24 (3H, s), 2.45–2.78 (2H, m), 3.17–3.36 (8H, m), 3.98 (1H, s), 6.87 (t, J=7.3 Hz), 6.99 (2H, d, J=8.6 Hz), 7.28 (2H, dd, J=7.3, 8.6 Hz).

EXAMPLE 117

4-(2-methoxyphenyl)phenyl-1-(2,2,4,6,7-pentamethyl-3-(pyrrolidinyl)-2,3-dihydro-1-benzofuran-5-yl)piperazine hydrochloride Using pyrrolidine and 5-(4-(2-methoxyphenyl)pyrazine-1-yl)-2,2,4,6,7-pentamethyl-2,3-dihydro-benzofuran-3-ol obtained in Reference Example 31, the free base was obtained in the same manner as in Example 57. The free base was treated with a 4N hydrogenchloride in ethyl acetate (10 ml) to obtain the title compound. Yield 62%. Amorphous powder.

$^1$H-NMR (CDCl3) δ: 1.24 (3H, s), 1.48 (3H, s), 1.64–1.71 (4H, m), 2.08 (3H, s), 2.25 (3H, s), 2.27 (3H, s), 2.50–2.80 (2H, m), 3.07–3.38 (8H, m), 3.89 (3H, s), 3.98 (1H, s), 6.83–7.03 (4H, m).

EXAMPLE 118

1-(3,4-dimethoxyphenyl)-4-(2,2,4,6,7-pentamethyl-3-piperidino-2,3-dihydro-1-benzofuran-5-yl)piperazine Using 5-(4-(3,4-dimethoxyphenyl)piperazin-1-yl)-2,2,4,6,7-pentamethyl-1-benzofuran-3-ol obtained in Reference Example 37, the title compound was obtained in the same manner as in Example 57. Yield 34% mp. 134–135° C. (methanol).

$^1$H-NMR (CDCl3) δ: 1.17–1.90 (13H, m), 2.07 (3H, s), 2.25 (3H, s), 2.29 (3H, s), 2.35 (1H, br s), 2.78 (1H, br s), 2.92 (1H, br s), 3.07–3.39 (8H, m), 3.66 (1H, s), 3.85 (3H, s), 3.89 (3H, s), 6.52 (1H, dd, J=8.4, 2.7 Hz), 6.65 (1H, d, J=2.7 Hz), 6.81 (1H, d, J=8.4 Hz).

EXAMPLE 119

1-(3,4-dimethoxyphenyl)-4-(2,2,4,6,7-pentamethyl-3-(pyrrolidinyl)-2,3-dihydro-1-benzofuran-5-yl)piperazine Using 5-(4-(3,4-dimethoxyphenyl)piperazin-1-yl)-2,2,4,6,7-pentamethyl-1-benzofuran-3-ol obtained in Reference Example 37 and pyrrolidine, the title compound was obtained in the same manner as in Example 57. Yield 39% mp. 128–130° C. (methanol).

$^1$H-NMR (CDCl3) δ: 1.24 (3H, s), 1.48 (3H, s), 1.60–1.72 (4H, m), 2.08 (3H, s), 2.22 (3H, s), 2.25 (3H, s), 2.48–2.79 (4H, m), 3.30–3.78 (8H, m), 3.85 (3H, s), 3.89 (3H, s), 3.98 (1H, s), 6.52 (1H, dd, J=8.7, 2.7 Hz), 6.64 (1H, d, J=2.7 Hz), 6.81 (1H, d, J=8.7 Hz).

EXAMPLE 120

1-(2,2,4,6,7-pentamethyl-3-piperidino-2,3-dihydro-1-benzofuran-5-yl)-4-(4-(trifluoromethyl)phenyl)piperazine Using 2,2,4,6,7-pentamethyl-5-(4-(4-(trifluoromethyl)phenyl)piperazin-1-yl)-1-benzofuran-3-ol obtained in Reference Example 38 and piperidine, the title compound was obtained in the same manner as in Example 57. Yield 61% mp. 182–183° C. (methanol).

$^1$H-NMR (CDCl3) δ: 1.10–1.82 (13H, m), 2.07 (3H, s), 2.23 (3H, s), 2.28 (3H, s), 2.38 (1H, br s), 2.78 (1H, br s), 2.92 (1H, br s), 3.18–3.42 (8H, m), 3.66 (1H, s), 6.98 (2H, d, J=8.7 Hz), 7.49 (2H, d, J=8.7 Hz).

EXAMPLE 121

1-(2,2,4,6,7-pentamethyl-3-(pyrrolidinyl)-2,3-dihydro-1-benzofuran-5-yl)-4-(4-(trifluoromethyl)phenyl)piperazine Using 2,4,6,7-pentamethyl-5-(4-(4-(trifluoromethyl)phenyl)piperazin-1-yl)-1-benzofuran-3-ol obtained in Reference Example 38 and pyrrolidine, the title compound was obtained in the same manner as in Example 57.

Yield 66% mp. 140–141° C. (methanol).

¹H-NMR (CDCl3) δ: 1.24 (3H, s), 1.48 (3H, s), 1.60–1.78 (4H, m), 2.07 (3H, s), 2.21 (3H, s), 2.23 (3H, s), 2.46–2.78 (4H, m), 3.18–3.45 (8H, m), 3.98 (1H, s), 6.97 (2H, d, J=8.4 Hz), 7.48 (2H, d, J=8.4 Hz).

EXAMPLE 122

1-(4-methoxyphenyl)-4-(2,2,4,6,7-pentamethyl-3-(6-methylpyridine-3-yl)-2,3-dihydro-1-benzofuran-5-yl)piperazine n-butyllithium (hexane solution 1.60 M, 2.90 mL, 4.65 mmol) was added dropwise to a solution of 5-bromo-2-methylpyridine (0.80 g, 4.65 mmol) in diethyl ether (20 ml) under argon atmosphere at −70° C. or less and the mixture was stirred for 30 minutes. A solution of 1-(2,2,4,6,7-pentamethyl-2,3-dihydro-1-benzofuran-3-on-5-yl)-4-(4-methoxyphenyl)piperazine (734 mg, 1.86 mmol) obtained in Reference Example 13 in THF (5 ml) was added dropwise to the reaction mixture at −70° C. or less and the mixture was allowed to warm to 0° C. and stirred under ice cooling for 30 minutes. The resulting mixture was poured into water and extracted with ethyl acetate. The organic extract was washed with water and saturated aqueous sodium chloride, dried over anhydrous sodium sulfate, and concentrated under reduced pressure. The residue was crystallized from hexane to obtain 520 mg of 5-(4-(4-methoxyphenyl)piperazin-1-yl)-(2,2,4,6,7-pentamethyl-3-(6-methylpyridine-3-yl)-2,3-dihydro-1-benzofuran-3-ol. The compound was added to trifluoroacetic acid (5.0 mL) under ice cooling and the mixture was allowed to warm to room temperature and then triethylsilane (0.5 mL, 3.2 mmol) was added. The mixture was stirred for 15 minutes and concentrated under reduced pressure. The residue was made to basic by saturated aqueous sodium bicarbonate and extracted with ethyl acetate. The organic extract was washed with water and saturated aqueous sodium chloride, dried over anhydrous sodium sulfate, and concentrated under reduced pressure. The residue was crystallized from hexane to obtain 370 mg (yield 42%) of the title compound. mp. 131–133° C. (methanol).
¹H-NMR (CDCl3) δ: 1.02 (3H, s), 1.51 (3H, s), 1.90 (3H, s), 2.15 (3H, s), 2.28 (3H, s), 2.54 (3H, s), 3.08–3.26 (8H, m), 3.78 (3H, s), 4.10 (1H, s), 6.82–7.10 (6H, m), 8.23 (1H, br s).

EXAMPLE 123

(−)-1-(4-methoxyphenyl)-4-(2,2,4,6,7-pentamethyl-3-(pyrrolidinyl)-2,3-dihydro-1-benzofuran-5-yl)piperazine 1-(4-methoxyphenyl)-4-(2,2,4,6,7-pentamethyl-3-(pyrrolidinyl)-2,3-dihydro-1-benzofuran-5-yl)piperazine obtained in Example 99, was separated in high performance liquid chromatography by the method shown below, and the title compound of having a short retention time was obtained.
System: Hitachi L-7100, L-7405
Column: CHIRALCEL OJ (4.6 (i, d)×250 mm) made by Daicel Kagaku Kogyo KK)
Mobile phase: hexane/ethanol=95/5, flow rate: 0.5 m L/min,
column temperature: 25° C.
One shot: 10 μl
mp. 93–94° C. (ethanol).
$[\alpha]_D$=−9.3° (c=1.01, chloroform).
¹H-NMR (CDCl3) δ: 1.23 (3H, s), 1.48 (3H, s), 1.62–1.77 (4H, m), 2.07 (3H, s), 2.22 (3H, s), 2.24 (3H, s), 2.44–2.78 (4H, m), 3.07–3.39 (8H, m), 3.78 (3H, s), 3.98 (1H, s), 6.85 (2H, d, J=9.0 Hz), 6.97 (2H, d, J=9.0 Hz).

EXAMPLE 124

(+)-1-(4-methoxyphenyl)-4-(2,2,4,6,7-pentamethyl-3-(pyrrolidinyl)-2,3-dihydro-1-benzofuran-5-yl)piperazine 1-(4-methoxyphenyl)-4-(2,2,4,6,7-pentamethyl-3-(pyrrolidinyl)-2,3-dihydro-1-benzofuran-5-yl)piperazine obtained in Example 99, was separated in high performance liquid chromatography by the method shown below, and the title compound of having a long retention time was obtained.
System: Hitachi L-7100, L-7405
Column: CHIRALCEL OJ (4.6 (i, d)×250 mm) made by Daicel Kagaku Kogyo KK)
Mobile phase: hexane/ethanol=95/5, flow rate: 0.5 m L/min, column temperature: 25° C.
One shot: 10 μl
mp. 90–92° C. (ethanol).
$[\alpha]_D$=+8.8° (c=0.87, chloroform).
¹H-NMR (CDCl3) δ: 1.23 (3H, s), 1.48 (3H, s), 1.62–1.78 (4H, m), 2.07 (3H, s), 2.22 (3H, s), 2.24 (3H, s), 2.44–2.80 (4H, m), 3.09–3.35 (8H, m), 3.78 (3H, s), 3.98 (1H, s), 6.85 (2H, d, J=9.0 Hz), 6.97 (2H, d, J=9.0 Hz).

EXAMPLE 125

3-(6-fluoropyridine-3-yl)-5-(4-benzylpiperazin-1-yl)-2,2,4,6,7-pentamethyl-2,3-dihydro-1-benzofuran-3-ol Using 2-fluoro-5-bromopyridine and 5-(4-benzyl piperazin-1-yl)-2,2,4,6,7-pentamethyl-2,3-dihydro-1-benzofuran-3(2H)-one obtained in Reference Example 41, the title compound was synthesized in the same manner as in Example 33. Yield 79%. mp. 105–109° C. (hexane).
¹H-NMR (CDCl3) δ: 0.89 (3H, s), 1.50 (3H, s), 1.93 (3H, s), 2.12 (3H, s), 2.20 (1H, br), 2.26 (3H, s), 2.43–2.60 (4H, m), 3.00–3.15 (4H, m), 3.55 (2H, s), 6.91 (1H, br), 7.20–7.40 (5H, m), 7.85 (2H, br).

EXAMPLE 126

4-benzyl-1-(3-(6-fluoropyridine-3-yl)-2,2,4,6,7-pentamethyl-2,3-dihydro-1-benzofuran-5-yl)piperazine Using 3-(6-fluoropyridine-3-yl)-5-(4-benzylpiperazin-1-yl)-2,2,4,6,7-pentamethyl-2,3-dihydro-1-benzofuran-3-ol obtained in Example 125, the title compound was synthesized in the same manner as in Example 46. Yield 78%. mp. 76–79° C. (hexane).
¹H-NMR (CDCl3) δ: 1.02 (3H, s), 1.49 (3H, s), 1.87 (3H, s), 2.12 (3H, s), 2.24 (3H, s), 2.45–2.58 (4H, m), 2.98–3.12 (4H, m), 3.55 (2H, s), 4.10 (1H, s), 6.80 (1H, dd, J=2.8, 8.2 Hz), 7.20–7.40 (6H, m), 7.91 (1H, br).

EXAMPLE 127

1-(3-(6-fluoropyridine-3-yl)-2,2,4,6,7-pentamethyl-2,3-dihydro-1-benzofuran-5-yl)piperazine A mixture of 10% palladium carbon (50% water, 183 mg), 4-benzyl-1-(3-(6-fluoropyridine-3-yl)-2,2,4,6,7-pentamethyl-2,3-dihydro-1-benzofuran-5-yl)piperazine (1.83 g, 4 mmol) obtained in Example 126 and ammonium formate (505 mg, 8 mmol) in methanol (50 ml) was refluxed for 2 hours under nitrogen atmosphere. The resulting mixture was cooled to room temperature and the catalyst was removed by filtration. The filtrate was concentrated under reduced pressure. The residue was diluted with ethyl acetate. The organic layer was washed with saturated aqueous sodium bicarbonate, and dried over anhydrous sodium sulfate. The solvent was removed by distillation under reduced pressure. The residue was purified with basic silica gel column chromatography (ethyl acetate) to obtain 1.3 g (yield 88%) of the title compound as an amorphous powder.

$^1$H-NMR (CDCl3) δ: 1.03 (3H, s), 1.50 (3H, s), 1.79 (1H, br), 1.88 (3H, s), 2.13 (3H, s), 2.26 (3H, s), 2.83–3.05 (8H, m), 4.11 (1H, s), 6.81 (1H, dd, J=2.9, 8.7 Hz), 7.23 (1H, br), 7.92 (1H, br).

EXAMPLE 128

1-benzyl-4-(2,2,4,6,7-pentamethyl-3-(pyrrolidinyl)-2,3-dihydro-1-benzofuran-5-yl)piperazine dihydrochloride Using pyrrolidine and 5-(4-benzyl piperazin-1-yl)-2,2,4,6,7-pentamethyl-2,3-dihydro-1-benzofuran-3-ol obtained in Reference Example 42, the free base was obtained in the same manner as in Example 57. The free base was treated with a 4 N hydrochloric acid in ethyl acetate solution (10 ml) to obtain the title compound. Yield 93%. mp. 224–227° C. (decomposition) (ethyl acetate-ethanol).

$^1$H-NMR (CDCl3) δ: 1.22 (3H, s), 1.47 (3H, s), 1.60–1.75 (4H, m), 2.06 (3H, s), 2.19 (3H, s), 2.22 (3H, s), 2.45–2.60 (4H, m), 2.61–2.77 (2H, m), 3.02–3.20 (4H, m), 3.56 (2H, s), 3.96 (1H, s), 7.21–7.42 (5H, m).

EXAMPLE 129

4-(4-fluorophenyl)-1-(3-(6-fluoropyridine-3-yl)-2,2,4,6,7-pentamethyl-2,3-dihydro-1-benzofuran-5-yl)piperazine Using fluorobenzene and 1-(3-(6-fluoropyridine-3-yl)-2,2,4,6,7-pentamethyl-2,3-dihydro-1-benzofuran-5-yl)piperazine obtained in Example 127, the title compound was obtained in the same manner as in Example 16. Yield 50%. Amorphous powder.

$^1$H-NMR (CDCl3) δ: 1.03 (3H, s), 1.51 (3H, s), 1.90 (3H, s), 2.14 (3H, s), 2.27 (3H, s), 3.10–3.26 (8H, m) 4.11 (1H, s), 6.81 (1H, dd, J=2.7, 8.3 Hz), 6.83–7.00 (4H, m), 7.20 (1H, br), 7.93 (1H, br).

EXAMPLE 130

1-(4-methoxyphenyl)-4-(2,2,4,6,7-pentamethyl-3-(4-methylbenzyl)oxy-2,3-dihydro-1-benzofuran-5-yl)piperazine Using α-bromo-p-xylene and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 74. Yield 68%. mp. 84–85° C. (diisopropyl ether-methanol). $^1$H-NMR (CDCl$_3$) δ: 1.36 (3H, s), 1.59 (3H, s), 2.07 (3H, s), 2.24 (3H, s), 2.25 (3H, s), 2.33 (3H, s), 3.05–3.35 (8H, m), 3.78 (3H, s), 4.49 (2H, s), 4.66 (1H, s), 6.86 (2H, d, J=9.2 Hz), 6.97 (2H, d, J=9.2 Hz), 7.13 (2H, d, J=8.2 Hz), 7.23 (2H, d, J=8.2 Hz).

EXAMPLE 131

1-(3-(6-fluoropyridine-3-yl)-2,2,4,6,7-pentamethyl-2,3-dihydro-1-benzofuran-5-yl)-4-(4-methoxyphenyl)methylpiperazine dihydrochloride 4-methoxybenzyl chloride (0.16 mL, 1.2 mmol) was added to a mixture of 1-(3-(6-fluoropyridine-3-yl)-2,2,4,6,7-pentamethyl-2,3-dihydro-1-benzofuran-5-yl)piperazine (369 mg, one mmol) obtained in Example 127 and potassium carbonate (138 mg, 1 mmol) in DMF (5 ml) and the mixture was stirred at room temperature for 3 hours. The resulting mixture was poured into water and extracted with ethyl acetate. The organic extract was washed three times using saturated aqueous sodium chloride, dried over anhydrous sodium sulfate, and the solvent was removed under reduced pressure. The residue was purified with silica gel column chromatography (hexane/ethyl acetate=4/1) to obtain 365 mg (yield 75%) of free salt of title compound. Thereafter, it was treated with 4N hydrogenchloride in ethyl acetate to obtain the title compound as a hydrochloride salt. mp. 218–221° C. (decomposition) (ethyl acetate-ethanol).

$^1$H-NMR (CDCl3) δ: 1.02 (3H, s), 1.49 (3H, s), 1.87 (3H, s), 2.12 (3H, s), 2.24 (3H, s), 2.40–2.53 (4H, m), 2.90–3.10 (4H, m), 3.48 (2H, s), 3.80 (3H, s), 4.10 (1H, s), 6.76–6.95 (3H, m), 7.20–7.35 (3H, m), 7.91 (1H, br).

EXAMPLE 132

Tert-butyl 4-(2,2,4,6,7-pentamethyl-3-pyrrolidinyl-2,3-dihydro-1-benzofuran-5-yl)piperazinecarboxylate Using tert butyl 4-(3-hydroxy-2,2,4,6,7-pentamethyl-2,3-dihydro-1-benzofuran-5-yl)piperazinecarboxylate obtained in Reference Example 44 and pyrrolidine, the title compound was synthesized in the same manner as in Example 57. Yield 89%. mp. 127–128° C. (ethyl acetate-hexane).

$^1$H-NMR (CDCl3) δ: 1.22 (3H, s), 1.47 (3H, s), 1.49 (9H, s), 1.63–1.79 (4H, m), 2.06 (3H, s), 2.17 (3H, s), 2.19 (3H, s), 2.55 (2H, br), 2.66–2.74 (2H, m), 2.98–3.06 (4H, m), 3.42–3.59 (4H, m), 3.96 (1H, s).

EXAMPLE 133

Tert-butyl 4-(2,2,4,6,7-pentamethyl-3-piperidino-2,3-dihydro-1-benzofuran-5-yl)piperazinecarboxylate Using tert butyl 4-(3-hydroxy-2,2,4,6,7-pentamethyl-2,3-dihydro-1-benzofuran-5-yl)piperazinecarboxylate obtained in Reference Example 44 and piperidine, the title compound was synthesized in the same manner as in Example 57. Yield 89%. mp. 167–168° C. (ethyl acetate-hexane).

$^1$H-NMR (CDCl3) δ: 1.19 (3H, s), 1.45–1.83 (18H, m), 2.05 (3H, s), 2.20 (3H, s), 2.24 (3H, s), 2.30–2.43 (2H, br), 2.65–3.10 (6H, m), 3.45–3.58 (4H, m), 3.65 (1H, s).

EXAMPLE 134

(2,2,4,6,7-pentamethyl-3-pyrrolidinyl-2,3-dihydro-1-benzofuran-5-yl)piperazine

A solution of 4N hydrogenchloride in ethyl acetate (20 ml) was added to a solution of tert butyl 4-(2,2,4,6,7- pentamethyl-3-pyrrolidinyl-2,3-dihydro-1-benzofuran-5-yl)piperazinecarboxylate (3.55 g, 8 mmol) obtained in Example 132 in THF (20 mL) and ethyl acetate (20 ml) and the mixture was stirred at 60° C. for 3 hours. The resulting mixture was cooled to 0° C. made to weakly alkaline using 1N sodium hydroxide aqueous, and extracted with ethyl acetate. The organic extract was washed using saturated aqueous sodium chloride, dried over anhydrous sodium sulfate, and the solvent was removed under reduced pressure. The residue was purified with basic silica gel column chromatography (ethyl acetate) to obtain 2.72 g (yield 100%) of the title compound as an amorphous powder.

$^1$H-NMR (CDCl3) δ: 1.22 (3H, s), 1.47 (3H, s), 1.63–1.72 (4H, m), 2.06 (3H, s), 2.20 (3H, s), 2.21 (3H, s), 2.50–2.74 (4H, m), 3.04–3.27 (8H, m) 3.97 (1H, s).

EXAMPLE 135 methyl 4-(((5-(4-(4-methoxyphenyl)piperazin-1-yl)-2,2,4,6,7-pentamethyl-2,3-dihydro-1-benzofuran-3-yl)oxy)methyl)benzoate Using methyl 4-(bromomethyl)benzoate and 5-(4-(4-methoxyphenyl)piperazin-1-yl)-2,2,4,6,7-pentamethyl-2,3-dihydro-1-benzofuran-3-ol obtained in Reference Example 18, the title compound was synthesized in the same manner as in Example 94. Oily material. Yield 76%. $^1$H-NMR (CDCl3) δ: 1.36 (3H, s), 1.59 (3H, s), 2.09 (3H, s), 2.26 (6H, s), 3.10–3.30 (8H, m), 3.79 (3H, s), 3.91 (3H, s), 4.57 (2H, s), 4.69 (1H, s), 6.86 (2H, d, J=9.2 Hz), 6.97 (2H, d, J=9.2 Hz), 7.39 (2H, d, J=8.0 Hz), 7.99 (2H, d, J=8.0 Hz).

EXAMPLE 136

4-(2,2,4,6,7-pentamethyl-3-pyrrolidinyl-2,3-dihydro-1-benzofuran-5-yl)-1-(phenylethyl)piperazine dihydrochloride Methanesulfonyl chloride (0.09 mL, 1.2 mmol) was added to a solution of phenethyl alcohol (0.14 mL, 1.2 mmol) and triethylamine (0.21 mL, 1.5 mmol) in acetonitrile (5 ml) at room temperature. The mixture was stirred for 1 hour, and then (2,2,4,6,7-pentamethyl-3-pyrrolidinyl-2,3-dihydro-1-benzofuran-5-yl)piperazine obtained in Example 134 (343 mg, 1 mmol) was added. After stirring for 16 hours at room temperature, the reaction mixture was concentrated under reduced pressure. The residue was diluted with water and extracted with ethyl acetate. The organic extract was washed with saturated aqueous sodium bicarbonate and saturated aqueous sodium chloride, dried over anhydrous sodium sulfate, and the solvent was removed under reduced pressure. The residue was purified with basic silica gel column chromatography (ethyl acetate/hexan=4/1) to obtain 166 mg as a free base. The free base was treated with 4N hydrogenchloride in ethyl acetate to obtain 96 mg (yield 18%) of the title compound. mp. 176–180° C. (decomposition) (ethanol-ethyl acetate).

$^1$H-NMR (CDCl3) δ: 1.23 (3H, s), 1.48 (3H, s), 1.60–1.75 (4H, m), 2.06 (3H, s), 2.21 (3H, s), 2.23 (3H, s), 2.45–2.76 (10H, m), 2.80–2.95 (2H, m), 3.03–3.26 (4H, m), 3.97 (1H, s), 7.18–7.38 (5H, m).

EXAMPLE 137

1-(4-methoxyphenylethyl)-4-(2,2,4,6,7-pentamethyl-3-pyrrolidinyl-2,3-dihydro-1-benzofuran-5-yl)piperazine dihydrochloride Using 4-methoxyphenethylalcohol, the title compound was obtained in the same manner as in Example 136. Yield 24% mp. 190–195° C. (decomposition) (ethanol-ethyl acetate).

$^1$H-NMR (CDCl3) δ: 1.23 (3H, s), 1.48 (3H, s), 1.60–1.73 (4H, m), 2.07 (3H, s), 2.20 (3H, s), 2.23 (3H, s), 2.45–2.87 (12H, m), 3.03–3.24 (4H, m), 3.79 (3H, s), 3.97 (1H, s), 6.85 (2H, d, J=8.7 Hz), 7.15 (2H, d, J=8.7 Hz).

EXAMPLE 138

1-(4-fluorobenzyl)-4-(2,2,4,6,7-pentamethyl-3-pyrrolidinyl-2,3-dihydro-1-benzofuran-5-yl)piperazine dihydrochloride Using 4-fluorobenzyl chloride and (2,2,4,6,7-pentamethyl-3-pyrrolidinyl-2,3-dihydro-1-benzofuran-5-yl)piperazine obtained in Example 134, the free base was obtained in the same manner as in Example 2. The free base was treated with 4N hydrogenchloride in ethyl acetate (10 mL) to obtain the title compound. Yield 25% mp. 227–232° C. (decomposition) (ethanol-ethyl acetate).

$^1$H-NMR (CDCl3) δ: 1.22 (3H, s), 1.47 (3H, s), 1.60–1.71 (4H, m), 2.06 (3H, s), 2.18 (3H, s), 2.21 (3H, s), 2.45–2.59 (6H, m), 2.63–2.77 (2H, m), 3.00–3.18 (4H, m), 3.53 (2H, s), 3.96 (1H, s), 6.00 (2H, t, J=8.6 Hz), 7.30–7.35 (2H, m).

EXAMPLE 139

1-(3-methoxyphenylethyl)-4-(2,2,4,6,7-pentamethyl-3-pyrrolidinyl-2,3-dihydro-1-benzofuran-5-yl)piperazine dihydrochloride To a mixture of potassium carbonate (207 mg, 1.1 mmol) and (2,2,4,6,7-pentamethyl-3-pyrrolidinyl-2,3-dihydro-1-benzofuran-5-yl)piperazine obtained in Example 134 in acetonitrile (5 ml) was added 3-methoxyphenethyl methanesulfonate (253 mg) at room temperature. After the mixture was stirred for 16 hours, the resulting mixture was concentrated under reduced pressure. The residue was diluted with water and extracted with ethyl acetate. The organic extract was washed saturated aqueous sodium bicarbonate and saturated aqueous sodium chloride, dried over anhydrous sodium sulfate, and the solvent was removed under reduced pressure. The residue was purified with basic silica gel column chromatography (ethyl acetate/hexane=4/1) to obtain 186 mg as a free base. The free base was treated with 4N hydrogenchloride in ethyl acetate (10 mL) to obtain 137 mg (yield 25%) of the title compound. mp. 183–185° C. (decomposition) (ethanol-ethyl acetate).

$^1$H-NMR (CDCl3) δ: 1.23 (3H, s), 1.48 (3H, s), 1.60–1.70 (4H, m), 2.06 (3H, s), 2.20 (3H, s), 2.23 (3H, s), 2.40–2.76 (10H, m), 2.81–2.88 (2H, m), 3.05–3.27 (4H, m), 3.80 (3H, s), 3.97 (1H, s), 6.83–6.92 (2H, m), 7.21 (1H, t, J=7.8 Hz)

EXAMPLE 140

6-(4-(4-methoxyphenyl)piperazin-1-yl)-2,2,4,5,7-pentamethyl-3-(4-methylphenyl)-2,3-dihydro-1-benzofuran-3-ol Using 4-bromotoluene and 6-(4-(4-methoxyphenyl)piperazin-1-yl-2,2,4,5,7-pentamethyl-2,3-dihydro-1-benzofuran-3(2H)-one obtained in Reference Example 25, the title compound was synthesized in the same manner as in Example 33. Yield 87% mp. 162–164° C.

$^1$H-NMR (CDCl3) δ: 0.86 (3H, s), 1.52 (3H, s), 1.88 (3H, s), 2.07 (1H, s), 2.19 (3H, s), 2.24 (3H, s), 2.35 (3H, s), 3.00–3.52 (8H, m), 3.79 (3H, s), 6.20–8.20 (4H, m), 6.86 (2H, d, J=9.1 Hz), 6.98 (2H, d, J=9.1 Hz).

EXAMPLE 141

4-(4-methoxyphenyl)-1-(2,2,4,5,7-pentamethyl-3-(4-methylphenyl)-2,3-dihydro-1-benzofuran-6-yl)piperazine Using 6-(4-(4-methoxyphenyl)piperazin-1-yl)-2,2,4,5,7-pentamethyl-3-(4-methylphenyl)-2,3-dihydro-1-benzofuran-3-ol obtained in Example 140, the title compound was synthesized in the same manner as in Example 46. Yield 85% mp. 160–162° C. (ethanol).

$^1$H-NMR (CDCl3) δ: 1.00 (3H, s), 1.49 (3H, s), 1.81 (3H, s), 2.16 (3H, s), 2.25 (3H, s), 2.31 (3H, s), 3.00–3.52 (8H, m), 3.79 (3H, s), 4.10 (1H, s), 6.40–7.40 (4H, m), 6.86 (2H, d, J=9.2 Hz), 6.98 (2H, d, J=9.2 Hz).

EXAMPLE 142

3-benzyl-5-(4-(4-methoxyphenyl)-1-piperazinyl)-2,2,4,6,7-pentamethyl-2,3-dihydro-1-benzofuran-3-ol Using 4-(4-methoxyphenyl)-1-(2,2,4,6,7-pentamethyl-2,3-dihydro-1-benzofuran-3-on-5-yl)piperazine obtained in Reference Example 13 and benzyl magnesium chloride, the title compound was obtained in the same manner as in Example 43. Yield 70% mp. 152–153° C. (ethyl acetate-hexane).

$^1$H-NMR (CDCl3) δ: 1.27 (3H, s), 1.39 (3H, s), 1.55 (3H, s), 1.58 (1H, s), 2.09 (3H, s), 2.23 (3H, s), 2.92–3.22 (10H, m), 3.77 (3H, s), 6.84 (2H, d, J=9.0 Hz), 6.86–6.97 (4H, m), 7.12–7.26 (3H, m).

EXAMPLE 143

1-(3-benzyl-2,2,4,6,7-pentamethyl-2,3-dihydro-1-benzofuran-5-yl)-4-(4-methoxyphenyl)piperazine Using 3-benzyl-5-(4-(4-methoxyphenyl)-1-piperazinyl)-2,2,4,6,7-pentamethyl-2,3-dihydro-1-benzofuran-3-ol obtained in Example 142, the title compound was obtained in the same manner as in Example 46. Yield 59% mp. 146–148° C. (ethyl acetate-hexane).

$^1$H-NMR (CDCl3) δ: 1.27 (3H, s), 1.43 (3H, s), 1.80 (3H, s), 2.10 (3H, s), 2.24 (3H, s), 2.75 (1H, dd, J=14.4, 6.3 Hz), 2.90 (1H, dd, J=14.4, 8.4 Hz), 3.00–3.30 (9H, m), 3.78 (3H, s), 6.84 (2H, d, J=9.0 Hz), 6.98 (2H, d, J=9.0 Hz), 7.07–7.28 (5H, m).

EXAMPLE 144

1-(4-methoxyphenyl)-4-(2,2,4,6,7-pentamethyl-3-(5-methylpyridine-2-yl)-2,3-dihydro-1-benzofuran-5-yl)piperazine Using 4-(4-methoxyphenyl)-1-(2,2,4,6,7-pentamethyl-2,3-dihydro-1-benzofuran-3-on-5-yl)piperazine obtained in Reference Example 13 and 2-bromo-5-methylpyridine, the title compound was obtained in the same manner as in Example 122. Yield 20% mp. 186–187° C. (ethyl acetate-hexane).

$^1$H-NMR (CDCl3) δ: 1.03 (3H, s), 1.54 (3H, s), 1.90 (3H, s), 2.14 (3H, s), 2.28 (3H, s), 2.30 (3H, s), 3.07–3.30 (8H, m), 3.77 (3H, s), 4.34 (1H, s), 6.64 (1H, d, J=8.4 Hz), 6.83 (2H, d, J=9.0 Hz), 6.94 (2H, d, J=9.0 Hz), 7.33 (1H, d, J=8.4 Hz), 8.37 (1H, s).

EXAMPLE 145

1-(4-methoxyphenyl)-4-(2,2,4,6,7-pentamethyl-3-(1-pyrrolidinylmethyl)-2,3-dihydro-1-benzofuran-5-yl)piperazine To a solution of (5-(4-[4-methoxyphenyl]piperazin-1-yl)-2,2,4,6,7-pentamethyl-2,3-dihydro-1-benzofuran-3-yl)methyl methanesulfononate (0.35 g, 0.716 mmol) obtained in Reference Example 40 in acetonitrile (10 ml) was added potassium carbonate (396 mg, 2.86 mmol) and pyrrolidine (0.12 mL, 1.43 mmol). The mixture was refluxed for 16 hours. The resulting mixture was diluted with water and extracted with ethyl acetate. The organic extract was washed with water and saturated aqueous sodium chloride, dried over anhydrous sodium sulfate, and concentrated under reduced pressure. The residue was purified with basic silica gel column chromatography (hexane/ethyl acetate=5/1) to obtain 175 mg (yield 53%) of the title compound via recrystallization (ethyl acetate-hexane). mp. 94–96° C. (methanol).

$^1$H-NMR (CDCl3) δ: 1.33 (3H, s), 1.59 (3H, s), 1.62–1.82 (4H, m), 2.07 (3H, s), 2.17–2.32 (7H, m), 2.38–2.51 (2H, m), 2.55–2.65 (2H, m), 2.81–2.90 (1H, m), 3.02–3.35 (9H, m), 3.78 (3H, s), 6.85 (2H, d, J=9.0 Hz), 6.96 (2H, d, J=9.0 Hz).

EXAMPLE 146

1-(4-methoxyphenyl)-4-(2,2,4,6,7-pentamethyl-3-(piperidinomethyl)-2,3-dihydro-1-benzofuran-5-yl)piperazine Using (5-(4-[4-methoxyphenyl]piperazin-1-yl)-2,2,4,6,7-pentamethyl-2,3-dihydro-1-benzofuran-3-yl)methyl methanesulfononate obtained in Reference Example 40, the title compound was obtained in the same manner as in Example 145. Yield 75% mp. 144–145° C. (methanol).

$^1$H-NMR (CDCl3) δ: 1.33 (3H, s), 1.40–1.70 (9H, m), 2.07 (3H, s), 2.18–2.35 (9H, m), 2.42–2.62 (3H, m), 3.02–3.35 (9H, m), 3.78 (3H, s), 6.85 (2H, d, J=9.0 Hz), 6.96 (2H, d, J=9.0 Hz).

EXAMPLE 147

1-(4-methoxyphenyl)-4-(2,2,4,6,7-pentamethyl-3-((4-methylphenoxy)methyl)-2,3-dihydro-1-benzofuran-5-yl)piperazine diethyl azodicarboxylate (40% toluene solution, 239 mg, 0.548 mmol) was added to a solution of (5-4-(4-methoxyphenyl)piperazin-1-yl)-2,2,4,6,7-pentamethyl-2,3-dihydro-1-benzofuran-3-yl)methanol (0.15 g, 0.365 mmol) obtained in Reference Example 39, 4-methylphenol (59 mg, 0.548 mmol), and triphenylphosphine (144 mg, 0.548 mmol) in THF (10 ml) with ice cooling and the mixture was stirred at room temperature for 3 hours. After the solvent was removed under reduced pressure, the residue was diluted with water and extracted with ethyl acetate. The organic extract was washed with 1N sodium hydroxide and water, dried over anhydrous sodium sulfate, and concentrated under reduced pressure. The residue was purified with silica gel column chromatography (hexane/ethyl acetate=10/1) to obtain 45 mg of the title compound via recrystallization (methanol) (yield 25%). mp. 149–150° C.

$^1$H-NMR (CDCl3) δ: 1.39 (3H, s), 1.55 (3H, s), 2.08 (3H, s), 2.24 (3H, s), 2.27 (3H, s), 2.31 (3H, s), 3.08–3.32 (8H, m), 3.36 (1H, d, J=6.3 Hz), 3.78 (3H, s), 3.95 (2H, d, J=6.3 Hz), 6.76 (2H, d, J=8.1 Hz), 6.85 (2H, d, J=9.0 Hz), 6.96 (2H, d, J=9.0 Hz), 7.06 (2H, d, J=8.1 Hz).

EXAMPLE 148

1-(3-((4-benzyloxy)methyl)-2,2,4,6,7-pentamethyl-2,3-dihydro-1-benzofuran-5-yl)-4-(4-methoxyphenyl)piperazine Sodium hydride (60%, 23 mg, 0.584 mmol) was added to a solution of (5-4-(4-methoxyphenyl)piperazin-1-yl)-2,2,4,6,7-pentamethyl-2,3-dihydro-1-benzofuran-3-yl) methanol (0.20 g, 0.487 mmol) obtained in Reference Example 39 in DMF (10 ml) was with ice cooling under argon atmosphere and the mixture was stirred at room temperature for 30 minutes. To the mixture was added dropwise benzyl bromide (92 mg, 0.536 mmol) with ice cooling. After the reaction mixture was stirred at 60° C. for 16 hours, the resulting mixture was diluted with water and extracted with ethyl acetate. The organic extract was washed with water and saturated aqueous sodium chloride, dried over anhydrous sodium sulfate, and concentrated under reduced pressure. The residue was purified with silica gel column chromatography (hexane/ethyl acetate=10/1) to obtain 155 mg (yield 64%) of the title compound via recrystallization (ethyl acetate-hexane). mp. 159–160° C.

$^1$H-NMR (CDCl3) δ: 1.33 (3H, s), 1.58 (3H, s), 2.06 (3H, s), 2.22 (6H, s), 3.05–3.31 (9H, m), 3.51 (2H, d, J=6.6 Hz), 3.78 (3H, s), 4.44 (1H, d, J=11.7 Hz), 4.50 (1H, d, J=11.7 Hz), 6.85 (2H, d, J=9.0 Hz), 6.96 (2H, d, J=9.0 Hz), 7.24–7.38 (5H, m).

EXAMPLE 149

5-(4-(4-methoxyphenyl)-1-piperazinyl)-2,2,4,6,7-pentamethyl-3-(2-phenylethyl)-2,3-dihydro-1-benzofuran-3-ol Using 4-(4-methoxyphenyl)-1-(2,2,4,6,7-pentamethyl-2,3-dihydro-1-benzofuran-3-on-5-yl)piperazine obtained in Reference Example 13 and phenethyl magnesium chloride, the title compound was obtained in the same manner as in Example 43. Yield 83% mp. 124–126° C. (methanol).

$^1$H-NMR (CDCl3) δ: 1.41 (3H, s), 1.59 (3H, s), 1.81 (1H, s), 2.08 (3H, s), 2.15 (1H, dt, J=13.2, 5.1 Hz), 2.25 (3H, s), 2.34 (1H, dt, J=13.2, 5.1 Hz), 2.42 (3H, s), 2.51 (1H, dt, J=13.2, 5.1 Hz), 2.73 (1H, dt, J=13.2, 5.1 Hz), 3.10–3.30 (8H, m), 3.78 (3H, s), 6.85 (2H, d, J=9.0 Hz), 6.96 (2H, d, J=9.0 Hz), 7.10–7.18 (3H, m), 7.20–7.28 (2H, m).

EXAMPLE 150

1-(4-methoxyphenyl)-4-(2,2,4,6,1-pentamethyl-3-(2-phenylethylidene)-2,3-dihydro-1-benzofuran-5-yl)piperazine Using 5-(4-(4-methoxyphenyl)-1-piperazinyl)-2,2,4,6,7-pentamethyl-3-(2-phenylethyl)-2,3-dihydro-1-benzofuran-3-ol obtained in Example 149, the title compound was obtained in the same manner as in Example 45. Yield 67% mp. 166–167° C. (ethanol).

$^1$H-NMR (CDCl3) δ: 1.65 (6H, s), 2.11 (3H, s), 2.27 (3H, s), 2.41 (3H, s), 3.08–3.32 (8H, m), 3.69 (2H, d, J=8.1 Hz), 3.78 (3H, s), 6.02 (1H, t, J=8.1 Hz), 6.85 (2H, d, J=9.0 Hz), 6.96 (2H, d, J=9.0 Hz), 7.18–7.37 (5H, m).

EXAMPLE 151

1-(4-methoxyphenyl)-4-(2,2,4,6,7-pentamethyl-3-(2-phenylethyl)-2,3-dihydro-1-benzofuran-5-yl)piperazine Using 5-(4-(4-methoxyphenyl)-1-piperazinyl)-2,2,4,6,7-pentamethyl-3-(2-phenylethyl)-2,3-dihydro-1-benzofuran-3-ol obtained in Example 149, the title compound was obtained in the same manner as in Example 46. Yield 59% mp. 92–94° C. (methanol).

$^1$H-NMR (CDCl3) δ: 1.31 (3H, s), 1.60 (3H, s), 1.70–1.90 (1H, m), 1.92–2.06 (1H, m), 2.08 (3H, s), 2.18 (3H, s), 2.23 (3H, s), 2.48–2.62 (2H, m), 2.91 (1H, dd, J=7.8, 3.0 Hz), 3.08–3.32 (8H, m), 3.78 (3H, s), 6.85 (2H, d, J=9.0 Hz), 6.96 (2H, d, J=9.0 Hz), 7.10–7.27 (5H, m).

EXAMPLE 152

(2,2,4,6,7-pentamethyl-3-piperidino-2,3-dihydro-1-benzofuran-5-yl)piperazine

A solution of 4N hydrogenchloride in ethyl acetate solution (10 ml) was added to a solution of tert butyl 4-(2,2,4,6,7-pentamethyl-3-piperidino-2,3-dihydro-1-benzofuran-5-yl)piperazine carboxylate (1.37 g, 3 mmol) obtained in Example 133 in THF (10 mL)-methanol (10 ml) and the mixture was stirred at 60° C. for 3 hours. After the reaction mixture was cooled to 0° C., the resulting mixture was made weakly alkaline using 1N sodium hydroxide and extracted with ethyl acetate. The organic extract was washed saturated aqueous sodium chloride, dried over anhydrous sodium sulfate, and the solvent was removed under reduced pressure. The residue was purified with basic silica gel column chromatography (ethyl acetate) to obtain 0.89 g (yield 83%) of the title compound as an amorphous powder.

$^1$H-NMR (CDCl3). Delta=1.15–1.93 (11H, m), 2.05 (3H, s), 2.21 (3H, s), 2.27 (3H, s), 2.35 (1H, br), 2.78 (1H, br), 2.95 (1H, br), 3.13–3.39 (8H, m), 3.66 (1H, s), 4.75 (2H, br).

EXAMPLE 153

1-benzyl-4-(2,2,4,6,7-pentamethyl-3-piperidino-2,3-dihydro-1-benzofuran-5-yl)piperazine dihydrochloride Using Benzyl chloride and (2,2,4,6,7-pentamethyl-3-piperidino-2,3-dihydro-1-benzofuran-5-yl)piperazine obtained in Example 152, the free base was obtained in the same manner as in Example 2. The free base was treated with a 4 N hydrogenchloride in ethyl acetate solution (10 ml) to obtain the title compound. Yield 64% Amorphous powder.

$^1$H-NMR (CDCl3) δ: 1.10–1.80 (12H, m), 2.05 (3H, s), 2.21 (3H, s), 2.26 (3H, s), 2.32 (1H, br), 2.48–2.60 (5H, br), 2.77 (1H, br), 2.93 (1H, br), 3.08–3.22 (4H, m), 3.58 (2H, s), 3.64 (1H, s), 7.25–7.40 (5H, m).

EXAMPLE 154

4-(((5-(4-[4-methoxyphenyl]piperazin-1-yl)-2,2,4,6,7-pentamethyl-2,3-dihydro-1-benzofuran-3-yl) oxy)methyl)benzoic acid To a solution of methyl 4-(((5-(4-[4-methoxyphenyl]piperazin-1-yl)-2,2,4,6,7-pentamethyl-2,3-dihydro-1-benzofuran-3-yl)oxy)methyl)benzoate (0.18 g, 0.33 mmol) obtained in Example 135 in methanol (1 mL)-THF (1 ml) was added 1N sodium hydroxide (0.5 mL). The mixture was stirred at room temperature for 16 hours. The reaction mixture was acidified with 1 N hydrochloric acid and extracted with ethyl acetate. The organic extract was washed with water and saturated aqueous sodium chloride and dried over anhydrous sodium sulfate. The residue was recrystallized from hexane-ethyl acetate to obtain 0.13 g (yield 75%) of the title compound. mp. 162–163° C.

$^1$H-NMR (CDCl3) δ: 1.36 (3H, s), 1.59 (3H, s), 2.09 (3H, s), 2.25 (6H, s), 3.05–3.35 (8H, m), 3.77 (3H, s), 4.56 (2H, dd, J=14.7, 12.0 Hz), 4.68 (1H, s), 6.84 (2H, d, J=9.0 Hz), 6.98 (2H, d, J=9.0 Hz), 7.39 (2H, d, J=7.8 Hz), 8.03 (2H, d, J=7.8 Hz).

Structural formulas of the compounds obtained in the aforementioned Examples are shown below.

Each symbol in the table has the following meaning.

Me: methyl
Et: ethyl
iPr: isopropyl
Ph: phenyl

TABLE 1
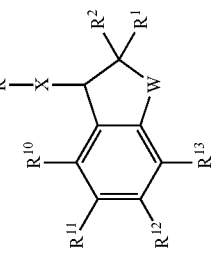
| Example Number | Structure | W | R1 | R2 | R3-X | R4 | R10 | R11 | R12 | R13 | Optical Isomer |
|---|---|---|---|---|---|---|---|---|---|---|---|
| 1 | 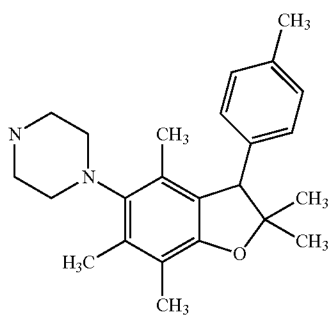 | O | Me | Me | 4-Me-Ph | H | Me | HN⟨piperazine⟩ | Me | Me | |
| 2 | 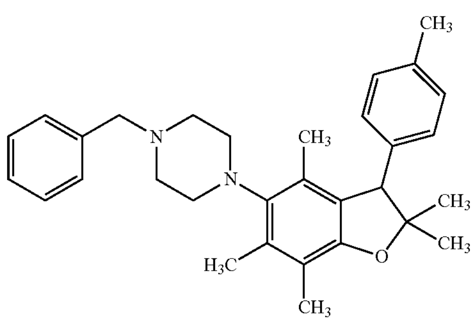 | O | Me | Me | 4-Me-Ph | H | Me | Bn-N⟨piperazine⟩ | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 3 | (structure) | O | Me | Me | 4-Me-Ph | H | Me | (4-MeO-benzyl-piperazinyl) | Me | Me | |
| 4 | (structure) | O | Me | Me | 4-Me-Ph | H | Me | (4-F-benzyl-piperazinyl) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 5 | 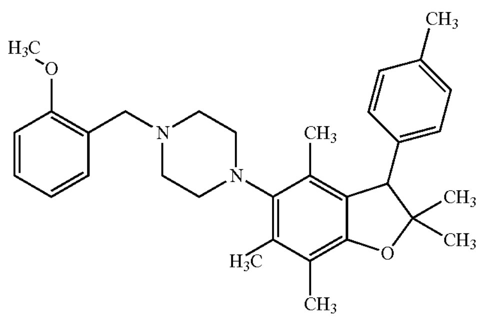 | O | Me | Me | 4-Me-Ph | H | Me | OMe (2-) | | Me | |
| 6 | 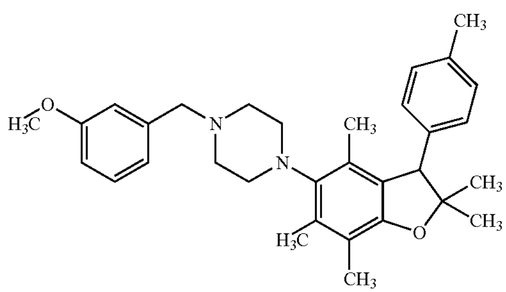 | O | Me | Me | 4-Me-Ph | H | Me | MeO (3-) | | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 7 | 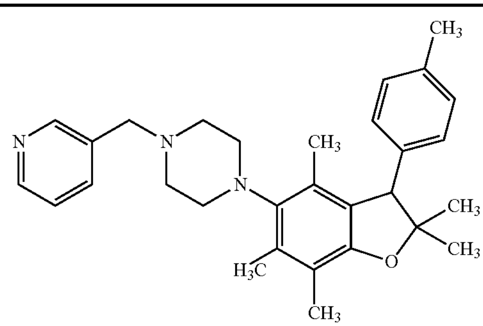 | O | Me | Me | 4-Me-Ph | H | Me | (3-pyridylmethyl-piperazinyl) | Me | Me | |
| 8 | 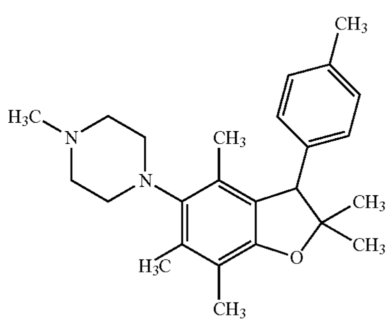 | O | Me | Me | 4-Me-Ph | H | Me | (4-methylpiperazinyl) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 9 | 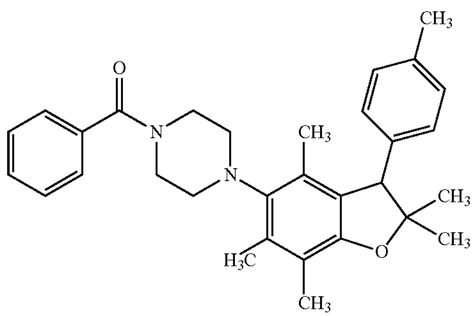 | O | Me | Me | 4-Me-Ph | H | Me | (4-benzoylpiperazin-1-yl) | Me | Me | |
| 10 | 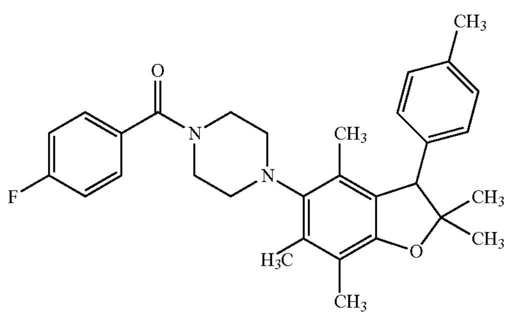 | O | Me | Me | 4-Me-Ph | H | Me | (4-(4-fluorobenzoyl)piperazin-1-yl) | Me | Me | |

TABLE 1-continued
| Example Number | Structure | W | R1 | R2 | R3-X | R4 | R10 | R11 | R12 | R13 | Optical Isomer |
|---|---|---|---|---|---|---|---|---|---|---|---|
| 11 | 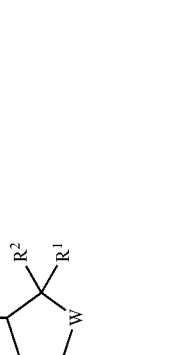 | O | Me | Me | 4-Me-Ph | H | Me | 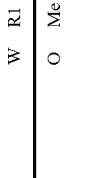 | Me | Me | |
| 12 | 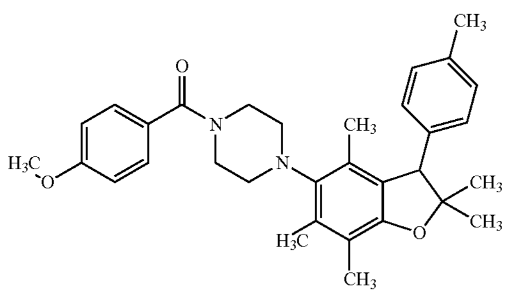 | O | Me | Me | 4-Me-Ph | H | Me |  | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 13 | (4-cyanobenzoyl-piperazinyl substituted 2,2,4,6,7-pentamethyl-3-(4-methylphenyl)-2,3-dihydrobenzofuran) | O | Me | Me | 4-Me-Ph | H | Me | (4-NC-C6H4-C(O)-piperazin-1-yl) | Me | Me | |
| 14 | (4-nitrophenyl-piperazinyl substituted 2,2,4,6,7-pentamethyl-3-(4-methylphenyl)-2,3-dihydrobenzofuran) | O | Me | Me | 4-Me-Ph | H | Me | (4-O2N-C6H4-piperazin-1-yl) | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 15 | 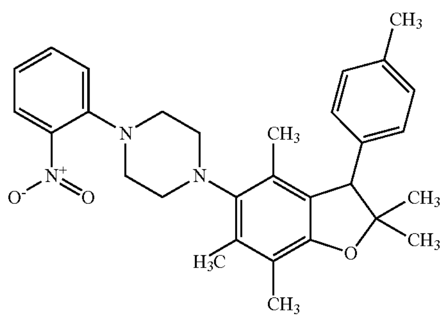 | O | Me | Me | 4-Me-Ph | H | Me | ![piperazine-2-nitrophenyl] | Me | Me | |
| 16 | 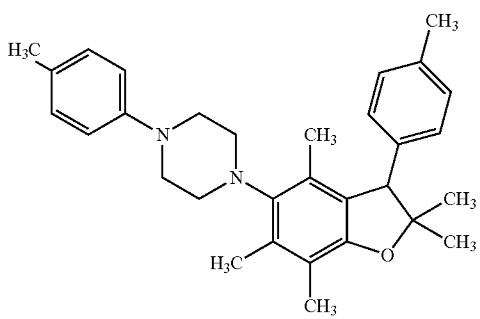 | O | Me | Me | 4-Me-Ph | H | Me | ![piperazine-4-methylphenyl] | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 17 | 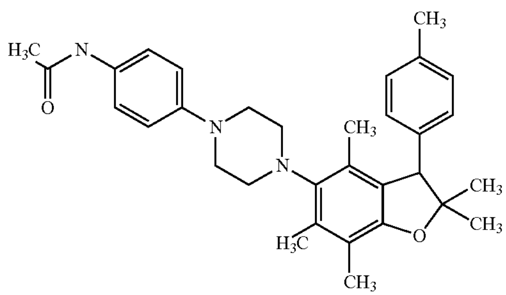 | O | Me | Me | 4-Me-Ph | H | Me | MeC(O)NH-C6H4- | piperazinyl-C6H4- (via R12 position with acetamide linker) | Me | |
| 18 | 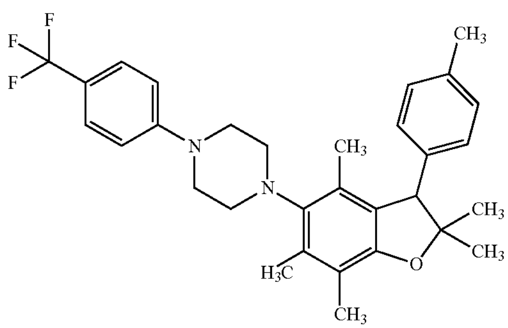 | O | Me | Me | 4-Me-Ph | H | Me | F3C-C6H4- | piperazinyl | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 19 | (structure with 3-(4-methylphenyl)-2,2-dimethyl-4,6,7-trimethyl benzofuran, 5-position bearing piperazinyl-(3,4-dimethoxyphenyl)) | O | Me | Me | 4-Me-Ph | H | Me | MeO (with additional MeO and piperazinyl-N-aryl substituent) | Me | Me | |
| 20 | (structure with 3-(4-methylphenyl)-2,2-dimethyl-4,6,7-trimethyl benzofuran, 5-position bearing piperazinyl-(4-cyanophenyl)) | O | Me | Me | 4-Me-Ph | H | Me | NC (with piperazinyl-N-aryl substituent) | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 21 | (structure) | O | Me | Me | 4-Me-Ph | H | Me | 3-pyridyl-piperazinyl | Me | Me | |
| 22 | (structure) | O | Me | Me | 4-Me-Ph | H | Me | 2-pyridyl-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 23 | 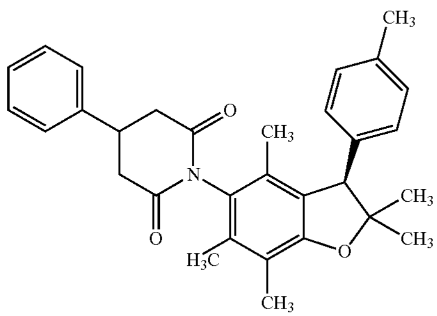 | O | Me | Me | 4-Me-Ph | H | Me | | Me | Me | R isomer |
| 24 | 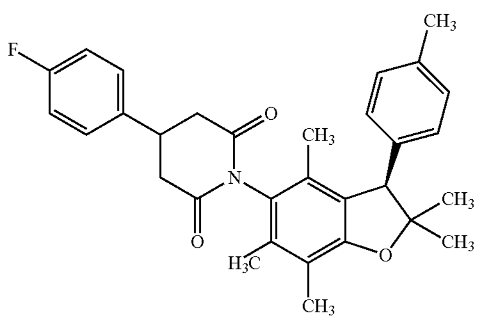 | O | Me | Me | 4-Me-Ph | H | Me | | Me | Me | R isomer |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 25 | 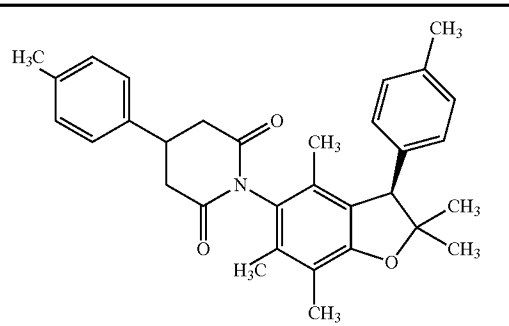 | O | Me | Me | 4-Me-Ph | H | Me | Me | Me | Me | R isomer |
| 26 | 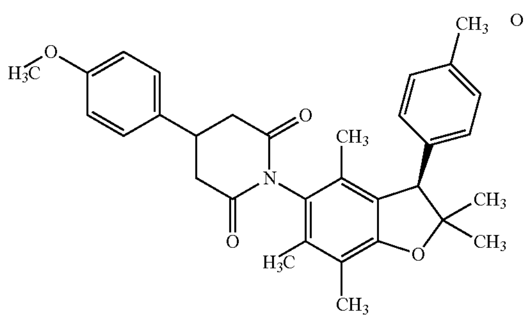 | O | Me | Me | 4-Me-Ph | H | Me | MeO | Me | Me | R isomer |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 27 | 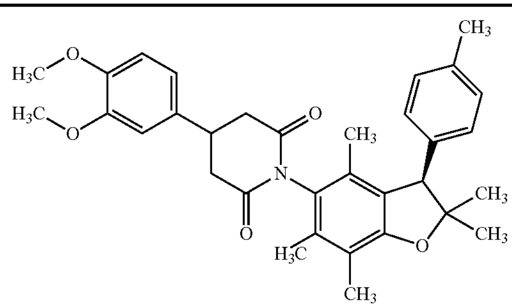 | O | Me | Me | 4-Me-Ph | H | Me | MeO | | Me | R isomer |
| 28 | 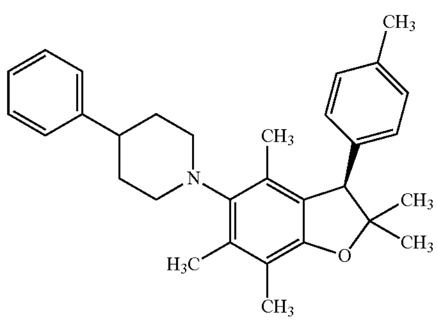 | O | Me | Me | 4-Me-Ph | H | Me | | Me | Me | R isomer |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 29 | 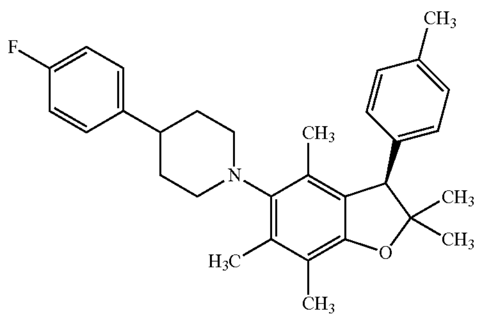 | O | Me | Me | 4-Me-Ph | H | Me | F | Me | Me | R-isomer |
| 30 | 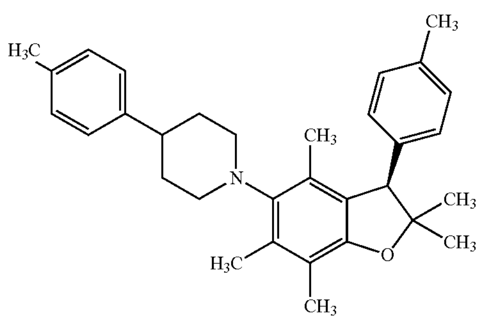 | O | Me | Me | 4-Me-Ph | H | Me | Me | Me | Me | R-isomer |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 31 | 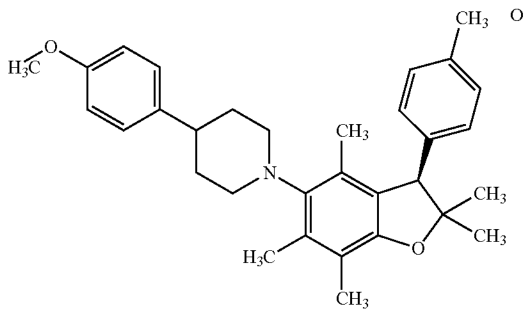 | O | Me | Me | 4-Me-Ph | H | Me | MeO | Me | Me | R isomer |
| 32 | 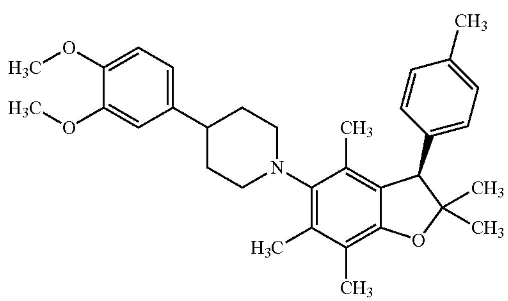 | O | Me | Me | 4-Me-Ph | H | Me | MeO | Me | Me | R isomer |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 33 | (structure shown) | O | Me | Me | 4-Me-Ph | OH | Me | MeO-C6H4-piperazinyl | Me | Me | |
| 34 | (structure shown) | O | Me | Me | 2-Naphthyl | OH | Me | MeO-C6H4-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 35 | (structure) | O | Me | Me | 4-Ph-Ph | OH | Me | MeO | Me | Me | |
| 36 | (structure) | O | Me | Me | 3-Thienyl | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 37 | 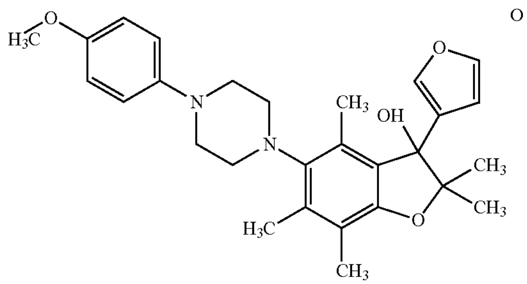 | O | Me | Me | 3-Furyl | OH | Me | MeO | Me | Me | |
| 38 | 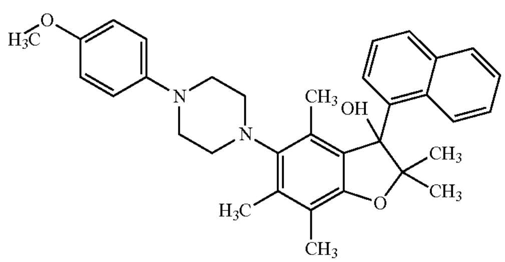 | O | Me | Me | 1-Naphthyl | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 39 | 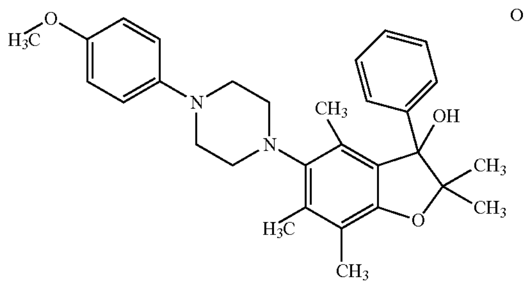 | O | Me | Me | Ph | OH | Me | MeO-C6H4-piperazinyl | Me | Me | |
| 40 | 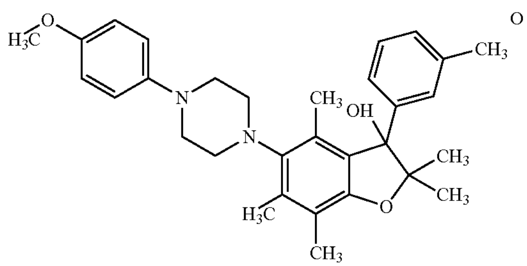 | O | Me | Me | 3-Me-Ph | OH | Me | MeO-C6H4-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 41 | 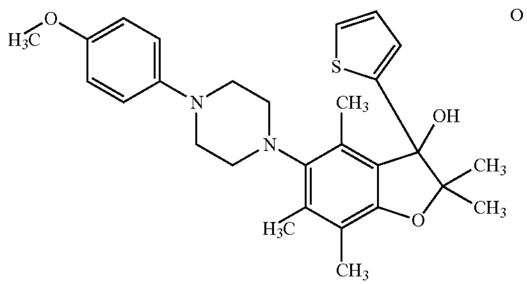 | O | Me | Me | 2-thienyl | OH | Me | MeO-C6H4-piperazinyl | Me | Me | |
| 42 | 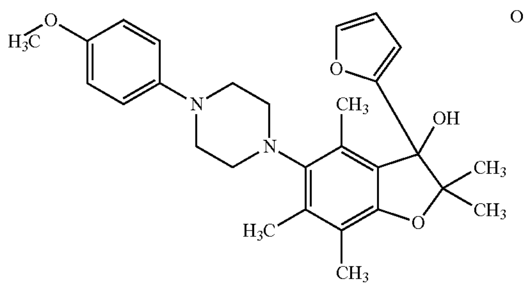 | O | Me | Me | 2-furyl | OH | Me | MeO-C6H4-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 43 | 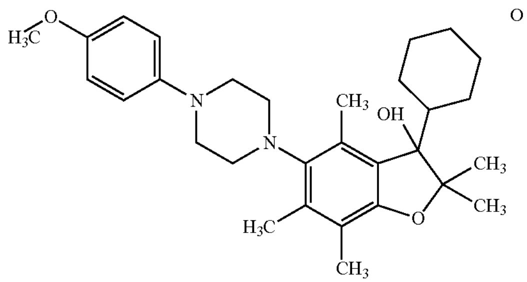 | O | Me | Me | c-hexyl | OH | Me | MeO | Me | Me | |
| 44 | 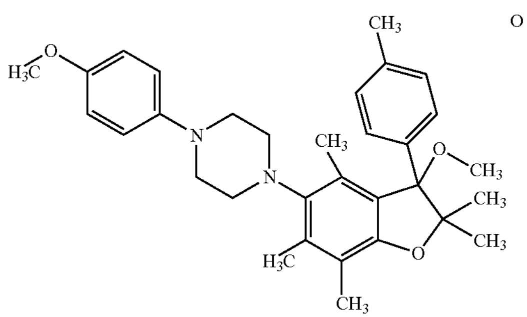 | O | Me | Me | 4-Me-Ph | Ome | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 45 | 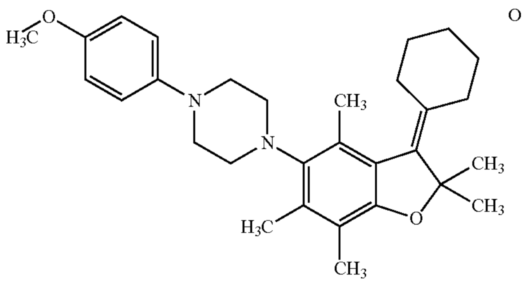 | O | Me | Me | c-hexyl | = | Me | MeO | Me | Me | |
| 46 | 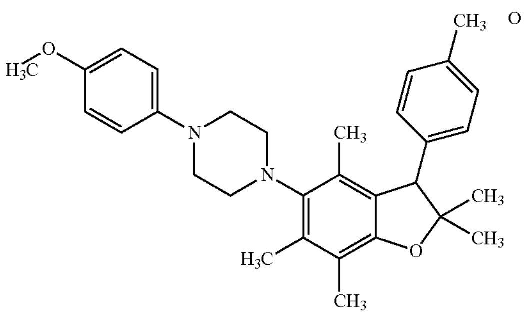 | O | Me | Me | 4-Me-Ph | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 47 | 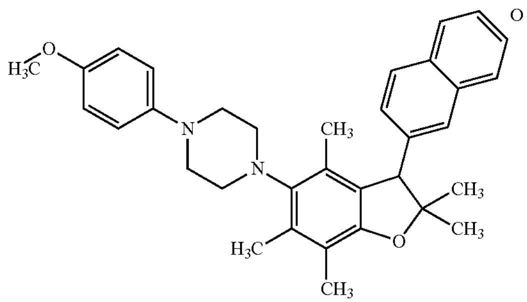 | O | Me | Me | 2-naphthyl | H | Me | MeO | Me | Me | |
| 48 | 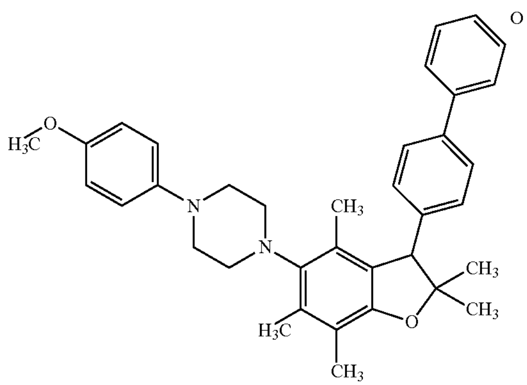 | O | Me | Me | 4-Ph-Ph | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 49 | 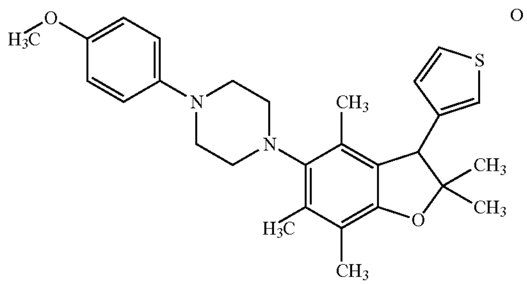 | O | Me | Me | 3-thienyl | H | Me | MeO-C6H4-piperazinyl | Me | Me | |
| 50 | 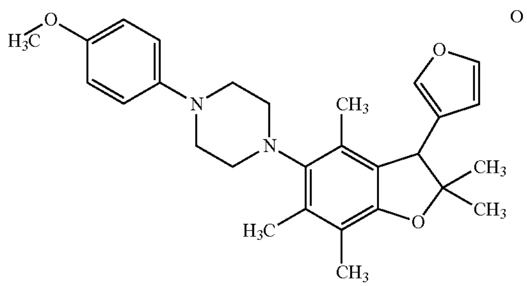 | O | Me | Me | 3-furyl | H | Me | MeO-C6H4-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 51 | 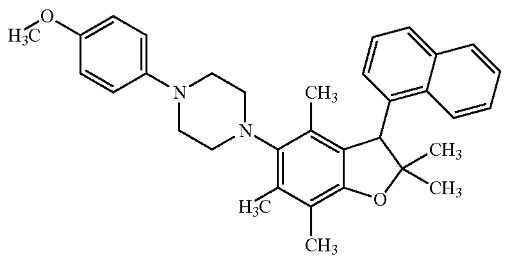 | O | Me | Me | 1-naphthyl | H | Me | MeO | Me | Me | |
| 52 | 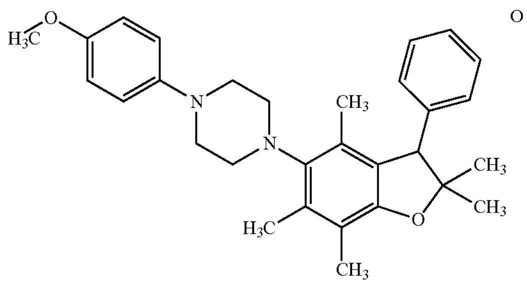 | O | Me | Me | Ph | H | Me | MeO | Me | Me | |

TABLE 1-continued
| Example Number | Structure | W | R1 | R2 | R3-X | R4 | R10 | R11 | R12 | R13 | Optical Isomer |
|---|---|---|---|---|---|---|---|---|---|---|---|
| 53 | 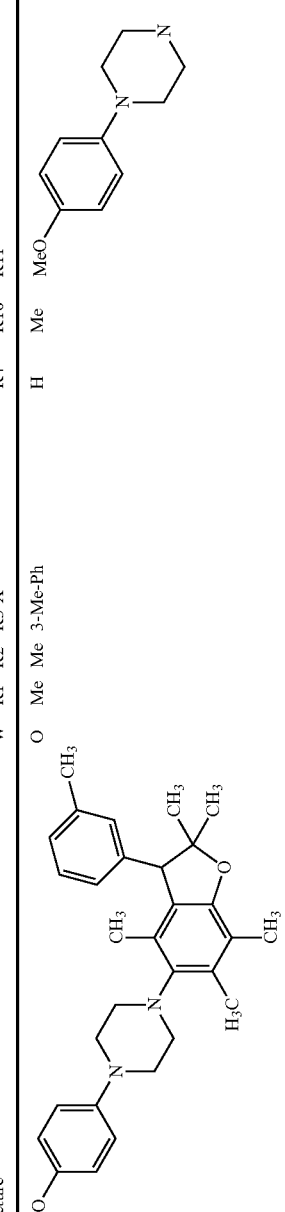 | O | Me | Me | 3-Me-Ph | H | Me | MeO-(4-piperazinyl-phenyl) | Me | Me | |
| 54 | 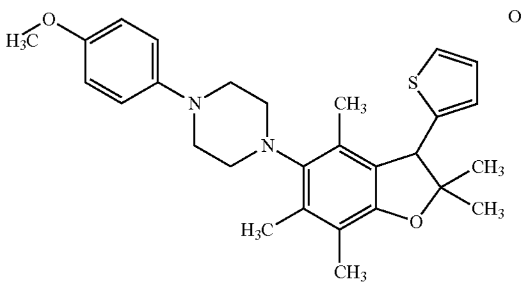 | O | Me | Me | 2-thienyl | H | Me | MeO-(4-piperazinyl-phenyl) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 55 | 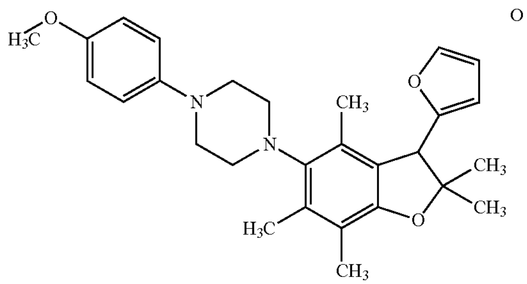 | O | Me | Me | 2-furyl | H | Me | MeO | Me | Me | |
| 56 | 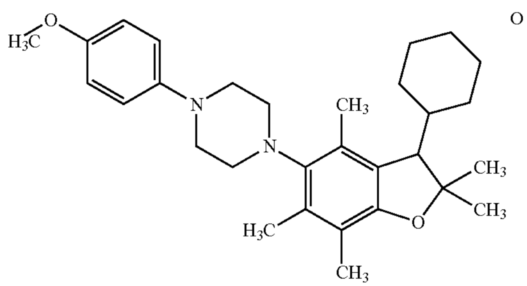 | O | Me | Me | c-hexyl | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 57 | 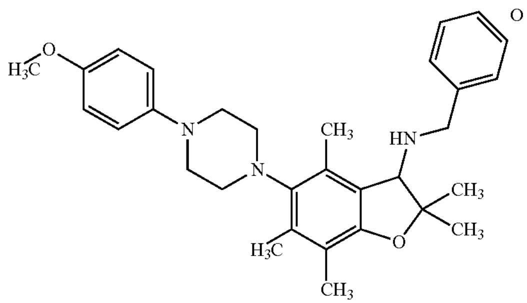 | O | Me | Me | benzyl-NH | H | Me | MeO-C6H4-piperazinyl | Me | Me | |
| 58 | 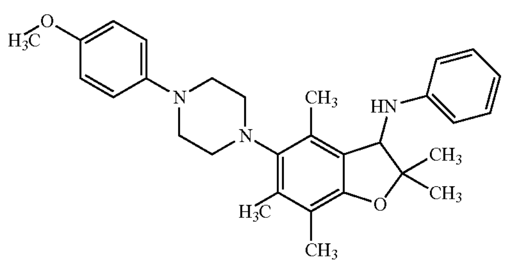 | O | Me | Me | Ph-NH | H | Me | MeO-C6H4-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 59 | 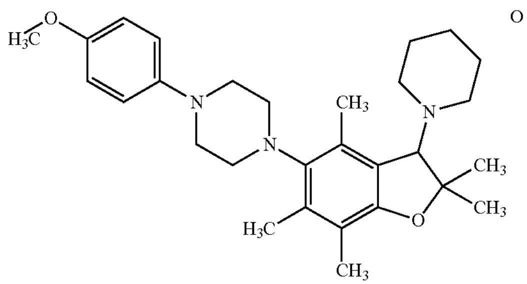 | O | Me | Me | piperindo | H | Me | MeO | Me | Me | |
| 60 | 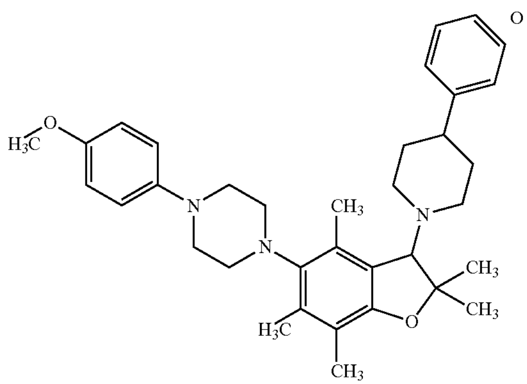 | O | Me | Me | 4-Ph-piperindo | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 61 | 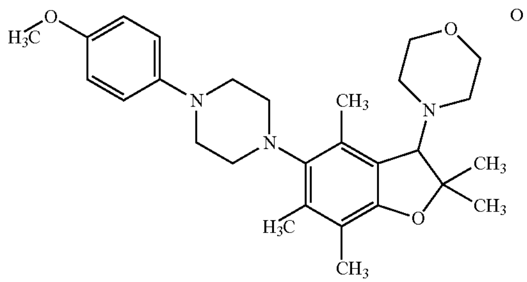 | O | Me | Me | morpholino | H | Me | MeO-C6H4-piperazinyl | Me | Me | |
| 62 | 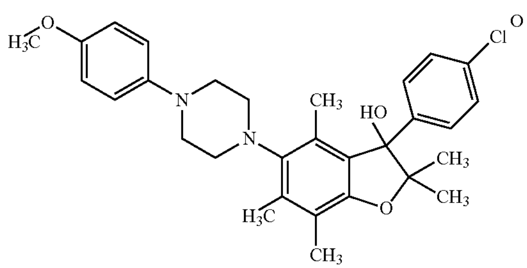 | O | Me | Me | 4-Cl-Ph | OH | Me | MeO-C6H4-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 63 | 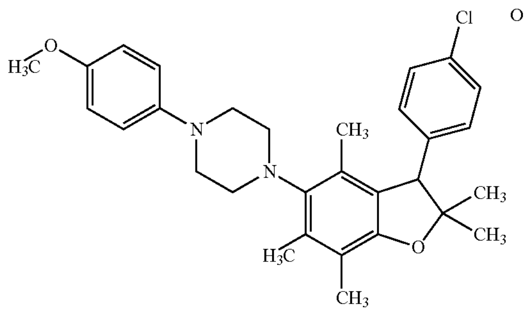 | O | Me | Me | 4-Cl-Ph | H | Me | MeO | Me | Me | |
| 64 | 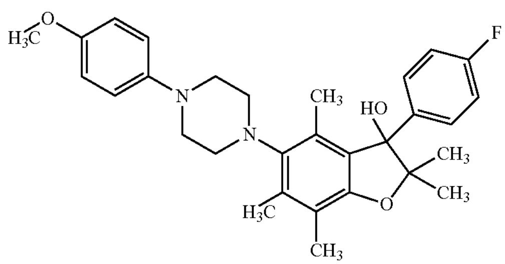 | O | Me | Me | 4-F-Ph | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 65 | 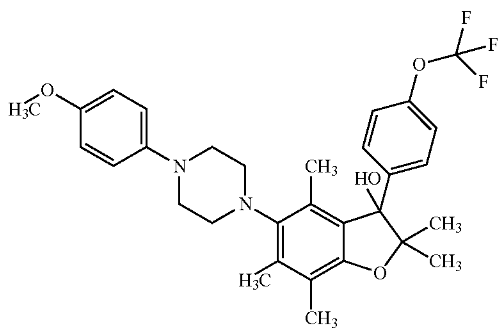 | O | Me | Me | 4-CF$_3$O-Ph | OH | Me | MeO | Me | Me | |
| 66 | 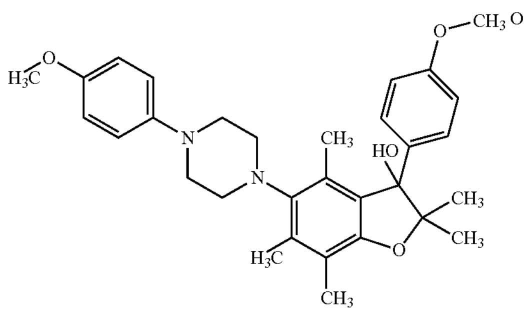 | O | Me | Me | 4-MeO-Ph | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 67 | 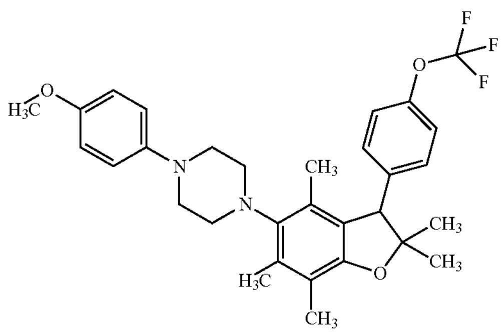 | O | Me | Me | 4-CF₃O-Ph | H | Me | MeO-Ph-N-piperazine | Me | Me | |
| 68 | 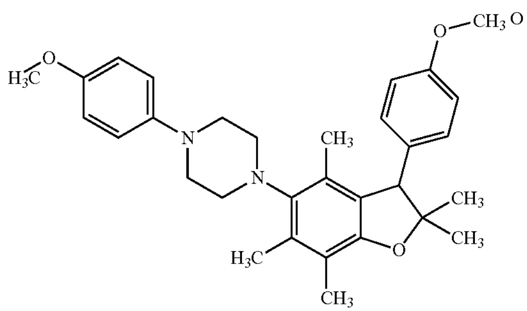 | O | Me | Me | 4-MeO-Ph | H | Me | MeO-Ph-N-piperazine | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 69 | 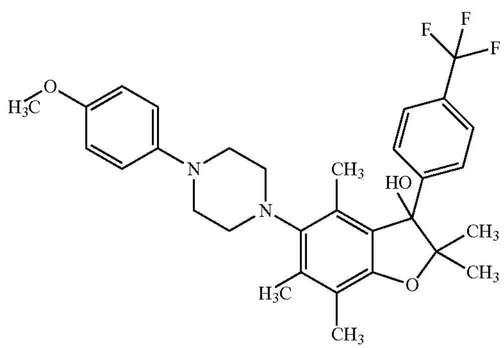 | O | Me | Me | 4-CF₃-Ph | OH | Me | MeO-(4-piperazinyl-Ph) | Me | Me | |
| 70 | 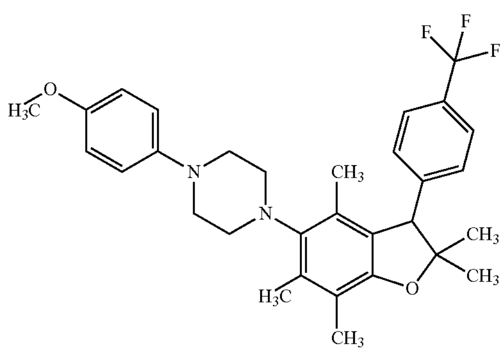 | O | Me | Me | 4-CF₃-Ph | H | Me | MeO-(4-piperazinyl-Ph) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 71 | 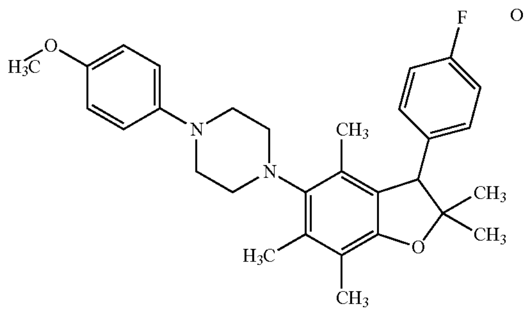 | O | Me | Me | 4-F-Ph | H | Me | MeO | Me | Me | |
| 72 | 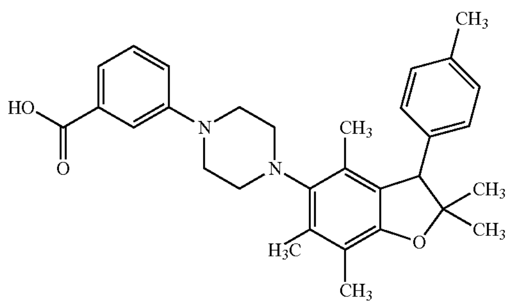 | O | Me | Me | 4-Me-Ph | H | Me | HO2C | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 73 | 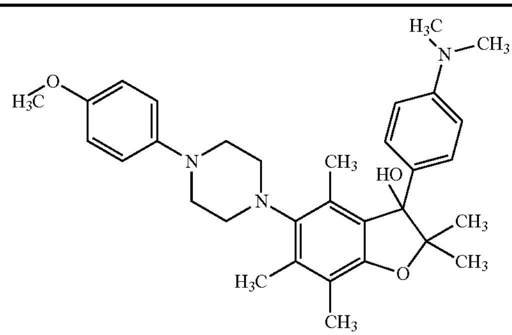 | O | Me | Me | 4-Me₂N-Ph | OH | Me | MeO | Me | Me | |
| 74 | 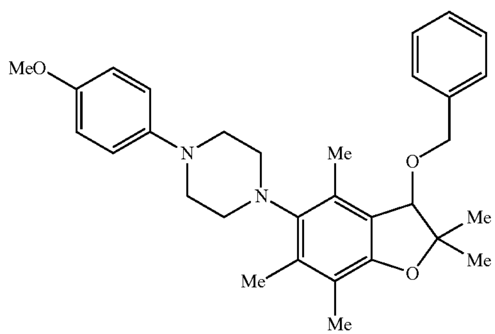 | O | Me | Me | PhCH₂O | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 75 | 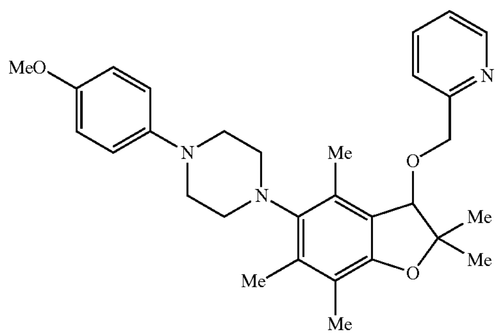 | O | Me | Me | 2-pyridylmethyloxy | H | Me | MeO-phenyl-piperazinyl | Me | Me | |
| 76 | 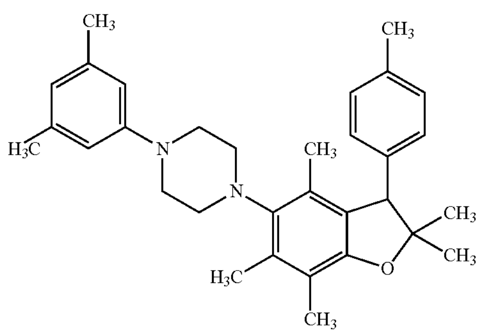 | O | Me | Me | 4-Me-Ph | H | Me | 3,5-diMe-phenyl-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 77 | 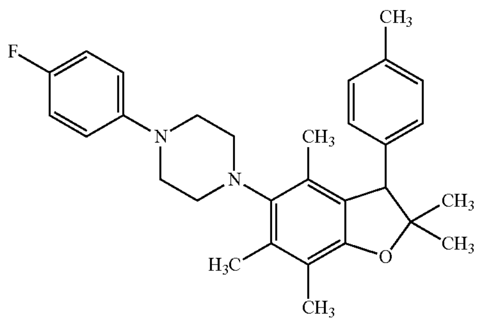 | O | Me | Me | 4-Me-Ph | H | Me | F | Me | Me | |
| 78 | 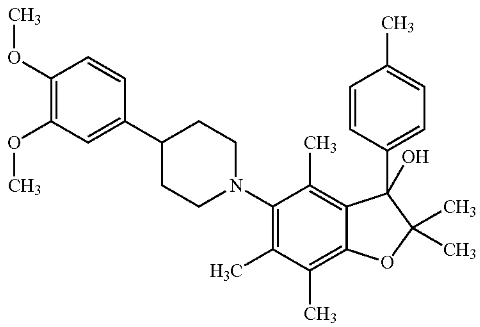 | O | Me | Me | 4-Me-Ph | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 79 | 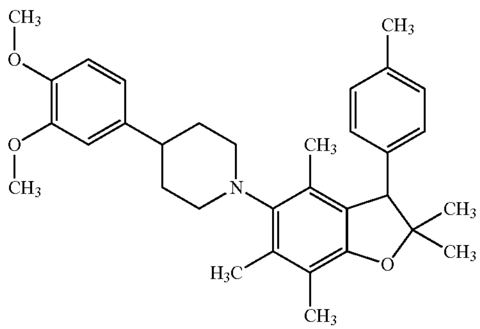 | O | Me | Me | 4-Me-Ph | H | Me | MeO | Me | Me | |
| 80 | 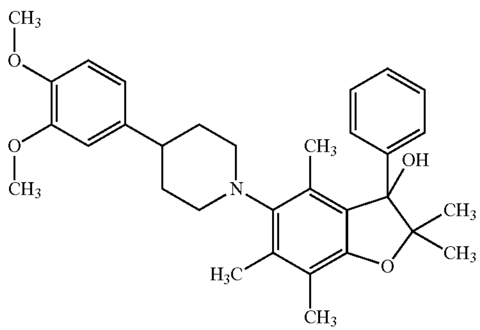 | O | Me | Me | Ph | OH | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 81 | 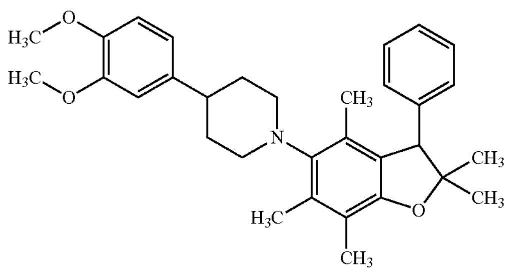 | O | Me | Me | Ph | H | Me | MeO | Me | Me | |
| 82 | 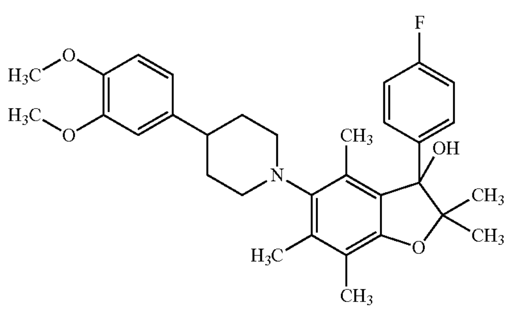 | O | Me | Me | 4-F-Ph | OH | Me | MeO | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 83 | (structure) | O | Me | Me | 4-iPr-Ph | H | Me | MeO (3,4-dimethoxyphenyl-piperidinyl) | Me | Me | |
| 84 | (structure) | O | Me | Me | 4-iPr-Ph | OH | Me | MeO (3,4-dimethoxyphenyl-piperidinyl) | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 85 | 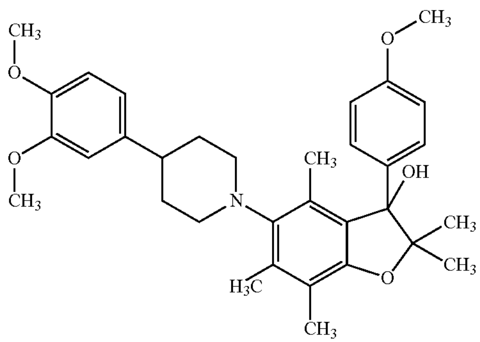 | O | Me | Me | 4-MeO-Ph | OH | Me | MeO | Me | Me | |
| 86 | 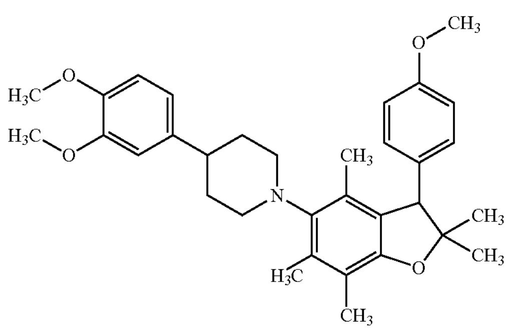 | O | Me | Me | 4-MeO-Ph | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 87 | 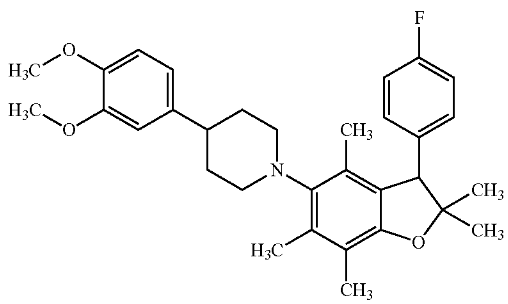 | O | Me | Me | 4-F-Ph | H | Me | MeO | | Me | |
| 88 | 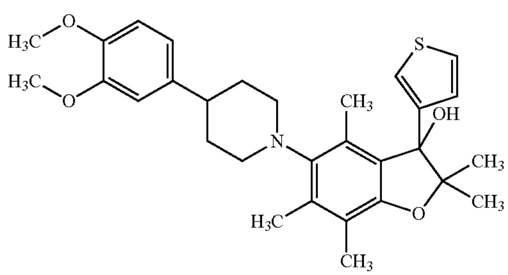 | O | Me | Me | 3-thienyl | OH | Me | MeO | | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 89 | ![structure] | O | Me | Me | 3-thienyl | H | Me | MeO-phenyl-piperidinyl | Me | Me | |
| 90 | ![structure] | O | Me | Me | Ph-NH | H | Me | MeO-phenyl-piperidinyl | Me | Me | |

TABLE 1-continued
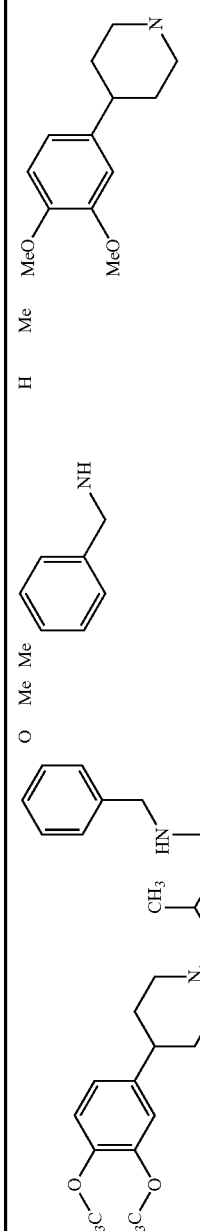
| Example Number | Structure | W | R1 | R2 | R3-X- | R4 | R10 | R11 | R12 | R13 | Optical Isomer |
|---|---|---|---|---|---|---|---|---|---|---|---|
| 91 | 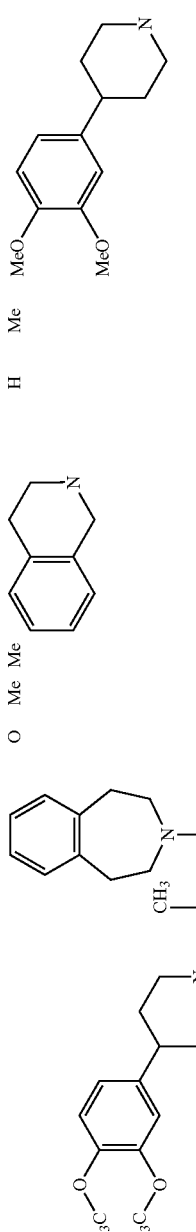 | O | Me | Me | benzylamino | H | Me | MeO, 4-(piperidin-4-yl)-2-MeO-phenyl | Me | Me | |
| 92 | 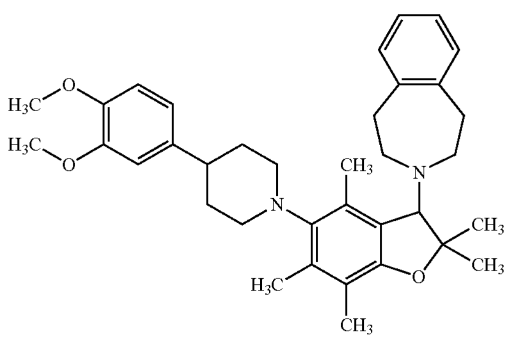 | O | Me | Me | 1,2,3,4-tetrahydroisoquinolin-2-yl | H | Me | MeO, 4-(piperidin-4-yl)-2-MeO-phenyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 93 | 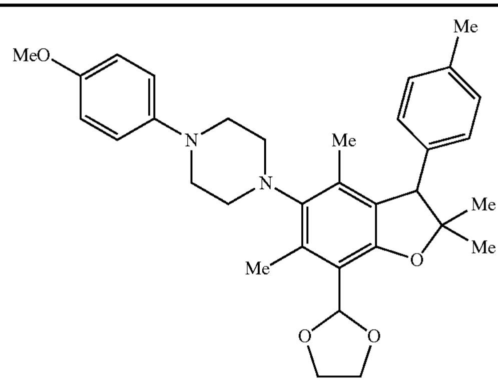 | O | Me | Me | 4-Me-Ph | H | Me | MeO-C6H4-piperazinyl | Me | 1,3-dioxolan-2-yl | |
| 94 | 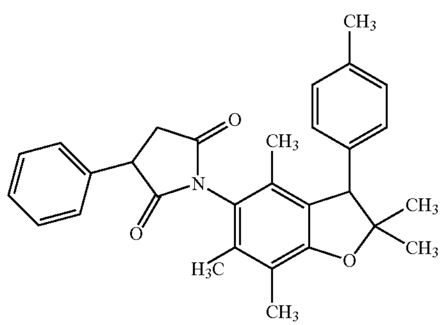 | O | Me | Me | 4-Me-Ph | H | Me | 3-phenylsuccinimido | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 95 | 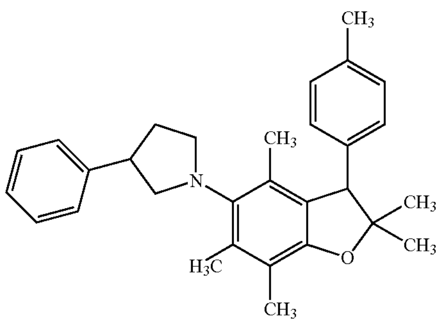 | O | Me | Me | 4-Me-Ph | H | Me | 3-phenylpyrrolidin-1-yl | Me | Me | |
| 96 | 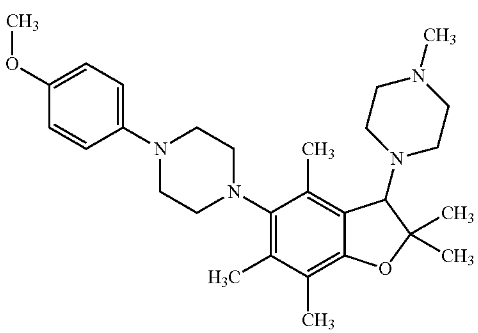 | O | Me | Me | 4-Me-piperidinyl | H | Me | 4-(4-methoxyphenyl)piperazin-1-yl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 97 | 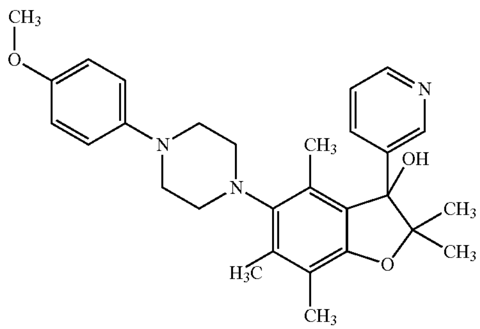 | O | Me | Me | 3-piridyl | OH | Me | MeO | Me | Me | |
| 98 | 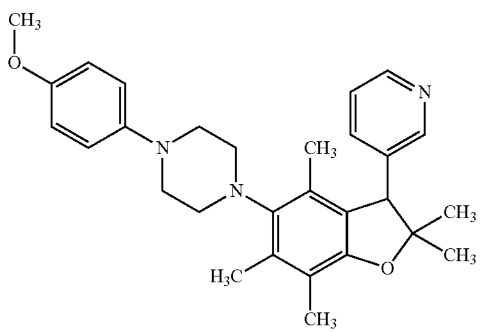 | O | Me | Me | 3-piridyl | H | Me | MeO | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 99 | 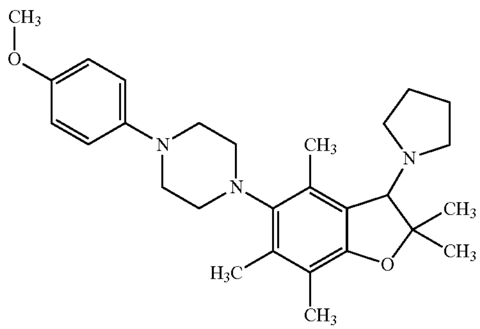 | O | Me | Me | pyrrolidinyl | H | Me | MeO | Me | Me | |
| 100 | 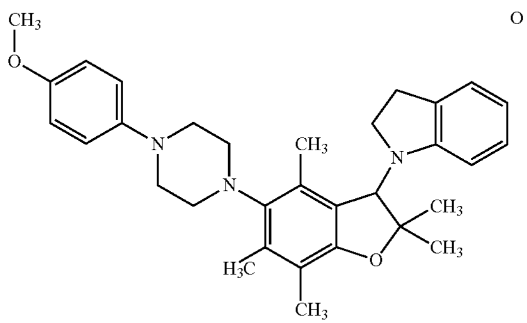 | O | Me | Me | indolinyl | H | Me | MeO | Me | Me | |

TABLE 1-continued
| Example Number | Structure | W | R1 | R2 | R3-X- | R4 | R10 | R11 | R12 | R13 | Optical Isomer |
|---|---|---|---|---|---|---|---|---|---|---|---|
| 101 | 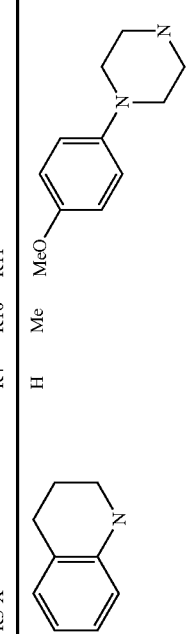 | O | Me | Me | 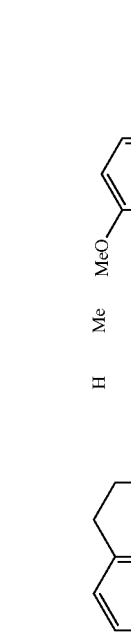 | H | Me | MeO<br> | Me | Me | |
| 102 | 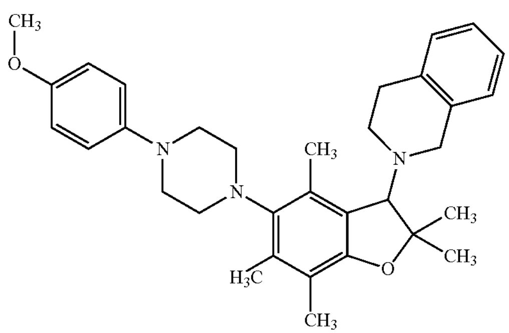 | O | Me | Me | 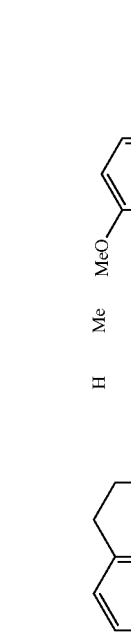 | H | Me | MeO<br> | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 103 | 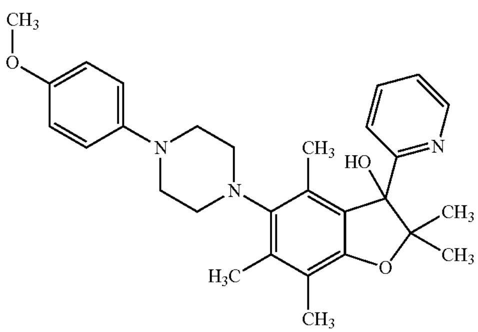 | O | Me | Me | 2-piridyl | OH | Me | MeO | Me | Me | |
| 104 | 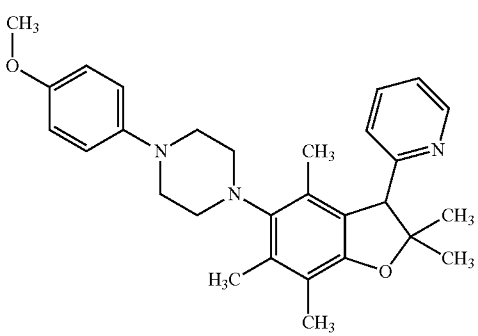 | O | Me | Me | 2-piridyl | H | Me | MeO | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 105 | 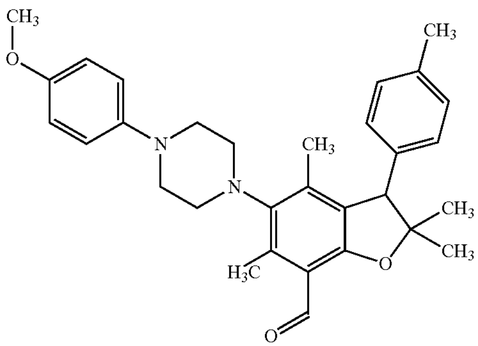 | O | Me | Me | 4-Me-Ph | H | Me | MeO | Me | CHO | |
| 106 | 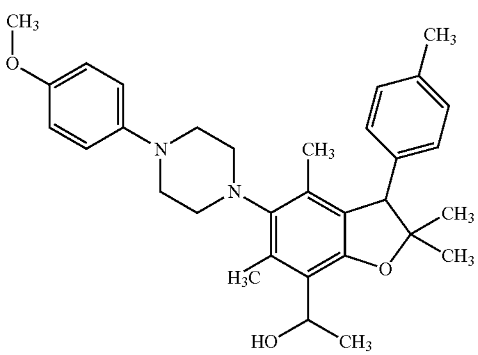 | O | Me | Me | 4-Me-Ph | H | Me | MeO | Me | CH(OH)CH₃ | |

TABLE 1-continued
| Example Number | Structure | W | R1 | R2 | R3-X- | R4 | R10 | R11 | R12 | R13 | Optical Isomer |
|---|---|---|---|---|---|---|---|---|---|---|---|
| 107 | 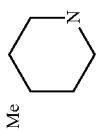 | O | Me | Me | 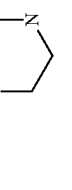 | H | Me | MeO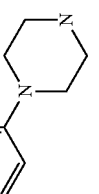 | Me | Me | |
| 108 | 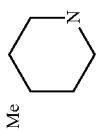 | O | Me | Me | 4-Et-piperazinyl | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 109 | 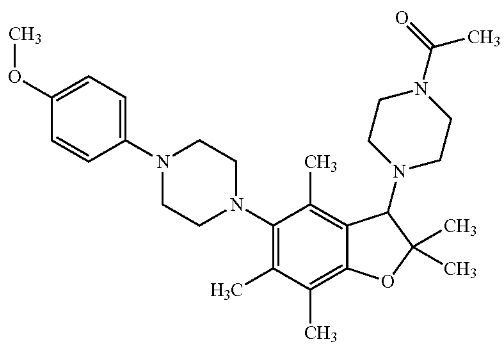 | O | Me | Me | 4-acetyl piperazinyl | H | Me | MeO | Me | Me | |
| 110 | 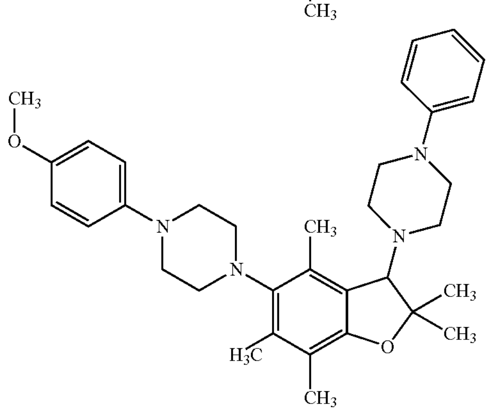 | O | Me | Me | 4-Ph piperazinyl | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 111 | 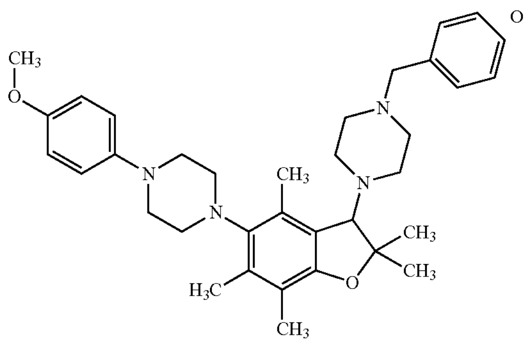 | O | Me | Me | benzylpiperazinyl | H | Me | MeO-phenyl-piperazinyl | Me | Me | |
| 112 | 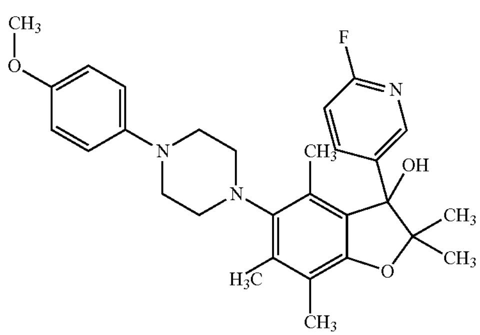 | O | Me | Me | 6-F-pyridin-3-yl | OH | Me | MeO-phenyl-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 113 | 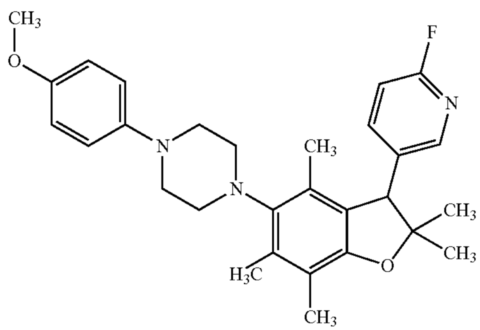 | O | Me | Me | 6-F-pyridin-3-yl | H | Me | MeO-(4-piperazinyl-phenyl) | Me | Me | |
| 114 | 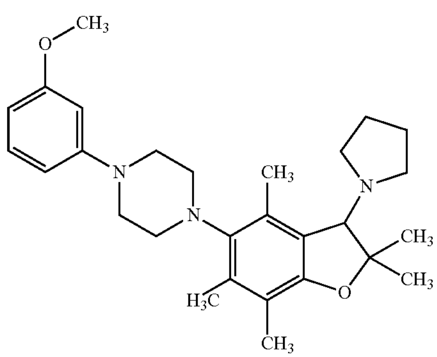 | O | Me | Me | pyrrolidinyl | H | Me | MeO-(3-piperazinyl-phenyl) | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 115 | 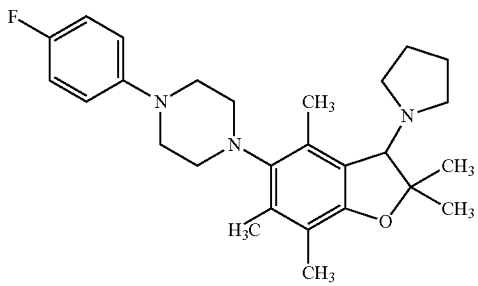 | O | Me | Me | pyrrolidinyl | H | Me | 4-F-phenylpiperazinyl | Me | Me | |
| 116 | 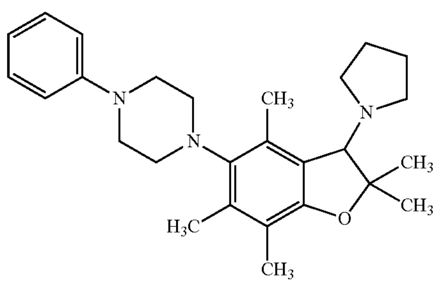 | O | Me | Me | pyrrolidinyl | H | Me | phenylpiperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 117 | ![structure] | O | Me | Me | pyrrolidinyl | H | Me | ![OMe-phenyl-piperazinyl] | Me | Me | |
| 118 | ![structure] | O | Me | Me | piperindo | H | Me | ![diOMe-phenyl-piperazinyl] | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 119 | 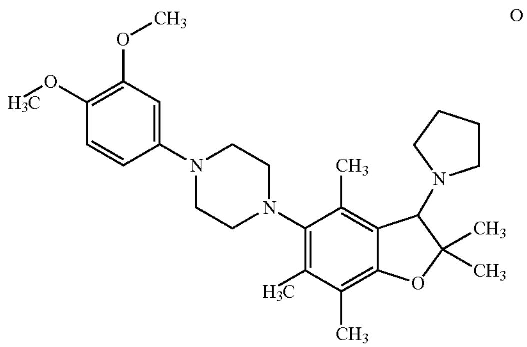 | O | Me | Me | pyrrolidinyl | H | Me | 3-OMe, 4-OMe-phenyl-piperazinyl | Me | Me | |
| 120 | 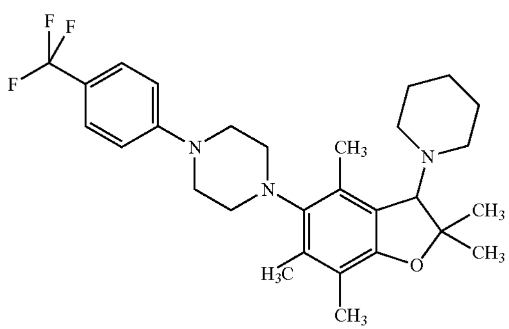 | O | Me | Me | piperindo | H | Me | 4-CF3-phenyl-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 121 | 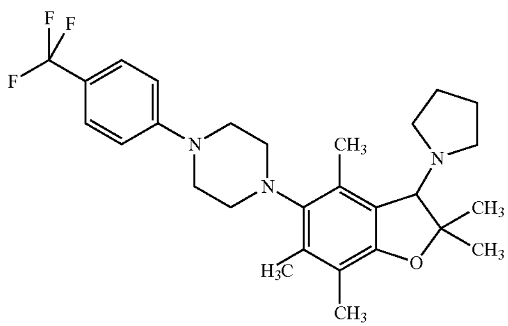 | O | Me | Me | pyrrolidinyl | H | Me | F3C-[4-piperazinyl-phenyl] | Me | Me | |
| 122 | 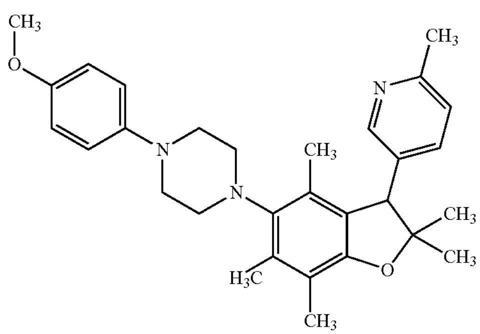 | O | Me | Me | 6-Me-pyridin-3-yl | H | Me | MeO-[4-piperazinyl-phenyl] | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 123 | 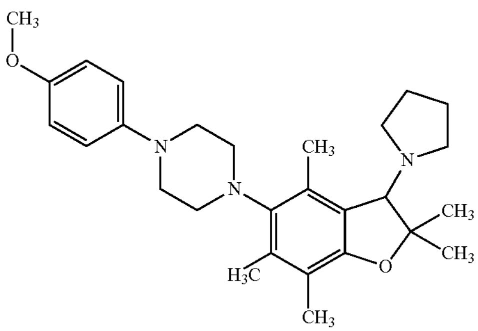 | O | Me | Me | pyrrolidinyl | H | Me | MeO | Me | Me | (−)-isomer |
| 124 | 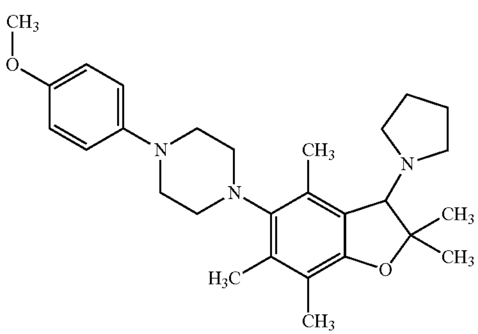 | O | Me | Me | pyrrolidinyl | H | Me | MeO | Me | Me | (+)-isomer |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 125 | 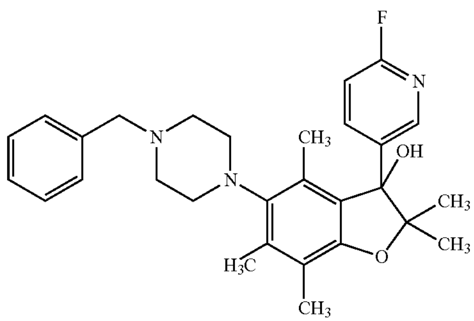 | O | Me | Me | 6-F-pyridin-3-yl | OH | Me | 4-benzylpiperazin-1-yl | Me | Me | |
| 126 | 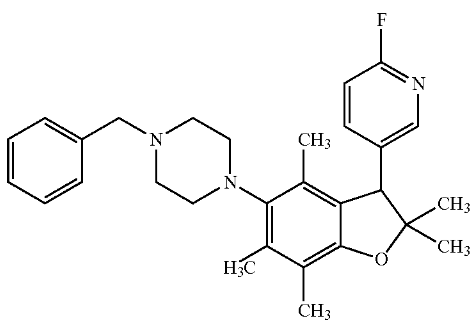 | O | Me | Me | 6-F-pyridin-3-yl | H | Me | 4-benzylpiperazin-1-yl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 127 | 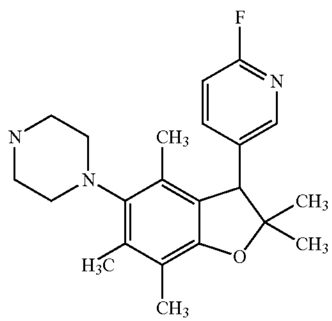 | O | Me | Me | 6-F-pyridin-3-yl | H | Me | piperazinyl | Me | Me | |
| 128 | 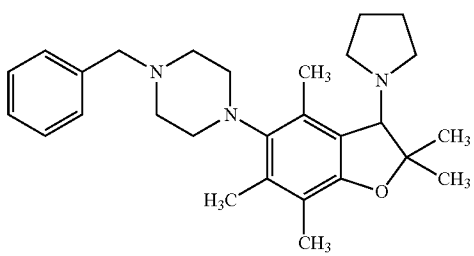 | O | Me | Me | pyrrolidinyl | H | Me | 4-benzylpiperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 129 | (structure) | O | Me | Me | 6-F-pyridin-3-yl | H | Me | (4-(4-fluorophenyl)piperazin-1-yl) | Me | Me | |
| 130 | (structure) | O | Me | Me | (4-methylbenzyl) | H | Me | (4-(4-methoxyphenyl)piperazin-1-yl) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 131 | 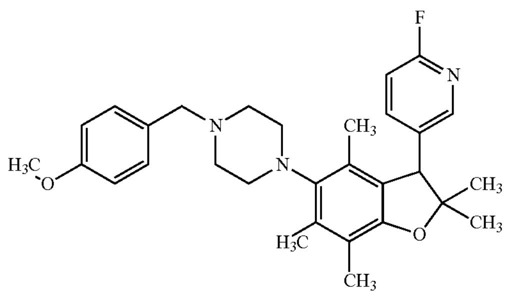 | O | Me | Me | 6-F-pyridin-3-yl | H | Me | | 4-(4-methoxybenzyl)piperazin-1-yl | Me | |
| 132 | 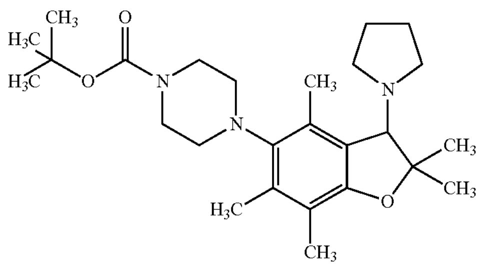 | O | Me | Me | pyrrolidinyl | H | Me | | 4-(2-methyl-2-propoxycarbonyl)piperazin-1-yl | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 133 | 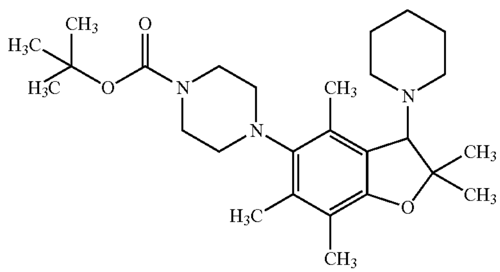 | O | Me | Me | piperindo | H | Me | (2-methyl-2-(piperazinylcarbonyloxy)propyl) | Me | Me | |
| 134 | 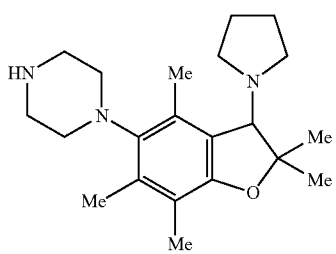 | O | Me | Me | pyrrolidinyl | H | Me | piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 135 | 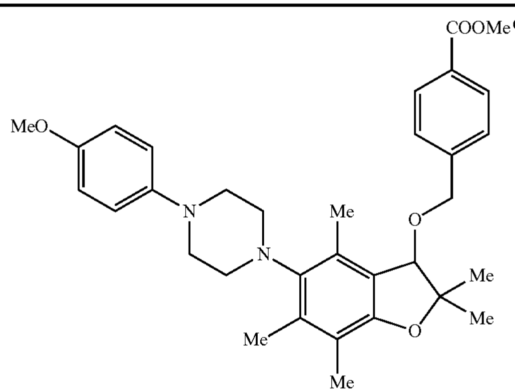 | COO | Me | Me | MeO₂C-C₆H₄-CH₂-O- | H | Me | MeO-C₆H₄-piperazinyl | Me | Me | |
| 136 | 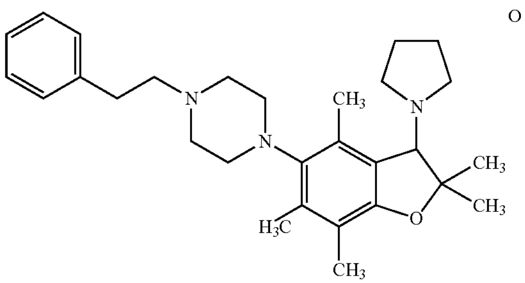 | O | Me | Me | pyrrolidinyl | H | Me | PhCH₂CH₂-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 137 | 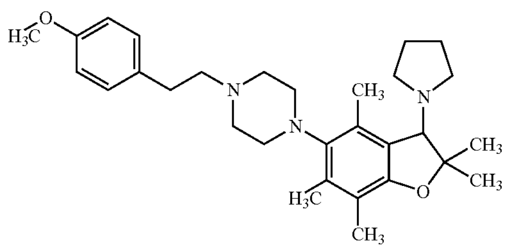 | O | Me | Me | pyrrolidinyl | H | Me | MeO-C6H4-CH2CH2-piperazinyl | Me | Me | |
| 138 | 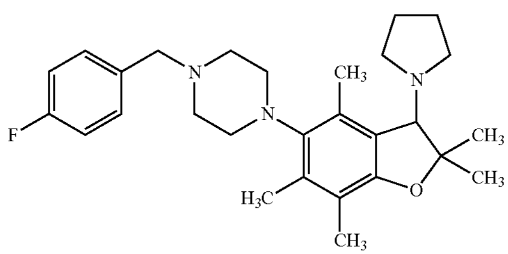 | O | Me | Me | pyrrolidinyl | H | Me | 4-F-C6H4-CH2-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 139 | 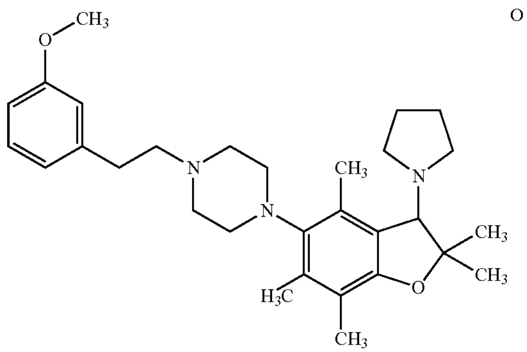 | O | Me | Me | pyrrolidinyl | H | Me | OMe | Me | Me | |
| 140 | 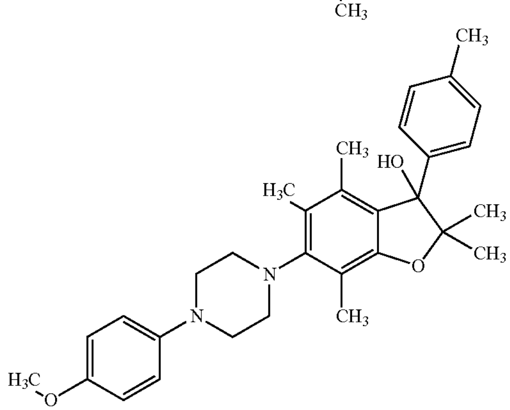 | O | Me | Me | 4-Me-Ph | OH | Me | Me | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 141 | 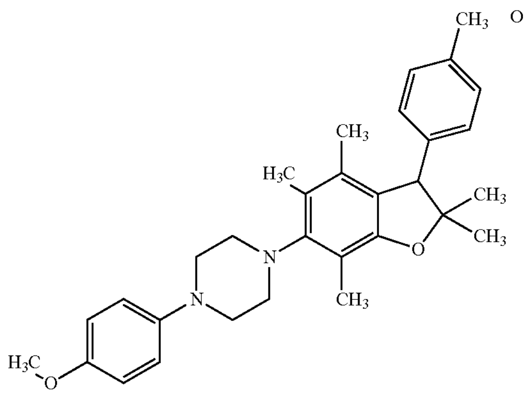 | O | Me | Me | 4-Me-Ph | H | Me | Me | MeO-C6H4-piperazinyl | Me | |
| 142 | 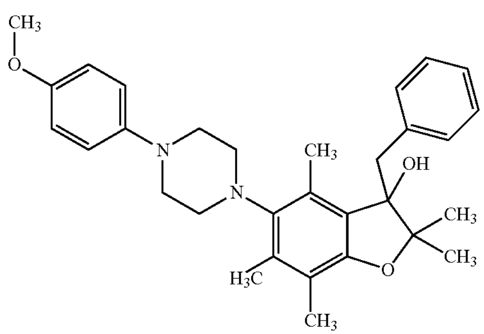 | O | Me | Me | Bn | OH | Me | MeO-C6H4-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 143 | 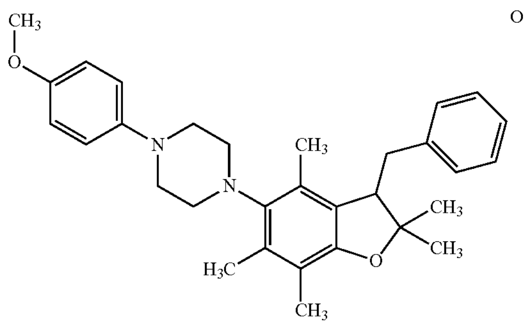 | O | Me | Me | Bn | H | Me | MeO-(4-piperazinyl-phenyl) | Me | Me | |
| 144 | 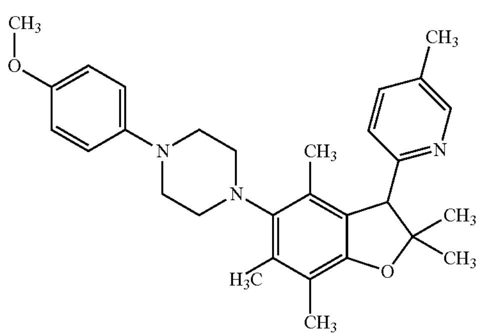 | O | Me | Me | 4-Me-pyridin-2-yl | H | Me | MeO-(4-piperazinyl-phenyl) | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 145 | 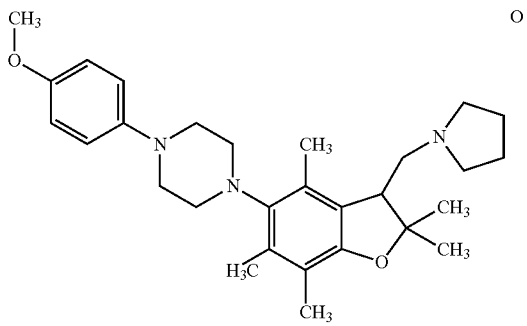 | O | Me | Me | pyrrolidinyl-NCH2 | H | Me | MeO-phenyl-piperazinyl | Me | Me | |
| 146 | 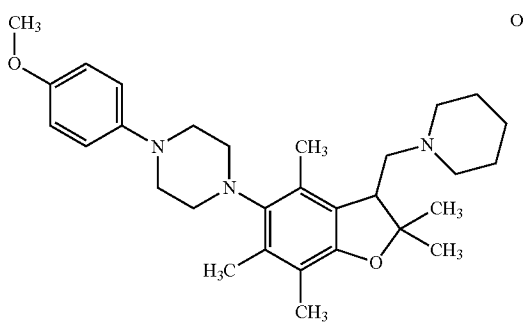 | O | Me | Me | piperidinyl-NCH2 | H | Me | MeO-phenyl-piperazinyl | Me | Me | |

TABLE 1-continued

| Example Number | Structure | W | R1 | R2 | R3-X | R4 | R10 | R11 | R12 | R13 | Optical Isomer |
|---|---|---|---|---|---|---|---|---|---|---|---|
| 147 | 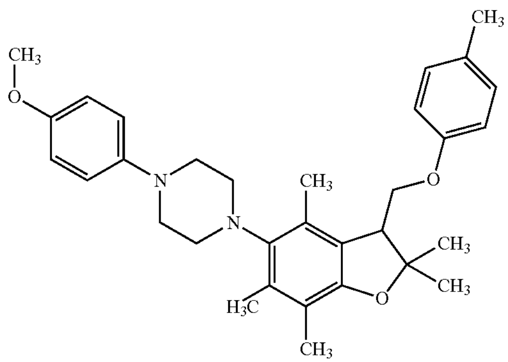 | O | Me | Me | 4-MePhOCH₂ | H | Me | MeO | Me | Me | |
| 148 | 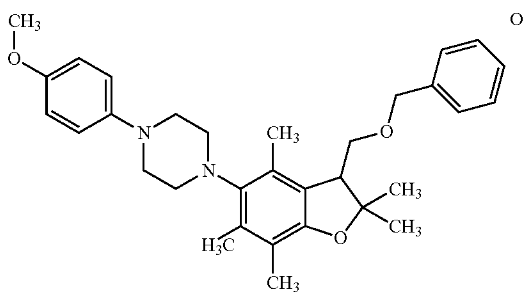 | O | Me | Me | PhCH₂OCH₂ | H | Me | MeO | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 149 | 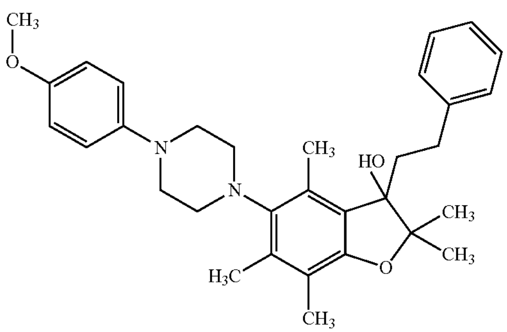 | O | Me | Me | PhCH₂CH₂ | OH | Me | MeO-C₆H₄-piperazinyl | Me | Me | |
| 150 | 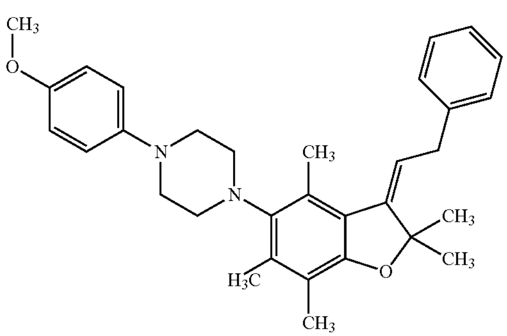 | O | Me | Me | PhCH₂CH | = | Me | MeO-C₆H₄-piperazinyl | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 151 | 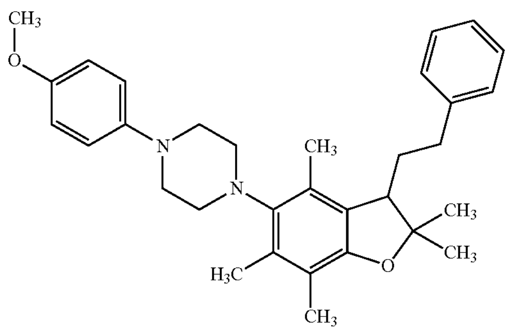 | O | Me | Me | PhCH₂CH₂ | H | Me | MeO-C₆H₄-piperazinyl | Me | Me | |
| 152 | 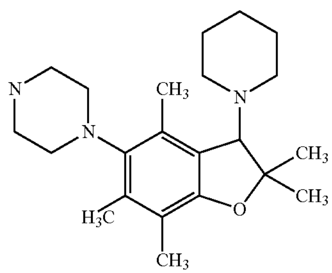 | O | Me | Me | piperindo | H | Me | piperazinyl-NH | Me | Me | |

TABLE 1-continued

| Example Number | Structure | W | R1 | R2 | R3-X- | R4 | R10 | R11 | R12 | R13 | Optical Isomer |
|---|---|---|---|---|---|---|---|---|---|---|---|
| 153 | ![structure] | O | Me | Me | piperindo | H | Me | benzylpiperazinyl | Me | Me | |
| 154 | ![structure] | O | Me | Me | HO₂C-C₆H₄-CH₂-O | H | Me | 4-methoxyphenylpiperazinyl | Me | Me | |

PREPARATION EXAMPLE 1

(1) Compound obtained in Example 2 10 mg.
(2) Lactose 34 mg.
(3) Corn starch 10.6 mg.
(4) Corn starch (paste) 5 mg.
(5) Magnesium stearate 0.4 mg.
(6) Carboxymethylcellulose calcium 20 mg.

Total 120 mg.

The aforementioned (1)–(6) are mixed together according to standard methods, and tabletted by a tabletting machine to produce tablets.

EXPERIMENTAL EXAMPLE 1

Cytoprotection activity against a PI-3 kinase inhibitor LY-294002 in human neuroblastoma SK-N-SH cells.

a) Experiment Materials

Human neuroblastoma SK-N-SH cells were purchased from American Type Cell Culture (ATCC). DMEM/F-12 culture medium and potassium/magnesium-free phosphate buffer saline (PBS(–)) were purchased from Nikken Biomedical Co., Ltd., N2 additives and EDTA solution were purchased from GIBCO BRL Company, fetal bovine serum (FCS) and a mixed solution of penicillin (5000 U/ml) and streptomycin (5 mg/ml) were purchased from BioWhittaker Inc., Alamarblue™ reagent was purchased from Wako Pure Chemical Industries Ltd., culture flasks were purchased from Falcon Company, collagen-coated 96-well multi-plates were purchased from Iwaki Glass Co., Ltd., and LY-294002 was purchased from Alexis Biochemicals, respectively. As for other reagents, commercially available guaranteed reagents were used.

b) Experimental Method (1) Cultivation of SK-N-SH Cells

A DMEM/F-12 culture medium which contains 5% FCS, 0.5% N2, 10 mM HEPES, and a 1% mixed solution of penicillin (5000 U/ml) and streptomycin (5 mg/ml) was used to subculture SK-N-SH cells in a carbon dioxide incubator under a mixed gas atmosphere consisting of 10% carbon dioxide/90% air. After being cultivated to a sub-confluent stage, the cells were detached with a PBS(–) solution containing 2.5 mM EDTA and seeded onto collagen-coated 96-well multi-plates in the proportion of $10^4/100$ μL well. After cultivation for 24 hours, the cultured cells were used in a cytotoxic test.

(2) Protective Activity with Respect to LY-294002-Induced Nerve Cell Cytotoxicity 80 μM of the culture medium of the SK-N-SH cells that were cultured as described above on the collagen-coated 96-well multi-plates was removed, and 40 μL each of LY-294002 having a final concentration of 30 μM and a test compound having a final concentration that was adjusted to be 1.0 μM were simultaneously added to initiate the cytotoxicity test. Note that each test compound used was diluted to a concentration of 10 mM with dimethyl sulfoxide, and the LY-294002 used was diluted to a concentration of 100 mM with dimethyl sulfoxide.

(3) Evaluation of the Survival Activity of the Cells

The survival activity of neural cells that were still living one day after the initiation of the cytotoxicity test was estimated by the reductive activity of Alamarblue™ reagent as an index. 20 μL of the culture medium was removed, 20 μL of Alamarblue™ reagent was added, and the amount of Alamarblue™ reagent reduced for 4 hours incubation was calorimetrically measured with a plate reader (WAKO SPECTRAMAX 250 Microplate Reader) (measurement wave length 570 nm, reference wave length 600 nm).

Cytoprotection activity was calculated by means of the following equation.

$$\text{Cytoprotection activity a test compound} = (A-B)/(C-B) \times 100 \ (\%)$$

A: The survival activity of a group consisting of a test compound and LY-294002
B: The survival activity of a group consisting of LY-294002
C: The survival activity of a control group (Results)

At least 4 wells for every 1 dose of a test compound was used to determine the cytoprotection activity of a test compound. The results are shown in Table 2.

TABLE 2

| Example compound | Cell protection activity (%). |
|---|---|
| 32 | 35.6 |
| 33 | 24.9 |
| 46 | 39.5 |
| 58 | 39.2 |
| 59 | 23.9 |
| 79 | 31.3 |
| 92 | 29.6 |

These results reveal that, like neurotrophic factors, compound (I) has protective activity against cytotoxicity of LY-294002, which is a PI-3 kinase inhibitor and causes neurodegeneration, and thereby suppresses neurodegeneration.

TEST EXAMPLE 2

Neurogenesis Enhancing Activity in Mixed Rat Glia Culture a) Experimental Materials Neonatal of SD rats were purchased from Japan Charles River Co, Ltd. A 40 mm nylon cell strainer was purchased from Beckton-Dickinson. DMEM/F12 culture medium, antibiotic, and N2 additive were purchased from Life Technology Corp. Anti β III-tubulin antibody was purchased from Sigma Corp. DAKO EnVision+/HRP kit was purchased from Dako Japan Corp. As for other reagents, commercially available guaranteed reagents were used.

b) Experimental Method

1. Mixed Rat Glia Culture

Rat mixed glia culture was prepared from the cerebrums of 2 day old neonatal SD rat. The neonates were anaesthetised with ice cooling, were decapitated, and their brains were quickly removed. The meninges were carefully removed, and the cerebral cortex was separated therefrom. The cerebral cortex was passed through 40 micron nylon mesh, and it was physically dissociated. Cell suspension was then layered in a cell dispersion liquid on serum, and the cells were fractionated by non-continuous density gradient centrifugation. The precipitate was washed twice with growth culture medium (10% FBS and antibiotic. added to DMEM/F12), and it was dispersed. Mixed glia culture was seeded and inoculated onto a collagen coated 96 well multiplate with $1 \times 10^5$ cells per well, and was cultured for five days.

2. Differentiation Assay

After culturing for five days, mixed glia culture was used in a differentiation assay. Growth culture medium was substituted with a serum-free medium (N2 supplememt and antibiotic added to DMEM/F12), and test compound was added simultaneously. After differentiation for five days, culture was fixed with 4% paraformaldehyde, and was immunostained with the mouse anti β III-tubulin monoclonal antibody and the DAKO EnVison+/HRP kit.

β III-tubulin positive cell area were quantified by image analysis, and was compared to when compound (I) was added (1 μM) and when it was not added (control). The results are shown in the table below.

TABLE 3

| Example compound | Differentiation/nacent promotion activity (%/control) |
|---|---|
| 32 | 371 |
| 33 | 448 |
| 46 | 842 |

The aforementioned results reveal that compound (I) has neurodifferentiating and neurogenic activity be β III-tubulin positive neural precursor cells.

INDUSTRIAL UTILITY

Compounds of the present invention, and salts or prodrugs thereof, have excellent nerve degeneration inhibitory activity and brain penetrability, have low toxicity, and are useful as agents for preventing/treating neurodegenerative diseases and the like. In addition, the compounds of the present invention have stem cell and/or neural precursor cell proliferation/differentiation promotion activity and are useful as neuropoiesis promotion agents or neuroregeneration promotion agents.

The invention claimed is:

1. A compound represented by the formula:

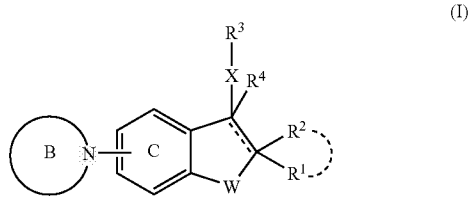

(I)

(wherein, $R^1$ and $R^2$ are the same or different and each represents a hydrogen atom, optionally substituted hydrocarbon group or optionally substituted heterocyclic group, or $R^1$ and $R^2$ may form, together with the adjacent carbon atom, a 3–8 membered iso- or heterocyclic group which may optionally substituted, $R^3$ represents an optionally substituted cyclic group, X represents a bond or a spacer of 1–3 atoms, and $R^4$ represents a hydrogen atom, an optionally substituted hydrocarbon group, optionally substituted hydroxy group, optionally substituted mercapto group which may have oxo, or an optionally substituted amino group, or $R^2$ and $R^4$ may link together to form a double bond, W represents an oxygen atom or a sulfur atom, ring B represents an optionally substituted 4–8 membered nitrogen-containing heterocyclic group, and ring C represents a benzene ring which may also be optionally substituted in addition to the group represented by ring B but not via a nitrogen atom, and═represents a single bond or a double bond), or a salt thereof.

2. The compound as defined in claim 1, wherein $R^1$ and $R^2$ are the same or different and represent (i) a hydrogen atom, (ii) C1–6 alkyl group, C2–6 alkenyl group, C2–6 alkynyl group, C3–8 cycloalkyl group or C6–14 aryl group each of which may have 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-$C_{1-6}$ alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 arylcarbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5-or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and a 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy, or (iii) 5–14 membered heterocyclic group containing, other than carbon atoms, 1–4 heteroatoms selected from nitrogen atoms, sulfur atoms, and oxygen atoms, optionally containing 1–5 substituents selected from (1) halogen, (2) C1–3 alkylenedioxy, (3) nitro, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6alkylamino, (15) mono-C6–14 arylamino, (16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 arylcarbonylamino, C1–6 alkoxy-carbonylamino, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally containing 1–3 substituents selected from C1–6 alkyl, C6–14 aryl and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo, and (24) C6–14 aryloxy, or (iv) $R^1$ and $R^2$, together with the adjacent carbon atom, may form C3–8 cycloalkane or 3–8 membered heterocyclic group containing, other than carbon atoms, 1–4 heteroatoms selected from nitrogen atoms, sulfur atoms, and oxygen atoms, which may respectively be substituted with 1–5 substituents selected from the following, (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6alkyl-carbamoyl, di-C1–6 alkyl-carbamoyl, thiocarbamoyl, C6–14 aryl-carbamoyl, 5- or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino, and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally substituted with 1–3 substituents which are selected from C1–6 alkyl, C6–14 aryl and a 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy;

$R^3$ represents (1) C6–14 aryl, (2) optionally halogenated C3–8 cycloalkyl or (3) 5–10 membered heterocyclic group containing, other than carbon atoms, 1–4 heteroatoms selected from nitrogen atoms, sulfur atoms, and oxygen atoms, which may respectively be substituted with 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5 or 6 membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 arylcarbonylamino, C1–6 alkoxy-carbonylamino, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14aryl, and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy X is a bond,

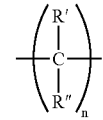

(wherein, R' and R'' represent a hydrogen atom, C1–6 alkyl group, C3–8 cycloalkyl group or C6–14 aryl group, and n is an integer of 1–3, and when n is 2 or 3, R' and R'' may be different in each repeating unit), —CO—, —O—, —S—, —SO—, —SO$_2$— or NR$^5$— (wherein, R$^5$ represents a hydrogen atom or C1–6 alkyl group, C2–6 alkenyl group, C2–6 alkynyl group, C3–8 cycloalkyl group, C6–14 aryl group, each of which may respectively contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy which is selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino optionally containing 1–3 substituents selected from C1–6 alkyl, C6–14 aryl and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo, and (24) C6–14 aryloxy), and a divalent group combining 1–3 of these may be formed;

$R^4$ represents a hydrogen atom or C1–6 alkyl group, C2–6 alkenyl group, C2–6 alkynyl group or C3–8 cycloalkyl group, C6–14 aryl group, hydroxy group, mercapto group which may have oxo, or amino group, which may respectively be substituted with include 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (II) optionally halogenated C1–6 alkylthio or mercapto, (12) hydroxy, (13) amino, (14) mono-C1–6 alkylamino, (15) mono-C6–14-arylamino, (16) di-C1–6 alkylamino, (17) di-C6–14 arylamino, (18) the acyl which is selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5-or 6-membered heterocyclic carbamoyl containing, other than carbon atoms, 1–4 heteroatoms selected from nitrogen atoms, sulfur atoms, and oxygen atoms, C1–6 alkylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino, and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy, or $R^2$ and $R^4$ may link together to form a double bond, and ring B is a 4—8 membered nitrogen-containing ring which may be substituted via —Y—with 1—5 substituents selected from (i) a hydrogen atom, (ii) halogen, (iii) oxo, and (iv) C1–6 alkyl group, C2–6 alkenyl group, C2–6 alkynyl group, C3–8 cycloalkyl group, C6–14 aryl group or 5–10 membered aromatic heterocyclic group containing, other than carbon atoms, 1–4 heteroatoms selected from nitrogen atoms, sulfur atoms, and oxygen atoms, and which may respectively be substituted with 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5 or 6 membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy; wherein Y is a bond, —CO—, —O—, —S—, —SO—, SO$_2$— or NR$^6$— (in the formula, R$^6$ represents a hydrogen atom or C1–6 alkyl group, C2–6 alkenyl group, C2–6 alkynyl group, C3–8 cycloalkyl group, C6–14 aryl group, which may respectively contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6–14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl which includes 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl, and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy), and;

ring C represents a benzene ring which may further be substituted with, in addition to ring B, 1–3 substituents selected from (1) halogen, (2) C1–3 alkylenedioxy, (3) nitro, (4) cyano, (5) optionally halogenated C1–8 alkyl, (6) optionally halogenated C2–8 alkenyl, (7) option halogenated C2–8 alkynyl, (8) optionally halogenated C3–8 cycloalkyl, (9) optionally halogenated C6–14 aryl, (10) optionally halogenated C1–6 alkoxy, (11) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl containing, other than carbon atoms, 1–4 heteroatoms selected from nitrogen atoms, sulfur atoms, and oxygen atoms, C1–6 alkyl-sulfonyl, C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino and C6–14 arylsulfonyl amino, (19) 4–8 membered saturated cyclic amino optionally containing 1–3 substituents selected from C1–6 alkyl, C6–14 aryl, and 5–10 membered aromatic heterocyclic group containing, other than carbon atoms, 1–4 heteroatoms selected from nitrogen atoms, sulfur atoms, and oxygen atoms, (20) 5–10 membered aromatic heterocyclic group containing, other than carbon atoms, 1–4 heteroatoms selected from nitrogen atoms, sulfur atoms, and oxygen atoms, and (21) sulfo.

3. The compound as defined in claim 1, wherein W is an oxygen atom.

4. The compound as defined in claim 1, wherein X is a bond.

5. The compound as defined in claim 1, wherein X is

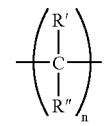

(wherein, R' and R" represent a hydrogen atom, C1–6 alkyl group, C3–8 cycloalkyl group or C6–14 aryl group, and n is an integer of 1–3, and when n is 2 or 3, R' and R" may be different in each repeating unit).

6. The compound as defined in claim 1, wherein ≡is a single bond.

7. The compound as defined in claim 1, wherein R3 is a optionally substituted C6–14 aryl group.

8. The compound as defined in claim 1, wherein R3 is an optionally substituted heterocyclic group.

9. The compound as defined in claim 1, wherein X is a bond, and R3 is an optionally substituted phenyl group.

10. The compound as defined in claim 1, wherein X is a bond, R3 is a phenyl group which may respectively contain 1–5 substituents selected from (1) halogen, (2) optionally halogenated C1–6 alkyl, (3) optionally halogenated C6–14 aryl, (4) optionally halogenated C1–6 alkoxy, and (5) di-C$_{1-6}$ alkylamino.

11. The compound as defined in claim 1, wherein X is a bond, R3 is a 5–8 membered heterocyclic group containing 1–3 nitrogen atoms, as heteroatoms, on the ring structure, and which may also contain 1–5 substituents selected from (1) halogen, (2) C1–3 alkylenedioxy, (3) nitro, (4) cyano, (5) optionally halogenated C1–6 alkyl, (6) optionally halogenated C2–6 alkenyl, (7) optionally halogenated C2–6 alkynyl, (8) optionally halogenated C3–8 cycloalkyl, (9) optionally halogenated C6–14 aryl, (10) optionally halogenated C1–6 alkoxy, (11) optionally halogenated C1–6 alkylthio or mercapto, (12) hydroxy, (13) amino, (14) mono-C1–6 alkylamino, (15) mono-C6–14 arylamino, (16) di-C1–6 alkylamino, (17) di-C6 14 arylamino, (18) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbonyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (19) acylamino selected from formyl amino, C1–6 alkyl-carbonylamino, C6–14 aryl-carbonylamino, C1–6 alkoxy-carbonylamino, C1–6 alkylsulfonyl amino and C6–14 arylsulfonyl amino, (20) acyloxy selected from C1–6 alkyl-carbonyloxy, C6–14 aryl-carbonyloxy, C1–6 alkoxy-carbonyloxy, mono-C1–6 alkyl-carbamoyloxy, di-C1–6 alkyl-carbamoyloxy, C6–14 aryl-carbamoyloxy and nicotinoyloxy, (21) 4–8 membered saturated cyclic amino which may contain 1–3 substituents selected from C1–6 alkyl, C6–14 aryl and 5–10 membered aromatic heterocyclic group containing, other than carbon atoms, 1–4 heteroatoms selected from nitrogen atoms, sulfur atoms, and oxygen atoms, (22) 5–10 membered aromatic heterocyclic group containing, other than carbon atoms, 1–4 heteroatoms selected from nitrogen atoms, sulfur atoms, and oxygen atoms, (23) sulfo and (24) C6–14 aryloxy.

12. The compound as defined in claim 1, wherein X is a bond, and $R^3$ is piperidino, morpholino, piperazinyl, pyridyl or pyrrolidinyl group which may respectively contain 1–3 substituents selected from (1) halogen, (2) optionally halogenated C1–6 alkyl, (3) optionally halogenated C6–14 aryl and (4) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl and C7–16 aralkyloxy-carbonyl.

13. The compound as defined in claim 1, wherein ring B is substituted with 1–4 substituents (that may be respectively the same or different when a plural substituents substitute) represented by the formula —Y—Ar [wherein, Y represents —$(CH_2)_m$— (m represents an integer of 1 to 6), —CO—, —O—, —S—, —SO—, —$SO_2$— or —$NR^6$— (wherein $R^6$ represents a hydrogen atom or optionally substituted hydrocarbon group) or a bond, and Ar represents optionally substituted aromatic group].

14. The compound as defined in claim 1, wherein ring B is a piperidine ring, piperazine ring or pyrrolidine ring.

15. The compound as defined in claim 1, wherein ring B is substituted in the 5 position of a (dihydro) benzo thiophene ring or a (dihydro) benzofuran ring.

16. The compound as defined in claim 13, wherein the aromatic ring represented by Ar is a optionally substituted phenyl group.

17. The compound as defined in claim 13, wherein Y is a bond.

18. The compound as defined in claim 1, wherein R1 and R2 are respectively C1–6 alkyl group.

19. The compound as defined in claim 1, wherein R4 is a hydrogen atom.

20. The compound as defined in claim 1, wherein ring C further is substituted with, in addition to ring B, 1–3 substituents selected from (1) halogen, (2) C1–3 alkylenedioxy, (3) nitro, (4) cyano, (5) optionally halogenated C1–8 alky (6) optionally halogenated C2–8 alkenyl, (7) optionally halogenated C2–8 alkynyl, (8) optionally halogenated C3–8 cycloalkyl, (9) optionally halogenated C6–14 aryl, (10) optionally halogenated C1–6 alkoxy, (11) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, 5- or 6-membered heterocyclic carbamoyl containing, other than carbon atoms, 1–4 heteroatoms selected from nitrogen atoms, sulfur atoms, and oxygen atoms, mono-C1–6 alkyl-carbamoyl, di-C1–6 alkyl-carbamoyl, C6–14 aryl-carbamoyl, thiocarbamoyl, 5- or 6-membered heterocyclic carbamoyl containing, other than carbon atoms, 1–4 heteroatoms selected from nitrogen atoms, sulfur atoms, and oxygen atoms, C1–6 alkylsulfonyl, C6–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonylamino, and C6–14 arylsulfonylamino, (19) 4–8 membered saturated cyclic amino which may contain 1–3 substituents selected from C1–6 alkyl, C6–14 aryl, and 5–10 membered aromatic heterocyclic group containing, other than carbon atoms, 1–4 heteroatoms selected from nitrogen atoms, sulfur atoms, and oxygen atoms, (20) 5–10 membered aromatic heterocyclic group containing, other than carbon atoms, 1–4 heteroatoms selected from nitrogen atoms, sulfur atoms, and oxygen atoms, and (21) sulfo.

21. The compound as defined in claim 1, wherein ring C further is, substituted with, in addition to ring B, 1–3 substituents selected from (1) halogen, (2) C1–3 alkylenedioxy, (3) nitro, (4) cyano, (5) C1–8 alkyl, (6) C2–8 alkenyl, (7) C2–8alkynyl, (8) optionally halogenated C3–8 cycloalkyl, (9) optionally halogenated C6–14 aryl, (10) C1–6 alkoxy, (11) hydroxy, (12) amino, (13) mono-C1–6 alkylamino, (14) mono-C6–14 arylamino, (15) di-C1–6 alkylamino, (16) di-C6–14 arylamino, (17) acyl selected from formyl, carboxy, carbamoyl, C1–6 alkyl-carbonyl, C3–8 cycloalkyl-carbonyl, C1–6 alkoxy-carbonyl, C6–14 aryl-carbonyl, C7–16 aralkyl-carbonyl, C6–14 aryloxy-carbonyl, C7–16 aralkyloxy-carbonyl, mono-C1–6 alkyl-carbamoyl, di-C1–6 alkyl-carbamoyl, C6–14 aryl-carbamoyl, thiocarbamoyl, C1–6 alkylsulfonyl, C1–14 arylsulfonyl, C1–6 alkylsulfinyl and C6–14 arylsulfinyl, (18) acylamino selected from formyl amino, C1–6 alkyl-carboxamide, C6–14 aryl-carboxamide, C1–6 alkoxy-carboxamide, C1–6 alkylsulfonyl amino, and C6–14 arylsulfonyl amino and (19) sulfo.

22. The compound as defined in claim 1, wherein ring C further is substituted with, in addition to ring B, 1 to 3 C1–6 alkyl groups.

23. The compound as defined in claim 1, wherein ring C further is substituted with, in addition to ring B, 3 C1–6 alkyl groups.

24. The compound as defined in claim 1, wherein ring C is substituted with, in addition to ring B, 3 methyl groups.

25. The compound as defined in claim 1, wherein the compound represented by formula:

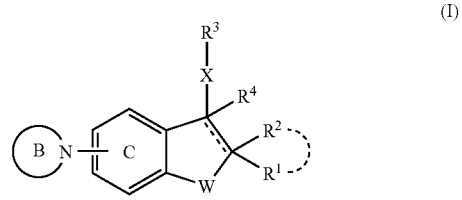

(I)

is 4-(3,4-dimethoxyphenyl)-1-(2,2,4,6,7-pentamethyl-3-(4-methylphenyl)-2,3-dihydro-1-benzofuran-5-yl) piperazine, (3R)-4-(4-methoxyphenyl)-1-(2,2,4,6,7-pentamethyl-3-(4-methylphenyl)-2,3-dihydro-1-benzofuran-5-yl) piperidine, 1-(2,2,4,6,7-pentamethyl-3-(4-methylphenyl)-2,3-dihydro-1-benzofuran-5-yl)-4-(4-methoxyphenyl) piperazine,
N-phenyl-5-(4-(4-methoxyphenyl) piperazin-1-yl)-2,2,4,6,7-pentamethyl-2,3-dihydro-1-benzofuran-3-amine,
4-(4-methoxyphenyl)-1-(2,2,4,6,7-pentamethyl-3-piperidino-2,3-dihydro-1-benzofuran-5-yl) piperazine,
1-(3-(4-(trifluoromethyl) phenyl)-2,2,4,6,7-pentamethyl-2,3-dihydro-1-benzofuran-5-yl)-4-(4-methoxyphenyl) piperazine,
4-(3,4-dimethoxyphenyl)-1-(3-(4-(methylphenyl)-2,2,4,6,7-pentamethyl-2,3-dihydro-1-benzofuran-5-yl) piperidine,
1-(3-(4-isopropylphenyl)-2,2,4,6,7-pentamethyl-2,3-dihydro-1-benzofuran-5-yl)-4-(3,4-dimethoxyphenyl) piperidine,
1-(4-methoxyphenyl)-4-(2,2,4,6,7-pentamethyl-3-[pyrrolidin-1-yl]-2,3-dihydro-1-benzofuran-5-yl) piperazine,
1-(5-(4-(4-methoxyphenyl)1-piperazinyl)-(2,2,4,6,7-pentamethyl-2,3-dihydro-1-benzofuran-3-yl) indoline,
1-(4-methoxyphenyl)-4-(2,2,4,6,7-pentamethyl-3-pyridine-2-yl-2,3-dihydro-1-benzofuran-5-yl) piperazine,
1-(3-(6-fluoropyridin-3-yl)-2,2,4,6,7-pentamethyl-2,3-dihydro-1-benzofuran-5-yl)-4-(4-methoxyphenyl) piperazine,
1-(3,4-dimethoxyphenyl)-4-(2,2,4,6,7-pentamethyl-3-piperidino-2,3-dihydro-1-benzofuran-5-yl) piperazine,
1-(4-methoxyphenyl)-4-(2,2,4,6,7-pentamethyl-3-(6-methyl-3-pyridinyl)-2,3-dihydro-1-benzofuran-5-yl) piperazine,
4-(4-methoxyphenyl)-1-(2,2,4,5,7-pentamethyl-3-(4-methylphenyl)-2,3-dihydro-1-benzofuran-6-yl) piperazine,
1-(3-benzyl-2,2,4,6,7-pentamethyl-2,3-dihydro-1-benzofuran-5-yl)-4-(4-methoxyphenyl) piperazine,
1-(4-methoxyphenyl)-4-(2,2,4,6,7-pentamethyl-3-((4-methylphenoxy) methyl)-2,3-dihydro-1-benzofuran-5-yl) piperazine,
4-(4-methoxyphenylmethyl)-1-(2,2,4,6,7-pentamethyl-3-(4-methylphenyl)-2,3-dihydro-1-benzofuran-5-yl)piperazine,
4-(2-methoxyphenylmethyl)-1-(2,2,4,6,7-pentamethyl-3-(4-methylphenyl)-2,3-dihydro-1-benzofuran-5-yl)piperazine,
4-(3-methoxyphenylmethyl)-1-(2,2,4,6,7-pentamethyl-3-(4-methylphenyl)-2,3-dihydro-1-benzofuran-5-yl)piperazine,
1-(3-(6-fluoropyridine-3-yl)-2,2,4,6,7-pentamethyl-2,3-dihydro-1-benzofuran-5-yl)-4-(4-methoxyphenyl)methylpiperazine,
1-(4-methoxyphenylethyl)-4-(2,2,4,6,7-pentamethyl-3-pyrrolidinyl-2,3-dihydro-1-benzofuran-5-yl)piperazine, or
1-(3-methoxyphenylethyl)-4-(2,2,4,6,7-pentamethyl-3-pyrrolidinyl-2,3-dihydro-1-benzofuran-5-yl)piperazine.

26. A method for treating Parkinson's disease, Alzheimer's disease, ALS or Huntingdon's disease in a mammal, comprising the administration of a compound of claim 1 to a mammal requiring treatment of Parkinson's disease, Alzheimer's disease, ALS or Huntington's disease.

27. A method for the treatment of depression, anxiety, maniac depression or PTSD in a mammal, comprising the administration of a compound of claim 1 to a mammal requiring treatment of depression, anxiety, manic depression or PTSD.

28. A method of inhibiting neurodegeneration which comprises administering a compound represented by the formula

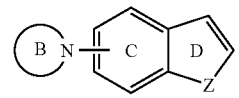

(wherein, ring B represents an optionally substituted 5–8 membered nitrogen-containing heterocyclic group, ring C represents a benzene ring which may further contain substituents in addition to the group represented by ring B, ring D represents an optionally substituted 5-membered ring, Z represents a carbon atom, nitrogen atom, oxygen atom or sulfur atom, and≡represents a single bond or a double bond), or a salt thereof to a mammal in need thereof.

29. The method as defined in claim 28, wherein Z is an oxygen atom.

30. The method as defined in claim 28, which is for treating neurodegenerative diseases.

31. The inhibitor as defined in claim 28, which is for treating Alzheimer's disease, Parkinson's disease, ALS or Huntington's disease.

32. The method as defined in claim 28, which is for treating mild cognitive impairment or mild memory loss.

33. A method of activating PKB which comprises administering a compound represented by the formula

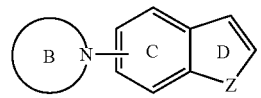

wherein ring B represents an optionally substituted 5–8 membered nitrogen-containing heterocyclic group, ring C represents a benzene ring which may further contain substituents in addition to the group represented by ring B, ring D represents an optionally substituted 5-membered ring, Z represents a carbon atom, nitrogen atom, oxygen atom or sulfur atom, and≡represents a singly bond or a double bond, or a salt thereof to a mammal in need thereof.

34. A method of promoting neurogenesis or neuroregeneration which comprises administering a compound represented by the formula

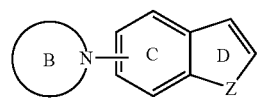

wherein ring B represents an optionally substituted 5–8 membered nitrogen containing heterocyclic group, ring C represents a benzene ring which may further contain substituents in addition to the group represented by ring B, ring D represents an optionally substituted 5-membered ring, Z represents a carbon atom, nitrogen atom, oxygen atom or sulfur atom, and≡represents a single bon or a double bond, or a salt thereof to a mammal in need thereof.

35. The method as defined in claim 34, which is for promoting a proliferation/differentiation of stem cells and/or neural precursor cells.

36. The agent as defined in claim 34, wherein Z is an oxygen atom.

37. The method as defined in claim 35, wherein the stem cells are embryonic stem cells or neural stem cells.

38. The method as defined in claim 34, which is for promoting a proliferation/differentiation of neural stem cells and/or neural cell grafts.

39. The method as defined in claim 34, which is for promoting a proliferation/differentiation of neural stem cells and/or neural cells for transplantation.

40. The method as defined in claim 34, which is for promoting a proliferation/differentiation of endogenous neural stem cells.

41. The method as defined in claim 34, which is for treating central nervous system diseases.

42. A method of promoting proliferation/differentiation of stem cells and/or neural precursor cells for neural stem cell culture which comprises administering a compound represented by the formula

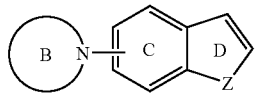

wherein ring B represents an optionally substituted 5–8 membered nitrogen-containing heterocyclic group, ring C represents a benzene ring which may further contain substituents in addition to the group represented by ring B, ring D represents an optionally substituted 5-membered ring, Z represents a carbon atom, nitrogen atom, oxygen atom or sulfur atom, and≡represents a singly bond or a double bond, or a salt thereof.

43. The method as defined in claim 42, wherein Z is an oxygen atom.

44. A process for producing a compound represented by the formula:

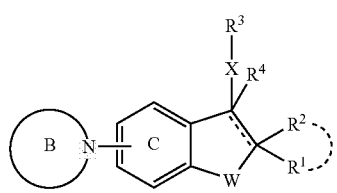

(I)

wherein $R^1$ and $R^2$ are the same of or different and each represents a hydrogen atom, optionally substituted hydrocarbon group or optionally substituted heterocyclic group, or $R^1$ and $R^2$ may form, together with the adjacent carbon atom, a 3–8 membered iso- or heterocyclic group which may optionally substituted, $R^3$ represents an optionally substituted cyclic group, X represents a bond or a spacer of 1–3 atoms, and $R^4$ represents a hydrogen atom, an optionally substituted hydrocarbon group, optionally substituted hydroxy group, optionally substituted mercapto group which may have oxo, or an optionally substituted amino group, or $R^2$ and $R^4$ may link together to form a double bond, W represents an oxygen atom or a sulfur atom, ring B represents an optionally substituted 4–8 membered nitrogen-containing heterocyclic group, and ring C represents a benzene ring which may also be optionally substituted in addition to the group represented by ring B but not via a nitrogen atom, and≡represents a singly bond or a double bond, or salts thereof, comprising the step of reacting a compound represented by the formula:

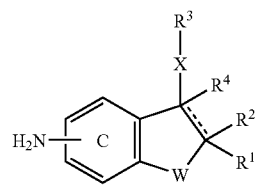

(wherein each symbol has the same meaning as defined above) or a salt thereof with a compound represented by the formula:

$$L^1\text{-}E\text{-}L^2$$

(wherein, $L^1$ and $L^2$ represent leaving groups, and E represents a partial sequence of the ring structure of ring B other than the nitrogen atom) or a salt thereof.

45. The production process as defined in claim 44, in which the reaction occurs in the presence of base.

46. A pharmaceutical composition comprising the compound as defined in claim 1 and a pharmacologically acceptable carrier.

* * * * *